United States Patent
Tamiya et al.

(10) Patent No.: US 11,530,205 B2
(45) Date of Patent: Dec. 20, 2022

(54) GLP-1 RECEPTOR MODULATORS

(71) Applicant: RECEPTOS LLC, New York, NY (US)

(72) Inventors: Junko Tamiya, Carlsbad, CA (US); Philip Turnbull, San Diego, CA (US); Brahmachary Enugurthi, San Diego, CA (US); Liming Huang, San Diego, CA (US); Adam R. Yeager, La Mesa, CA (US); Thomas Fowler, Leicestershire (GB); Greg P. Iacobini, Nottinghamshire (GB); Matthew Richard Crittall, Nottinghamshire (GB)

(73) Assignee: Receptos LLC, New York, NY (US)

( * ) Notice: Subject to any disclaimer, the term of this patent is extended or adjusted under 35 U.S.C. 154(b) by 0 days.

(21) Appl. No.: 16/608,134

(22) PCT Filed: Apr. 26, 2018

(86) PCT No.: PCT/US2018/029597
§ 371 (c)(1),
(2) Date: Oct. 24, 2019

(87) PCT Pub. No.: WO2018/200833
PCT Pub. Date: Nov. 1, 2018

(65) Prior Publication Data
US 2021/0371409 A1  Dec. 2, 2021

Related U.S. Application Data

(60) Provisional application No. 62/491,892, filed on Apr. 28, 2017.

(51) Int. Cl.
| | | |
|---|---|---|
| *C07D 413/12* | (2006.01) | |
| *C07D 239/26* | (2006.01) | |
| *C07D 401/12* | (2006.01) | |
| *C07D 403/12* | (2006.01) | |
| *C07D 405/12* | (2006.01) | |
| *C07D 409/12* | (2006.01) | |
| *C07D 417/12* | (2006.01) | |

(52) U.S. Cl.
CPC ......... *C07D 413/12* (2013.01); *C07D 239/26* (2013.01); *C07D 401/12* (2013.01); *C07D 403/12* (2013.01); *C07D 405/12* (2013.01); *C07D 409/12* (2013.01); *C07D 417/12* (2013.01)

(58) Field of Classification Search
CPC .. C07D 413/12; C07D 239/26; C07D 401/12; C07D 403/12; C07D 405/12; C07D 409/12; C07D 417/12
See application file for complete search history.

(56) References Cited

U.S. PATENT DOCUMENTS

| | | | | |
|---|---|---|---|---|
| 9,474,755 | B2* | 10/2016 | Boehm | A61K 31/155 |
| 9,598,430 | B2* | 3/2017 | Boehm | C07D 409/14 |
| 9,700,543 | B2* | 7/2017 | Boehm | A61P 25/00 |
| 9,795,613 | B2* | 10/2017 | Boehm | A61P 1/16 |
| 9,839,664 | B2* | 12/2017 | Boehm | C07D 401/14 |
| 10,034,886 | B2* | 7/2018 | Boehm | C07D 207/08 |
| 10,259,823 | B2* | 4/2019 | Boehm | A61K 31/415 |
| 2017/0114072 | A1* | 4/2017 | Yang | C07D 401/12 |
| 2017/0216392 | A1* | 8/2017 | Boehm | C07K 5/06139 |
| 2017/0313717 | A1* | 11/2017 | Boehm | C07D 417/04 |
| 2018/0021346 | A1* | 1/2018 | Boehm | A61K 31/551 |
| | | | | 544/333 |

FOREIGN PATENT DOCUMENTS

| | | |
|---|---|---|
| WO | 2012/166951 A1 | 12/2012 |
| WO | 2013/090454 A2 | 6/2013 |
| WO | 2014/201172 A1 | 12/2014 |

OTHER PUBLICATIONS

Madsbad; Diabetes, Obesity and Metabolism, 2016, 18, 317-332. doi: 10.1111/dom.12596 (Year: 2016).*

* cited by examiner

*Primary Examiner* — Daniel R Carcanague
(74) *Attorney, Agent, or Firm* — Seed IP Law Group LLP

(57) ABSTRACT

Compounds are provided that modulate the glucagon-like peptide 1 (GLP-1) receptor, as well as products containing such compounds, and methods of their use and synthesis. Such compounds have the structure of Formula (I) below: (I) or pharmaceutically acceptable salts thereof, wherein A, J, $W^1$, Y, Z, $R^1$, $R^2$, $R^3$ and $R^4$ are as defined herein.

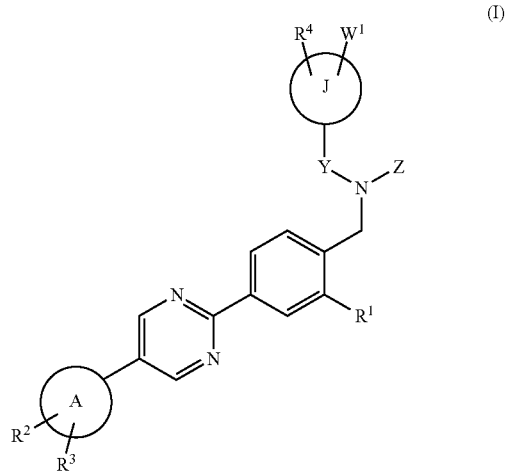

18 Claims, No Drawings
Specification includes a Sequence Listing.

GLP-1 RECEPTOR MODULATORS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 800059 418USPC SEQUENCE LISTING.txt. The text file is 1 KB, was created on Jun. 9, 2021, and is being submitted electronically via EFS-Web.

TECHNICAL FIELD

The disclosure is directed to compounds that modulate the glucagon-like peptide 1 (GLP-1) receptor, as well as to related products and methods for their use and synthesis.

BACKGROUND

Glucagon-like peptide 1 receptor (GLP-1R) belongs to Family B1 of the seven-transmembrane G protein-coupled receptors, and its natural agonist ligand is the peptide hormone glucagon-like peptide-1 (GLP-1). GLP-1 is a peptide hormone arising by its alternative enzymatic cleavage from proglucagon, the prohormone precursor for GLP-1, which is highly expressed in enteroendocrine cells of the intestine, the alpha cells of the endocrine pancreas (islets of Langerhans), and the brain (Kieffer T. J. and Habener, J. F. Endocrin. Rev. 20:876-913 (1999); Drucker, D. J., Endocrinology 142:521-7 (2001); Holst, J. J., Diabetes Metab. Res. Rev. 18:430-41 (2002)). The initial actions of GLP-1 observed were on the insulin-producing cells of the islets, where it stimulates glucose-dependent insulin secretion. Subsequently, multiple additional anti diabetogenic actions of GLP-1 were discovered including the stimulation of the growth and inhibition of the apoptosis of pancreatic beta cells (Drucker, D. J., Endocrinology 144:5145-8 (2003); Holz, G. G. and Chepurny O. G., Curr. Med. Chem. 10:2471-83 (2003); List, J. F. and Habener, J. F., Am. J. Physiol. Endocrinol. Metab. 286:E875-81 (2004)).

On activation, GLP-1 receptors couple to the a subunit of G protein, with subsequent activation of adenylate cyclase and increase of cAMP levels, thereby potentiating glucose-stimulated insulin secretion. Therefore, GLP-1 is an attractive target to lower blood glucose levels and preserve the β-cells of the pancreas of diabetic patients. Glucagon has been used for decades in medical practice within diabetes and several glucagon-like peptides are being developed for various therapeutic indications. GLP-1 analogs and derivatives are being developed for the treatment for patients suffering from diabetes.

While advances have been made in this field, there remains a significant need for modulators of the GLP-1 receptor, particularly GLP-1 receptor agonists, as well as for products and methods related to the same. The present disclosure fulfills these and other needs, as described in more detail in the following detailed description.

SUMMARY OF INVENTION

The present invention is directed to compounds adapted to act as modulators of the GLP-1 receptor, particularly GLP-1 receptor agonists, as well as to related products and methods of their preparation and their use, such as in treatment of a malcondition mediated by GLP-1 receptor, or when modulation of GLP-1 receptor is medically indicated.

In one embodiment, compounds are provided having the structure of Formula (I):

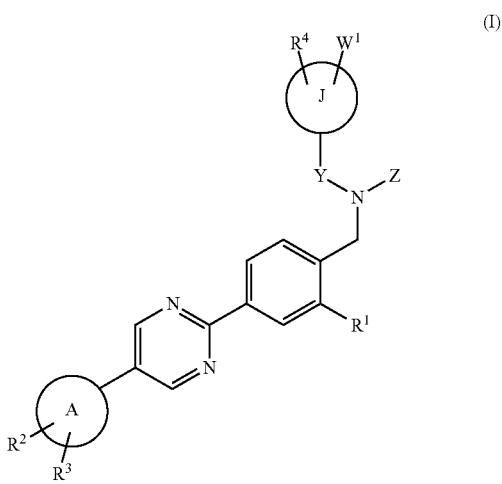

or a pharmaceutically acceptable salts thereof, wherein A, J, $W^1$, Y, Z, $R^1$, $R^2$, $R^3$ and $R^4$ are as defined below.

In one embodiment, the compounds of Formula (I) include, but are not limited to, hydrates, hydrates and/or isotopes thereof, as well as stereoisomers to the extent such compounds contain one or more chiral centers.

In one embodiment, a pharmaceutical composition comprising a compound of Formula (I) together with at least one pharmaceutically acceptable carrier, diluent or excipient is provided.

In one embodiment, a method of modulation of a GLP-1 receptor is provided comprising contacting the receptor with a compound of Formula (I), or a pharmaceutical composition comprising a compound of Formula (I).

In one embodiment, a method is provided for treatment of a malcondition in a subject for which modulation of a GLP-1 receptor is medically indicate, comprising administering to the subject a compound of Formula (I), or a pharmaceutical composition comprising a compound of Formula (I).

In one embodiment, the malcondition is type I diabetes, type II diabetes, gestational diabetes, obesity, excessive appetite, insufficient satiety, or metabolic disorder.

In one embodiment, the malcondition is non-alcoholic fatty liver disease (NAFLD) and/or non-alcoholic steatohepatitis (NASH).

In one embodiment, methods for synthesis of compounds of Formula (I) are provided, including preparation of intermediates associated with such methods.

DETAILED DESCRIPTION OF THE INVENTION

As mentioned above, the present invention provides compounds which modulate the GLP-1 receptor, particularly GLP-1 receptor agonists, as well as to methods of their preparation and use in the treatment of conditions mediated by the GLP-1 receptor, including (but not limited to) type I diabetes, type II diabetes, gestational diabetes, obesity, excessive appetite, insufficient satiety, metabolic disorder, non-alcoholic fatty liver disease (NAFLD) and/or non-alcoholic steatohepatitis (NASH).

In one embodiment, compounds are provided having the structure of Formula (I):

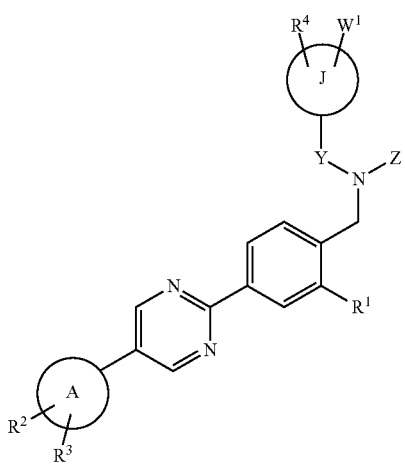

or a pharmaceutically acceptable salts thereof, wherein:
J is null or has the structure:

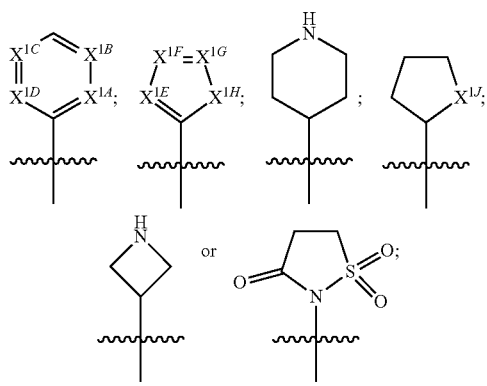

each of $X^{1A}$, $X^{1B}$, $X^{1C}$, $X^{1D}$, $X^{1E}$, $X^{1F}$ and $X^{1G}$ is C, CH or N;
$X^{1H}$ is O or S;
$X^{1J}$ is $CH_2$ or NH;
$R^1$ is H, alkyl or alkoxy;
Y is —C(O)—, —$CH_2$—, —C(O)—$CH_2$—, —$CH_2$—C(O)—, —C(O)—$(CR^aR^b)_n$—$N(R^c)$—C(O)—$(CR^aR^b)_n$—, —C(O)—$(CR^aR^b)_n$—$N(R^d)$— where $R^d$ may form a fused ring with J or with a fused $J$-$R^4$—$W^1$ ring system,
—C(O)—$(CR^aR^b)_n$—$N(R^c)$—C(O)—$(CR^aR^b)_n$—$N(R^c)$—$S(O)_k$—$(CR^aR^b)_n$—, —C(O)—$(CR^aR^b)_n$—$N(R^c)$—C(O)—$(CR^aR^b)$—$N(R^d)$— where $R^d$ may form a fused ring with J or with a fused $J$-$R^4$—$W^1$ ring system, or —C(O)—$(CR^aR^b)_n$—$N(R^c)$—$S(O)_k$—$(CR^aR^b)$—;
Z is —$(CR^aR^b)_n$—C(O)—$R^7$;
$R^7$ is —$OR^{30}$, —$NR^{31}R^{32}$, —$NH(CR^aR^b)_n$—C(O)—$R^7$, —$NHSO_2R^7$ or —(CO)—NH—$SO_2$—$R^7$, or $R^{31}$;
each $R^{30}$ is independently H or alkyl;
each $R^{31}$ and $R^{32}$ is independently H or $C_1$-$C_6$ alkyl optionally substituted with one or more $R^{33}$, or taken together with the N atom to which they are attached can form a 3- to 7-membered heterocyclic ring;

each $R^{33}$ is independently halo, hydroxyl, alkoxy, perhaloalkyl, perhaloalkoxy, carboxyl, —C(O)O—$R^{30}$, —$OR^{30}$, —$N(R^{30})_2$ or heterocyclyl;
each $R^4$ is independently H, alkyl, alkoxy, or alkyl substituted with one or more $R^{43}$, halogen, perhaloalkyl, perhaloalkoxy, —CN, —$OR^{40}$ or —$NR^{41}R^{42}$;
each $R^{41}$ and $R^{42}$ is independently H, alkyl, —$(CH_2)_n$—C(O)O—$R^{40}$, —C(O)—$R^{40}$, aryl, heteroaryl; or $R^{41}$ and $R^{42}$, taken together with the N atom to which they are attached, can form a 3- to 7-membered heterocyclic ring;
each $R^{43}$ is independently H, halo, hydroxyl, —$NR^{41}R^{42}$, or alkoxy;
$W^1$ is —$(CR^aR^b)_{i1}$-$L^1$—$(CR^aR^b)_{j1}$—$R^{60}$ or $R^4$; or $W^1$ and $R^4$ taken together comprise a 5- or 6-membered carbocyclic or heterocyclic ring fused with the ring to which $W^1$ and $R^4$ are attached and optionally having one, two or three heteroatoms where each such heteroatom is independently selected from O, N, and S, and where any ring atom of such heterocyclic ring may be optionally substituted with one or more —$L^4$—$R^{13}$ or $R^{13}$; or $W^1$ is a 5- or 6-membered heterocyclic ring fused with a phenyl ring and having one, two or three heteroatoms where each such heteroatom is independently selected from O, N, and S, and where any ring atom of such fused heterocyclic ring and phenyl ring moiety may be optionally substituted with one or more $R^{14}$;
$L^1$ is —O—, —C(O)—, —OC(O)—, —C(O)O—, —$NR^{10}$—, —$C(O)NR^{10}$—, —$N(R^{10})$—$(CH_2)_n$—C(O)—, —$N(R^{10})$—C(O)—$N(R^{10})$—, —$N(R^{10})$—$S(O)_2$—, —$S(O)_2$—$NR^{10}$—, or —$N(S(O)_2$—$(CH_2)_n$—$R^{60})_2$;
$R^{60}$ is $R^{13}$, —O—$(CH_2)_n$—$R^{13}$, or $R^{10}$;
each $R^{10}$, $R^{11}$ and $R^{12}$ is independently H or alkyl;
$R^{13}$ is cycloalkyl, heterocycloalkyl, aryl, or heteroaryl, or a fused bicycle or tricycle of any two or three of such ring moieties, or $R^{13}$ and $R^{10}$ taken together with the N atom to which they are attached form a heterocyclic ring, where any ring atom of $R_{13}$ may be optionally substituted with one or more $R^{14}$ or $R^{15}$;
each $R^{14}$ is independently H, alkyl, halo, hydroxy, cyano, alkoxy, perhaloalkyl, and perhaloalkoxy, —$OR^{10}$, —$(CH_2)_n$—$C(O)OR^{10}$, —$SR^{10}$, —SO—$R^{10}$, —$S(O)_2$—$R^{10}$, —$(CH_2)_n$—$NR^{11}R^{12}$, —NH—C(O)—$(CH_2)_n$—$R^{12}$, —$N(R^{11})$—C(O)—$(CH_2)_n$—$R^{12}$, or —$NH(CH_2)_n$—$R^{12}$;
$R^{15}$ is cycloalkyl, heterocycloalkyl, aryl, or heteroaryl, or a fused bicycle of any two of such ring moieties, where any ring atom of $R^{15}$ may be optionally substituted with one or more $R^{14}$;
each $R^5$ is independently H, alkyl, alkoxy, alkyl substituted with one or more $R_{53}$, halogen, perhaloalkyl, perhaloalkoxy, —CN, —$OR^{50}$, or —$NR^{51}R^{52}$;
each $R^{40}$ and $R^{50}$ is independently H or alkyl;
each $R^{51}$ and $R^{52}$ is independently H or alkyl, —$(CH_2)_n$—C(O)O—$R^{50}$, —C(O)—$R^{50}$, aryl, heteroaryl, or two taken together with the N atom to which they are attached can form a 3- to 7-membered heterocyclic ring;
each $R^a$ and $R^b$ is independently H, hydroxy, alkyl, or aralkyl optionally substituted with hydroxyl; or both $R^a$ and $R^b$ attached to the same carbon are, taken together, oxo, or cycloalkyl;
each $R^c$ and $R^d$ is independently H, hydroxy, alkyl, —$S(O)_k$—$R^7$ or —C(O)—$R^7$;

A is cycloalkyl;

R² is alkyl, haloalkyl, cycloalkyl, heterocycloalkyl, aryl, heteroaryl, or a fused bicycle of any two of such ring moieties, where any ring atom of R₂ may be optionally substituted with one or more R³;

each R³ is independently H, alkyl, or perhaloalkyl;

each n is independently 0, 1, 2, 3 or 4; and each $i_1$, $i_2$, $j_1$ and $j_2$ is independently 0, 1, 2, 3 or 4.

In one embodiment, the compounds of Formula (I) include, but are not limited to, hydrates, hydrates and/or isotopes thereof. The compounds of Formula (I) also include stereoisomers to the extent that the compounds of Formula (I) contain one or more chiral centers.

As used herein, the terms listed below have the following meaning.

"Alkyl" groups include straight chain and branched alkyl groups having from 1 to about 20 carbon atoms, and typically from 1 to 12 carbons ($C_1$-$C_{12}$ alkyl), or, in some embodiments, from 1 to 8 carbon atoms ($C_1$-$C_8$ alkyl), or, in some embodiments, from 1 to 4 carbon atoms ($C_1$-$C_4$ alkyl). In the case of cycloalkyl groups, such groups have from 3-20 carbon atoms. Examples of straight chain alkyl groups include, but are not limited to, methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups.

"Alkenyl" groups include straight and branched chain alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH═CH₂, —CH═CH(CH₃), —CH═C(CH₃)₂, —C(CH₃)═CH₂, —C(CH₃)═CH(CH₃), —C(CH₂CH₃)═CH₂, —CH═CHCH₂CH₃, —CH═CH(CH₂)₂CH₃, —CH═CH(CH₂)₃CH₃, —CH═CH(CH₂)₄CH₃, vinyl, cyclohexenyl, cyclopentenyl, cyclohexadienyl, butadienyl, pentadienyl, and hexadienyl among others.

"Cycloalkyl" groups are alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. In some embodiments, cycloalkyl groups are partially unsaturated, including, for example, but not limited to cyclohexenyl, cyclopentenyl, and cyclohexadienyl groups. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Aryl" groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like).

"Aralkyl" groups are alkyl, alkenyl or alkynyl groups as defined above in which a hydrogen atom of an alkyl, alkenyl or alkynyl group is replaced with an aryl group as defined above. Representative aralkyl groups include benzyl (—CH₂phenyl), phenylethyl (—CH₂CH₂phenyl) and phenylethylene (—CH═CHphenyl) groups and fused (cycloalkylaryl)alkyl groups such as 4-ethyl-indanyl.

"Heterocyclyl" or "heterocyclic" groups include aromatic and non-aromatic ring moieties containing 3 or more ring members, of which one or more is a heteroatom such as, but not limited to, N, O, S, or P. In some embodiments, heterocyclyl groups include 3 to 20 ring members, whereas other such groups have 3 to 15 ring members, including for example single ring systems containing 5, 6 or 7 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a C₂-heterocyclyl can be a 5-ring with two carbon atoms and three heteroatoms, a 6-ring with two carbon atoms and four heteroatoms, and so forth. Likewise a C₄-heterocyclyl can be a 5-ring with one heteroatom, a 6-ring with two heteroatoms, and so forth. The number of carbon atoms plus the number of heteroatoms sums up to equal the total number of ring atoms.

The term "heterocyclyl" includes fused ring species including those having fused aromatic and non-aromatic groups. The phrase also includes polycyclic and/or bridging ring systems containing a heteroatom such as, but not limited to, quinuclidyl and 7-azabicyclo[2.2.1]heptane, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrazinyl, pyrimidinyl, pyridazinyl, thiadiazolyl, oxadiazolyl, imidazolinyl, hexahydropyrimidinyl, diazepanyl, triazinyl, imidazolyl, pyrrolidinyl, furanyl, tetrahydrofuranyl, tetrahydro-2H-pyranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heteroaryl" groups are aromatic ring moieties containing 5 or more ring members, of which, one or more is a heteroatom such as, but not limited to, N, O, and S. A heteroaryl group designated as a C₂-heteroaryl can be a 5-ring with two carbon atoms and three heteroatoms, a 6-ring with two carbon atoms and four heteroatoms and so forth. Likewise a C₄-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, pyridinyl, pyridazinyl, pyrimidyl, pyrazyl, pyrazinyl, pyrimidinyl, thiadiazolyl, imidazolyl, oxadiazolyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl (1,2,4-oxadiazolyl, 1,3,4-oxadiazolyl), thiadiazolyl (1,2,4-thiadiazolyl, 1,3,4-thiadiazolyl), isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl, pyrimidinyl (2-pyrimidinyl, 4-pyrimidinyl, 5-pyrimidinyl, 6pyrimidinyl), pyrazinyl, pyridazinyl (3-pyridazinyl, 4-pyridazinyl, 5-pyridazinyl), prazolo[1,5-α]pyridinyl, quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), isobenzofuranyl, 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), benzo[d]isoxazolyl, carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

When two "R" groups are said to be joined together or taken together to form a ring, it is meant that together with the carbon atom or a non-carbon atom (e.g., nitrogen atom), to which they are bonded, they may form a ring system. In general, they are bonded to one another to form a 3- to 7-membered ring, or a 5- to 7-membered ring. Non-limiting specific examples are the cyclopentyl, cyclohexyl, cycloheptyl, piperidinyl, piperazinyl, pyrolidinyl, pyrrolyl, pyridinyl.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, n-heptyloxy, n-octyloxy n-nonyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-IT, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each. Accordingly, any compound substituted with an amino group can be viewed as an amine.

An "ammonium" ion includes the unsubstituted ammonium ion NH$_4^+$, but unless otherwise specified, it also includes any protonated or quaternarized forms of amines.

Thus, trimethylammonium hydrochloride and tetramethylammonium chloride are both ammonium ions, and amines, within the meaning herein.

The term "amide" or "amido" includes C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H). A "carboxamido" group is a group of the formula C(O)NR$_2$, wherein R can be H, alkyl, aryl, etc.

The term "carbonyl," refers to a —C(O)— group.

"Halo," "halogen," and "halide" include fluorine, chlorine, bromine and iodine.

The term "perhaloalkyl" refers to an alkyl group where all of the hydrogen atoms are replaced by halogen atoms. Perhaloalkyl groups include, but are not limited to, —CF$_3$ and —C(CF$_3$)$_3$. The term "haloalkyl" refers to an alkyl group where some but not necessarily all of the hydrogen atoms are replaced by halogen atoms. Haloalkyl groups include but are not limited to —CHF$_2$ and —CH$_2$F.

The term "perhaloalkoxy" refers to an alkoxy group where all of the hydrogen atoms are replaced by halogen atoms. Perhaloalkoxy groups include, but are not limited to, —OCF$_3$ and —OC(CF$_3$)$_3$. The term "haloalkoxy" refers to an alkoxy group where some but not necessarily all of the hydrogen atoms are replaced by halogen atoms. Haloalkoxy groups include but are not limited to —OCHF$_2$ and —OCH$_2$F.

In one embodiment, compounds are provided having the structure of Formula (II):

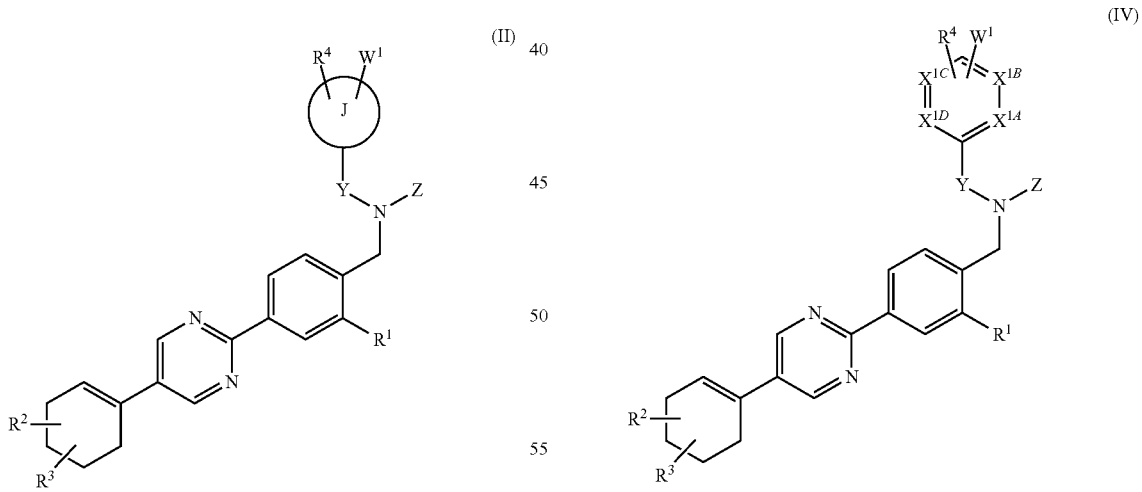

wherein J, W$^1$, Y, Z, R$^1$, R$^2$, R$^3$ and R$^4$ are as defined for Formula (I) above.

In one embodiment, compounds are provided having the structure of Formula (III):

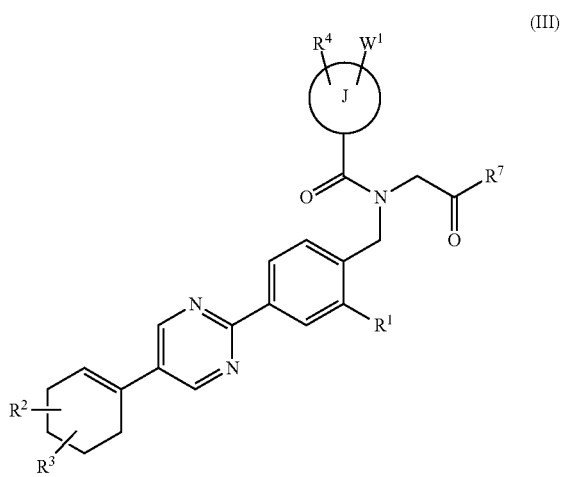

wherein J, W$^1$, R$^1$, R$^2$, R$^3$, R$^4$, and R$^7$ are as defined for Formula (I) above In one embodiment, compounds are provided having the structure of Formula (IV):

(IV)

wherein W$^1$, Y, Z, X$^{1A}$, X$^{1B}$, X$^{1C}$, X$^{1D}$, R$^1$, R$^2$, R$^3$ and R$^4$ are as defined for Formula (I) above.

In one embodiment, compounds are provided having the structure of Formula (V):

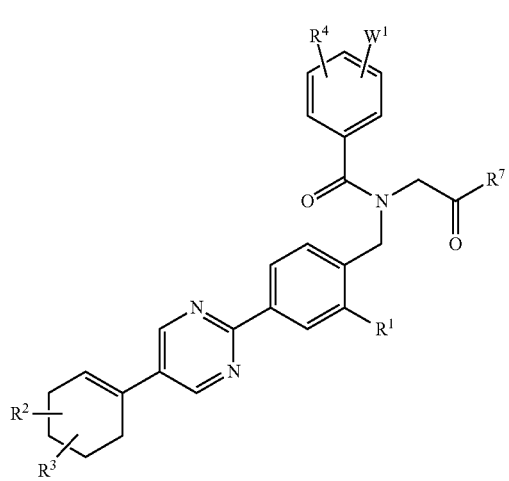

(V)

wherein $W^1$, $R^1$, $R^2$, $R^3$, $R^4$, and $R^7$ are as defined for Formula (I) above.

In one embodiment, compounds are provided having the structure of Formula (VI):

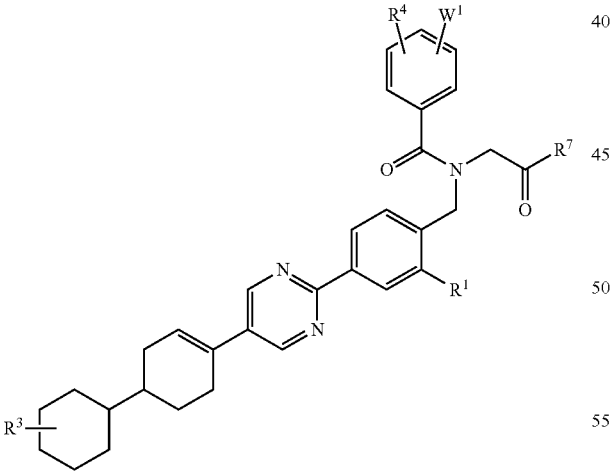

(VI)

wherein $W^1$, $R^3$, $R^4$, and $R^7$ are as defined for Formula (I) above.

In one embodiment, compounds are provided having the structure of Formula (VII):

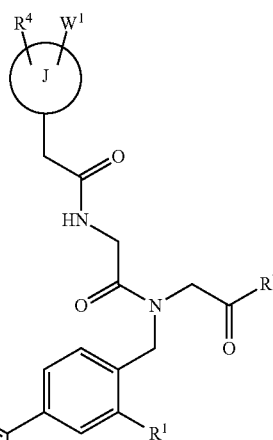

(VII)

wherein J, $W^1$, $R^1$, $R^2$, $R^3$, $R^4$, and $R^7$ are as defined for Formula (I) above.

In one embodiment, compounds are provided having the structure of Formula (VIII):

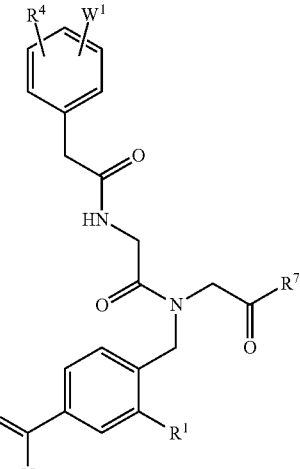

(VIII)

wherein $W^1$, $R^1$, $R^2$, $R^3$, $R^4$, and $R^7$ are as defined for Formula (I) above.

In one embodiment, compounds are provided having the structure of Formula (IX):

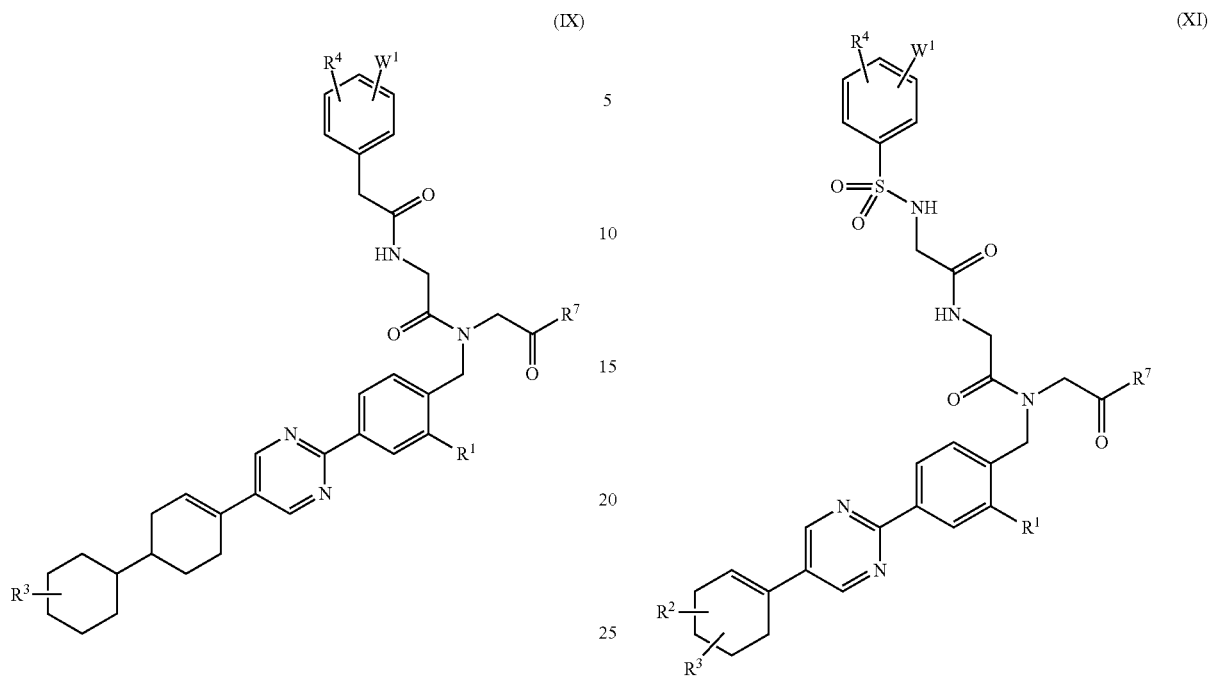

wherein $W^1$, $R^1$, $R^3$, $R^4$, and $R^7$ are as defined for Formula (I) above.

In one embodiment, compounds are provided having the structure of Formula (X):

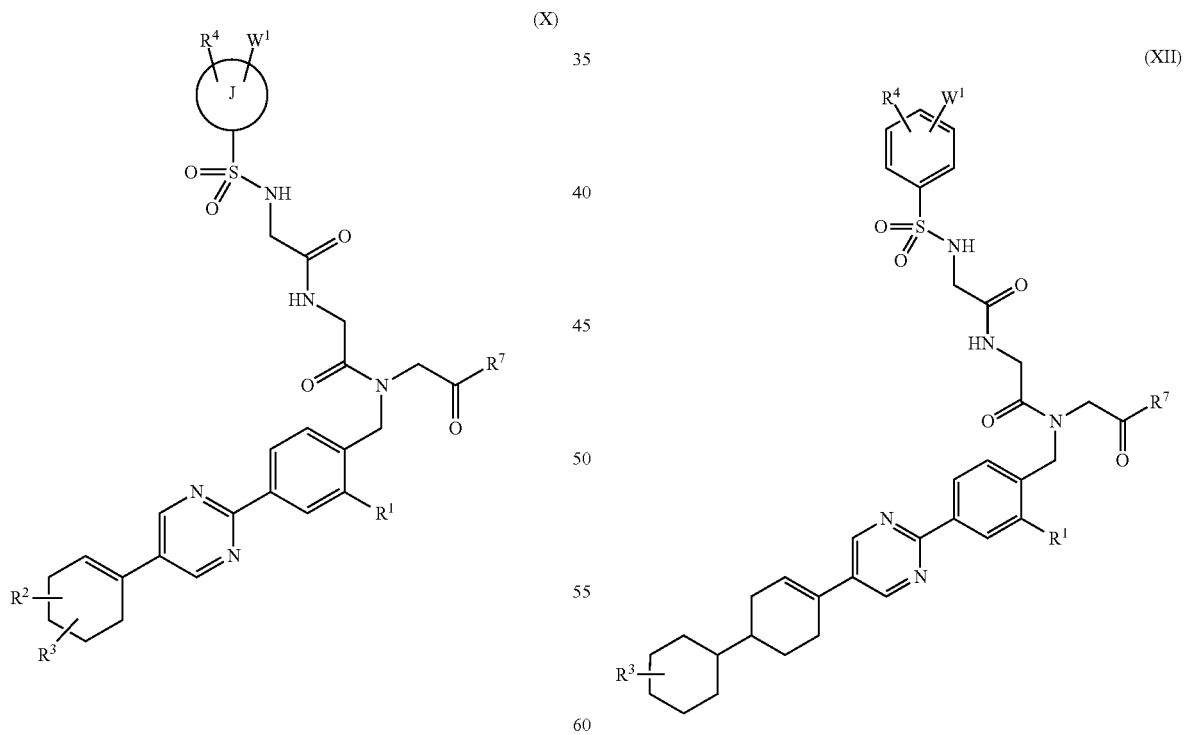

wherein J, $W^1$, $R^1$, $R^2$, $R^3$, $R^4$, and $R^7$ are as defined for Formula (I) above.

In one embodiment, compounds are provided having the structure of Formula (XI):

wherein $W^1$, $R^1$, $R^2$, $R^3$, $R^4$, and $R^7$ are as defined for Formula (I) above.

In one embodiment, compounds are provided having the structure of Formula (XII):

wherein $W^1$, $R^1$, $R^3$, $R^4$, and $R^7$ are as defined for Formula (I) above.

The compounds of any one of Formulas (II) through (XII) above include, but are not limited to, hydrates, hydrates and/or isotopes thereof, as well as stereoisomers to the extent such compounds contain one or more chiral centers.

The compounds of any one of Formulas (II) through (XII) above also include pharmaceutically acceptable salts.

In the following more specific embodiments, the various substituents (e.g., A, J, $W^1$, Y, Z, $R^1$, $R^2$, $R^3$, $R^4$, and $R^7$) are set forth in more detail with respect to the compounds of each of Formulas (I) through (XII) above, as applicable to the substituents being further defined. For example, reference to Y below is intended to further limit the compounds of Formulas (I), (II) and (IV) above, but not Formulas (III) or (V)-(XII) since the Y substituent has already been further defined in the same. Thus, reference to the substituents below is intended to further modify Formulas (I)-(XII) to the extent such formulas recite that particular substituent as a variable.

In one embodiment, Y is —C(O)—.
In one embodiment, Y is —C(O)—CH$_2$—.
In one embodiment, Y is —C(O)—CH$_2$—NH—C(O)—CH$_2$—.
In one embodiment, Y is —C(O)—CH$_2$—NH—C(O)—CH$_2$—NH—S(O)$_2$—CH$_2$—.
In one embodiment, Y is —C(O)—CH$_2$—NH—C(O)—CH$_2$—NH—.
In one embodiment, Y is —C(O)—CH$_2$—NH—C(O)—CH$_2$—NH—S(O)$_2$—CH$_2$—.
In one embodiment, Z is —CH$_2$C(O)OH.
In one embodiment, $W^1$ is attached to one of $X^{1A}$, $X^{1B}$, $X^{1C}$, $X^{1D}$, $X^{1E}$, $X^{1F}$ or $X^{1G}$.
In one embodiment, the ring atom of $X^{1A}$, $X^{1B}$, $X^{1C}$, $X^{1D}$, $X^{1E}$, $X^{1F}$ and $X^{1G}$ to which $W^1$ is attached is C.
In one embodiment, $W^1$ is attached to $X^{1G}$ and $X^{1G}$ is C.
In one embodiment, each of $X^{1A}$, $X^{1B}$, $X^{1C}$ and $X^{1D}$ is C or CH.
In one embodiment, one of $X^{1A}$, $X^{1B}$, $X^{1C}$ and $X^{1D}$ is N.
In one embodiment, two of $X^{1A}$, $X^{1B}$, $X^{1C}$, and $X^{1D}$ is N.
In one embodiment, one of $X^{1E}$, $X^{1F}$ and $X^{1G}$ is N.
In one embodiment, $X^{1F}$ is N.
In one embodiment, $X^{1H}$ is O.
In one embodiment, $X^{1H}$ is S.
In one embodiment, $W^1$ is attached in the para position.
In one embodiment, $W^1$ is —(CR$^a$R$^b$)$_{i1}$-L$^1$—(CR$^a$R$^b$)$_{j1}$—R$^{60}$.
In one embodiment, $W^1$ is —NH—C(O)—(CH$_2$)$_n$—R$^{60}$.
In one embodiment, $W^1$ is —NH—C(O)—CH$_2$—R$^{60}$.
In one embodiment, $W^1$ is —OR$^{10}$, —NHCO(CH$_2$)$_n$—R$^{60}$, —N(CH$_3$)CO(CH$_2$)$_n$—R$^{60}$ or —NH(CH$_2$)$_n$—R$^{60}$.
In one embodiment, i1 is 0, in another embodiment i1 is 1, and in a further embodiment i1 is 2.
In one embodiment, j1 is 0, in another embodiment j1 is 1, and in a further embodiment j1 is 2.
In one embodiment, $L^1$ is —NR$^{10}$C(O)—.
In one embodiment, $L^1$ is —NR$^{10}$—.
In one embodiment, $L^1$ is —N(R$^{10}$)SO$_2$—.
In one embodiment, $R^{10}$ is —H.
In one embodiment, $R^{60}$ is $R^{13}$.
In one embodiment, $R^{60}$ is —O—(CH$_2$)$_n$—R$^{13}$, in another embodiment $R^{60}$ is —O—R$^{13}$, and in a further embodiment $R^{60}$ is —O—CH$_2$—R$^{13}$.
In one embodiment, $R^{13}$ is aryl optionally substituted with one or more $R^{14}$, and in another embodiment $R^{13}$ is phenyl.
In one embodiment, $R^{13}$ is cycloalkyl or heterocycloalkyl, and in another embodiment, $R^{13}$ is cyclopentyl, cyclohexyl, thiazolyl, tetrahydrofuranyl, oxazolyl, thiophenyl, 1,2,4-oxadiazolyl, furanyl, tetrahydro-2H-pyranyl, or piperidinyl.
In one embodiment, $R^{13}$ is unsubstituted or substituted at one or more ring position with methyl, ethyl, isopropyl, t-butyl, —CF$_3$, methoxy, ethoxy, hydroxyl, —OCF$_3$, halogen (F, Cl, Br or I), methylthio or —SO$_2$CH$_3$. In another embodiment, $R^{13}$ is substituted with one or more of methyl, methoxy, F or —CF$_3$.

In one embodiment, $R^{13}$ is cycloalkyl, aryl or heteroaryl, where any ring atom of $R^{13}$ may be optionally substituted with $R^{14}$.

In one embodiment, each $R^{14}$ is independently H, alkyl, halo, alkoxy, perhaloalkyl or perhaloalkoxy. In another embodiment, $R^{14}$ is halo, alkoxy, perhaloalkyl or perhaloalkoxy. In a further embodiment, $R^{14}$ is alkoxy or perhaloalkyl.

In one embodiment, each $R^{31}$ and $R^{32}$ is independently H, alkyl or alkyl substituted with carboxyl. In another embodiment, at least one of $R^{31}$ and $R^{32}$ is H.

In one embodiment, $R^{60}$ is:

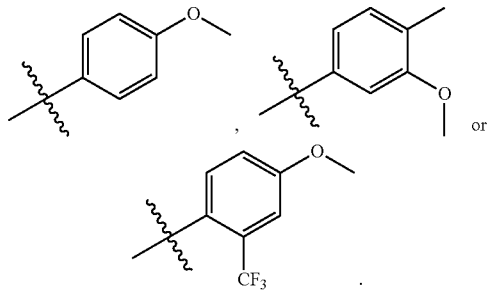

In one embodiment, each of $R^a$ and $R^b$ is H. In another embodiment, at least one of $R^a$ and $R^b$ is methyl.

In one embodiment, at least one of $R^a$ and $R^b$ is isopropyl.

In one embodiment, at least one of $R^a$ and $R^b$ is benzyl or hydroxybenzyl.

In one embodiment, at least one pair of $R^a$ and $R^b$ is, taken together, oxo or cycloalkyl.

In one embodiment, A is a fully saturated cycloalkyl. In another embodiment, A is a partially saturated cycloalkyl. In a further embodiment, A is a fully unsaturated cycloalkyl. In such embodiment, if there is unsaturation, the conjugation of the pi-electrons in the ring do not give rise to aromaticity. In another embodiment, A is cyclopropyl, cyclobutyl, cyclopentyl, cyclohexyl, cycloheptyl, cyclopropenyl, cyclobutenyl, cyclopentenyl, cyclohexenyl or cycloheptenyl.

In one embodiment, $R^2$ is alkyl. In another embodiment, $R^2$ is methyl, ethyl, isopropyl or t-butyl.

In one embodiment, $R^2$ is cycloalkyl. In another embodiment, $R^2$ is cyclopropyl, cyclobutyl, cyclopentyl, cyclohexyl, cycloheptyl, cyclopropenyl, cyclobutenyl, cyclopentenyl, cyclohexenyl or cycloheptenyl.

In one embodiment, $R^2$ is aryl. In another embodiment, $R^2$ is phenyl.

In one embodiment, $R^2$ is substituted with at least one $R^3$.

In one embodiment, $R^3$ is halo, alkyl, alkoxy, perhaloalkyl or perhaloalkoxy. In another embodiment, $R^3$ is methyl, ethyl, n-propyl, iso-propyl, n-butyl, iso-butyl, tert-butyl, n-pentyl or —CF$_3$.

In one embodiment, a compound is provided having the structure any one of compound numbers 1-153 as shown in the following Table 1, or a stereoisomer, hydrate, solvate, isotope or pharmaceutically acceptable salts thereof.

TABLE 1
| Representative Compounds | |
|---|---|
| Structure | Cpd. No. |
|  | 1 |
|  | 2 |

TABLE 1-continued

Representative Compounds

| Structure | Cpd. No. |
|---|---|
| 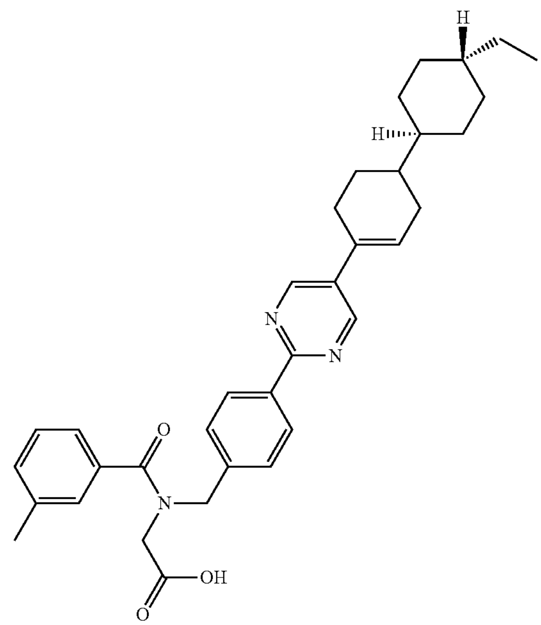 [SMILES: CC[C@H]1CC[C@H](C2CC=C(c3cnc(-c4ccc(CN(CC(=O)O)C(=O)c5cccc(C)c5)cc4)nc3)CC2)CC1] | 3 |
| 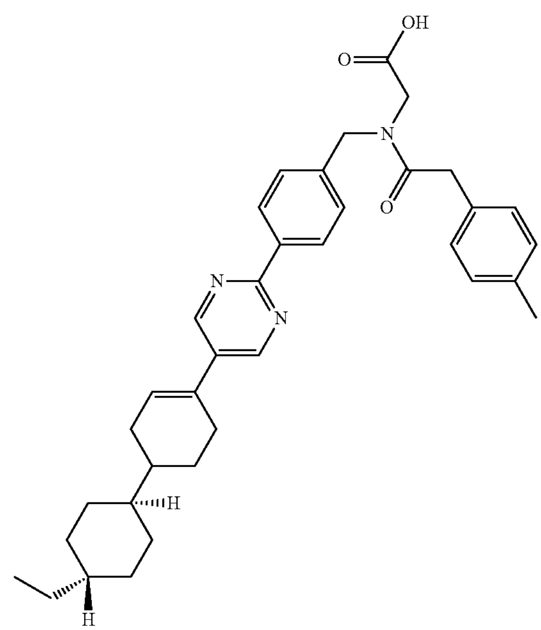 [SMILES: CC[C@H]1CC[C@H](C2CC=C(c3cnc(-c4ccc(CN(CC(=O)O)C(=O)Cc5ccc(C)cc5)cc4)nc3)CC2)CC1] | 4 |

TABLE 1-continued
Representative Compounds
| Structure | Cpd. No. |
|---|---|
| 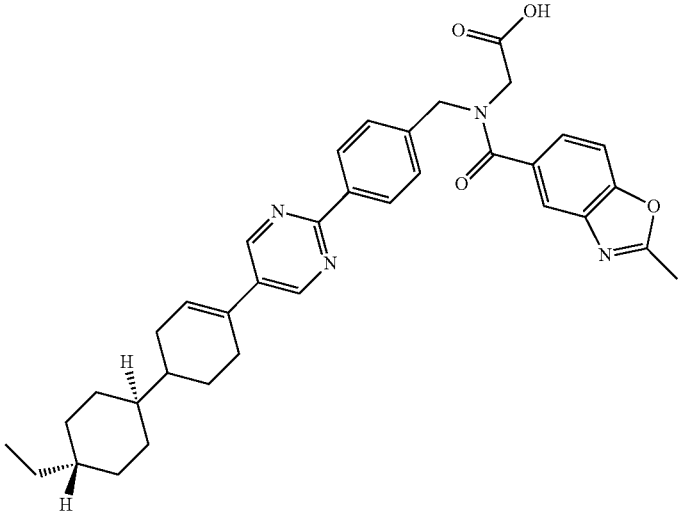 [SMILES: CC[C@H]1CC[C@H](C2CC=C(c3cnc(-c4ccc(CN(CC(=O)O)C(=O)c5ccc6oc(C)nc6c5)cc4)nc3)CC2)CC1] | 5 |
| 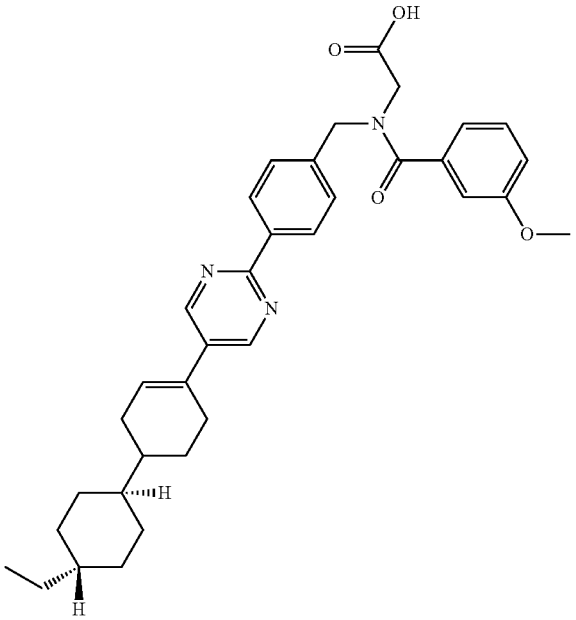 [SMILES: CC[C@H]1CC[C@H](C2CC=C(c3cnc(-c4ccc(CN(CC(=O)O)C(=O)c5cccc(OC)c5)cc4)nc3)CC2)CC1] | 6 |

TABLE 1-continued
Representative Compounds
| Structure | Cpd. No. |
|---|---|
| 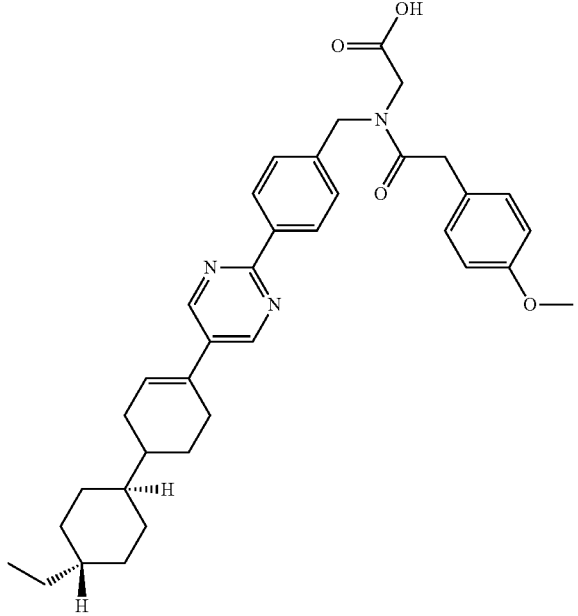 [SMILES: CC[C@H]1CC[C@H](C2CC=C(c3cnc(-c4ccc(CN(CC(=O)O)C(=O)Cc5ccc(OC)cc5)cc4)nc3)CC2)CC1] | 7 |
| 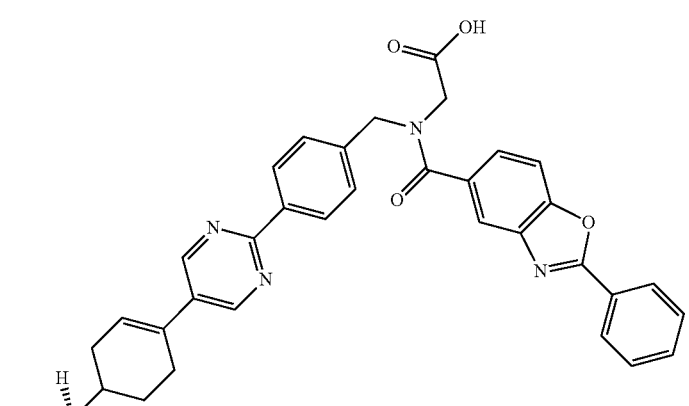 | 8 |

TABLE 1-continued
Representative Compounds
| Structure | Cpd. No. |
|---|---|
| 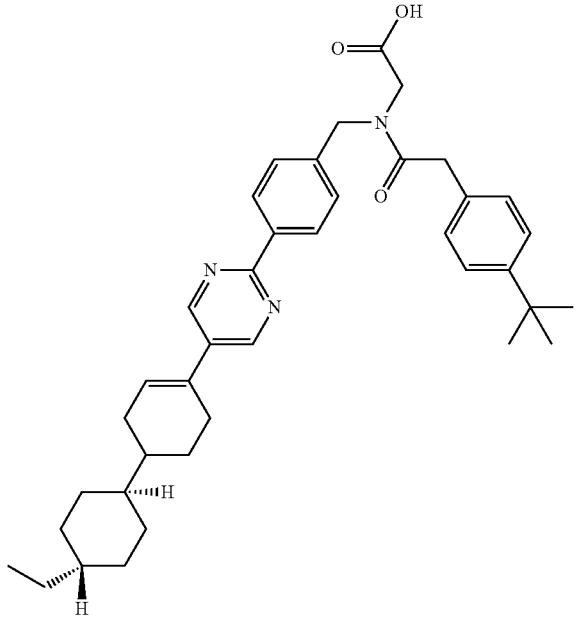 [SMILES: CC[C@H]1CC[C@H](C2CC=C(c3cnc(-c4ccc(CN(CC(=O)O)C(=O)Cc5ccc(C(C)(C)C)cc5)cc4)nc3)CC2)CC1] | 9 |
| 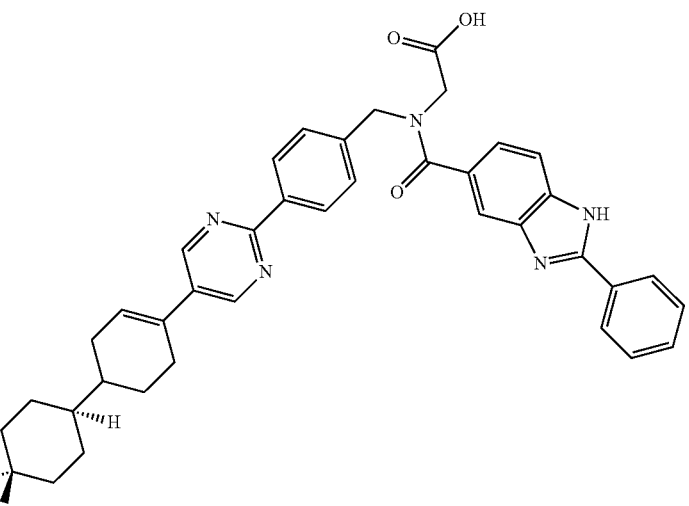 | 10 |

TABLE 1-continued
Representative Compounds
| Structure | Cpd. No. |
|---|---|
| 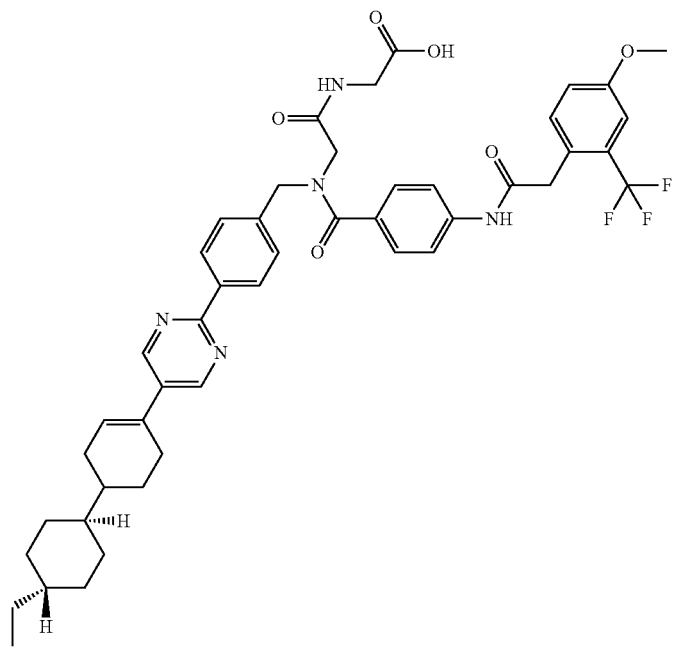 [SMILES: CC[C@H]1CC[C@H](C2CC=C(c3cnc(-c4ccc(CN(CC(=O)NCC(=O)O)C(=O)c5ccc(NC(=O)Cc6ccc(OC)cc6C(F)(F)F)cc5)cc4)nc3)CC2)CC1] | 11 |
| 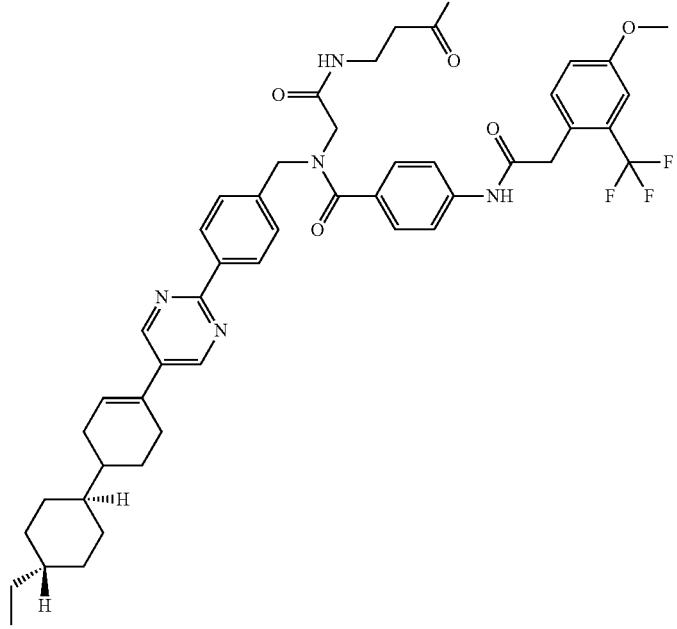 | 12 |

TABLE 1-continued
Representative Compounds
| Structure | Cpd. No. |
|---|---|
| 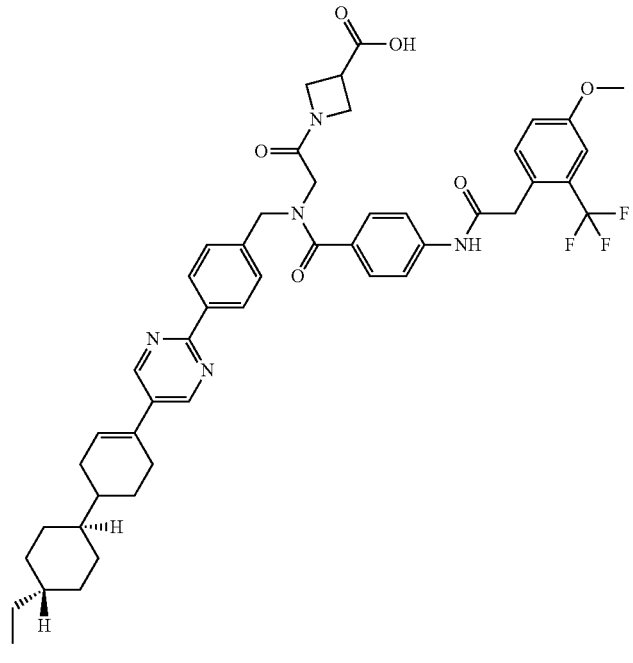 [SMILES: CC[C@H]1CC[C@H](C2CC=C(c3cnc(-c4ccc(CN(CC(=O)N5CC(C(=O)O)C5)C(=O)c5ccc(NC(=O)Cc6ccc(OC)cc6C(F)(F)F)cc5)cc4)nc3)CC2)CC1] | 13 |
| 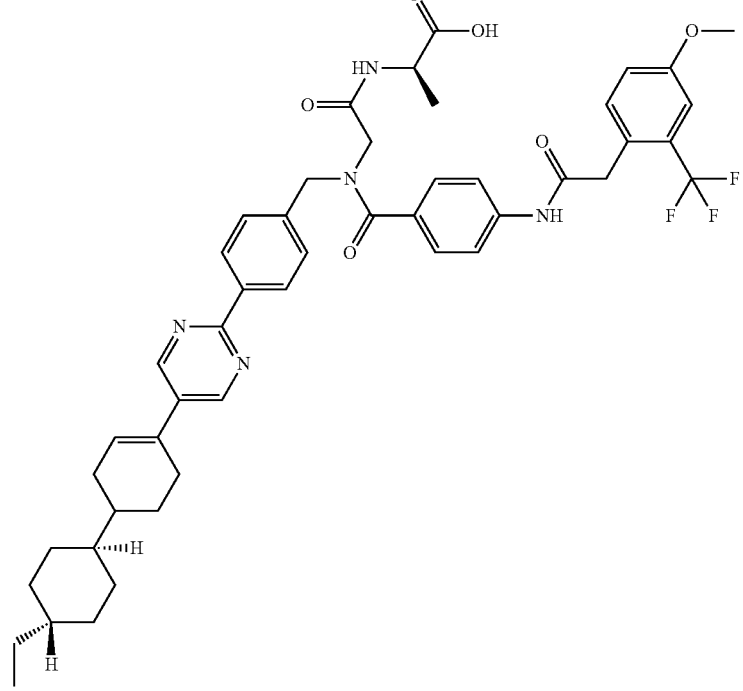 | 14 |

TABLE 1-continued

Representative Compounds

| Structure | Cpd. No. |
|---|---|
| 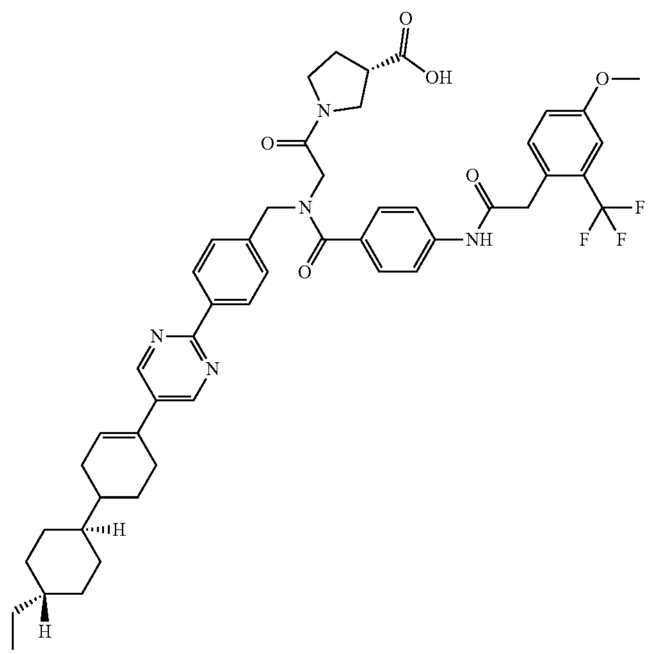 [SMILES: CC[C@H]1CC[C@H](C2CC=C(c3cnc(-c4ccc(CN(CC(=O)N5CC[C@H](C(=O)O)C5)C(=O)c5ccc(NC(=O)Cc6ccc(OC)cc6C(F)(F)F)cc5)cc4)nc3)CC2)CC1] | 15 |
| 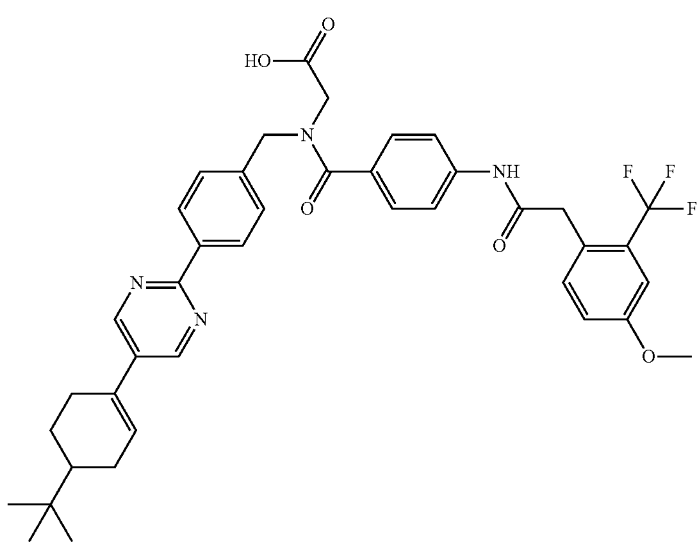 [SMILES: COc1ccc(CC(=O)Nc2ccc(C(=O)N(CC(=O)O)Cc3ccc(-c4ncc(C5=CCC(C(C)(C)C)CC5)cn4)cc3)cc2)c(C(F)(F)F)c1] | 16 |

TABLE 1-continued

Representative Compounds

| Structure | Cpd. No. |
|---|---|
| 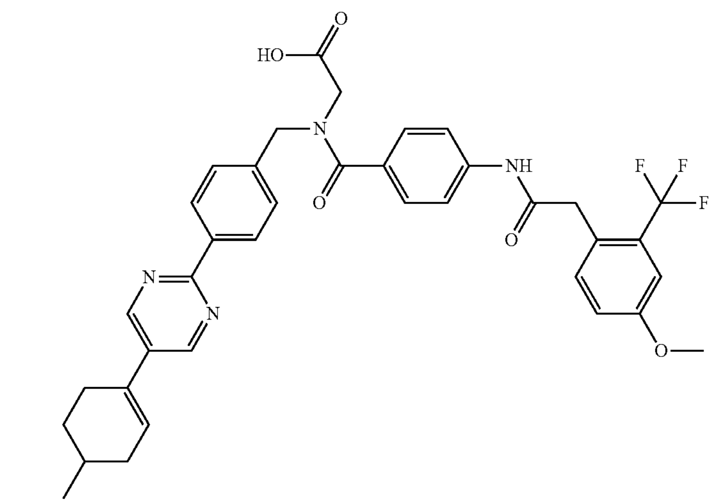 [SMILES: COc1ccc(CC(=O)Nc2ccc(C(=O)N(CC(=O)O)Cc3ccc(-c4ncc(C5=CCC(C)CC5)cn4)cc3)cc2)c(C(F)(F)F)c1] | 17 |
| 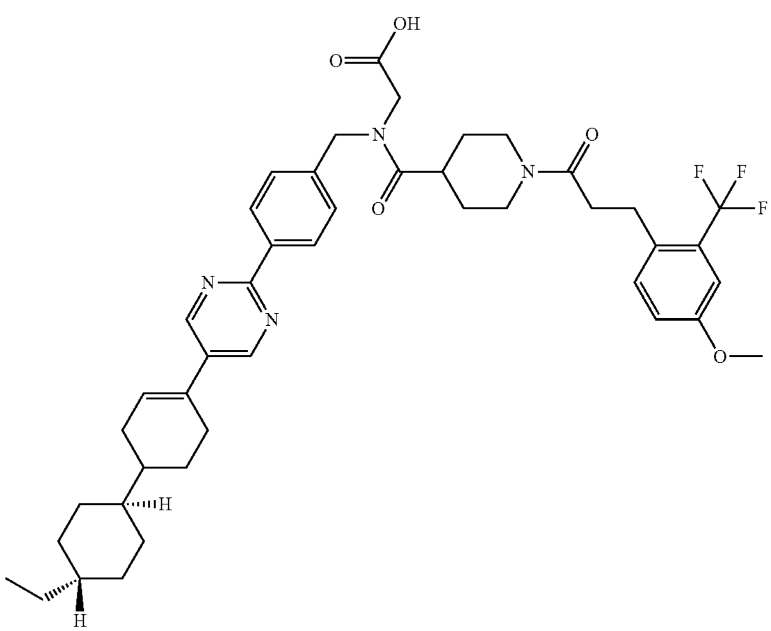 [SMILES: CC[C@H]1CC[C@H](C2CC=C(c3cnc(-c4ccc(CN(CC(=O)O)C(=O)C5CCN(C(=O)CCc6ccc(OC)cc6C(F)(F)F)CC5)cc4)nc3)CC2)CC1] | 18 |

TABLE 1-continued
Representative Compounds
| Structure | Cpd. No. |
|---|---|
| 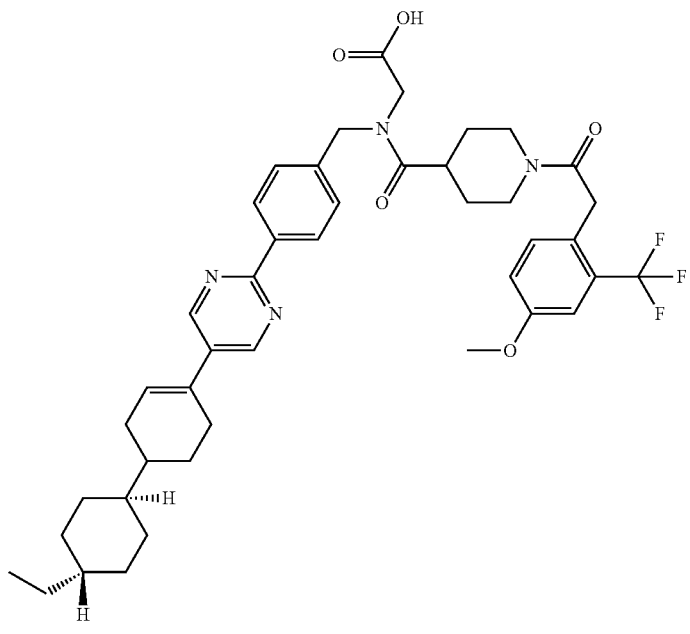 [SMILES: CC[C@H]1CC[C@H](C2CC=C(c3cnc(-c4ccc(CN(CC(=O)O)C(=O)C5CCN(C(=O)Cc6ccc(OC)cc6C(F)(F)F)CC5)cc4)nc3)CC2)CC1] | 19 |
| 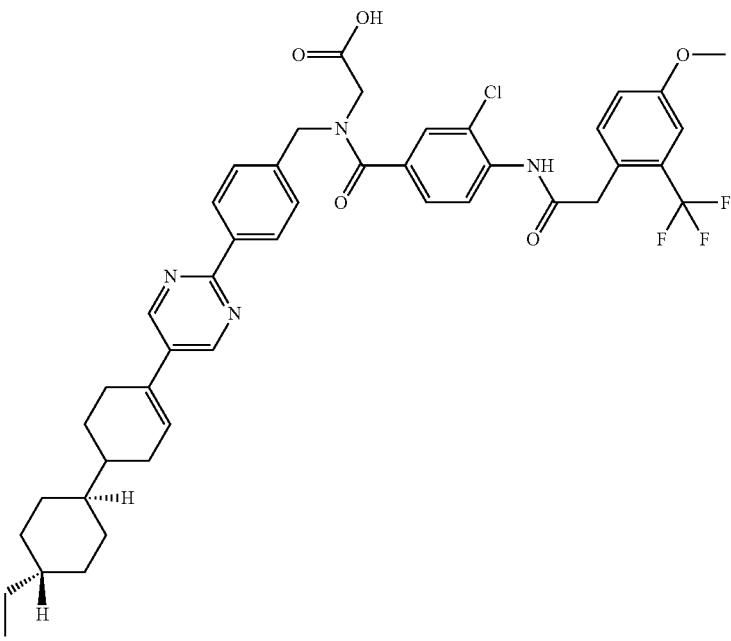 | 20 |

TABLE 1-continued

Representative Compounds

| Structure | Cpd. No. |
|---|---|
| 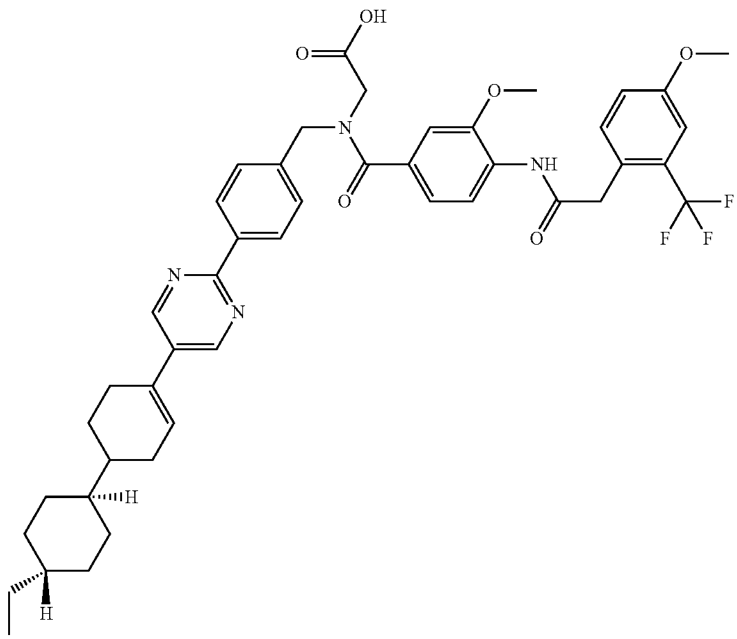 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)c(OC)c5)cc4)nc3)CC2)CC1] | 21 |
| 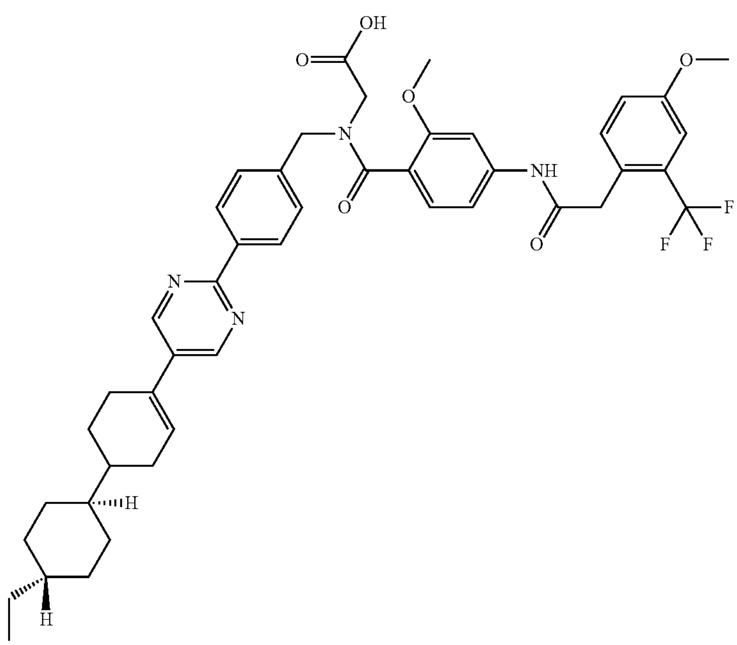 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)cc5OC)cc4)nc3)CC2)CC1] | 22 |

TABLE 1-continued
Representative Compounds
| Structure | Cpd. No. |
|---|---|
| 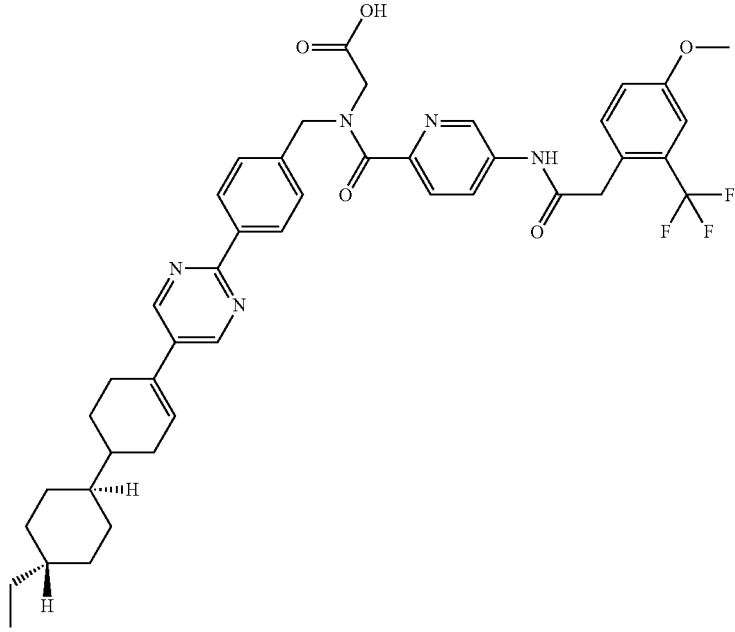 | 23 |
| 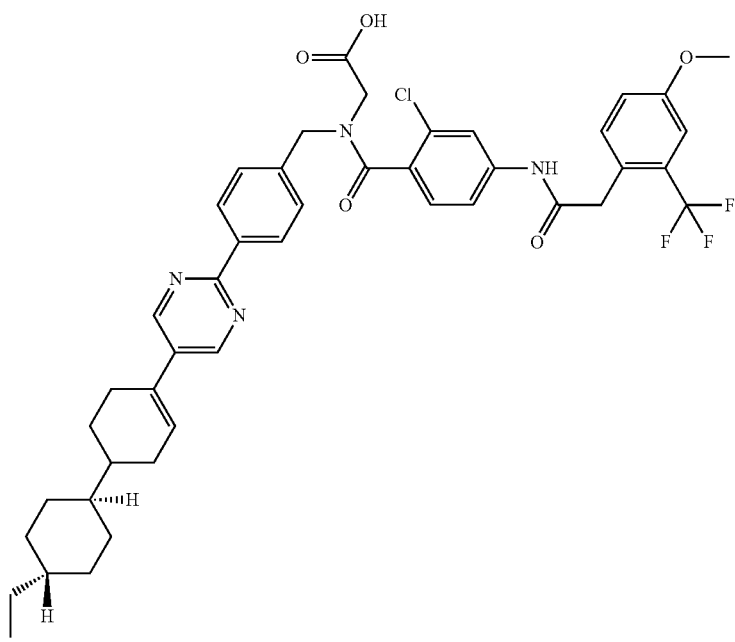 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)cc5Cl)cc4)nc3)CC2)CC1] | 24 |

TABLE 1-continued
Representative Compounds
| Structure | Cpd. No. |
|---|---|
| 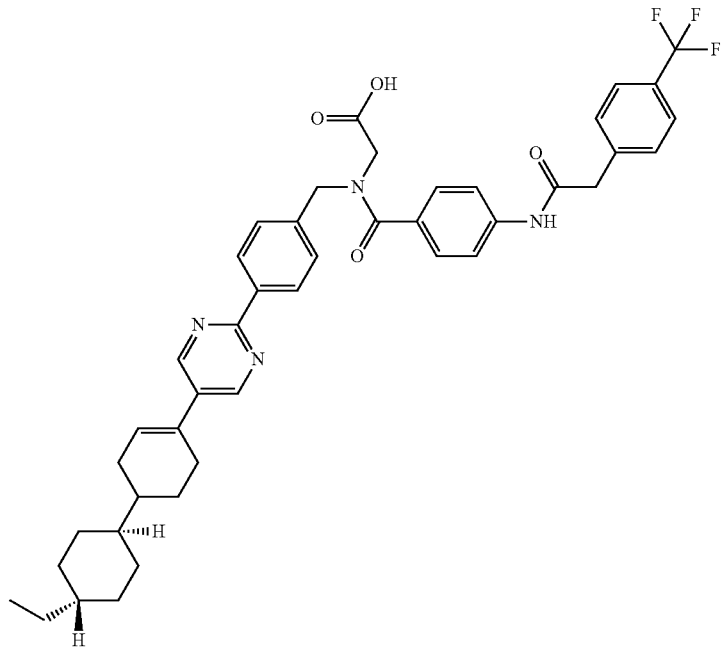 [SMILES: CC[C@H]1CC[C@H](C2CC=C(c3cnc(-c4ccc(CN(CC(=O)O)C(=O)c5ccc(NC(=O)Cc6ccc(C(F)(F)F)cc6)cc5)cc4)nc3)CC2)CC1] | 25 |
| 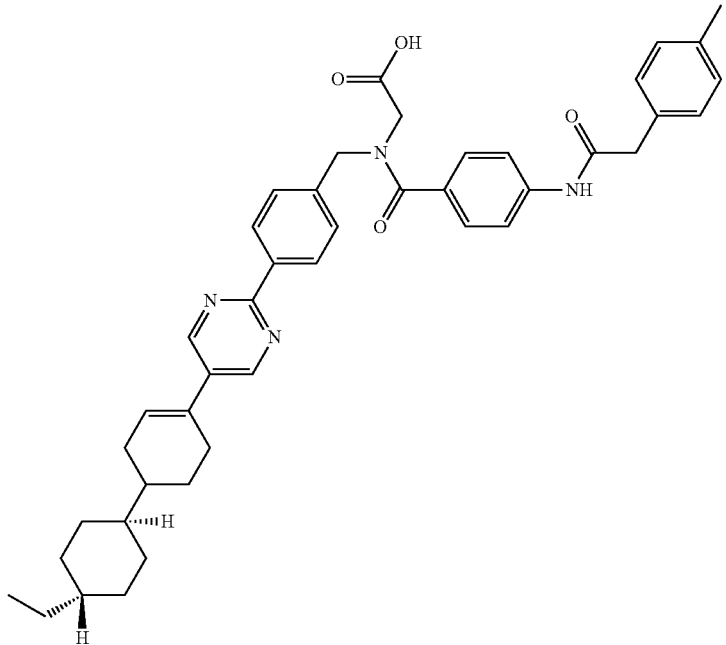 [SMILES: CC[C@H]1CC[C@H](C2CC=C(c3cnc(-c4ccc(CN(CC(=O)O)C(=O)c5ccc(NC(=O)Cc6ccc(C)cc6)cc5)cc4)nc3)CC2)CC1] | 26 |

TABLE 1-continued
Representative Compounds
| Structure | Cpd. No. |
|---|---|
| 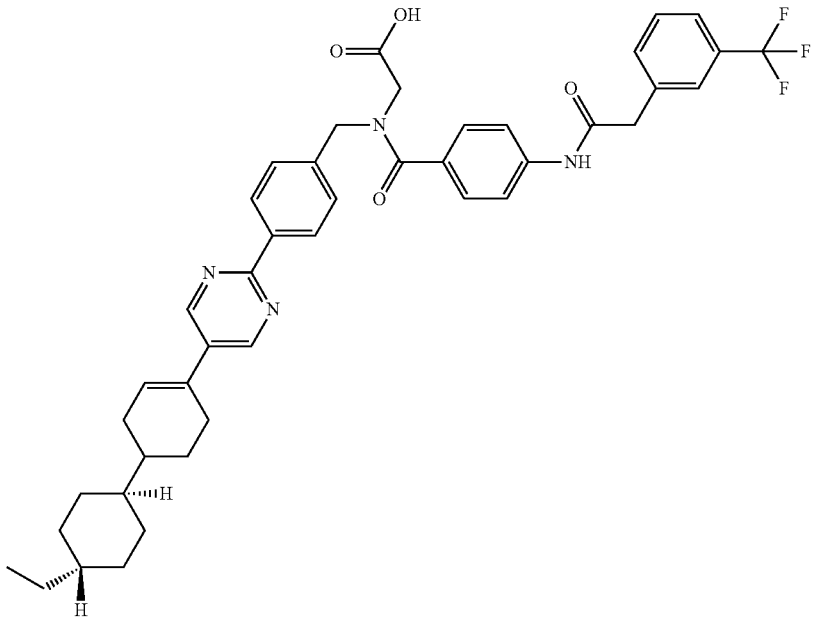 [SMILES: CC[C@H]1CC[C@H](C2CC=C(c3cnc(-c4ccc(CN(CC(=O)O)C(=O)c5ccc(NC(=O)Cc6cccc(C(F)(F)F)c6)cc5)cc4)nc3)CC2)CC1] | 27 |
| 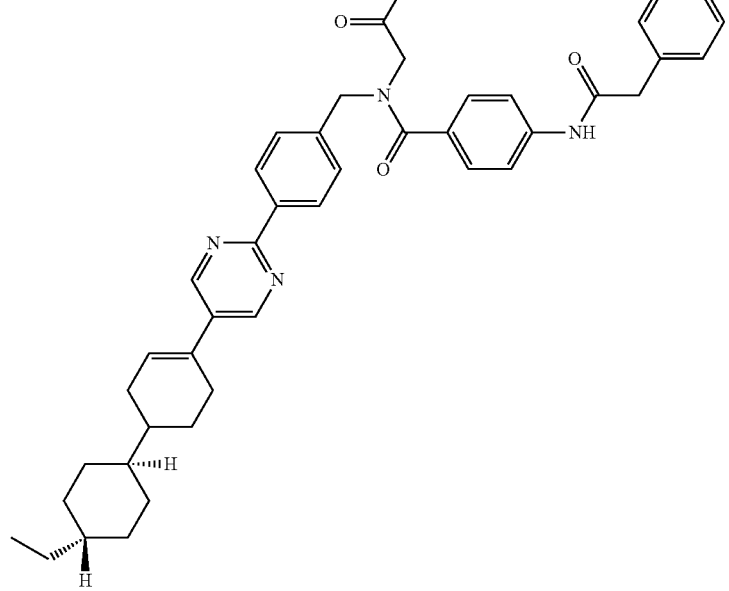 | 28 |

TABLE 1-continued
Representative Compounds
| Structure | Cpd. No. |
|---|---|
| 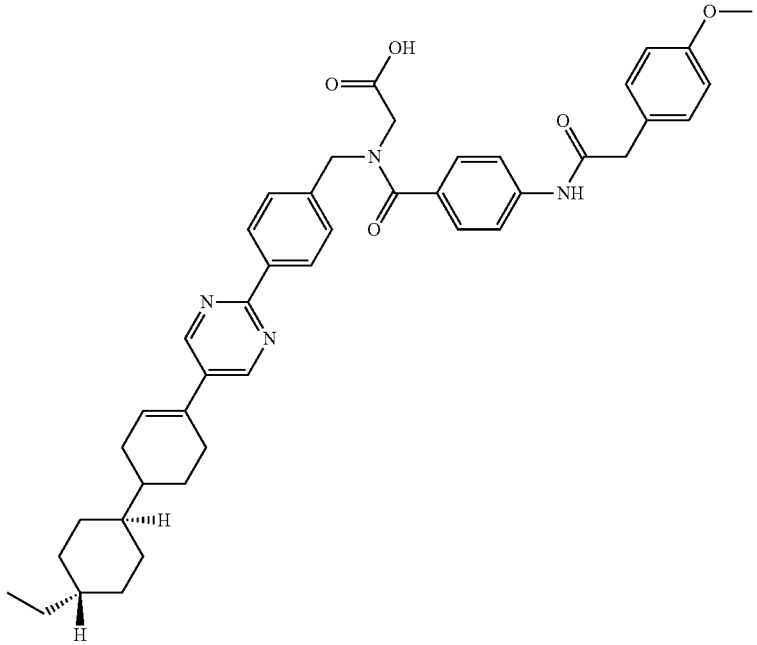 [SMILES: CC[C@H]1CC[C@H](C2CC=C(c3cnc(-c4ccc(CN(CC(=O)O)C(=O)c5ccc(NC(=O)Cc6ccc(OC)cc6)cc5)cc4)nc3)CC2)CC1] | 29 |
| 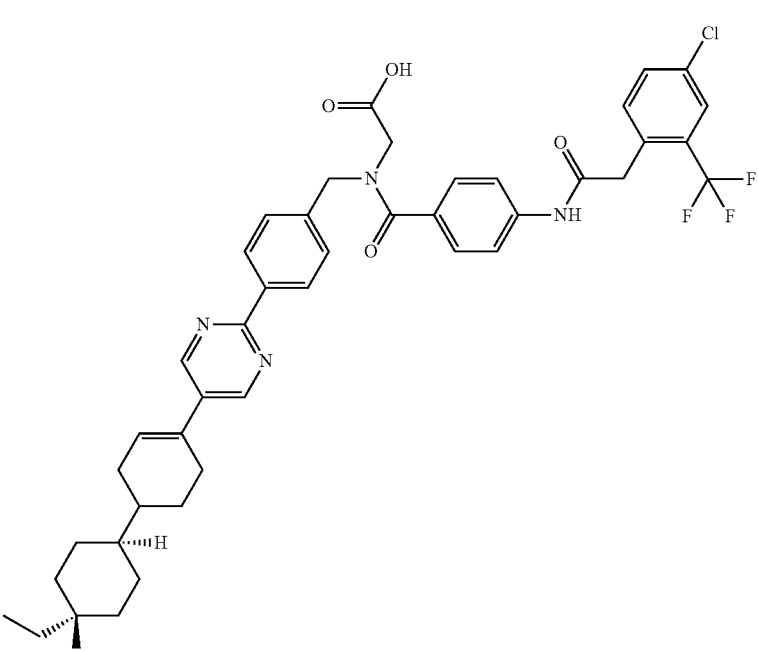 | 30 |

TABLE 1-continued
Representative Compounds
| Structure | Cpd. No. |
|---|---|
| 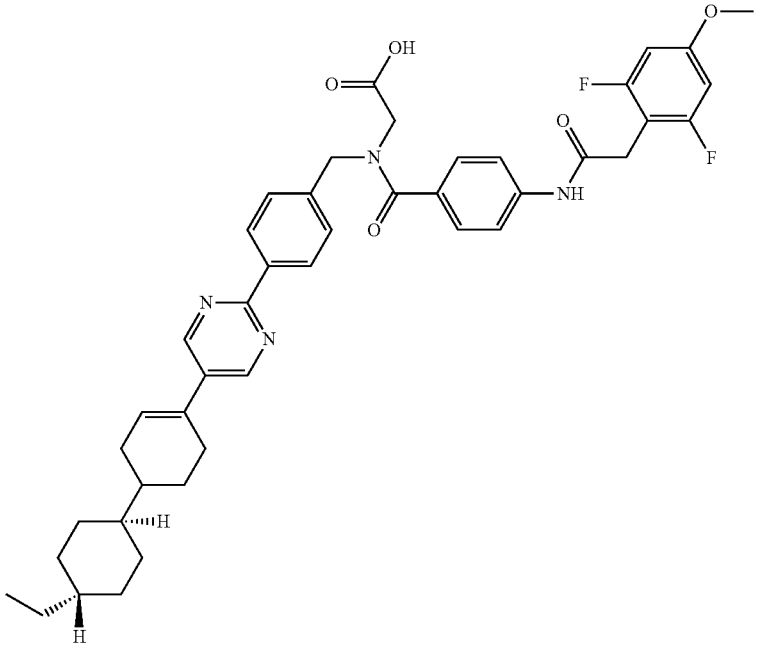 [SMILES: CC[C@H]1CC[C@H](C2CC=C(c3cnc(-c4ccc(CN(CC(=O)O)C(=O)c5ccc(NC(=O)Cc6c(F)cc(OC)cc6F)cc5)cc4)nc3)CC2)CC1] | 31 |
| 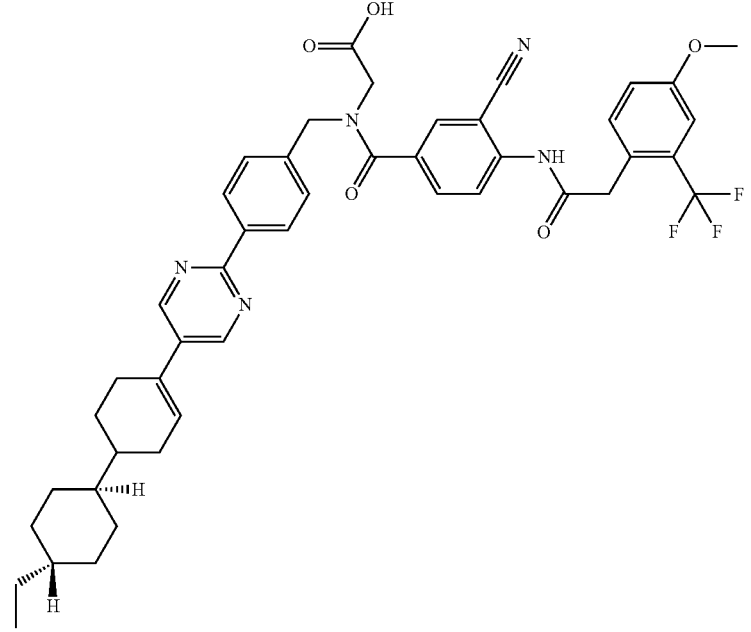 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)c(C#N)c5)cc4)nc3)CC2)CC1] | 32 |

TABLE 1-continued
Representative Compounds
| Structure | Cpd. No. |
|---|---|
| 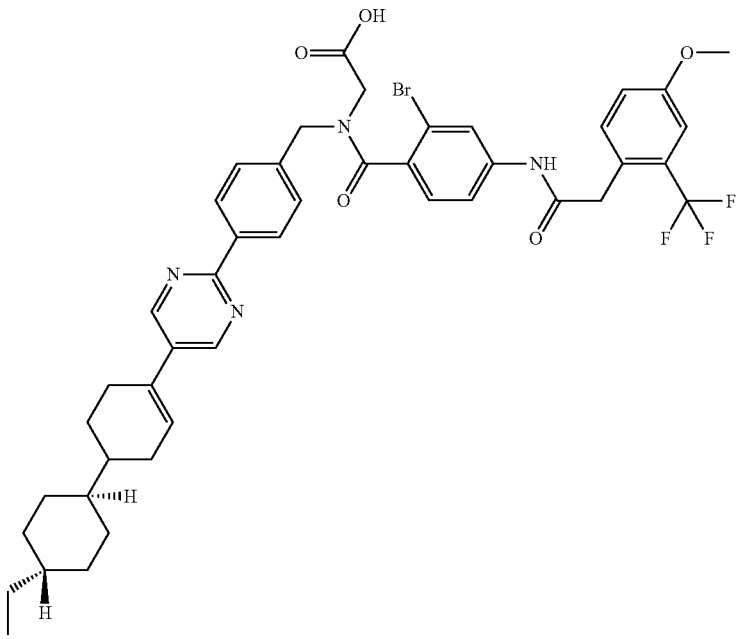 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)cc5Br)cc4)nc3)CC2)CC1] | 33 |
| 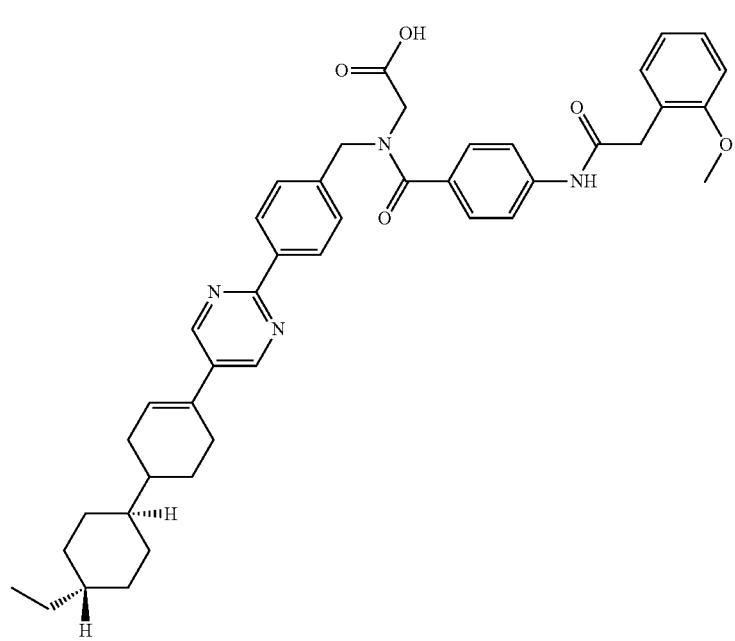 [SMILES: CC[C@H]1CC[C@H](C2CC=C(c3cnc(-c4ccc(CN(CC(=O)O)C(=O)c5ccc(NC(=O)Cc6ccccc6OC)cc5)cc4)nc3)CC2)CC1] | 34 |

TABLE 1-continued
Representative Compounds
| Structure | Cpd. No. |
|---|---|
| 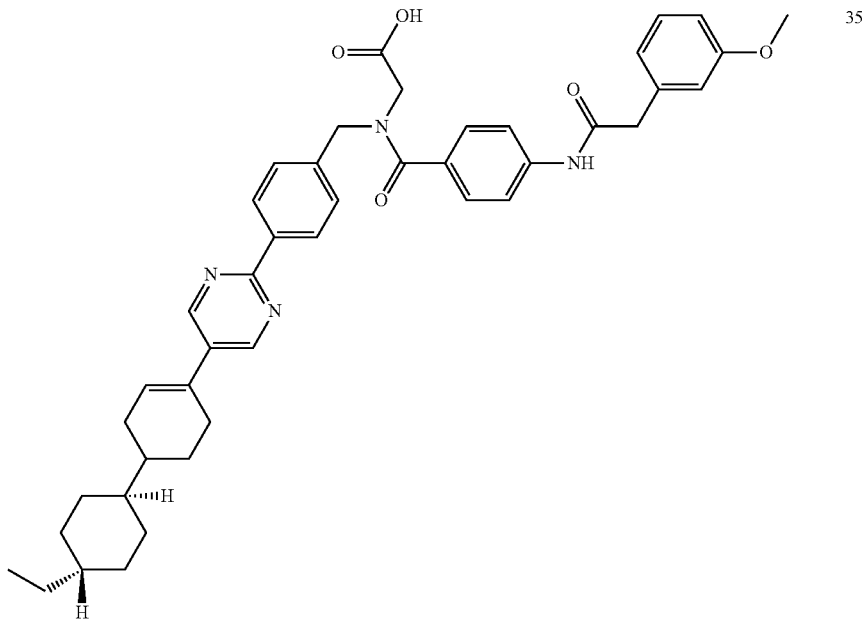 | 35 |
| 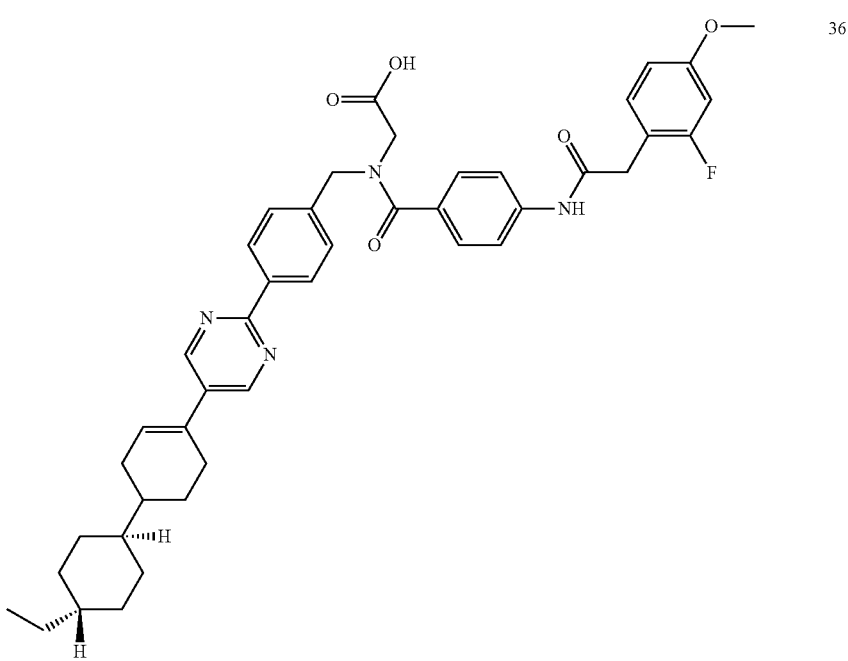 | 36 |

TABLE 1-continued
Representative Compounds
| Structure | Cpd. No. |
|---|---|
| 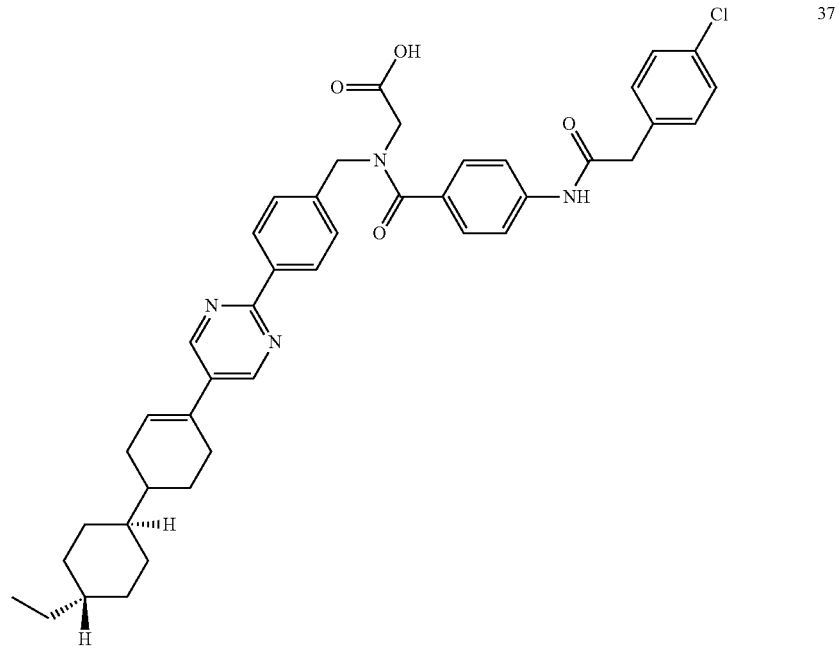 | 37 |
| 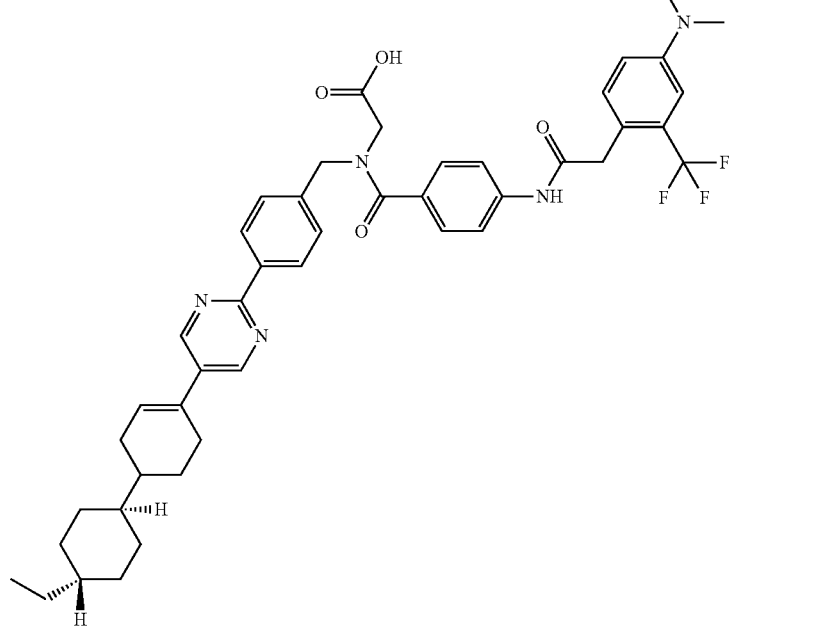 | 38 |

TABLE 1-continued
Representative Compounds
| Structure | Cpd. No. |
|---|---|
| 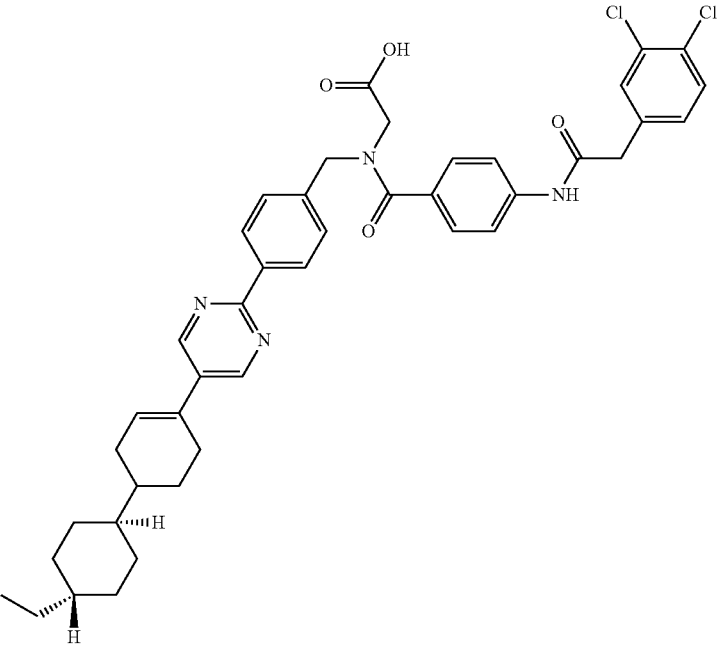 | 39 |
| 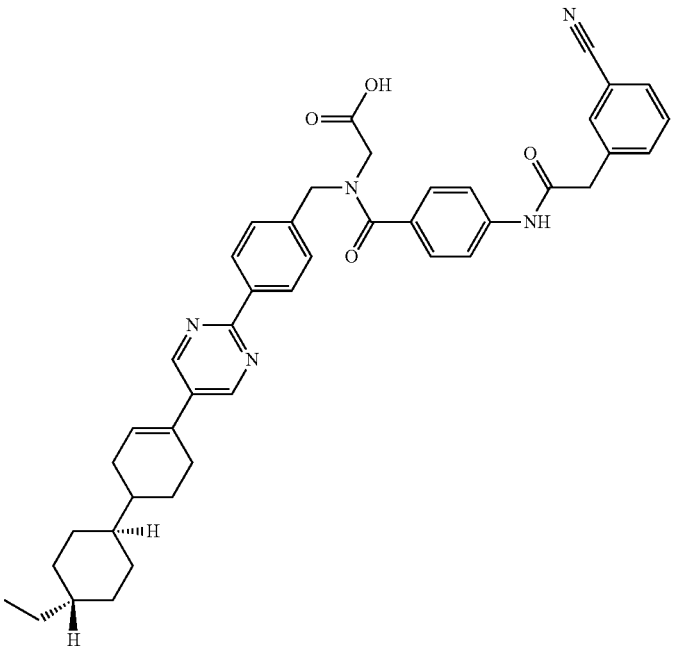 [SMILES: CC[C@H]1CC[C@H](C2CC=C(c3cnc(-c4ccc(CN(CC(=O)O)C(=O)c5ccc(NC(=O)Cc6cccc(C#N)c6)cc5)cc4)nc3)CC2)CC1] | 40 |

TABLE 1-continued
Representative Compounds
| Structure | Cpd. No. |
|---|---|
| 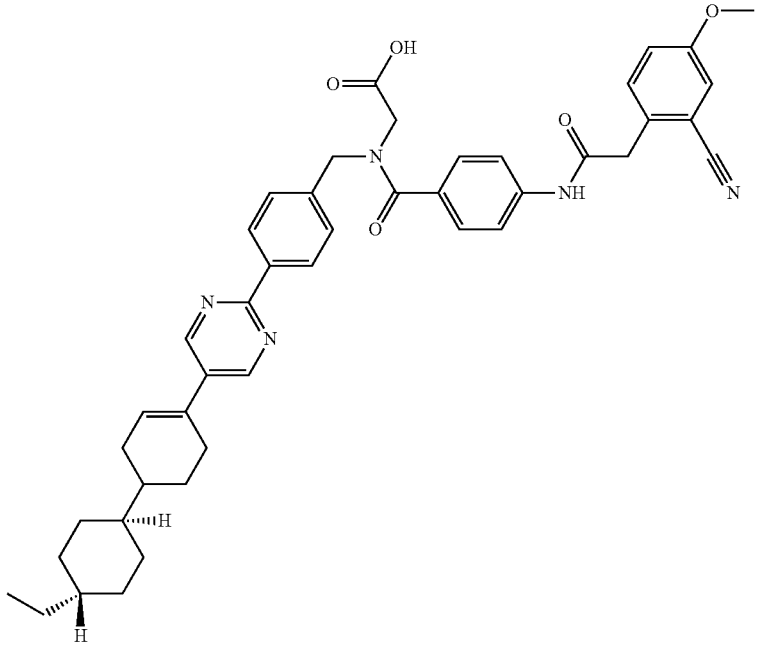 [SMILES: CC[C@H]1CC[C@H](C2CC=C(c3cnc(-c4ccc(CN(CC(=O)O)C(=O)c5ccc(NC(=O)Cc6ccc(OC)cc6C#N)cc5)cc4)nc3)CC2)CC1] | 41 |
| 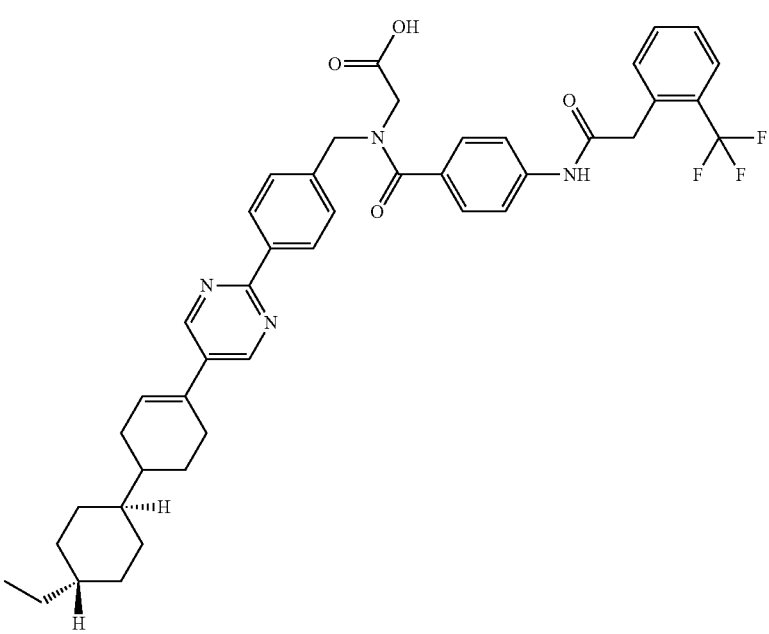 [SMILES: CC[C@H]1CC[C@H](C2CC=C(c3cnc(-c4ccc(CN(CC(=O)O)C(=O)c5ccc(NC(=O)Cc6ccccc6C(F)(F)F)cc5)cc4)nc3)CC2)CC1] | 42 |

TABLE 1-continued
Representative Compounds
| Structure | Cpd. No. |
| --- | --- |
| 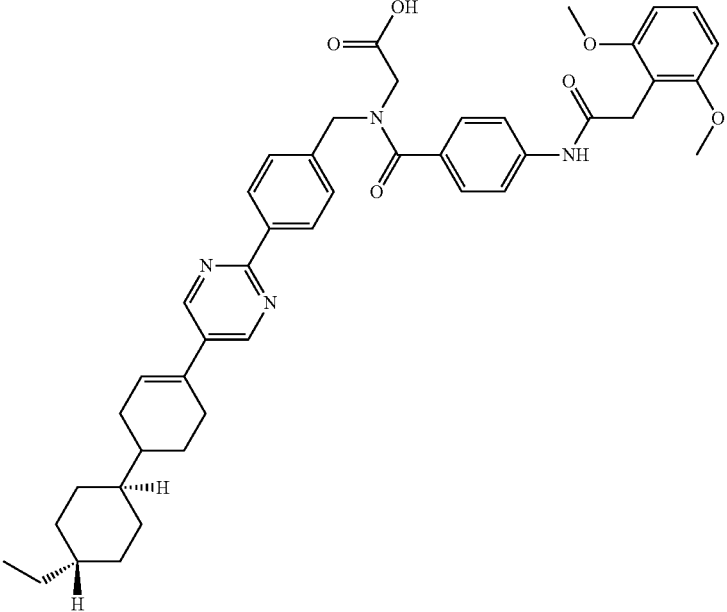 [SMILES: CC[C@H]1CC[C@H](C2CC=C(c3cnc(-c4ccc(CN(CC(=O)O)C(=O)c5ccc(NC(=O)Cc6c(OC)cccc6OC)cc5)cc4)nc3)CC2)CC1] | 43 |
| 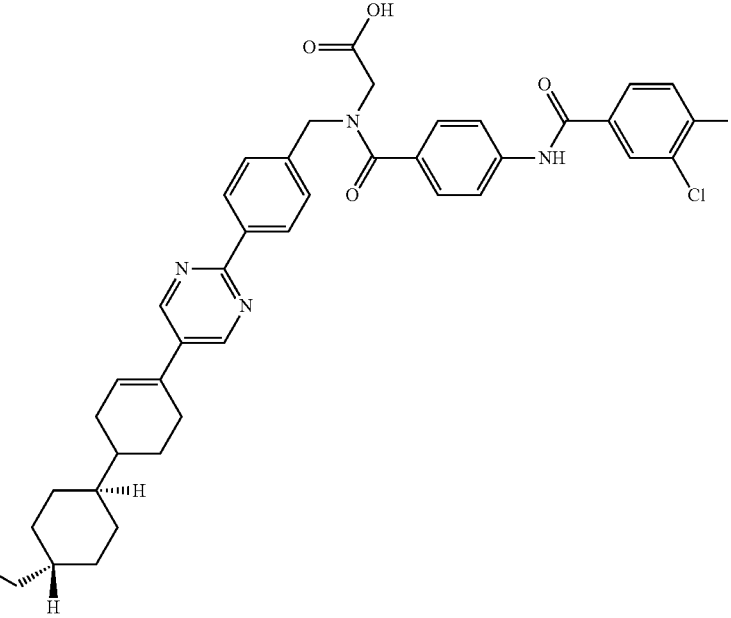 | 44 |

TABLE 1-continued

Representative Compounds

| Structure | Cpd. No. |
|---|---|
| 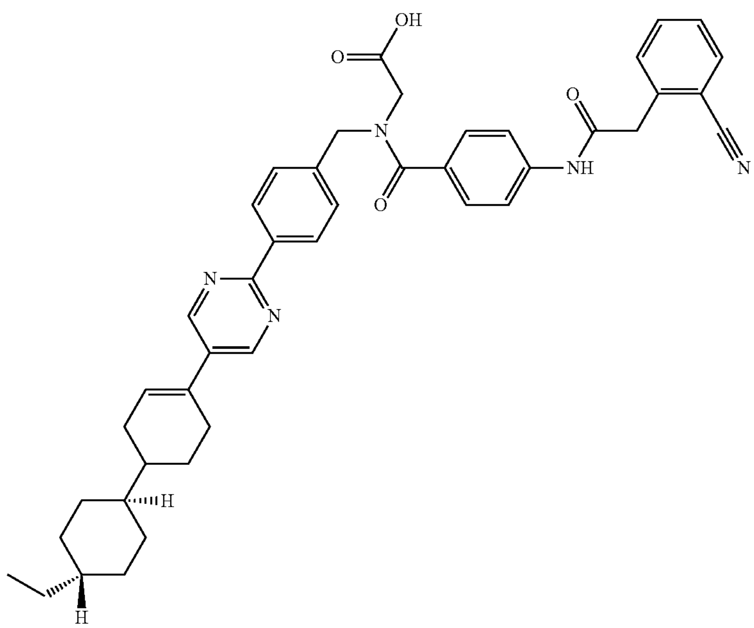 [SMILES: CC[C@H]1CC[C@H](C2CC=C(c3cnc(-c4ccc(CN(CC(=O)O)C(=O)c5ccc(NC(=O)Cc6ccccc6C#N)cc5)cc4)nc3)CC2)CC1] | 45 |
| 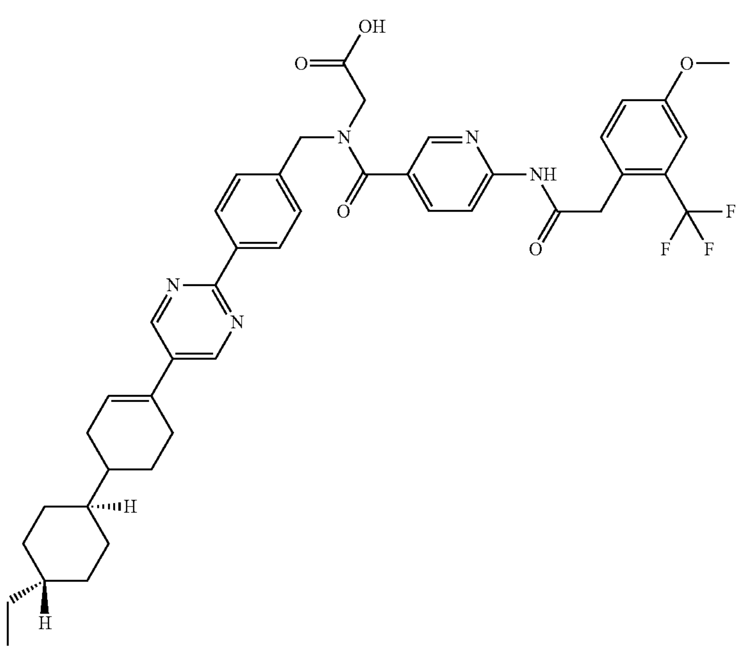 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)nc5)cc4)nc3)CC2)CC1] | 46 |

TABLE 1-continued
Representative Compounds
| Structure | Cpd. No. |
|---|---|
| 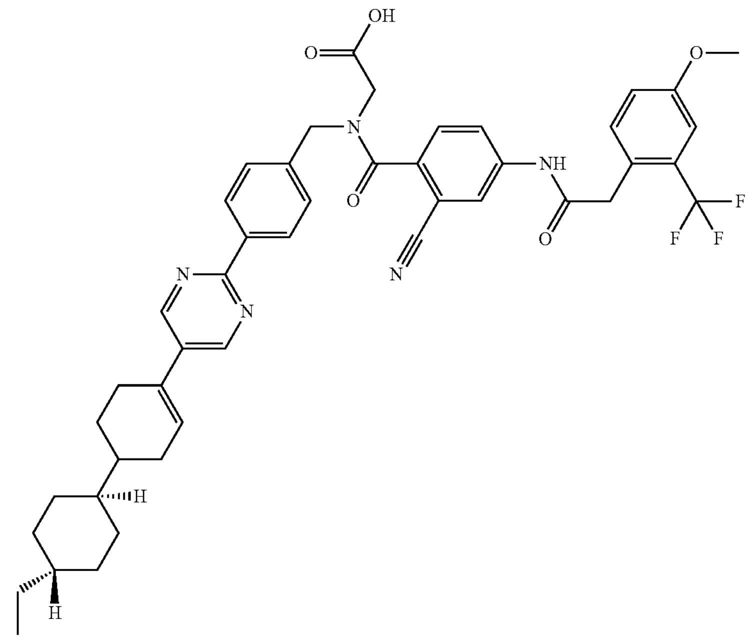 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)cc5C#N)cc4)nc3)CC2)CC1] | 47 |
| 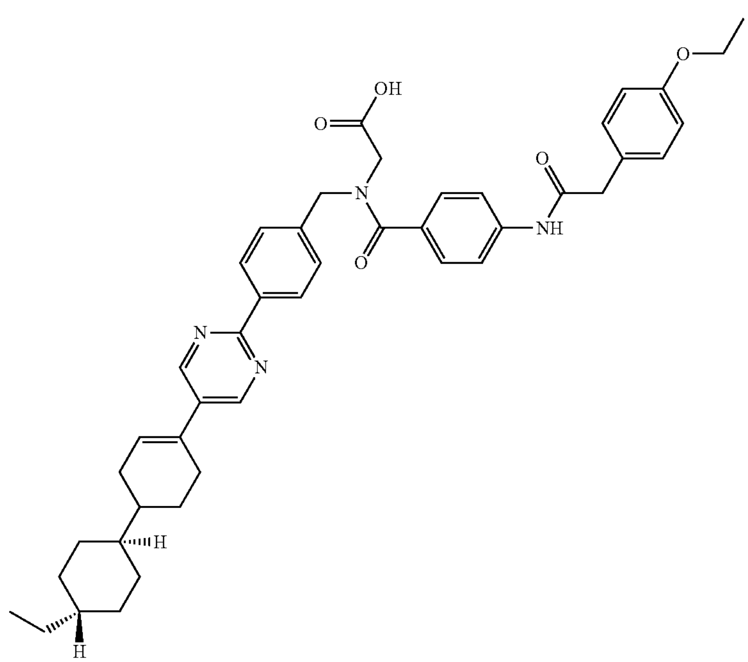 [SMILES: CCOc1ccc(CC(=O)Nc2ccc(C(=O)N(CC(=O)O)Cc3ccc(-c4ncc(C5=CCC([C@H]6CC[C@H](CC)CC6)CC5)cn4)cc3)cc2)cc1] | 48 |

TABLE 1-continued
Representative Compounds
| Structure | Cpd. No. |
|---|---|
| 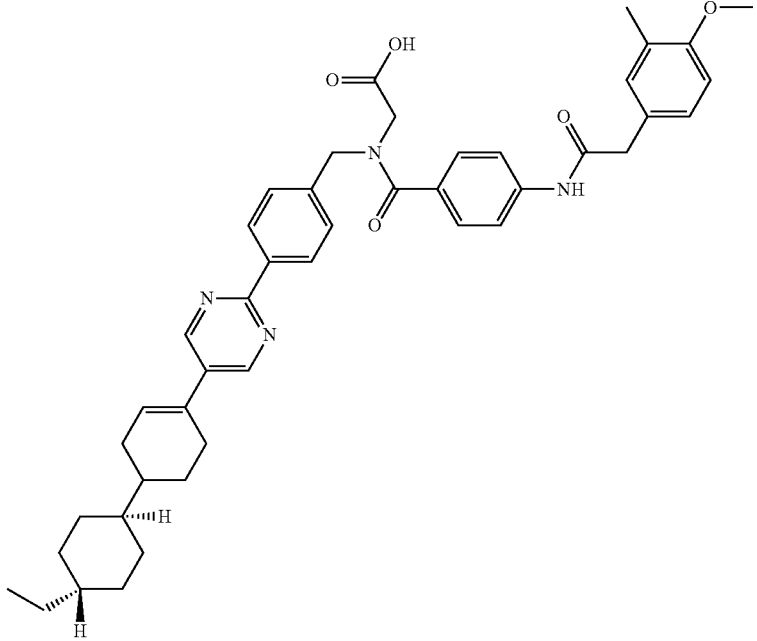 [SMILES: CC[C@H]1CC[C@H](C2CC=C(c3cnc(-c4ccc(CN(CC(=O)O)C(=O)c5ccc(NC(=O)Cc6ccc(OC)c(C)c6)cc5)cc4)nc3)CC2)CC1] | 49 |
| 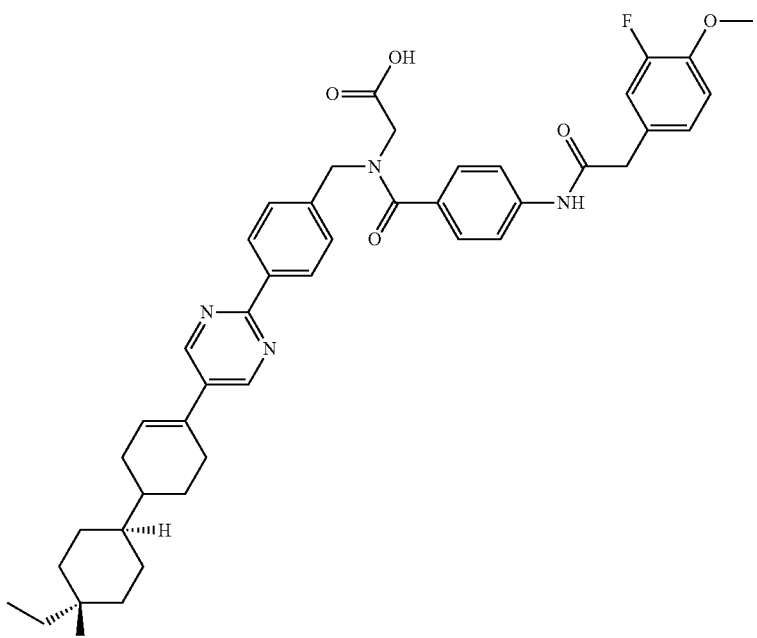 | 50 |

TABLE 1-continued

Representative Compounds

| Structure | Cpd. No. |
|---|---|
| 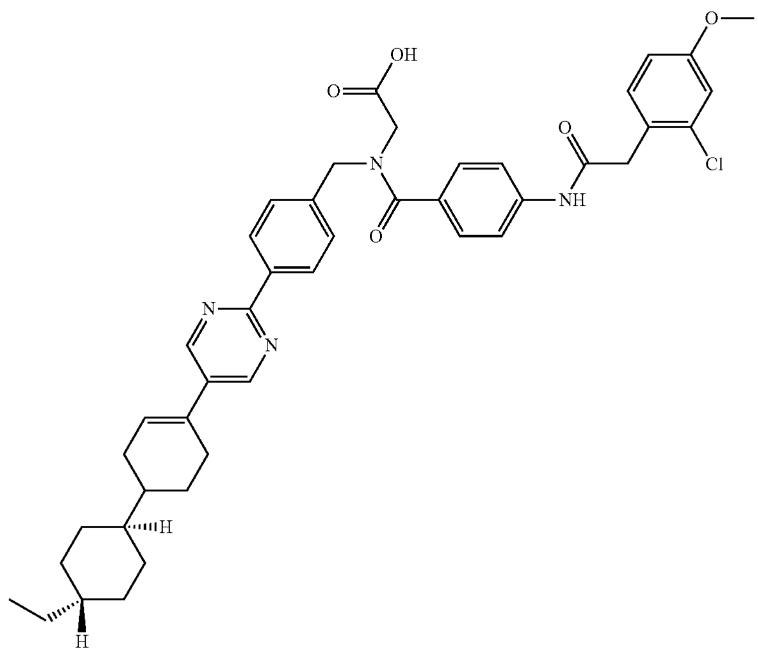 [SMILES: CC[C@H]1CC[C@H](C2CC=C(c3cnc(-c4ccc(CN(CC(=O)O)C(=O)c5ccc(NC(=O)Cc6ccc(OC)cc6Cl)cc5)cc4)nc3)CC2)CC1] | 51 |
| 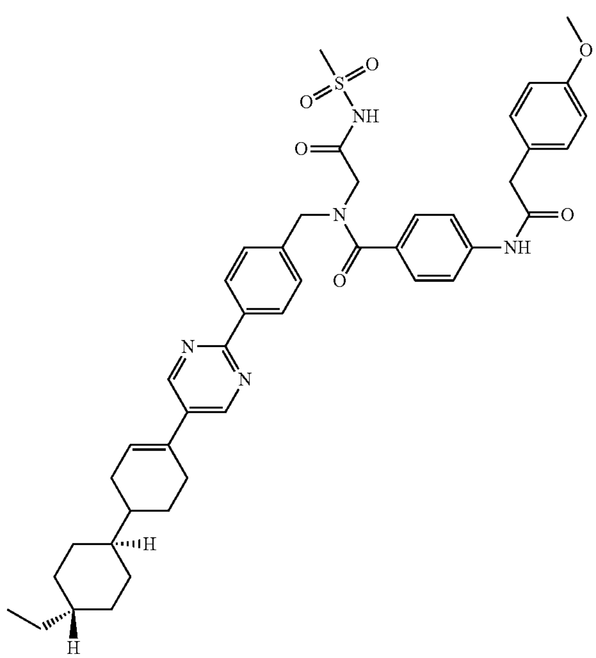 [SMILES: CC[C@H]1CC[C@H](C2CC=C(c3cnc(-c4ccc(CN(CC(=O)NS(C)(=O)=O)C(=O)c5ccc(NC(=O)Cc6ccc(OC)cc6)cc5)cc4)nc3)CC2)CC1] | 52 |

TABLE 1-continued
Representative Compounds
| Structure | Cpd. No. |
|---|---|
| 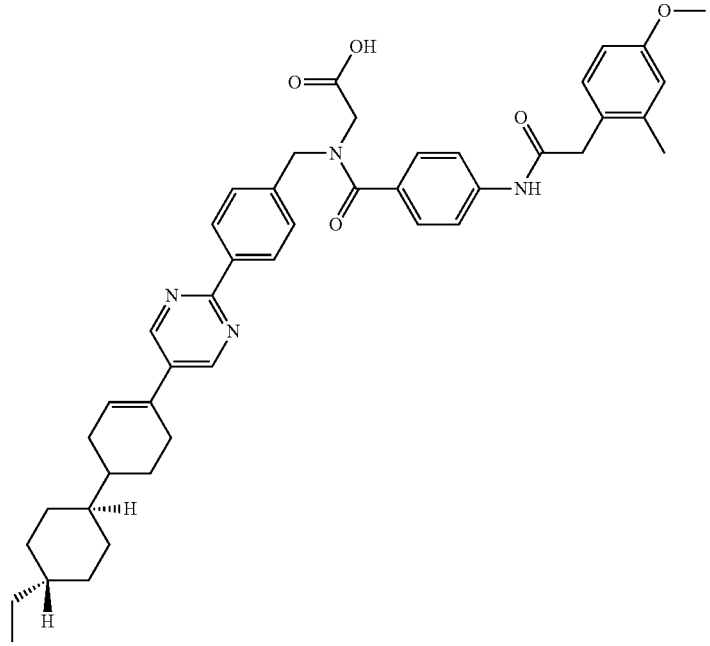 [SMILES: CC[C@H]1CC[C@H](C2CC=C(c3cnc(-c4ccc(CN(CC(=O)O)C(=O)c5ccc(NC(=O)Cc6ccc(OC)cc6C)cc5)cc4)nc3)CC2)CC1] | 53 |
| 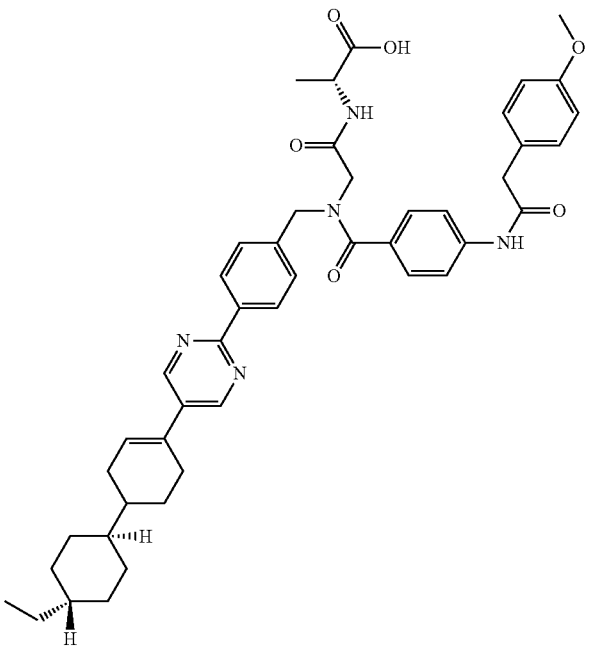 [SMILES: CC[C@H]1CC[C@H](C2CC=C(c3cnc(-c4ccc(CN(CC(=O)N[C@H](C)C(=O)O)C(=O)c5ccc(NC(=O)Cc6ccc(OC)cc6)cc5)cc4)nc3)CC2)CC1] | 54 |

TABLE 1-continued
Representative Compounds
| Structure | Cpd. No. |
|---|---|
| 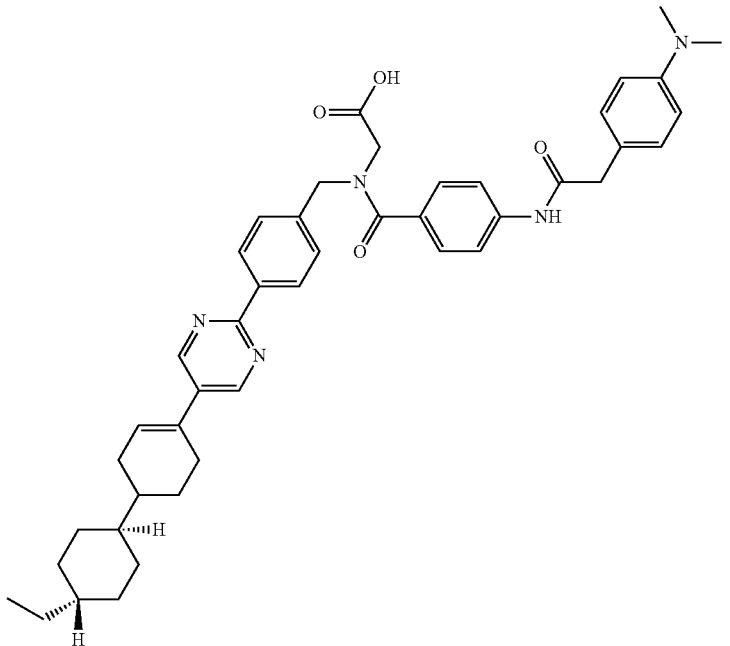 [SMILES: CC[C@H]1CC[C@H](C2CC=C(c3cnc(-c4ccc(CN(CC(=O)O)C(=O)c5ccc(NC(=O)Cc6ccc(N(C)C)cc6)cc5)cc4)nc3)CC2)CC1] | 55 |
| 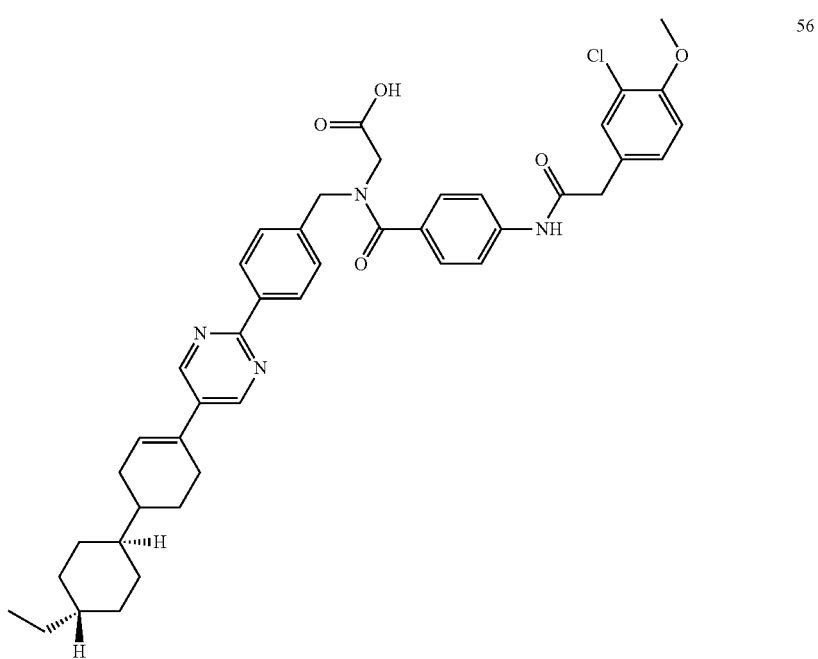 | 56 |

TABLE 1-continued
Representative Compounds
| Structure | Cpd. No. |
|---|---|
| 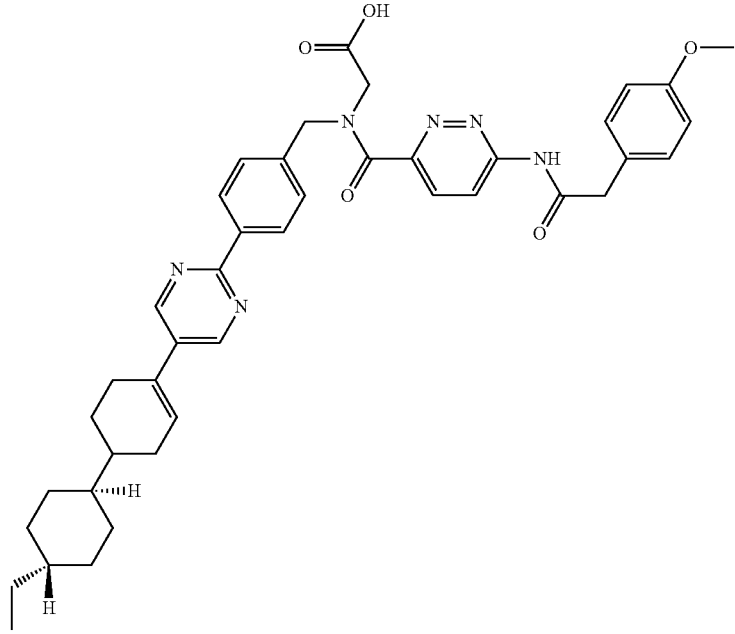 [SMILES: CC[C@H]1CC[C@H](C2CC=C(c3cnc(-c4ccc(CN(CC(=O)O)C(=O)c5ccc(NC(=O)Cc6ccc(OC)cc6)nn5)cc4)nc3)CC2)CC1] | 57 |
| 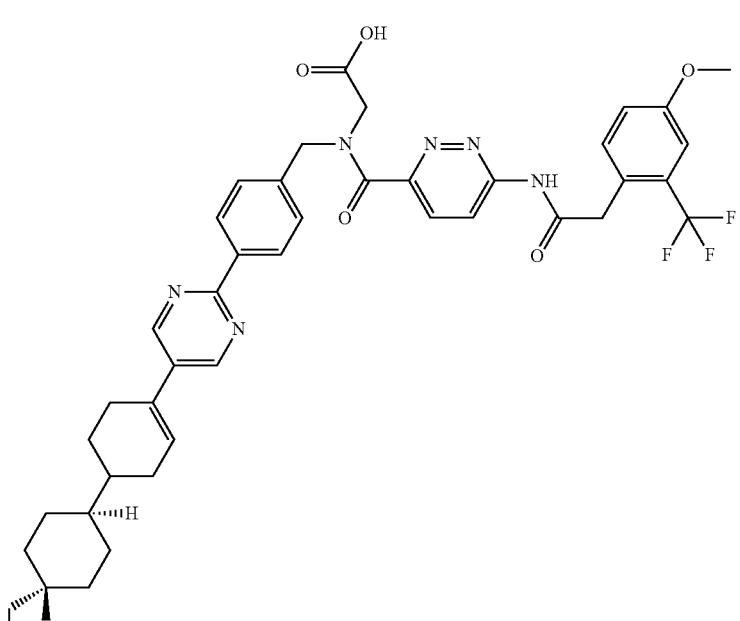 | 58 |

TABLE 1-continued
Representative Compounds
| Structure | Cpd. No. |
|---|---|
| 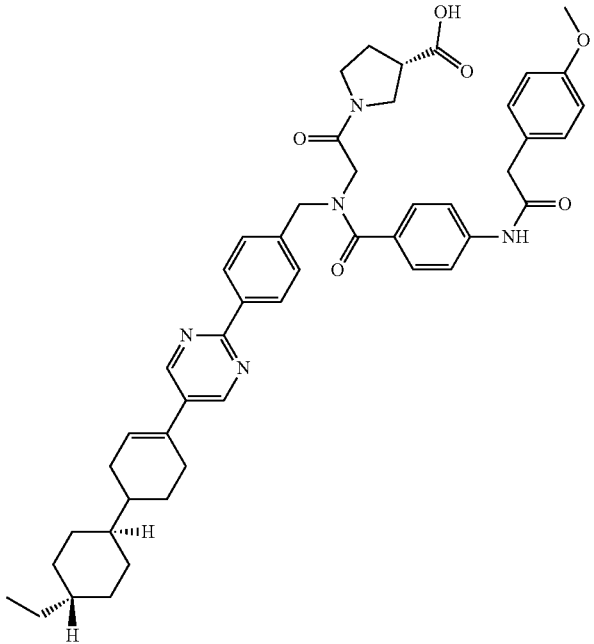 [SMILES: CC[C@H]1CC[C@H](C2CC=C(c3cnc(-c4ccc(CN(CC(=O)N5CC[C@H](C(=O)O)C5)C(=O)c5ccc(NC(=O)Cc6ccc(OC)cc6)cc5)cc4)nc3)CC2)CC1] | 59 |
| 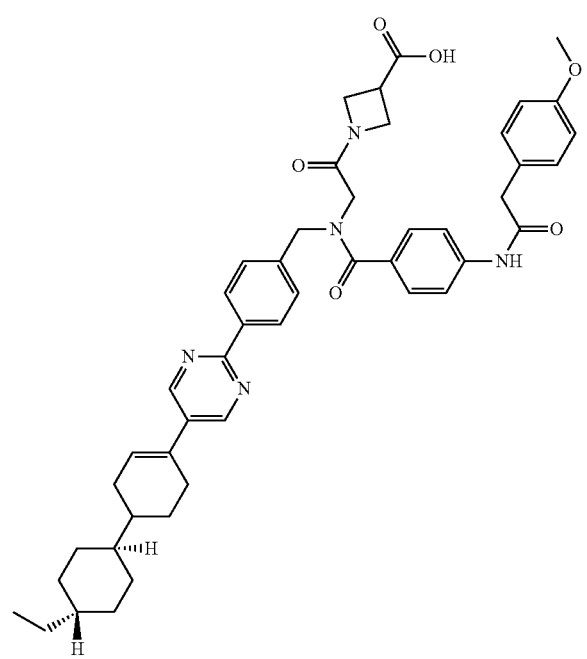 [SMILES: CC[C@H]1CC[C@H](C2CC=C(c3cnc(-c4ccc(CN(CC(=O)N5CC(C(=O)O)C5)C(=O)c5ccc(NC(=O)Cc6ccc(OC)cc6)cc5)cc4)nc3)CC2)CC1] | 60 |

TABLE 1-continued
Representative Compounds
| Structure | Cpd. No. |
|---|---|
| 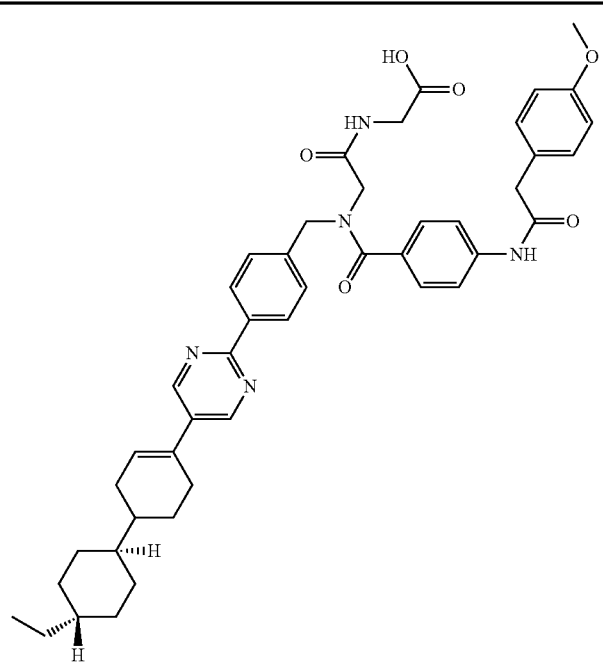 | 61 |
| 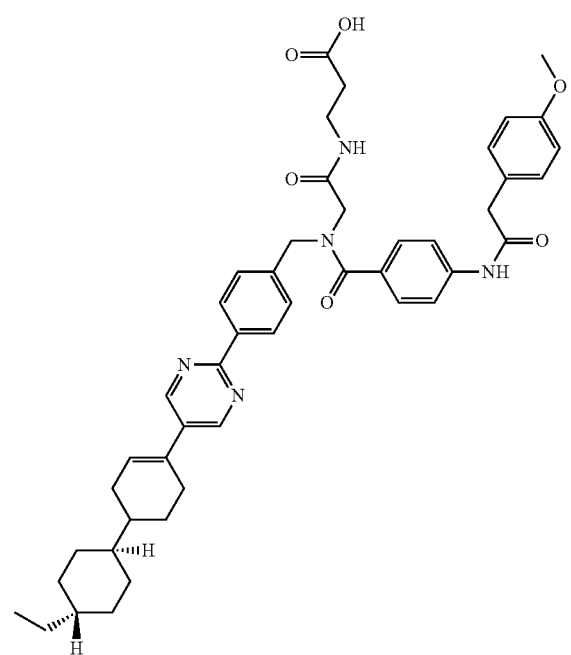 [SMILES: CC[C@H]1CC[C@H](C2CC=C(c3cnc(-c4ccc(CN(CC(=O)NCCC(=O)O)C(=O)c5ccc(NC(=O)Cc6ccc(OC)cc6)cc5)cc4)nc3)CC2)CC1] | 62 |

TABLE 1-continued
Representative Compounds
| Structure | Cpd. No. |
|---|---|
| 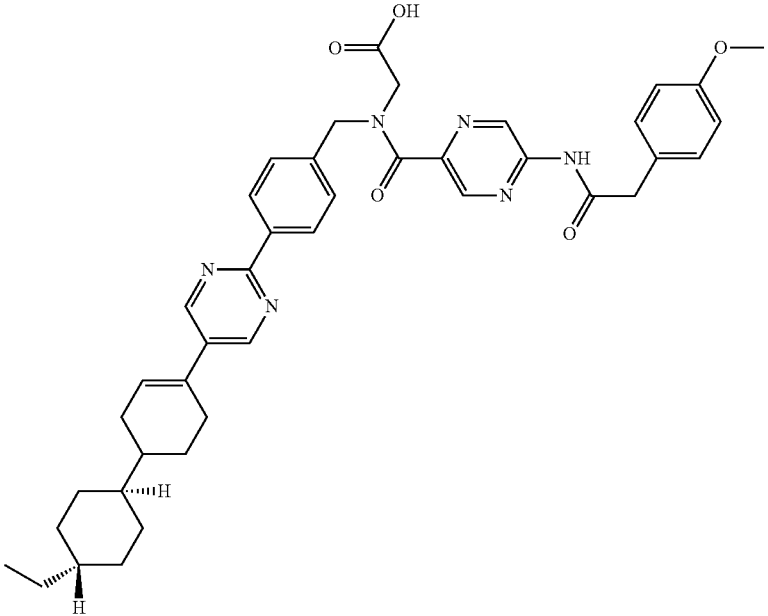 [SMILES: CC[C@H]1CC[C@H](C2CC=C(c3cnc(-c4ccc(CN(CC(=O)O)C(=O)c5cnc(NC(=O)Cc6ccc(OC)cc6)cn5)cc4)nc3)CC2)CC1] | 63 |
| 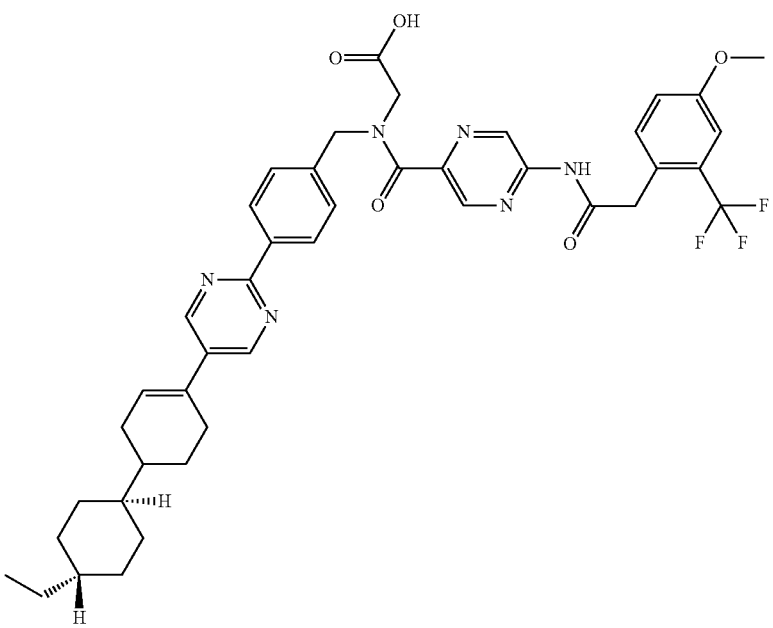 [SMILES: CC[C@H]1CC[C@H](C2CC=C(c3cnc(-c4ccc(CN(CC(=O)O)C(=O)c5cnc(NC(=O)Cc6ccc(OC)cc6C(F)(F)F)cn5)cc4)nc3)CC2)CC1] | 64 |

TABLE 1-continued
Representative Compounds
| Structure | Cpd. No. |
|---|---|
| 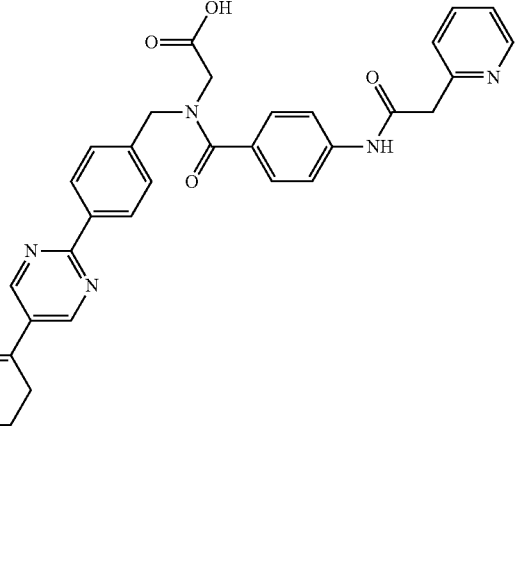 | 65 |
| 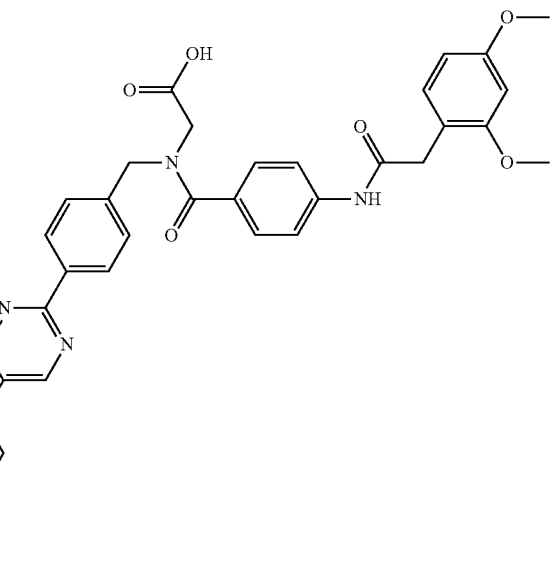 | 66 |

TABLE 1-continued
Representative Compounds
| Structure | Cpd. No. |
|---|---|
| 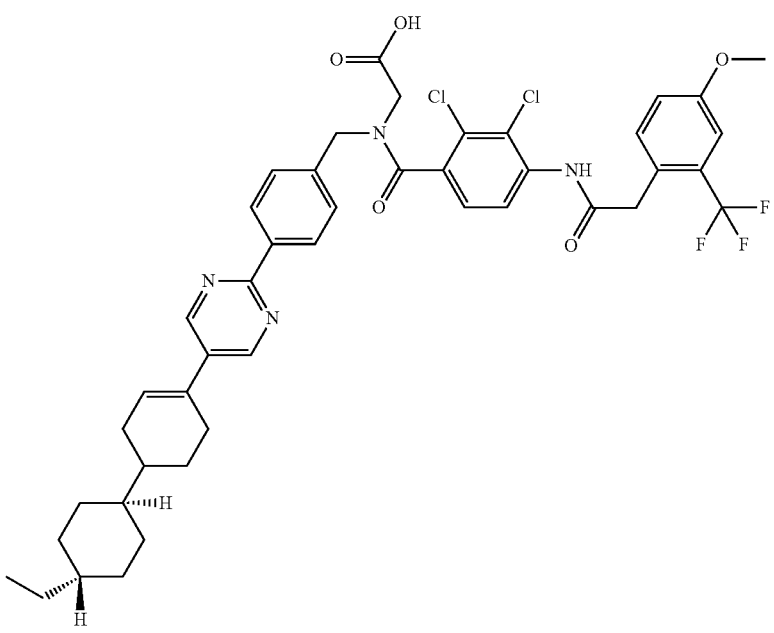 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)c(Cl)c5Cl)cc4)nc3)CC2)CC1] | 67 |
| 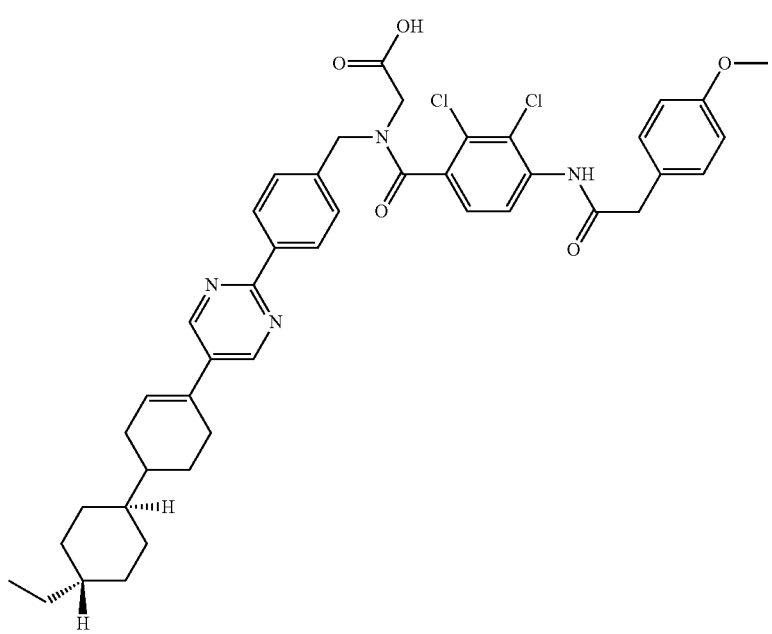 [SMILES: CC[C@H]1CC[C@H](C2CC=C(c3cnc(-c4ccc(CN(CC(=O)O)C(=O)c5ccc(NC(=O)Cc6ccc(OC)cc6)c(Cl)c5Cl)cc4)nc3)CC2)CC1] | 68 |

TABLE 1-continued
Representative Compounds
| Structure | Cpd. No. |
|---|---|
| 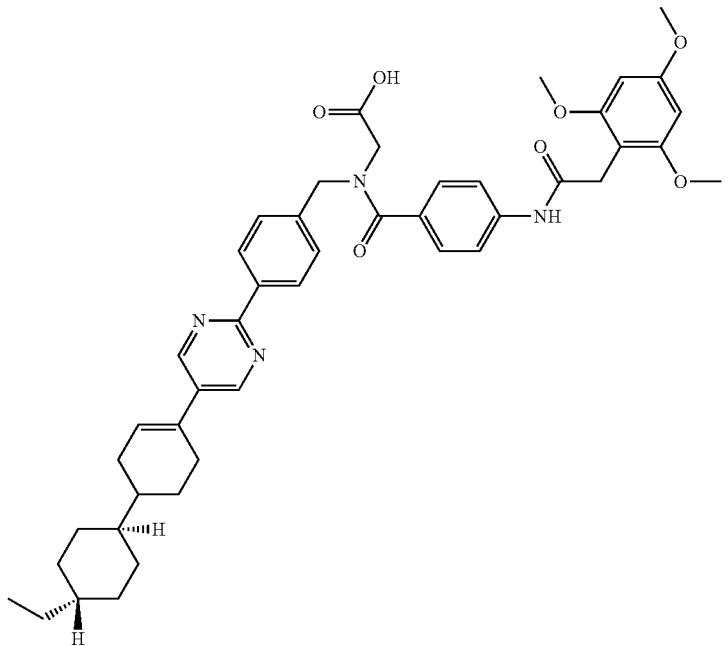 [SMILES: CC[C@H]1CC[C@H](C2CC=C(c3cnc(-c4ccc(CN(CC(=O)O)C(=O)c5ccc(NC(=O)Cc6c(OC)cc(OC)cc6OC)cc5)cc4)nc3)CC2)CC1] | 69 |
| 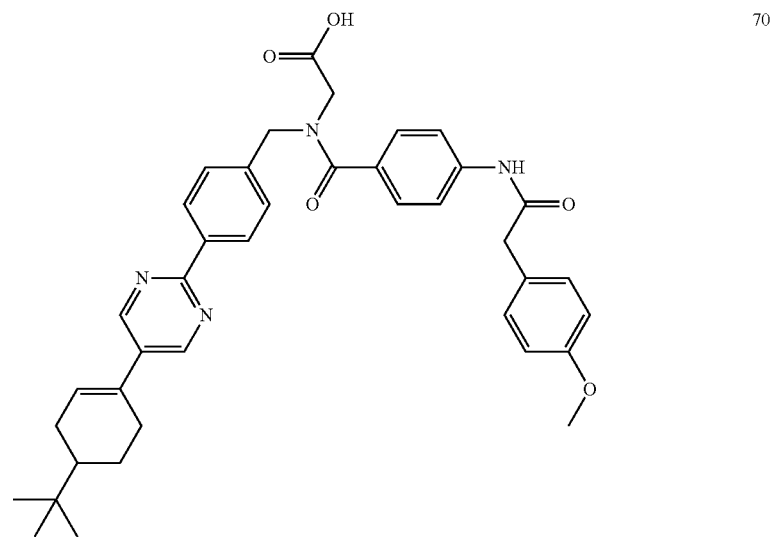 | 70 |

TABLE 1-continued
Representative Compounds
| Structure | Cpd. No. |
|---|---|
| 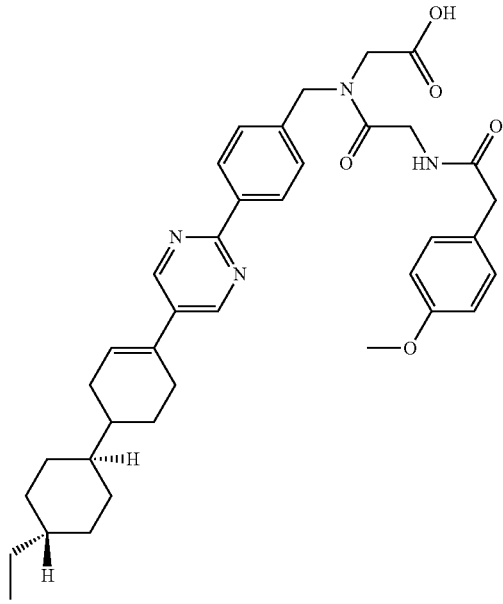 [SMILES: CC[C@H]1CC[C@H](C2CC=C(c3cnc(-c4ccc(CN(CC(=O)O)C(=O)CNC(=O)Cc5ccc(OC)cc5)cc4)nc3)CC2)CC1] | 71 |
| 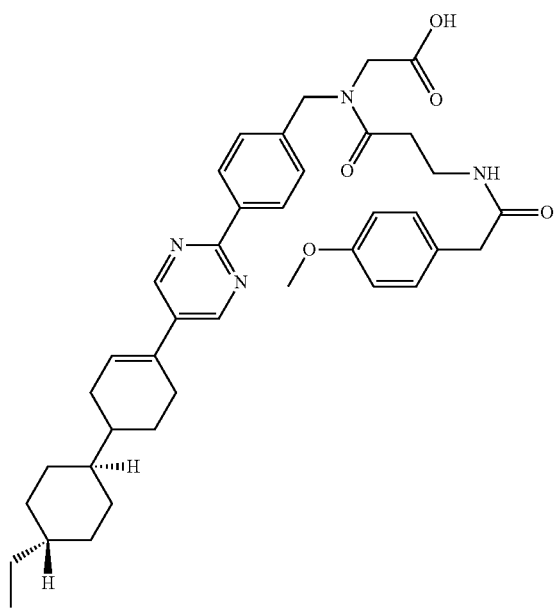 [SMILES: CC[C@H]1CC[C@H](C2CC=C(c3cnc(-c4ccc(CN(CC(=O)O)C(=O)CCNC(=O)Cc5ccc(OC)cc5)cc4)nc3)CC2)CC1] | 72 |

TABLE 1-continued

Representative Compounds

| Structure | Cpd. No. |
|---|---|
| 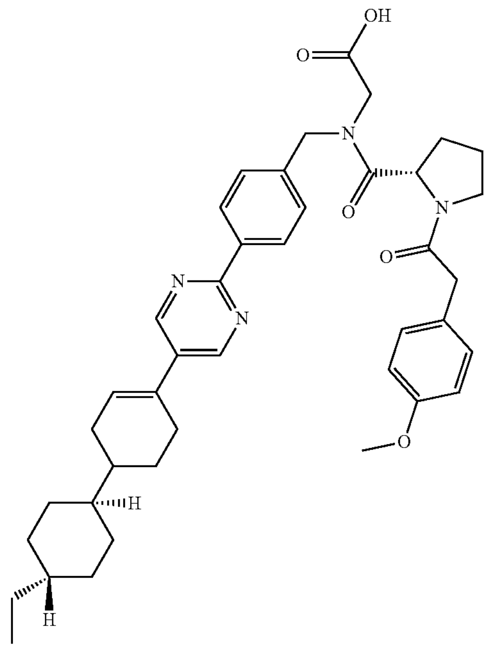 [SMILES: CC[C@H]1CC[C@H](C2CC=C(c3cnc(-c4ccc(CN(CC(=O)O)C(=O)[C@@H]5CCCN5C(=O)Cc5ccc(OC)cc5)cc4)nc3)CC2)CC1] | 73 |
| 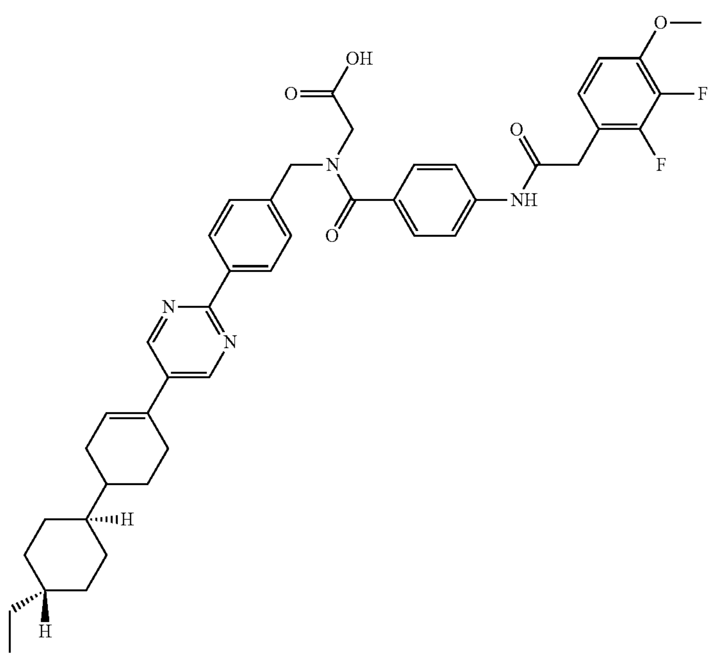 [SMILES: CC[C@H]1CC[C@H](C2CC=C(c3cnc(-c4ccc(CN(CC(=O)O)C(=O)c5ccc(NC(=O)Cc6ccc(OC)c(F)c6F)cc5)cc4)nc3)CC2)CC1] | 74 |

TABLE 1-continued
Representative Compounds
| Structure | Cpd. No. |
|---|---|
| 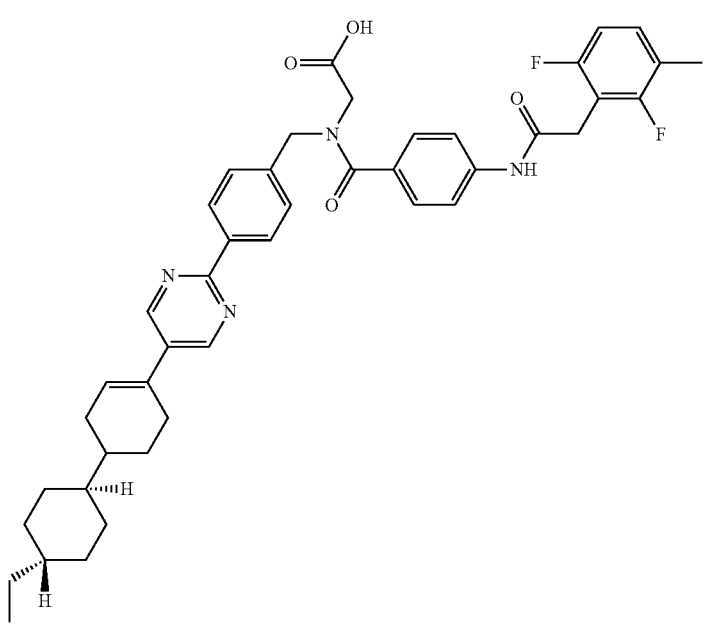 [SMILES: CC[C@H]1CC[C@H](C2CC=C(c3cnc(-c4ccc(CN(CC(=O)O)C(=O)c5ccc(NC(=O)Cc6c(F)ccc(C)c6F)cc5)cc4)nc3)CC2)CC1] | 75 |
| 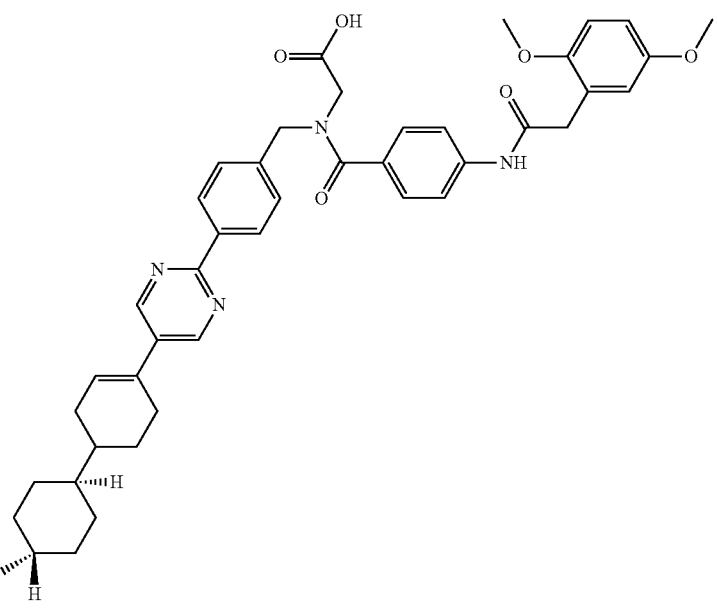 | 76 |

TABLE 1-continued
Representative Compounds
| Structure | Cpd. No. |
|---|---|
| 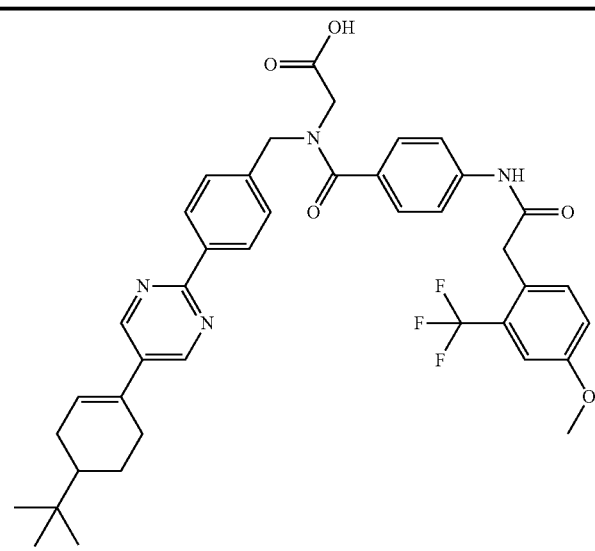 | 77 |
| 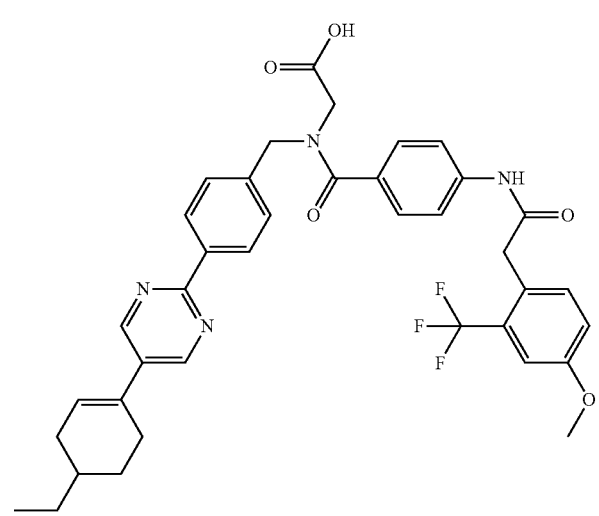 [SMILES: CCC1CC=C(c2cnc(-c3ccc(CN(CC(=O)O)C(=O)c4ccc(NC(=O)Cc5ccc(OC)cc5C(F)(F)F)cc4)cc3)nc2)CC1] | 78 |
| 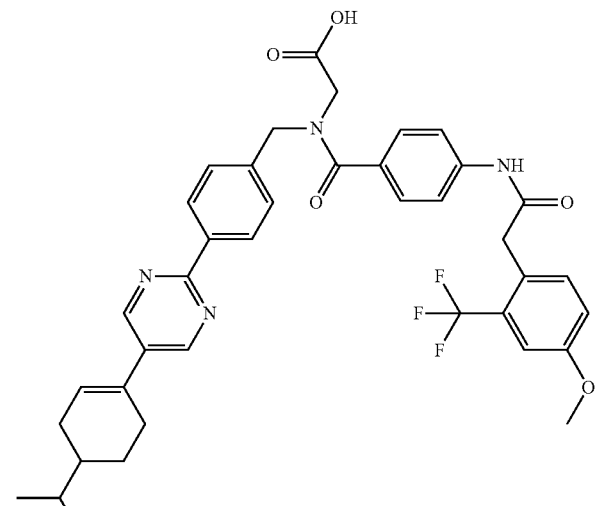 | 79 |

TABLE 1-continued
Representative Compounds
| Structure | Cpd. No. |
|---|---|
| 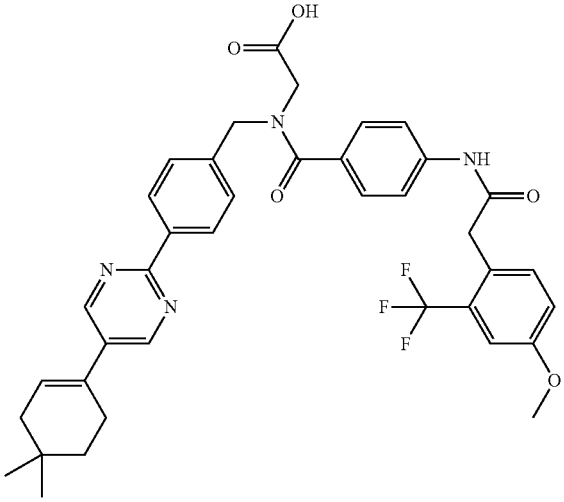 [SMILES: COc1ccc(CC(=O)Nc2ccc(C(=O)N(CC(=O)O)Cc3ccc(-c4ncc(C5=CCC(C)(C)CC5)cn4)cc3)cc2)c(C(F)(F)F)c1] | 80 |
| 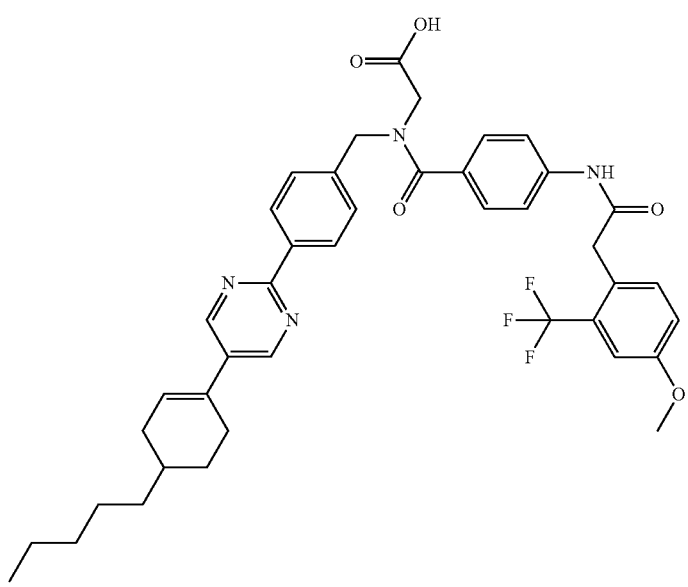 [SMILES: CCCCCC1CC=C(c2cnc(-c3ccc(CN(CC(=O)O)C(=O)c4ccc(NC(=O)Cc5ccc(OC)cc5C(F)(F)F)cc4)cc3)nc2)CC1] | 81 |

TABLE 1-continued
Representative Compounds
| Structure | Cpd. No. |
|---|---|
| 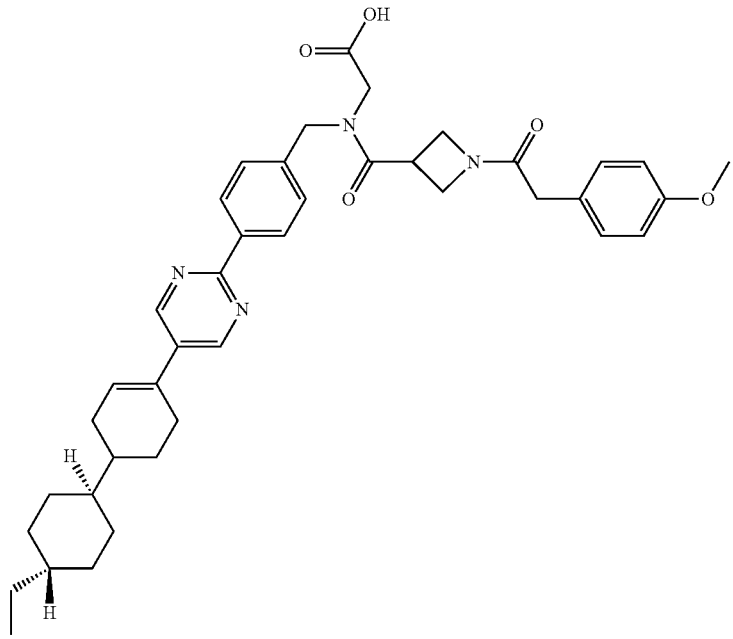 [SMILES: CC[C@H]1CC[C@H](C2CC=C(c3cnc(-c4ccc(CN(CC(=O)O)C(=O)C5CN(C(=O)Cc6ccc(OC)cc6)C5)cc4)nc3)CC2)CC1] | 82 |
| 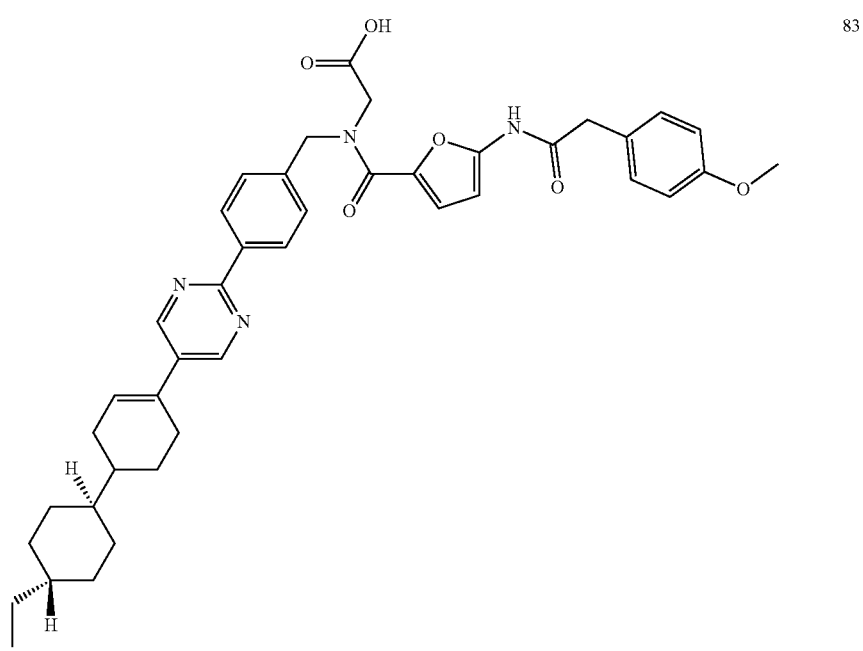 | 83 |

TABLE 1-continued
Representative Compounds
| Structure | Cpd. No. |
|---|---|
| 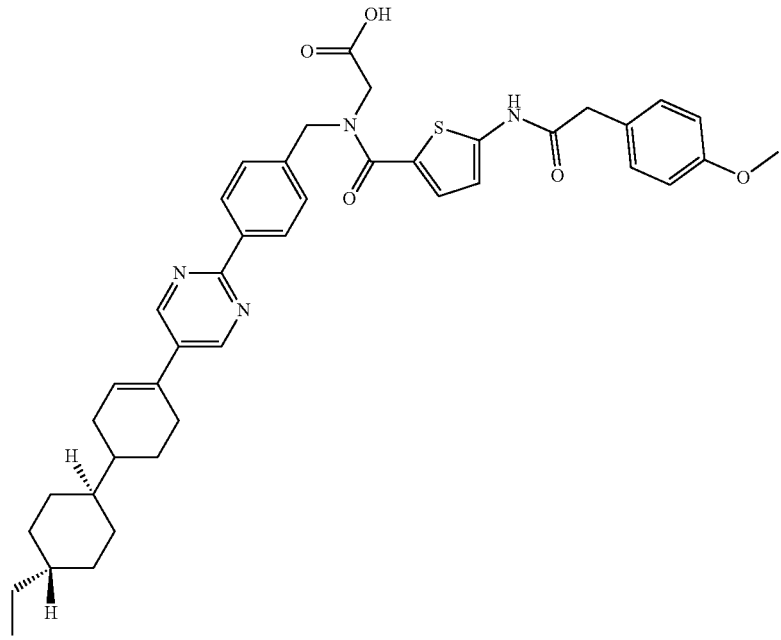 [SMILES: CC[C@H]1CC[C@H](C2CC=C(c3cnc(-c4ccc(CN(CC(=O)O)C(=O)c5ccc(NC(=O)Cc6ccc(OC)cc6)s5)cc4)nc3)CC2)CC1] | 84 |
| 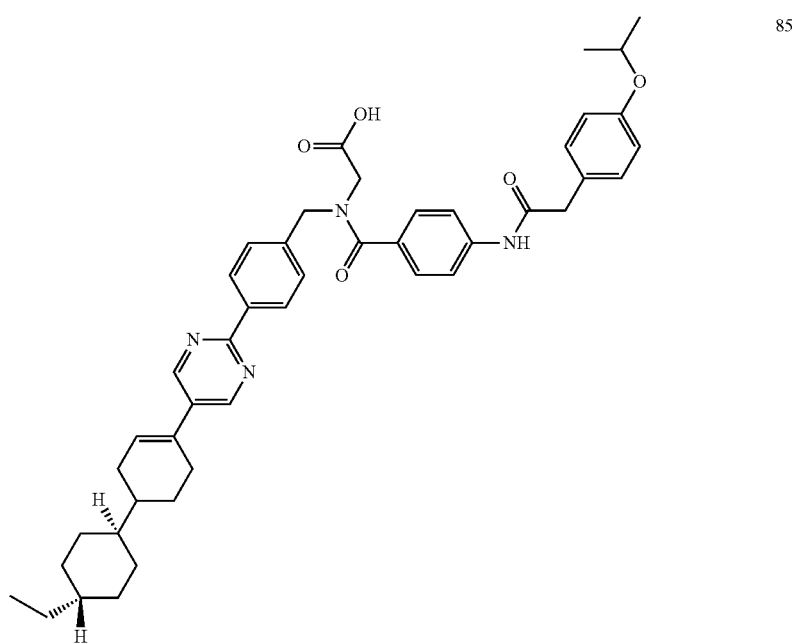 | 85 |

TABLE 1-continued

Representative Compounds

| Structure | Cpd. No. |
|---|---|
| 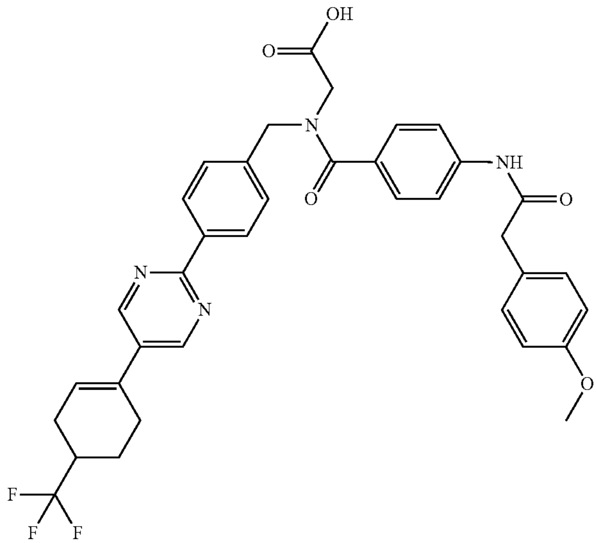 [SMILES: COc1ccc(CC(=O)Nc2ccc(C(=O)N(CC(=O)O)Cc3ccc(-c4ncc(C5=CCC(C(F)(F)F)CC5)cn4)cc3)cc2)cc1] | 86 |
| 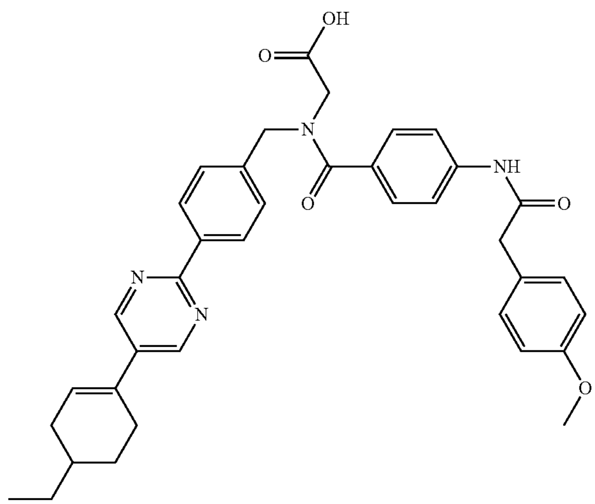 [SMILES: CCC1CC=C(c2cnc(-c3ccc(CN(CC(=O)O)C(=O)c4ccc(NC(=O)Cc5ccc(OC)cc5)cc4)cc3)nc2)CC1] | 87 |
| 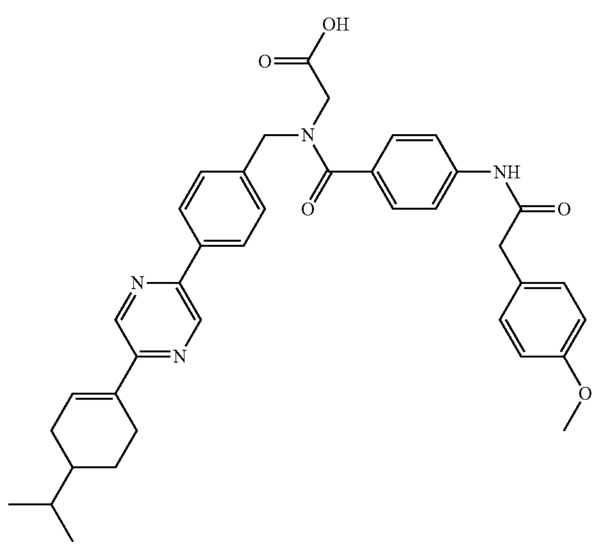 | 88 |

TABLE 1-continued

Representative Compounds

| Structure | Cpd. No. |
|---|---|
| 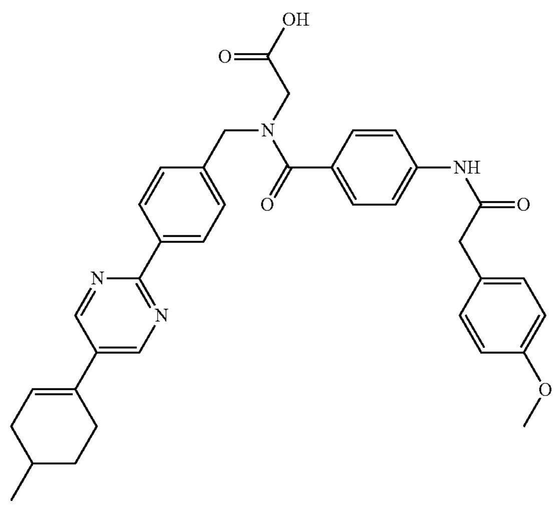 [SMILES: COc1ccc(CC(=O)Nc2ccc(C(=O)N(CC(=O)O)Cc3ccc(-c4ncc(C5=CCC(C)CC5)cn4)cc3)cc2)cc1] | 89 |
| 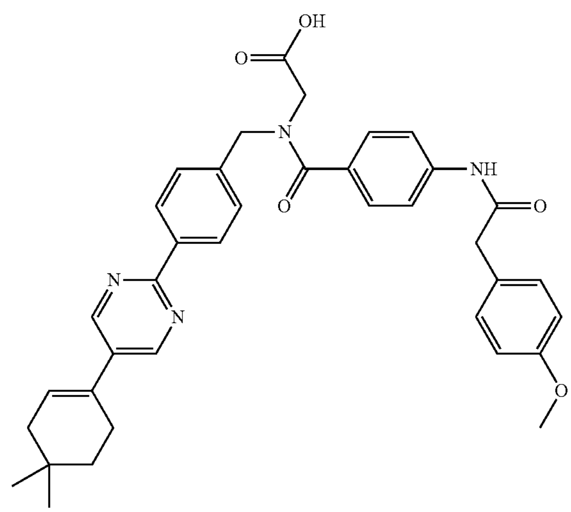 [SMILES: COc1ccc(CC(=O)Nc2ccc(C(=O)N(CC(=O)O)Cc3ccc(-c4ncc(C5=CCC(C)(C)CC5)cn4)cc3)cc2)cc1] | 90 |
| 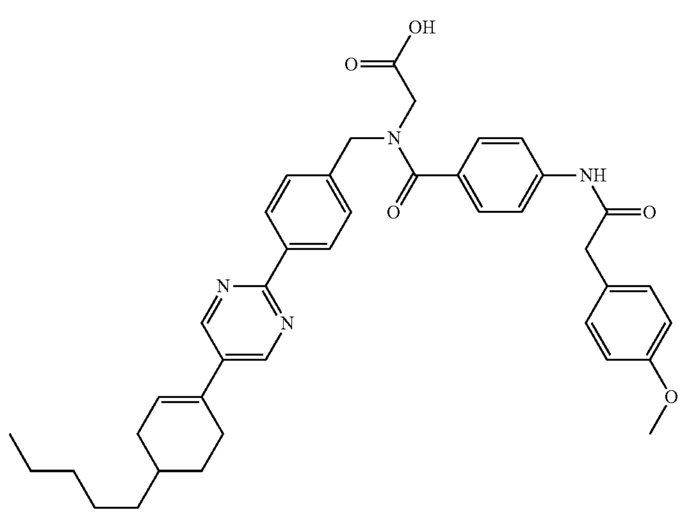 [SMILES: CCCCCC1CC=C(c2cnc(-c3ccc(CN(CC(=O)O)C(=O)c4ccc(NC(=O)Cc5ccc(OC)cc5)cc4)cc3)nc2)CC1] | 91 |

TABLE 1-continued
Representative Compounds
| Structure | Cpd. No. |
|---|---|
| 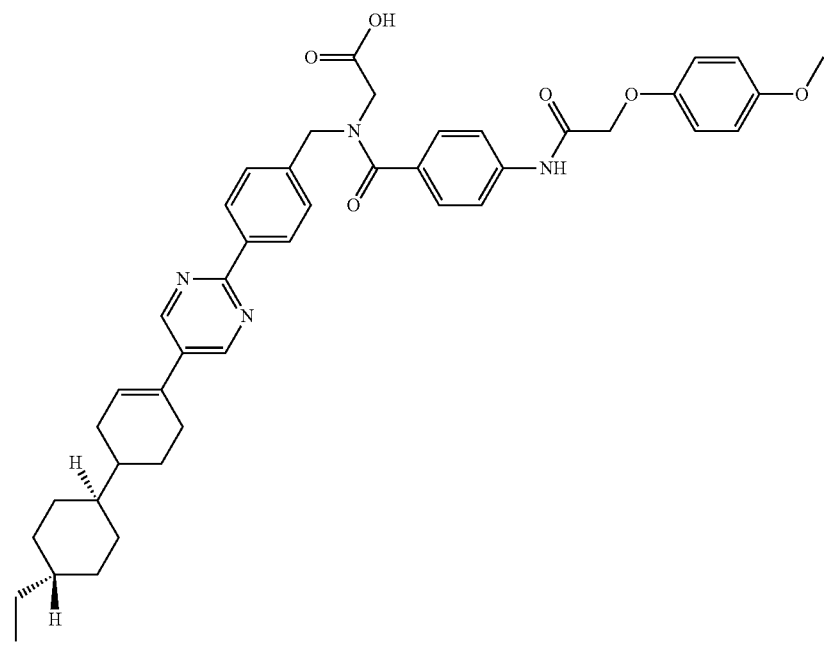 | 92 |
| 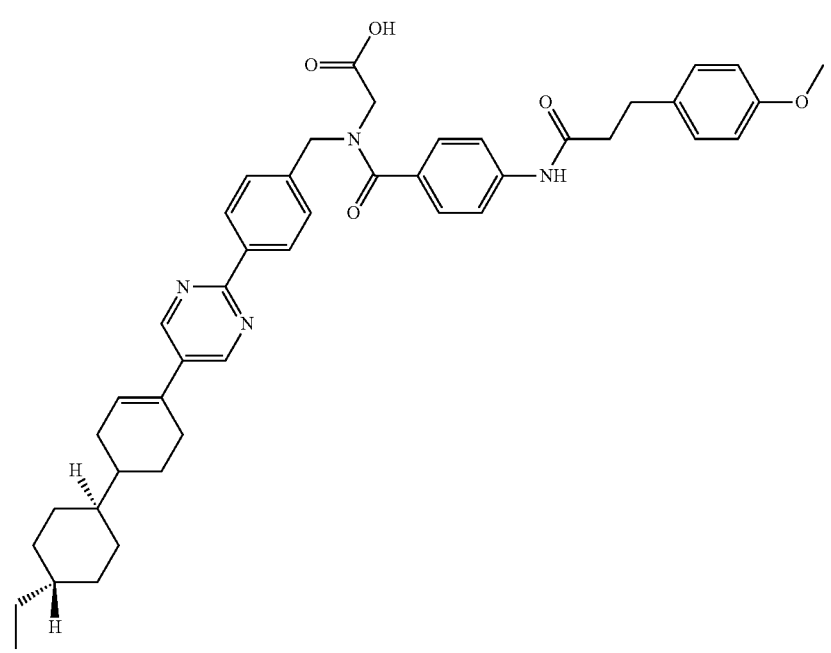 [SMILES: CC[C@H]1CC[C@H](C2CC=C(c3cnc(-c4ccc(CN(CC(=O)O)C(=O)c5ccc(NC(=O)COc6ccc(OC)cc6)cc5)cc4)nc3)CC2)CC1] | 93 |

TABLE 1-continued
Representative Compounds
| Structure | Cpd. No. |
|---|---|
| 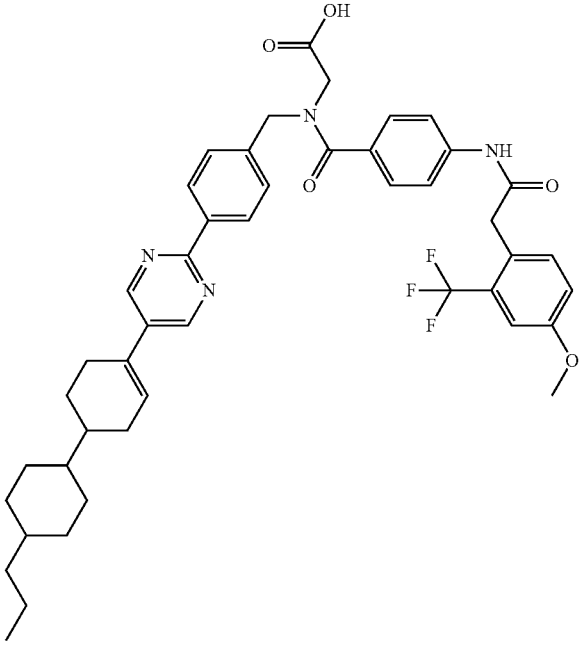 [SMILES: CCCC1CCC(C2CC=C(c3cnc(-c4ccc(CN(CC(=O)O)C(=O)c5ccc(NC(=O)Cc6ccc(OC)cc6C(F)(F)F)cc5)cc4)nc3)CC2)CC1] | 94 |
| 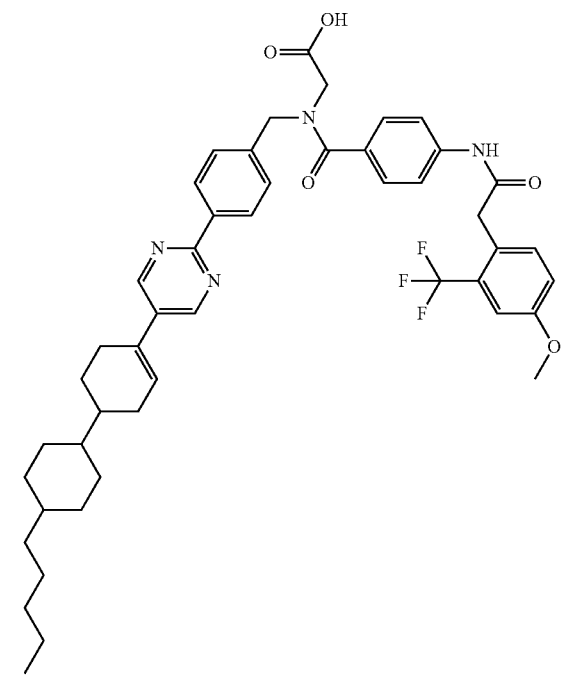 [SMILES: CCCCCC1CCC(C2CC=C(c3cnc(-c4ccc(CN(CC(=O)O)C(=O)c5ccc(NC(=O)Cc6ccc(OC)cc6C(F)(F)F)cc5)cc4)nc3)CC2)CC1] | 95 |

TABLE 1-continued
Representative Compounds
| Structure | Cpd. No. |
|---|---|
| 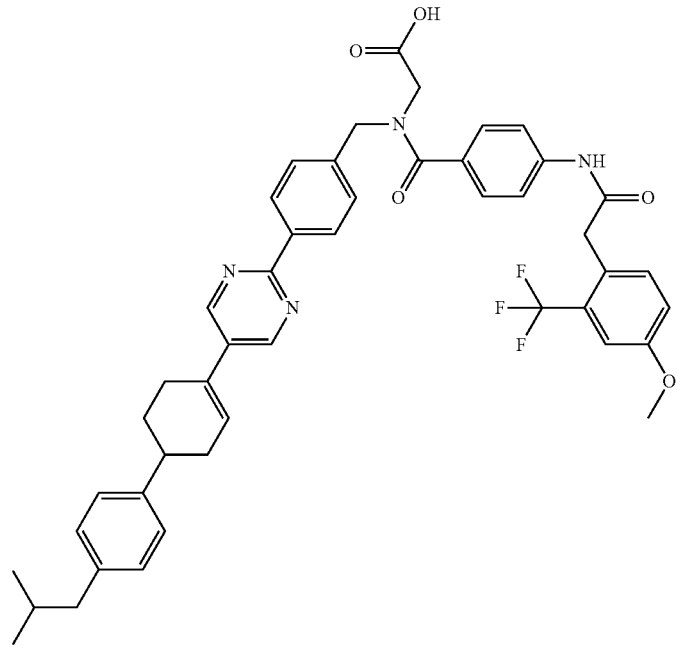 [SMILES: COc1ccc(CC(=O)Nc2ccc(C(=O)N(CC(=O)O)Cc3ccc(-c4ncc(C5=CCC(c6ccc(CC(C)C)cc6)CC5)cn4)cc3)cc2)c(C(F)(F)F)c1] | 96 |
| 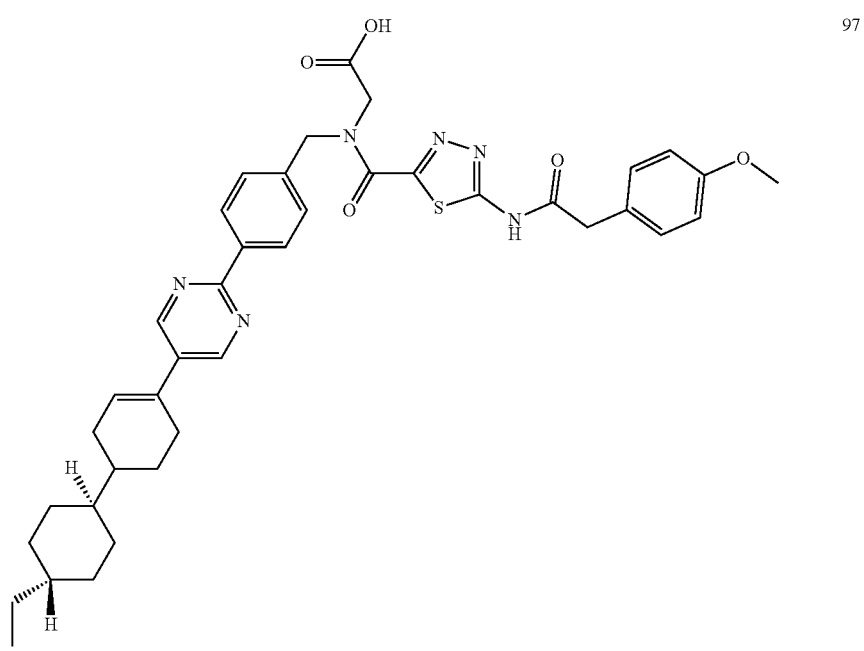 | 97 |

TABLE 1-continued

Representative Compounds

| Structure | Cpd. No. |
|---|---|
| 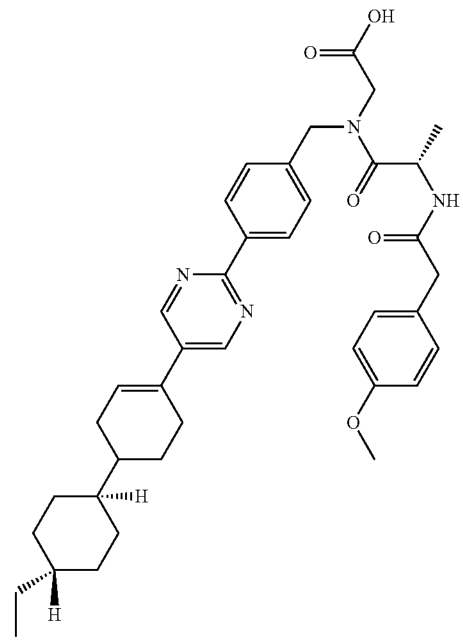 [SMILES: CC[C@H]1CC[C@H](C2CC=C(c3cnc(-c4ccc(CN(CC(=O)O)C(=O)[C@H](C)NC(=O)Cc5ccc(OC)cc5)cc4)nc3)CC2)CC1] | 98 |
| 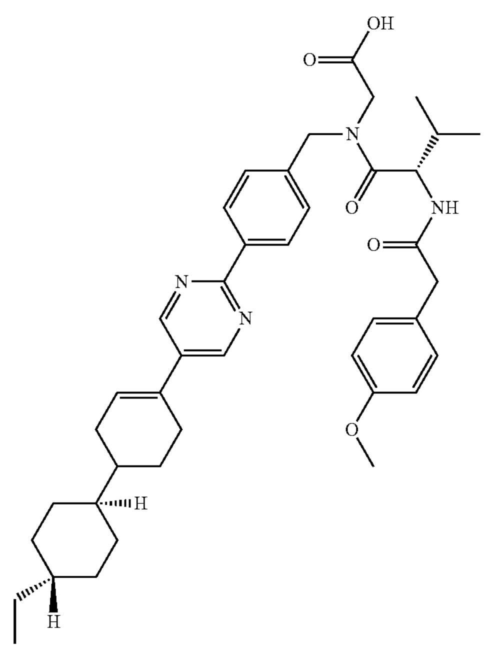 [SMILES: CC[C@H]1CC[C@H](C2CC=C(c3cnc(-c4ccc(CN(CC(=O)O)C(=O)[C@@H](NC(=O)Cc5ccc(OC)cc5)C(C)C)cc4)nc3)CC2)CC1] | 99 |

TABLE 1-continued
Representative Compounds
| Structure | Cpd. No. |
|---|---|
| 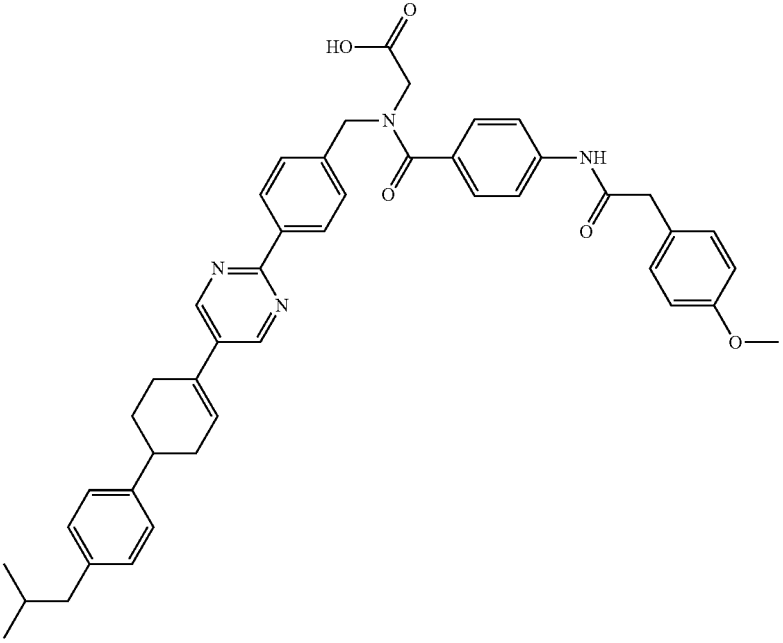 [SMILES: COc1ccc(CC(=O)Nc2ccc(C(=O)N(CC(=O)O)Cc3ccc(-c4ncc(C5=CCC(c6ccc(CC(C)C)cc6)CC5)cn4)cc3)cc2)cc1] | 100 |
| 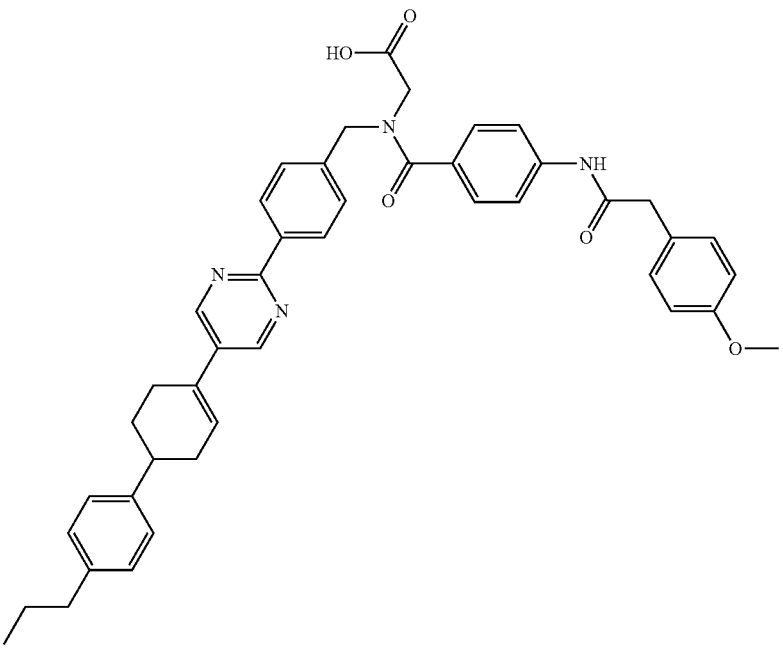 [SMILES: CCCc1ccc(C2CC=C(c3cnc(-c4ccc(CN(CC(=O)O)C(=O)c5ccc(NC(=O)Cc6ccc(OC)cc6)cc5)cc4)nc3)CC2)cc1] | 101 |

TABLE 1-continued
Representative Compounds
| Structure | Cpd. No. |
|---|---|
| 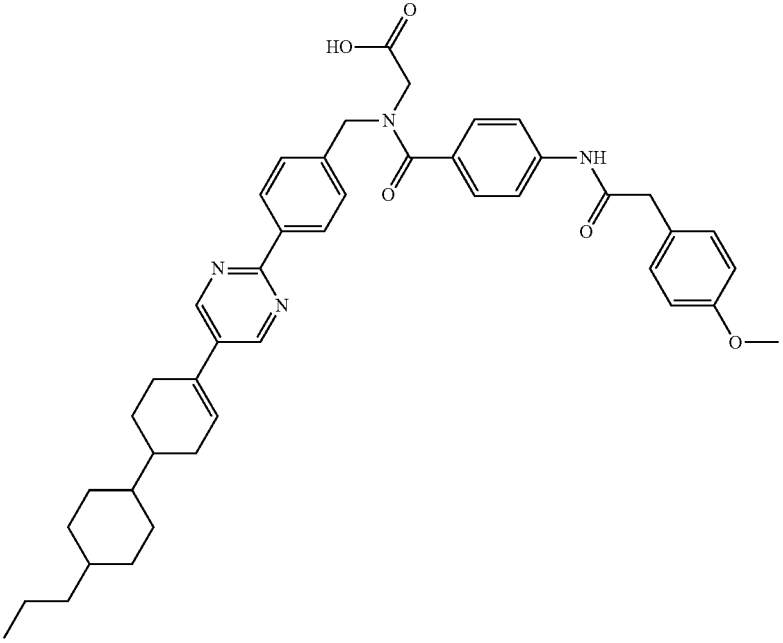 [SMILES: CCCC1CCC(C2CC=C(c3cnc(-c4ccc(CN(CC(=O)O)C(=O)c5ccc(NC(=O)Cc6ccc(OC)cc6)cc5)cc4)nc3)CC2)CC1] | 102 |
| 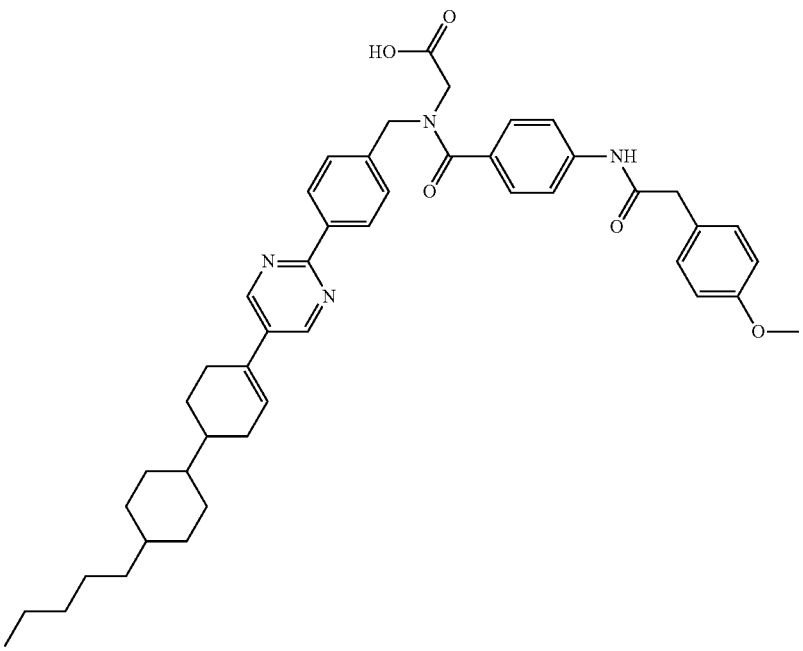 [SMILES: CCCCCC1CCC(C2CC=C(c3cnc(-c4ccc(CN(CC(=O)O)C(=O)c5ccc(NC(=O)Cc6ccc(OC)cc6)cc5)cc4)nc3)CC2)CC1] | 103 |

TABLE 1-continued
Representative Compounds
| Structure | Cpd. No. |
|---|---|
| 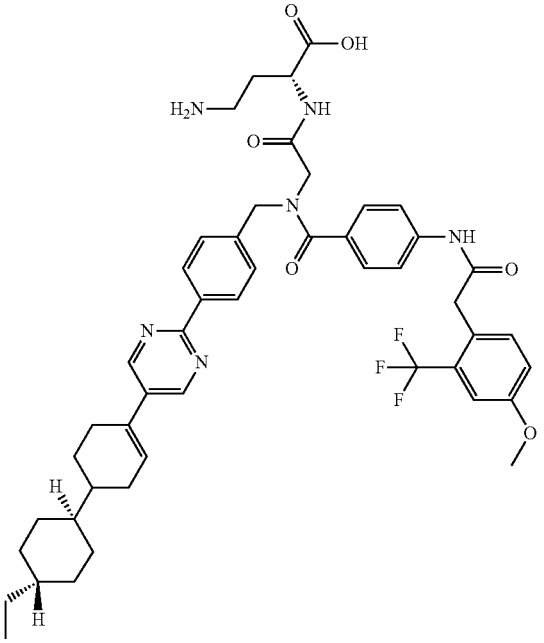 [SMILES: CC[C@H]1CC[C@H](C2CC=C(c3cnc(-c4ccc(CN(CC(=O)N[C@H](CCN)C(=O)O)C(=O)c5ccc(NC(=O)Cc6ccc(OC)cc6C(F)(F)F)cc5)cc4)nc3)CC2)CC1] | 104 |
| 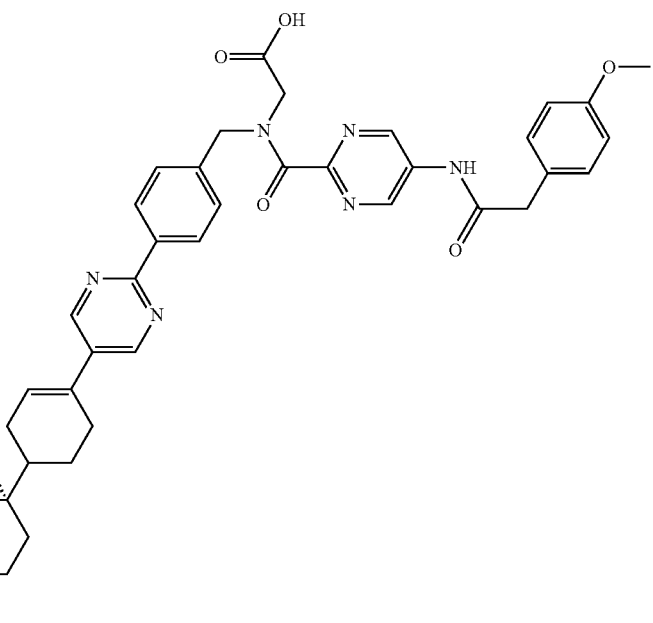 | 105 |

TABLE 1-continued
Representative Compounds
| Structure | Cpd. No. |
|---|---|
| 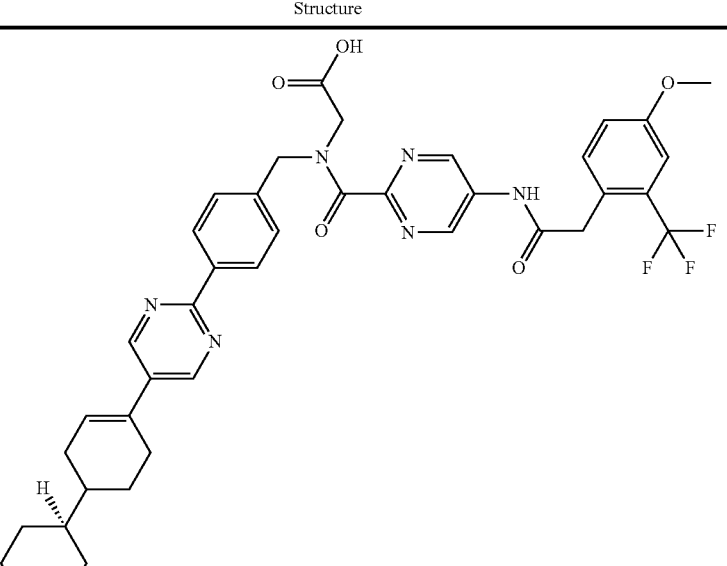 | 106 |
| 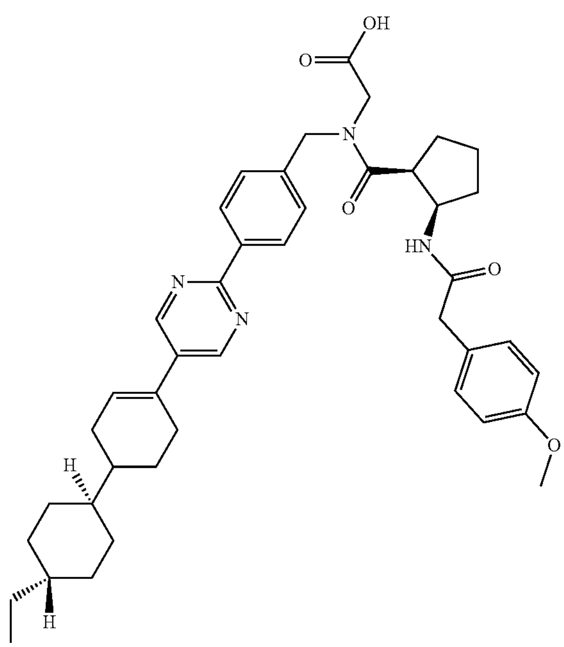 [SMILES: CC[C@H]1CC[C@H](C2CC=C(c3cnc(-c4ccc(CN(CC(=O)O)C(=O)[C@H]5CCC[C@H]5NC(=O)Cc5ccc(OC)cc5)cc4)nc3)CC2)CC1] | 107 |

TABLE 1-continued

Representative Compounds

| Structure | Cpd. No. |
|---|---|
| 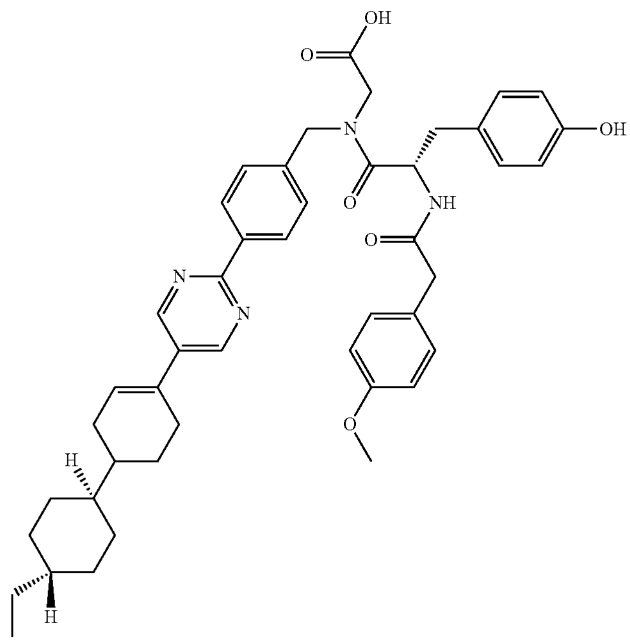 [SMILES: CC[C@H]1CC[C@H](C2CC=C(c3cnc(-c4ccc(CN(CC(=O)O)C(=O)[C@H](Cc5ccc(O)cc5)NC(=O)Cc5ccc(OC)cc5)cc4)nc3)CC2)CC1] | 108 |
| 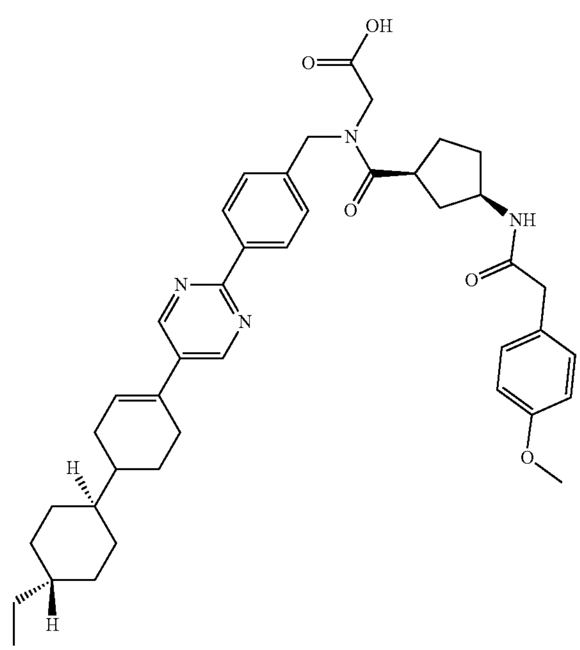 [SMILES: CC[C@H]1CC[C@H](C2CC=C(c3cnc(-c4ccc(CN(CC(=O)O)C(=O)[C@H]5CC[C@@H](NC(=O)Cc6ccc(OC)cc6)C5)cc4)nc3)CC2)CC1] | 109 |

TABLE 1-continued

Representative Compounds

| Structure | Cpd. No. |
|---|---|
| 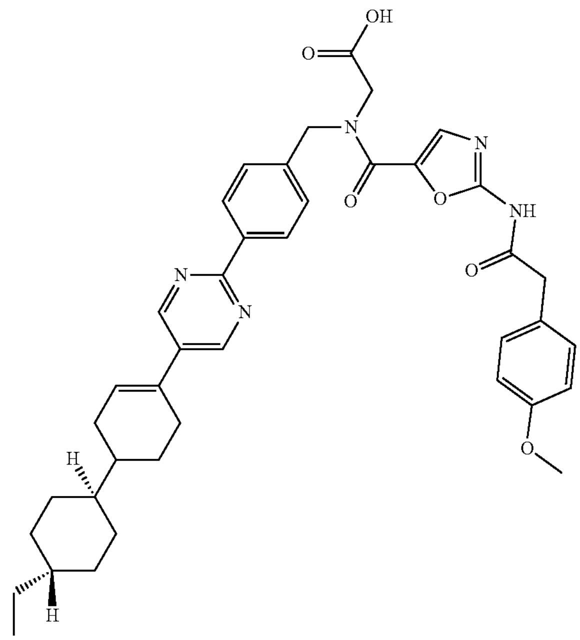 [SMILES: CC[C@H]1CC[C@H](C2CC=C(c3cnc(-c4ccc(CN(CC(=O)O)C(=O)c5cnc(NC(=O)Cc6ccc(OC)cc6)o5)cc4)nc3)CC2)CC1] | 110 |
| 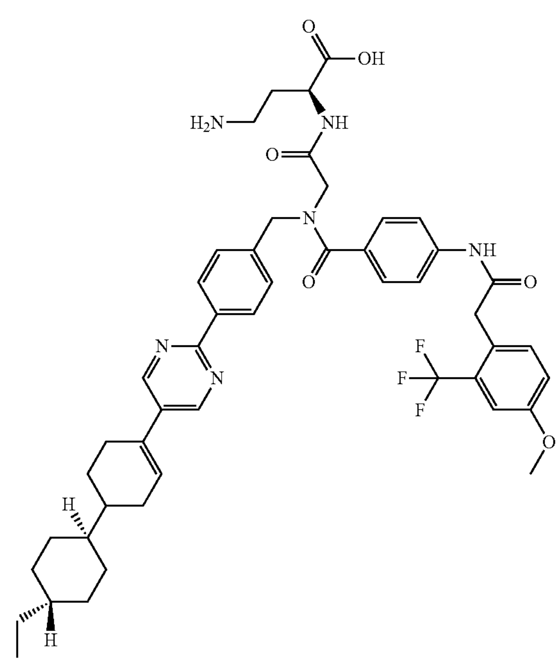 [SMILES: CC[C@H]1CC[C@H](C2CC=C(c3cnc(-c4ccc(CN(CC(=O)N[C@@H](CCN)C(=O)O)C(=O)c5ccc(NC(=O)Cc6ccc(OC)cc6C(F)(F)F)cc5)cc4)nc3)CC2)CC1] | 111 |

TABLE 1-continued

Representative Compounds

| Structure | Cpd. No. |
|---|---|
| 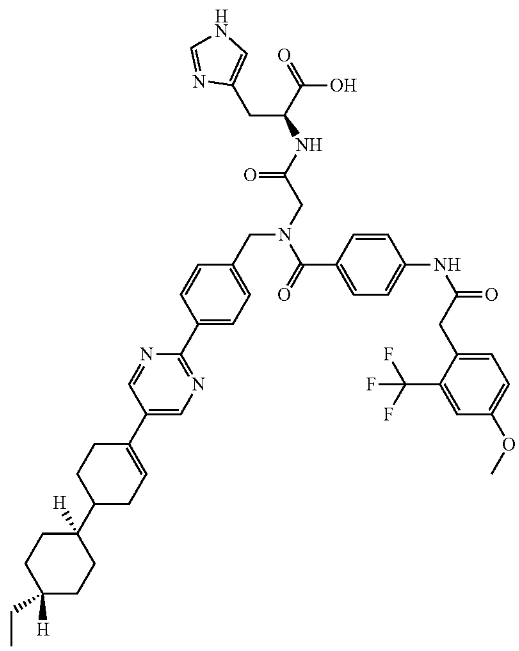 [SMILES: CC[C@H]1CC[C@H](C2CC=C(c3cnc(-c4ccc(CN(CC(=O)N[C@@H](Cc5c[nH]cn5)C(=O)O)C(=O)c5ccc(NC(=O)Cc6ccc(OC)cc6C(F)(F)F)cc5)cc4)nc3)CC2)CC1] | 112 |
| 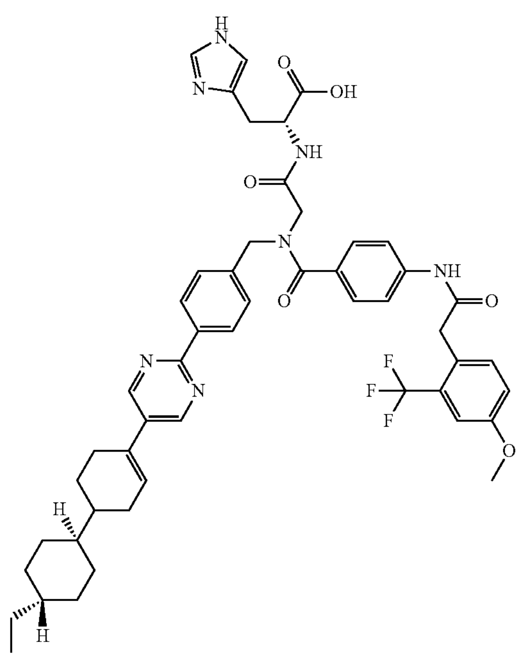 [SMILES: CC[C@H]1CC[C@H](C2CC=C(c3cnc(-c4ccc(CN(CC(=O)N[C@H](Cc5c[nH]cn5)C(=O)O)C(=O)c5ccc(NC(=O)Cc6ccc(OC)cc6C(F)(F)F)cc5)cc4)nc3)CC2)CC1] | 113 |

TABLE 1-continued
Representative Compounds
| Structure | Cpd. No. |
|---|---|
| 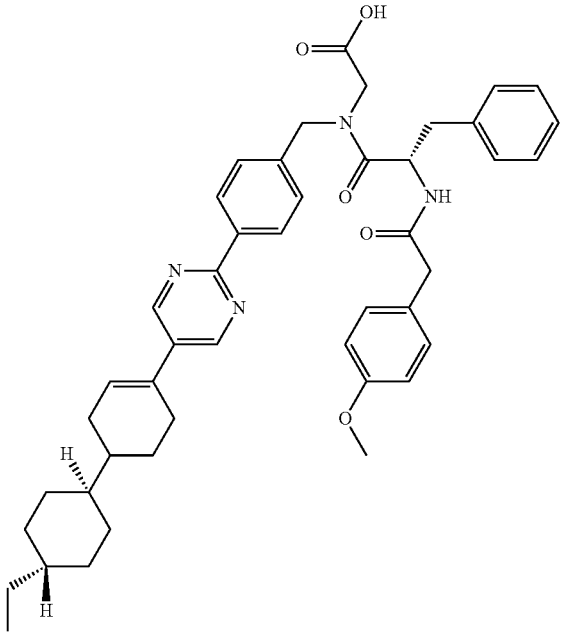 [SMILES: CC[C@H]1CC[C@H](C2CC=C(c3cnc(-c4ccc(CN(CC(=O)O)C(=O)[C@H](Cc5ccccc5)NC(=O)Cc5ccc(OC)cc5)cc4)nc3)CC2)CC1] | 114 |
| 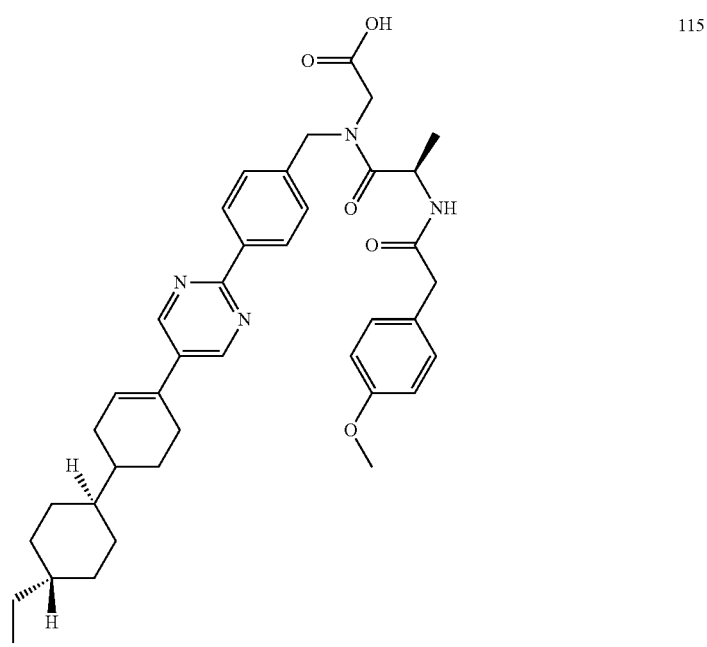 | 115 |

129 130
TABLE 1-continued
Representative Compounds
| Structure | Cpd. No. |
|---|---|
| 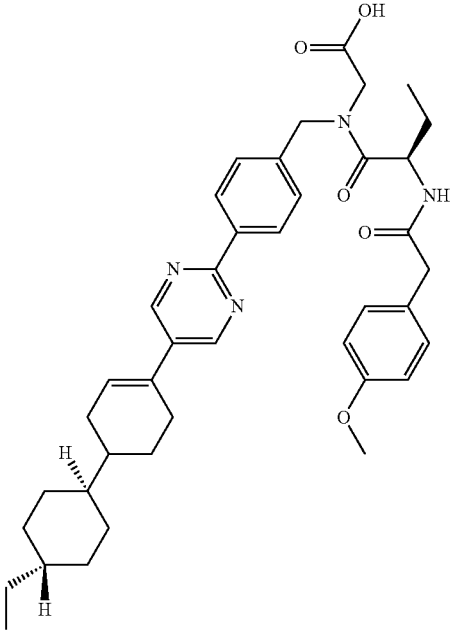 [SMILES: CC[C@@H](NC(=O)Cc1ccc(OC)cc1)C(=O)N(CC(=O)O)Cc1ccc(-c2ncc(C3=CCC([C@H]4CC[C@H](CC)CC4)CC3)cn2)cc1] | 116 |
| 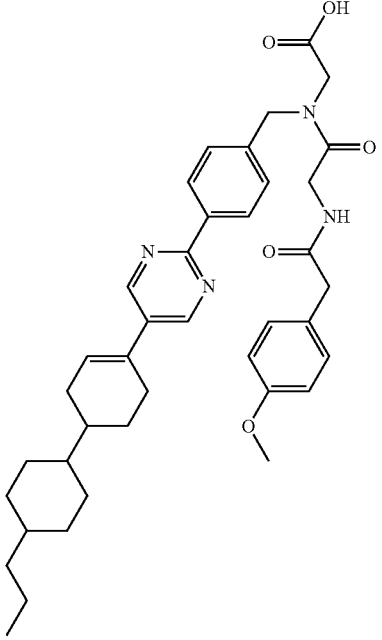 [SMILES: CCCC1CCC(C2CC=C(c3cnc(-c4ccc(CN(CC(=O)O)C(=O)CNC(=O)Cc5ccc(OC)cc5)cc4)nc3)CC2)CC1] | 117 |

TABLE 1-continued
Representative Compounds
| Structure | Cpd. No. |
|---|---|
| 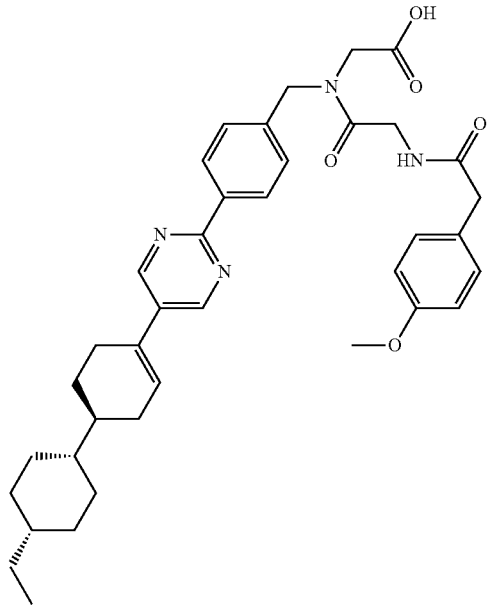 [SMILES: CC[C@H]1CC[C@@H]([C@@H]2CC=C(c3cnc(-c4ccc(CN(CC(=O)O)C(=O)CNC(=O)Cc5ccc(OC)cc5)cc4)nc3)CC2)CC1] | 118 |
| 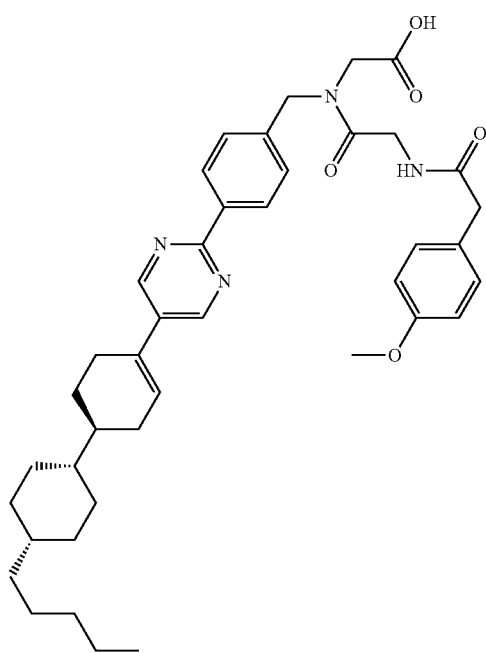 [SMILES: CCCCC[C@H]1CC[C@@H]([C@@H]2CC=C(c3cnc(-c4ccc(CN(CC(=O)O)C(=O)CNC(=O)Cc5ccc(OC)cc5)cc4)nc3)CC2)CC1] | 119 |

TABLE 1-continued
Representative Compounds
| Structure | Cpd. No. |
|---|---|
| 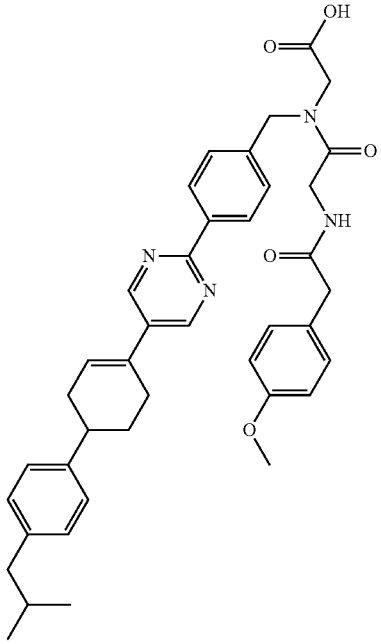 [SMILES: COc1ccc(CC(=O)NCC(=O)N(CC(=O)O)Cc2ccc(-c3ncc(C4=CCC(c5ccc(CC(C)C)cc5)CC4)cn3)cc2)cc1] | 120 |
| 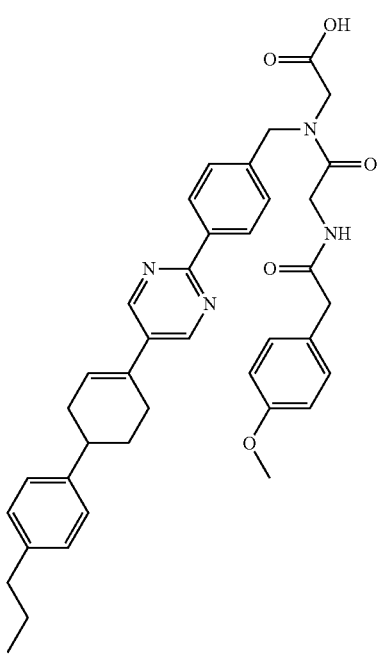 | 121 |

TABLE 1-continued
Representative Compounds
| Structure | Cpd. No. |
|---|---|
| 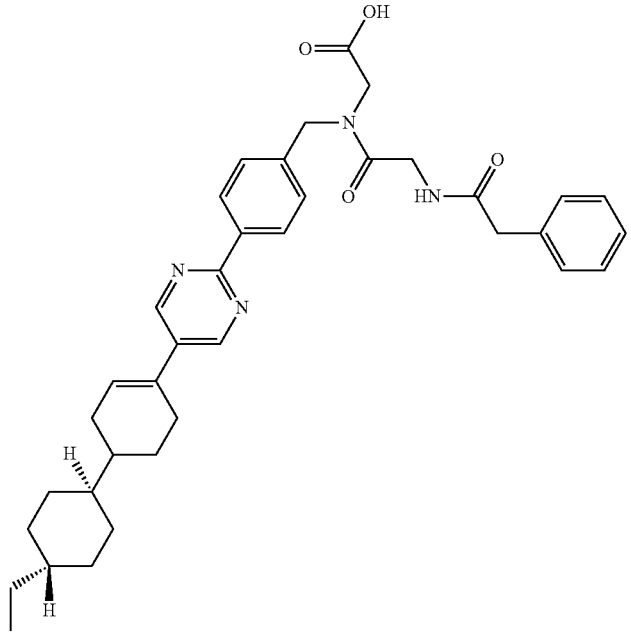 [SMILES: CC[C@H]1CC[C@H](C2CC=C(c3cnc(-c4ccc(CN(CC(=O)O)C(=O)CNC(=O)Cc5ccccc5)cc4)nc3)CC2)CC1] | 122 |
| 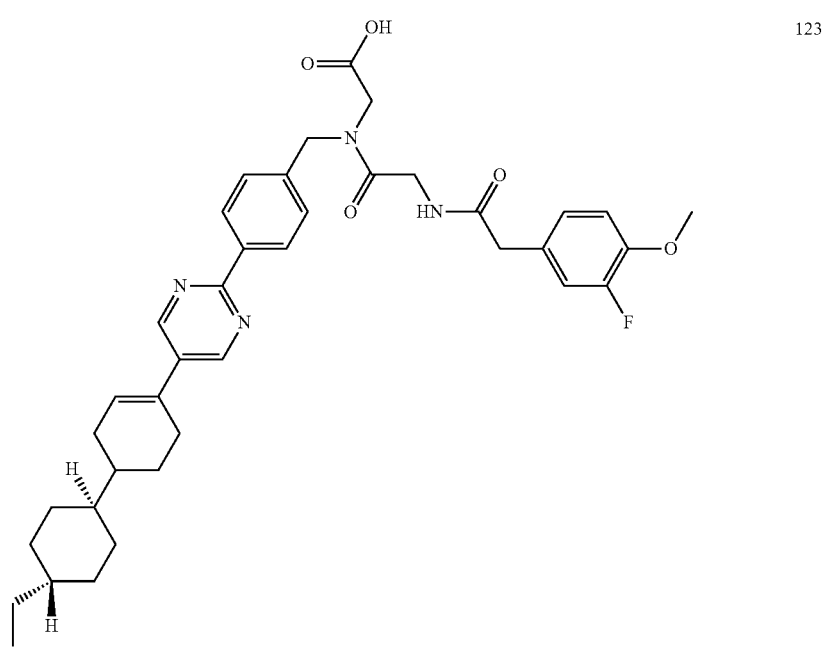 | 123 |

TABLE 1-continued
Representative Compounds
| Structure | Cpd. No. |
|---|---|
| 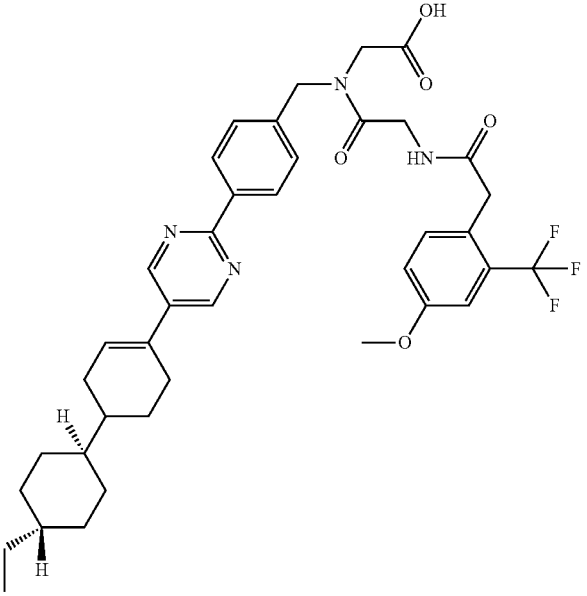 [SMILES: CC[C@H]1CC[C@H](C2CC=C(c3cnc(-c4ccc(CN(CC(=O)O)C(=O)CNC(=O)Cc5ccc(OC)cc5C(F)(F)F)cc4)nc3)CC2)CC1] | 124 |
| 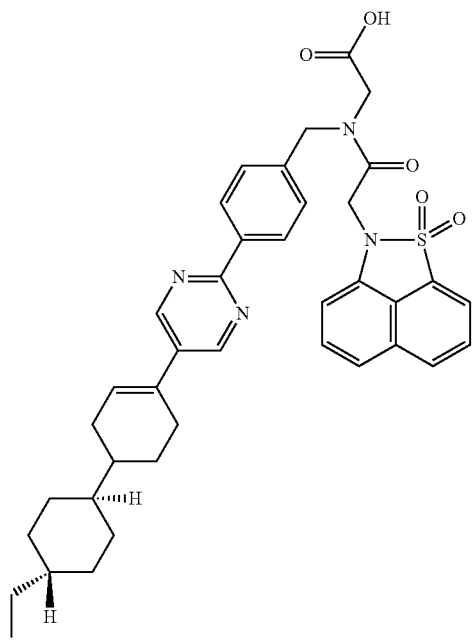 [SMILES: CC[C@H]1CC[C@H](C2CC=C(c3cnc(-c4ccc(CN(CC(=O)O)C(=O)CN5c6cccc7cccc(c67)S5(=O)=O)cc4)nc3)CC2)CC1] | 125 |

TABLE 1-continued

Representative Compounds

| Structure | Cpd. No. |
|---|---|
| 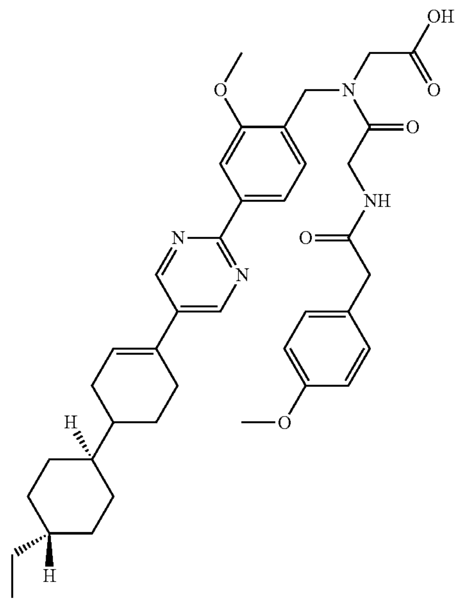 [SMILES: CC[C@H]1CC[C@H](C2CC=C(c3cnc(-c4ccc(CN(CC(=O)O)C(=O)CNC(=O)Cc5ccc(OC)cc5)c(OC)c4)nc3)CC2)CC1] | 126 |
| 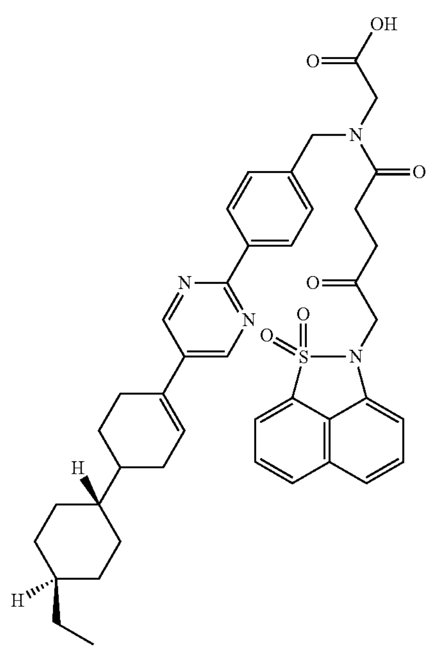 [SMILES: CC[C@H]1CC[C@H](C2CC=C(c3cnc(-c4ccc(CN(CC(=O)O)C(=O)CCC(=O)CN5c6cccc7cccc(c67)S5(=O)=O)cc4)nc3)CC2)CC1] | 127 |

TABLE 1-continued

Representative Compounds

| Structure | Cpd. No. |
|---|---|
| 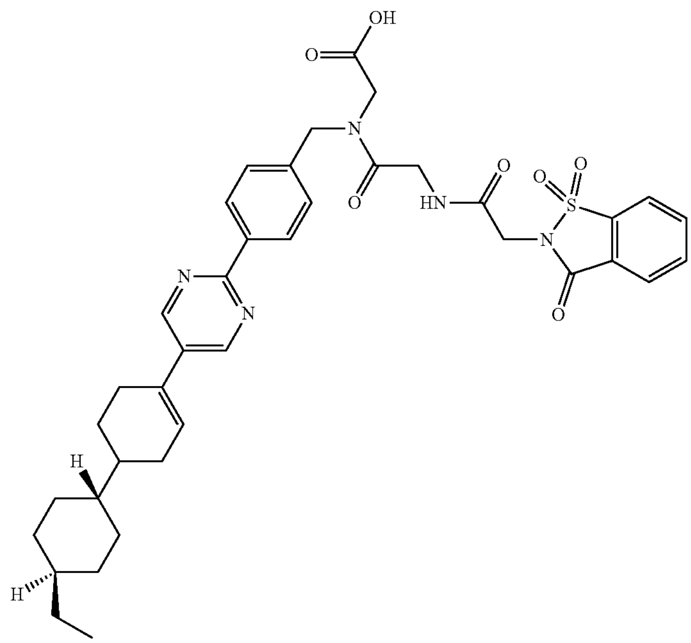 [SMILES: CC[C@H]1CC[C@H](C2CC=C(c3cnc(-c4ccc(CN(CC(=O)O)C(=O)CNC(=O)CN5C(=O)c6ccccc6S5(=O)=O)cc4)nc3)CC2)CC1] | 128 |
| 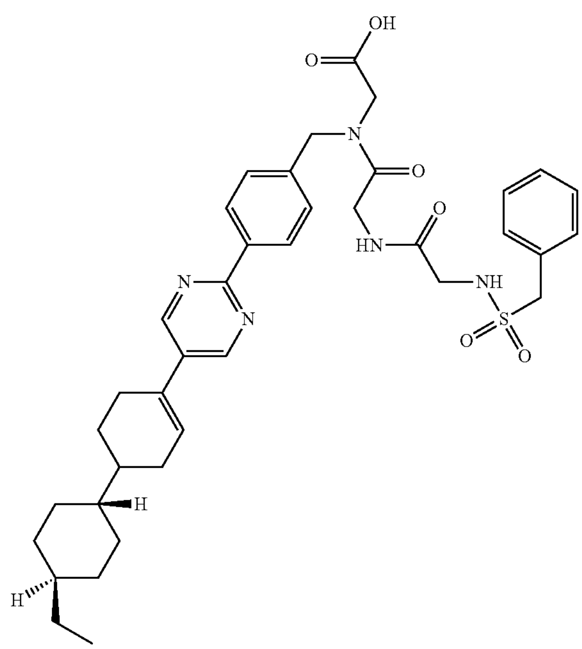 [SMILES: CC[C@H]1CC[C@H](C2CC=C(c3cnc(-c4ccc(CN(CC(=O)O)C(=O)CNC(=O)CNS(=O)(=O)Cc5ccccc5)cc4)nc3)CC2)CC1] | 129 |

TABLE 1-continued
Representative Compounds
| Structure | Cpd. No. |
|---|---|
| 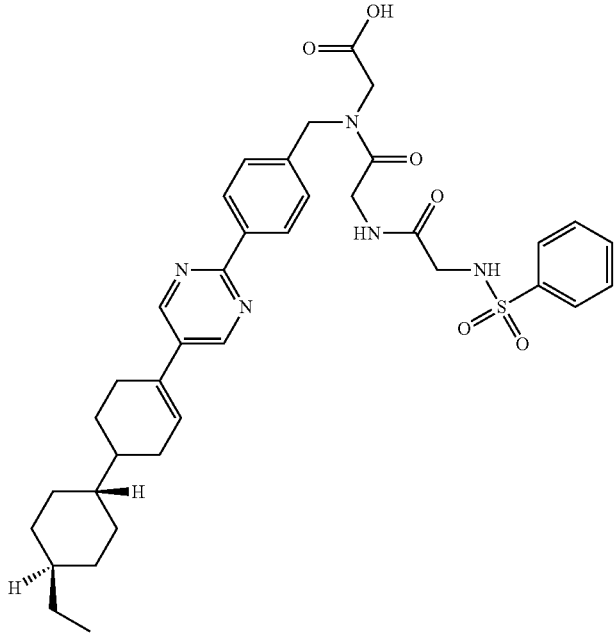 [SMILES: CC[C@H]1CC[C@H](C2CC=C(c3cnc(-c4ccc(CN(CC(=O)O)C(=O)CNC(=O)CNS(=O)(=O)c5ccccc5)cc4)nc3)CC2)CC1] | 130 |
| 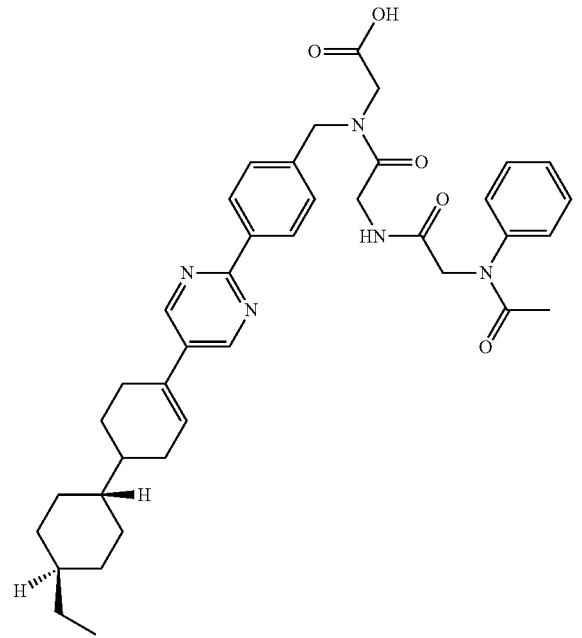 [SMILES: CC[C@H]1CC[C@H](C2CC=C(c3cnc(-c4ccc(CN(CC(=O)O)C(=O)CNC(=O)CN(C(C)=O)c5ccccc5)cc4)nc3)CC2)CC1] | 131 |

TABLE 1-continued

Representative Compounds

| Structure | Cpd. No. |
|---|---|
| 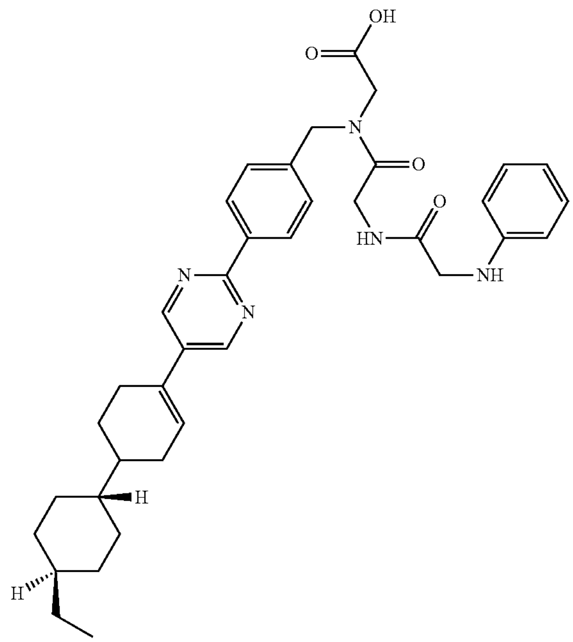 [SMILES: CC[C@H]1CC[C@H](C2CC=C(c3cnc(-c4ccc(CN(CC(=O)O)C(=O)CNC(=O)CNc5ccccc5)cc4)nc3)CC2)CC1] | 132 |
| 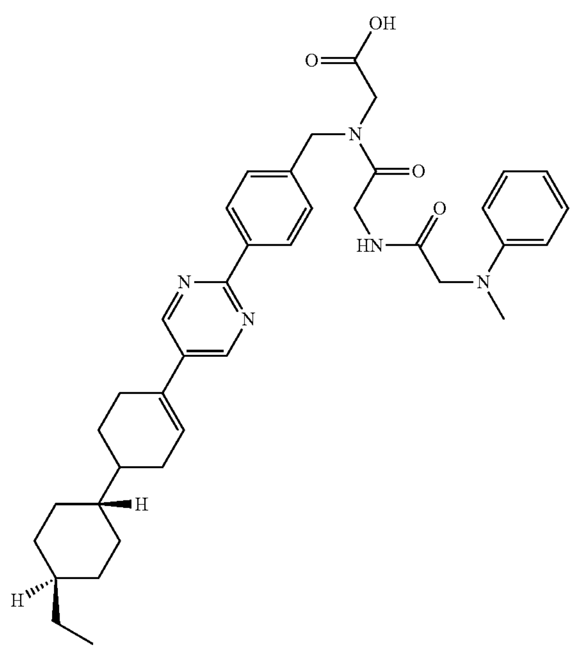 [SMILES: CC[C@H]1CC[C@H](C2CC=C(c3cnc(-c4ccc(CN(CC(=O)O)C(=O)CNC(=O)CN(C)c5ccccc5)cc4)nc3)CC2)CC1] | 133 |

//
TABLE 1-continued
Representative Compounds
| Structure | Cpd. No. |
|---|---|
| 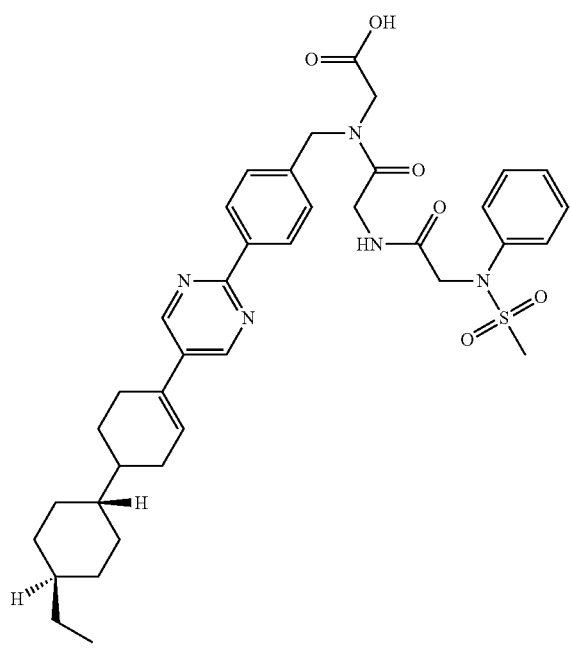 [SMILES: CC[C@H]1CC[C@H](C2CC=C(c3cnc(-c4ccc(CN(CC(=O)O)C(=O)CNC(=O)CN(c5ccccc5)S(C)(=O)=O)cc4)nc3)CC2)CC1] | 134 |
| 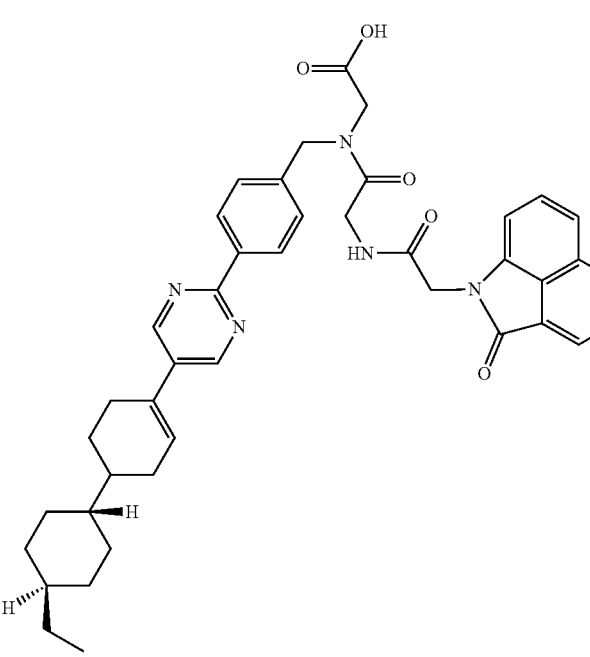 | 135 |

TABLE 1-continued
Representative Compounds
| Structure | Cpd. No. |
|---|---|
| 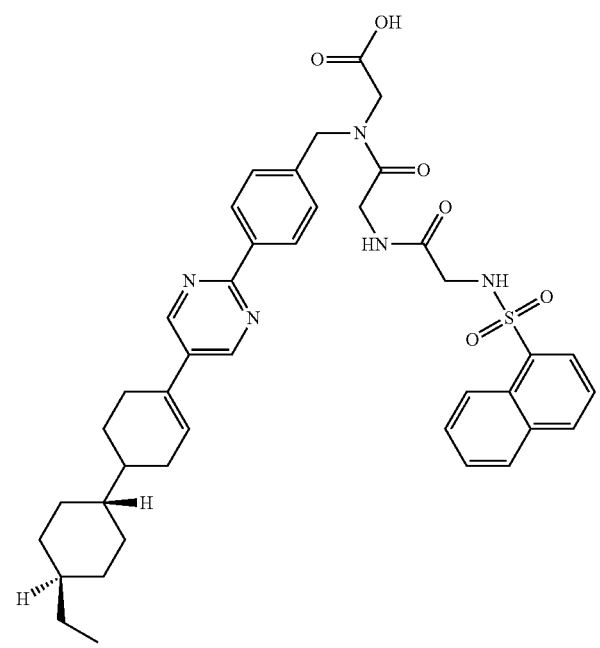 [SMILES: CC[C@H]1CC[C@H](C2CC=C(c3cnc(-c4ccc(CN(CC(=O)O)C(=O)CNC(=O)CNS(=O)(=O)c5cccc6ccccc56)cc4)nc3)CC2)CC1] | 136 |
| 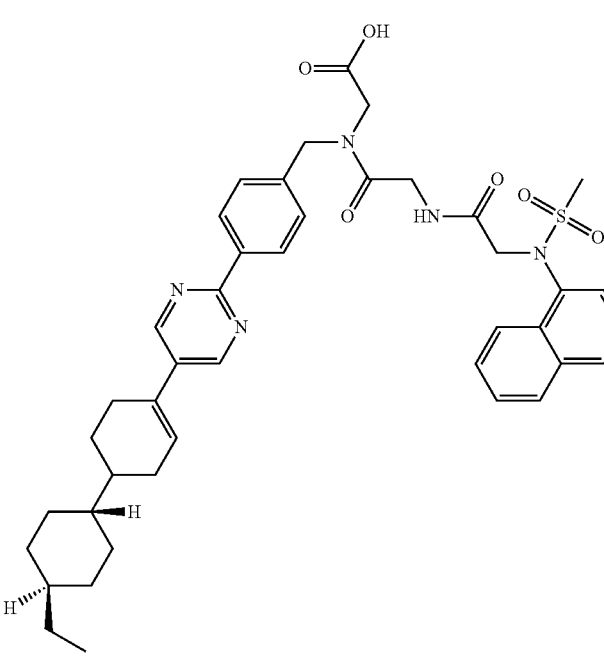 | 137 |

TABLE 1-continued
| Representative Compounds | |
|---|---|
| Structure | Cpd. No. |
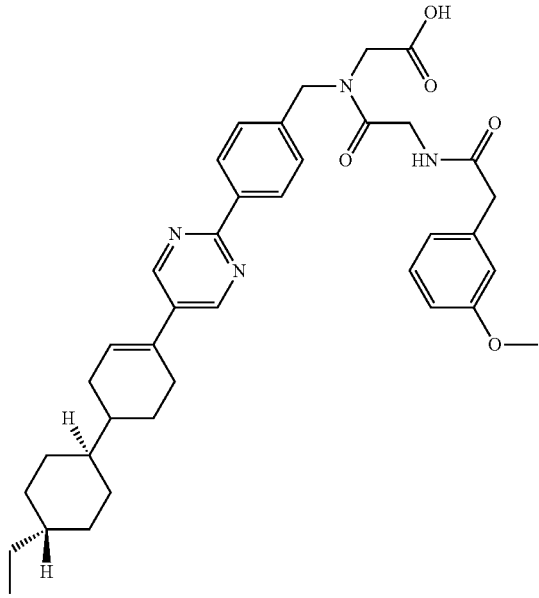 [SMILES: CC[C@H]1CC[C@H](C2CC=C(c3cnc(-c4ccc(CN(CC(=O)O)C(=O)CNC(=O)Cc5cccc(OC)c5)cc4)nc3)CC2)CC1]
138
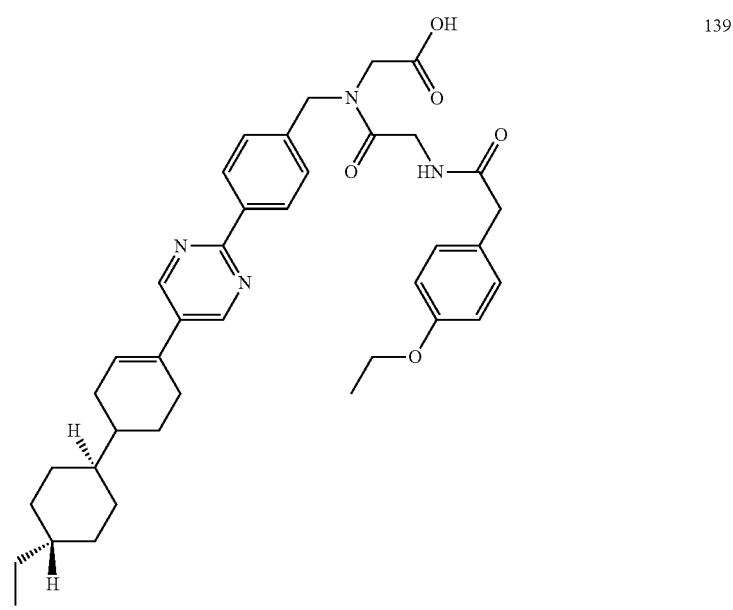
139

TABLE 1-continued
Representative Compounds
| Structure | Cpd. No. |
|---|---|
| 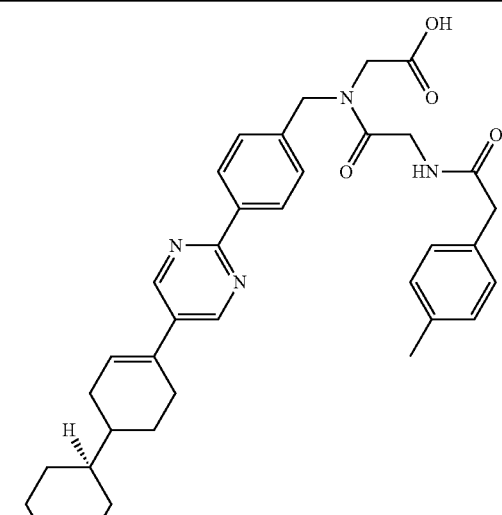 | 140 |
| 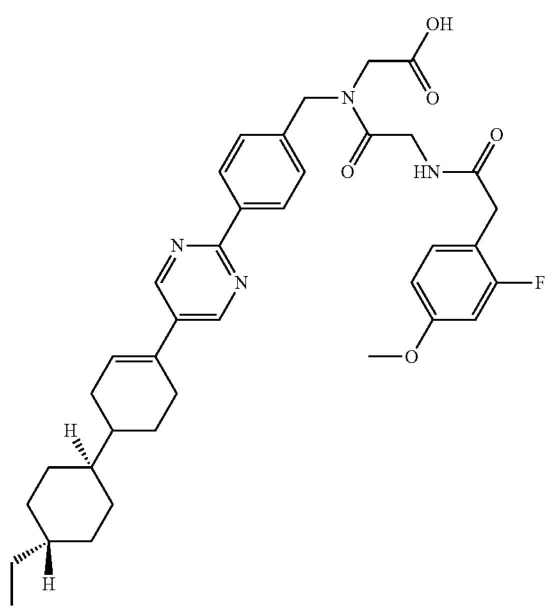 [SMILES: CC[C@H]1CC[C@H](C2CC=C(c3cnc(-c4ccc(CN(CC(=O)O)C(=O)CNC(=O)Cc5ccc(OC)cc5F)cc4)nc3)CC2)CC1] | 141 |

TABLE 1-continued
Representative Compounds
| Structure | Cpd. No. |
|---|---|
| 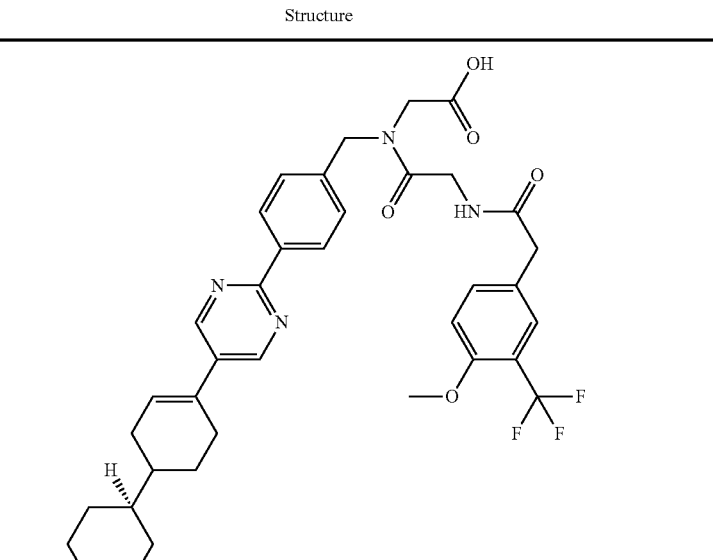 | 142 |
| 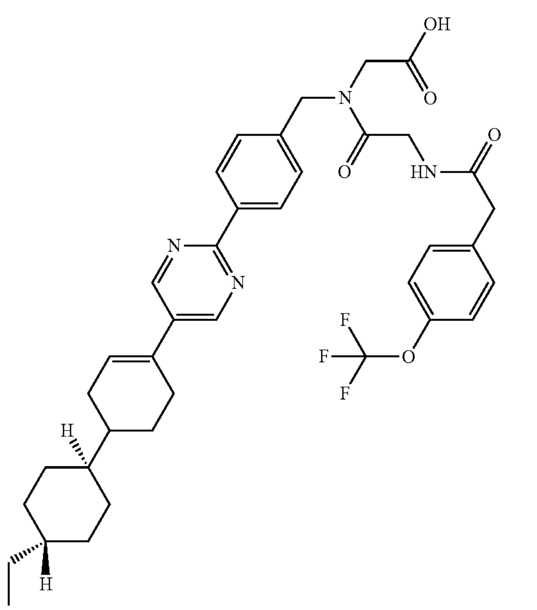 [SMILES: CC[C@H]1CC[C@H](C2CC=C(c3cnc(-c4ccc(CN(CC(=O)O)C(=O)CNC(=O)Cc5ccc(OC(F)(F)F)cc5)cc4)nc3)CC2)CC1] | 143 |

TABLE 1-continued
Representative Compounds
| Structure | Cpd. No. |
|---|---|
| 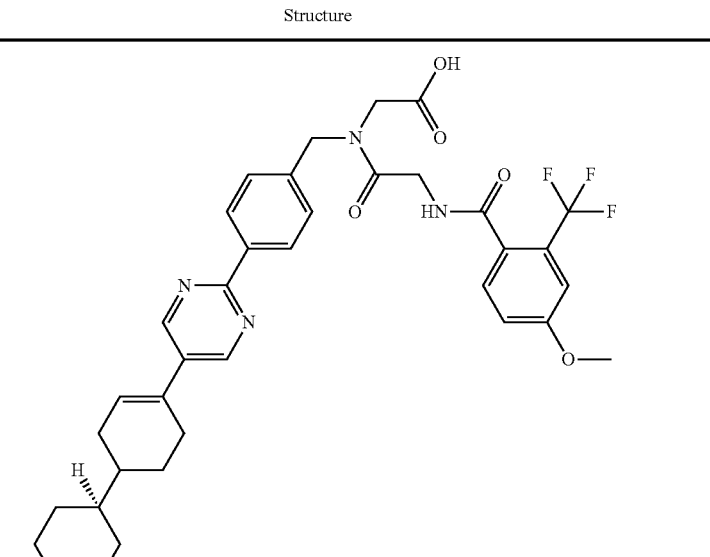 | 144 |
| 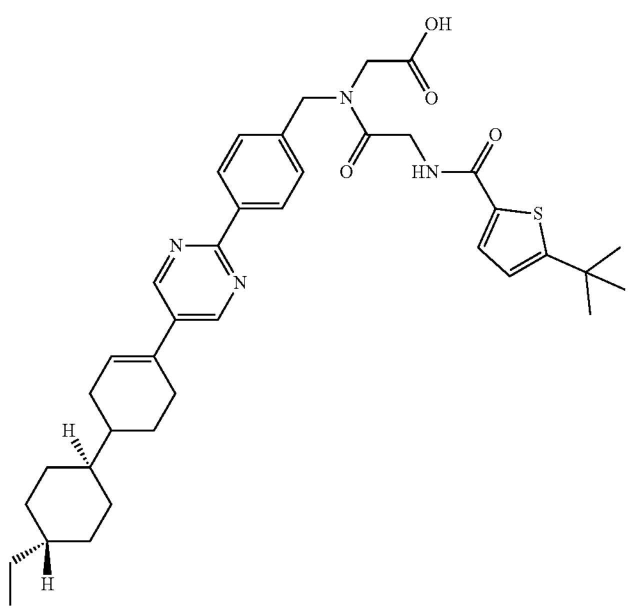 [SMILES: CC[C@H]1CC[C@H](C2CC=C(c3cnc(-c4ccc(CN(CC(=O)O)C(=O)CNC(=O)c5ccc(C(C)(C)C)s5)cc4)nc3)CC2)CC1] | 145 |

TABLE 1-continued
Representative Compounds
| Structure | Cpd. No. |
|---|---|
| 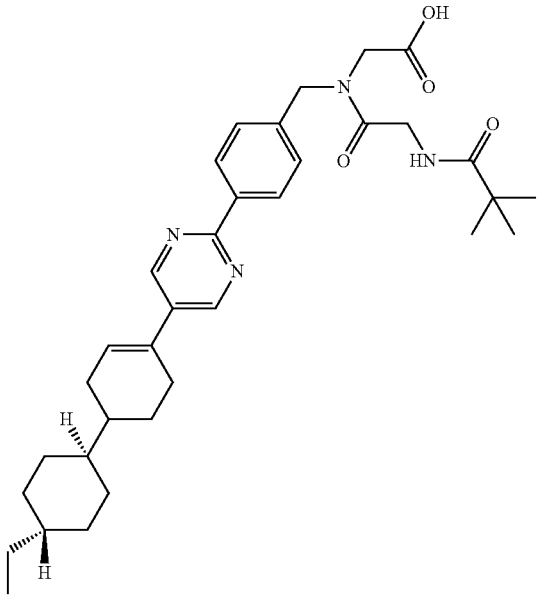 [SMILES: CC[C@H]1CC[C@H](C2CC=C(c3cnc(-c4ccc(CN(CC(=O)O)C(=O)CNC(=O)C(C)(C)C)cc4)nc3)CC2)CC1] | 146 |
| 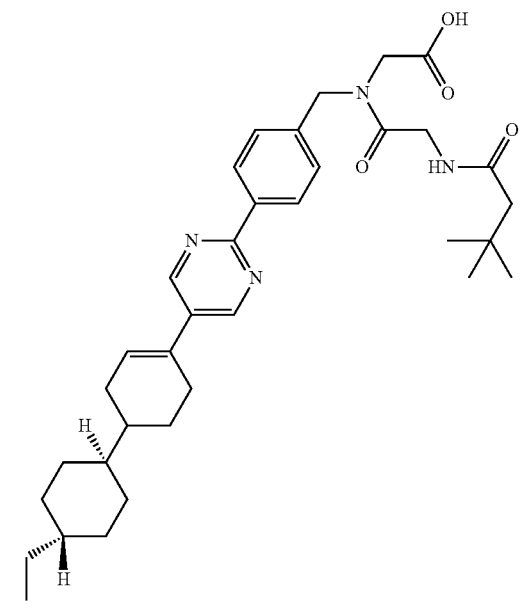 [SMILES: CC[C@H]1CC[C@H](C2CC=C(c3cnc(-c4ccc(CN(CC(=O)O)C(=O)CNC(=O)CC(C)(C)C)cc4)nc3)CC2)CC1] | 147 |

TABLE 1-continued

Representative Compounds

| Structure | Cpd. No. |
|---|---|
| 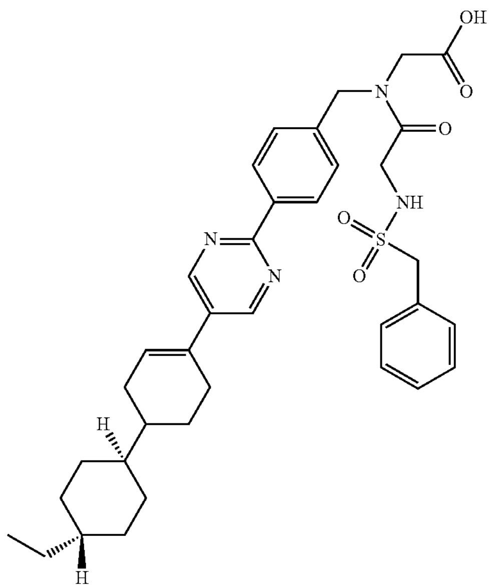 [SMILES: CC[C@H]1CC[C@H](C2CC=C(c3cnc(-c4ccc(CN(CC(=O)O)C(=O)CNS(=O)(=O)Cc5ccccc5)cc4)nc3)CC2)CC1] | 148 |
| 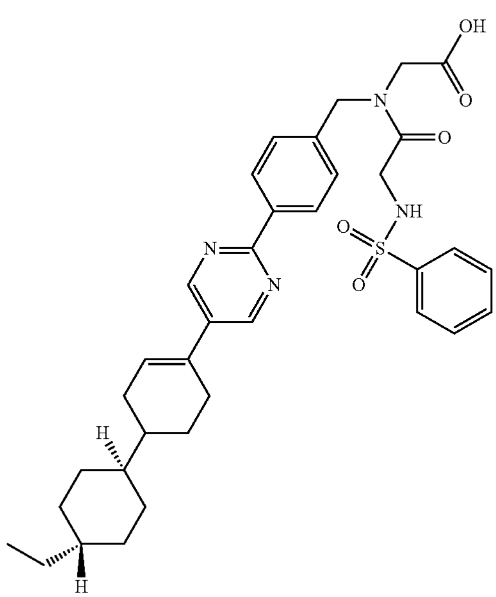 [SMILES: CC[C@H]1CC[C@H](C2CC=C(c3cnc(-c4ccc(CN(CC(=O)O)C(=O)CNS(=O)(=O)c5ccccc5)cc4)nc3)CC2)CC1] | 149 |

TABLE 1-continued

Representative Compounds

| Structure | Cpd. No. |
|---|---|
| 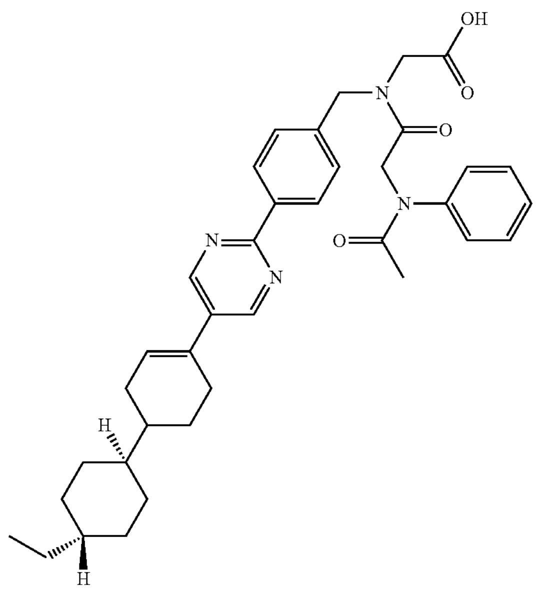 [SMILES: CC[C@H]1CC[C@H](C2CC=C(c3cnc(-c4ccc(CN(CC(=O)O)C(=O)CN(C(C)=O)c5ccccc5)cc4)nc3)CC2)CC1] | 150 |
| 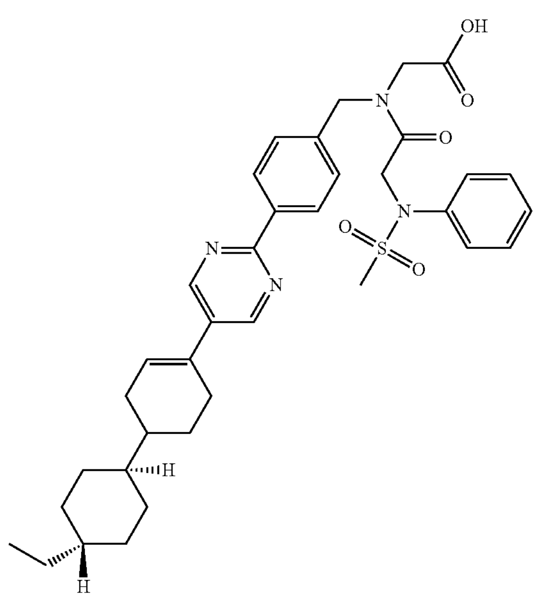 [SMILES: CC[C@H]1CC[C@H](C2CC=C(c3cnc(-c4ccc(CN(CC(=O)O)C(=O)CN(c5ccccc5)S(C)(=O)=O)cc4)nc3)CC2)CC1] | 151 |

TABLE 1-continued

Representative Compounds

| Structure | Cpd. No. |
|---|---|
| 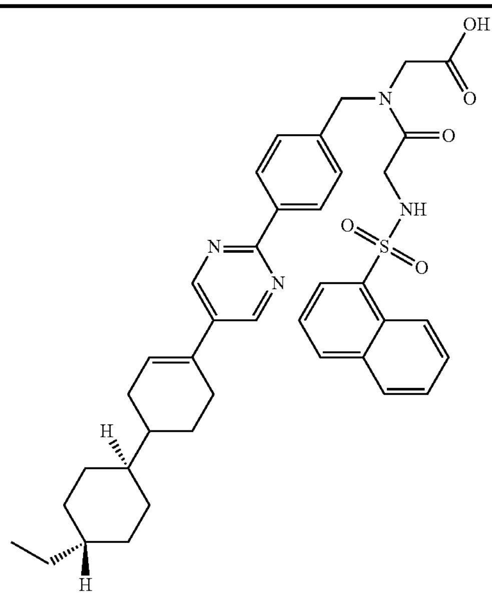 | 152 |
| 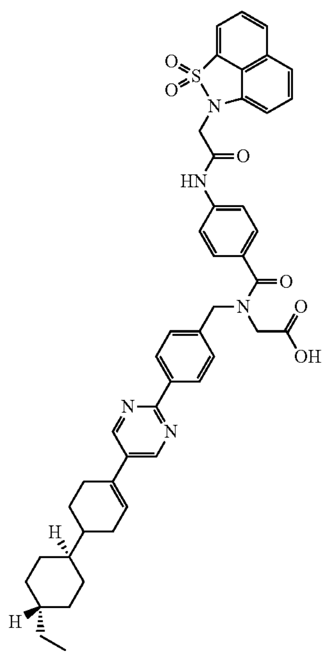 [SMILES: CC[C@H]1CC[C@H](C2CC=C(c3cnc(-c4ccc(CN(CC(=O)O)C(=O)c5ccc(NC(=O)CN6c7cccc8cccc(c78)S6(=O)=O)cc5)cc4)nc3)CC2)CC1] | 153 |

Compound Nos. 1-153 of Table 1 above include, but are not limited to, hydrates, hydrates and/or isotopes thereof, as well as pharmaceutically acceptable salts thereof.

A "salt" as is well known in the art includes an organic compound such as a carboxylic acid, a sulfonic acid, or an amine, in ionic form, in combination with a counter ion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like.

A "pharmaceutically acceptable salt" is a salt formed from a counter ion that has been approved for human consumption and is generally non-toxic.

Acid addition salts of the disclosed compounds include, for example, salts prepared by adding and inorganic acid or an organic acid. Examples of inorganic acids include, but are not limited to, hydrochloric, hydrobromic, hydriodic, nitric, carbonic, sulfuric, and phosphoric acids. Appropriate organic acids include, but are not limited to, aliphatic, cycloaliphatic, aromatic, araliphatic, heterocyclic, carboxylic and sulfonic classes of organic acids, representative examples of which include formic acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Base addition salts of the disclosed compounds include, but are not limited to, salts prepared by adding alkali metal, alkaline earth metal and transition metal salts such as, for example, calcium, magnesium, potassium, sodium and zinc salts. Representative base addition salts also include salts made from organic bases such as, for example, N,N'-dibenzylethylenediamine, chloroprocaine, choline, diethanolamine, ethylenediamine, meglumine (N-methylglucamine) and procaine.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form (i.e., a compound in water solution, while it may be hydrated, is not a hydrate as the term is used herein).

A "solvate" is a similar composition except that a solvent other than water replaces the water. For example, methanol or ethanol can form an "alcoholate", which can again be stoichiometric or non-stoichiometric. As the term is used herein a "solvate" refers to a solid form (i.e., a compound in solution in a solvent, while it may be solvated, is not a solvate as the term is used herein).

The term "isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon 13 and/or 14 atoms, wherein one or more hydrogen atoms are replaced with deuterium and/or tritium, and/or wherein one or more fluorine atoms are replaced by fluorine 19.

"Stereoisomers" include all chiral, enantiomeric, diastereomeric and/or racemic forms of a compound, unless a particular stereochemistry or isomeric form is specifically indicated. Compounds of the present invention include enriched or resolved optical isomers at any or all asymmetric atoms as are apparent from the depictions, at any degree of enrichment, including, for example, enrichment to a weight purity of 98%, 99%, 99.5% or 99.9%. Both racemic, enantiomeric and diastereomeric mixtures, as well as the individual optical isomers, can be synthesized so as to be substantially free of their enantiomeric or diastereomeric partners, and these are all within the scope of certain embodiments of the invention.

Enantiomers are sometimes called optical isomers because a pure enantiomer rotates plane-polarized light in a particular direction. If the light rotates clockwise, then that enantiomer is labeled "(+)" or "d" for dextrorotatory, its counterpart will rotate the light counterclockwise and is labeled "(-)" or "l" for levorotatory. Stereoisomers that differ at some stereocenters but not at others are not mirror images, so they are not enantiomers. Instead, they are referred to as diastereomers. A diastereomer is any stereoisomer that is not an enantiomer.

The terms "racemate" and "racemic mixture" are frequently used interchangeably. A racemate is an equal mixture of two enantiomers. A racemate is labeled "(±)" because it is not optically active (i.e., will not rotate plane-polarized light in either direction since its constituent enantiomers cancel each other out).

In certain representative embodiments, the "A" group of Formula (I) has the following structure, wherein the asterisk (*) denotes chiral carbon.

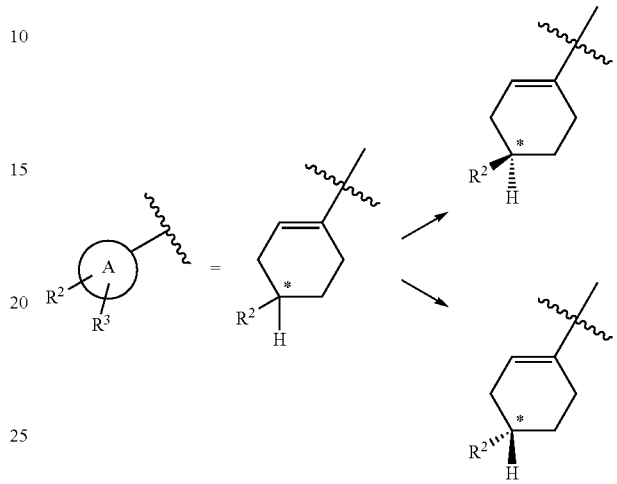

While the above disclosure depicts stereo confirmation at a single chiral center, it should be understood that the presence of multiple chiral centers allows for multiple combinations of stereoisomers (e.g, two chiral centers will give four possible orientations, and so forth). It is intended that compounds having the structure of any one of Formulas (I)-(XII) above include all stereoisomers arising from the presence of one or more chiral centers, including any and all enantiomeric and/or diastereomeric forms, at any degree of purity, as well as racemic mixtures of the same.

In a further representative embodiment, $R^2$ is cyclohexyl substituted with $R^3$, as illustrated below. In this embodiment, the noted hydrogen atoms can exist in a cis- or trans-configuration:

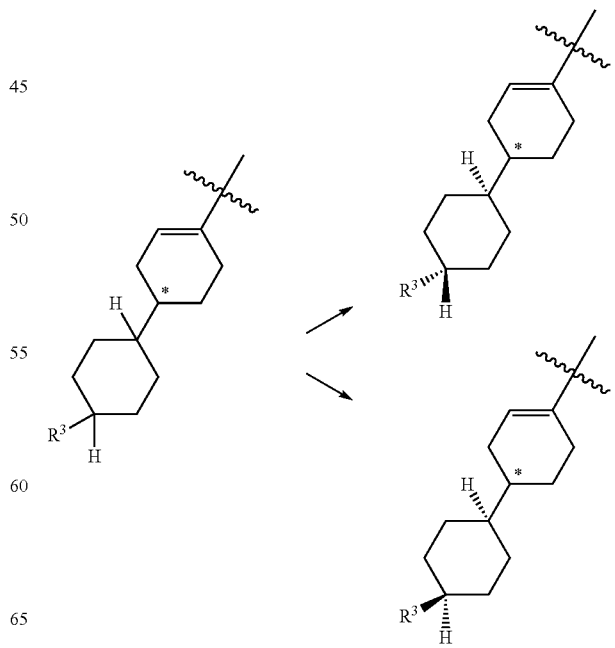

Accordingly, it is intended that compounds having the structure of any one of Formulas (I)-(XII) above also include stereoisomers involving geometric isomersism, such as the cis- and/or trans-isomers illustrated above.

It should also be understood that a prodrug is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. In one embodiment of the present invention, substances are provided that can be administered to a patient where the substance is converted in vivo by the action of biochemical reactions within the patient's body, such as enzymes, to a compound having the structure of any one of Formulas (I)-(XII), or a compound of Table 1.

In one embodiment, a pharmaceutical composition is provided comprising a compound of Formula (I)-(XII), a compound of Table 1, or a pharmaceutically acceptable salt thereof, in combination with at least one pharmaceutically acceptable carrier, diluent or excipient.

As use herein, a compound that "modulates" a GLP-1 receptor means that the compound interacts with the receptor, either directly or by way of an allosteric interaction, thereby activating, potentiating and/or agonizing the GLP-1 receptor for which it modulates.

In one embodiment, the present invention encompasses compounds that modulate GLP-1 receptor, with high affinity and specificity, an agonist manner or as an activator or a potentiator. In another embodiment, a compound of the invention acts as a positive allosteric modulator of GLP-1 receptor.

In one embodiment, the present invention provides a method for agonizing a GLP-1 receptor with a compound of the invention (i.e., an agonist). The method involves contacting the receptor with a suitable concentration of an inventive compound to bring about activation of the receptor. The contacting can take place in vitro, for example in carrying out an assay to determine the GLP-1 receptor activation activity of an inventive compound undergoing experimentation related to a submission for regulatory approval.

In one embodiment, the method for modulating a GLP-1 receptor, can also be carried out in vivo, that is, within the living body of a mammal, such as a human patient or a test animal. The inventive compound can be supplied to the living organism via one of the routes as described above (e.g., orally), or can be provided locally within the body tissues. In the presence of the inventive compound, activation of the receptor takes place and the effect thereof can be studied.

In one embodiment, a method is provided for modulation of a GLP-1 receptor by contacting the receptor with an effective amount of a compound of this invention, or a pharmaceutical composition comprising the same, wherein the GLP-1 receptor is disposed within a living mammal.

In one embodiment, a method is provided for treatment of a malcondition in a subject for which modulation of a GLP-1 receptor is medically indicated, by administering an effective amount of a compound of this invention to the subject at a frequency and for duration of time sufficient to provide a beneficial effect to the subject (e.g., patient).

"Treating" or "treatment" refers to an alleviation of symptoms associated with a disorder or disease, or inhibition of further progression or worsening of those symptoms, or prevention or prophylaxis of the disease or disorder.

"Effective amount" refers to an amount sufficient to produce a beneficial therapeutic effect on the patient. For example, "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as a modulator of GLP-1 activity. A therapeutically effective amount is also one in which any toxic or detrimental effects of compounds of the invention are outweighed by the therapeutically beneficial effects. For example, in the context of treating a malcondition mediated by activation of a GLP-1 receptor, a therapeutically effective amount of a GLP-1 receptor agonist is an amount sufficient to control the malcondition, to mitigate the progress of the malcondition, or to relieve the symptoms of the malcondition. The dosages and formulations for the other agents to be employed, where applicable, will be as set out in the latest edition of the *Physicians' Desk Reference*, incorporated herein by reference.

In one embodiment, a method is provided for treatment of a malcondition in a subject for which modulation of a GLP-1 receptor is medically indicated, by administering an effective amount of a compound of this invention to the subject at a frequency and for a duration of time sufficient to provide a beneficial effect to the subject, wherein the malcondition comprises type I diabetes, type II diabetes, gestational diabetes, obesity, excessive appetite, insufficient satiety, or metabolic disorder. In one embodiment, the subject is a patient or a human being. In certain embodiments, the human being is afflicted with, or at risk of developing, a disease or condition selected from the group consisting of type I diabetes, type II diabetes, gestational diabetes, obesity, excessive appetite, insufficient satiety, and metabolic disorder. In one embodiment, said disease is type I diabetes or type II diabetes.

In another embodiment, methods of treatment provided by the invention include administration of a compound of the invention to a subject (e.g., patient) for the treatment of non-alcoholic fatty liver disease (NAFLD) and/or non-alcoholic steatohepatitis (NASH). NAFLD is believed to be caused by the disruption of hepatic lipid homeostasis and, at least in a portion of patients, can progress to NASH. NAFLD is associated with insulin resistance in type 2 diabetes mellitus, and GLP1 increases insulin sensitivity and aids glucose metabolism. The compounds of this invention are beneficial in this context by serving to increase fatty acid oxidation, decrease lipogenesis, and/or improve hepatic glucose metabolism (see e.g., Lee et. al., Diabetes Metab. J. 36:262-267, 2012; Trevaskis et al. Am. J. Physiol. Gastrointest. Liver Physiol. 302:G762-G772, 2012; Kim et al. Korean J. Physiol. Pharmacol. 18:333-339, 2014; and see: Armstrong et. al, Journal of Hepatology 62:S187-S212, 2015 for results with Liraglutide in Phase II trials).

In one embodiment, methods are provided for use of a compound of this invention for preparation of a medicament adapted for treatment of a disorder or a malcondition wherein modulation of a GLP-1 receptor is medically indicated.

In one embodiment, the invention provides methods for synthesis of certain compounds including compounds of the invention as more fully illustrated herein. In certain other embodiments, the invention provides certain intermediate compounds associated with such methods of synthesis as illustrated herein.

Compounds of the invention can be synthesized using standard synthetic techniques known to those of skill in the art, including the general synthetic procedures set forth in the Schemes 1-20 below.

Scheme 1

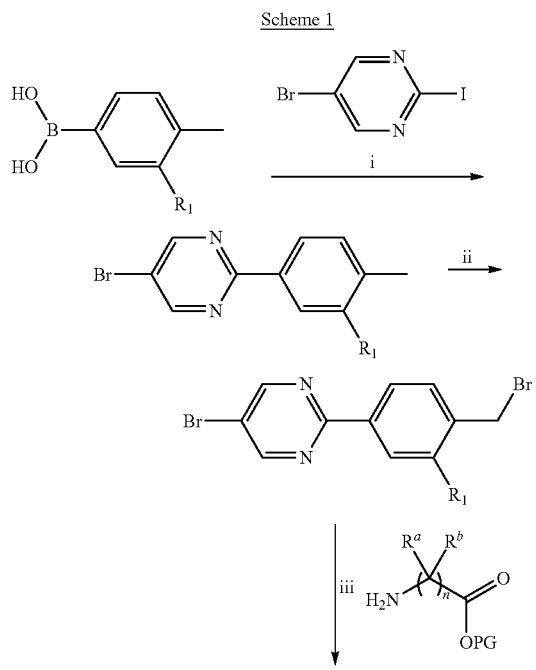

Scheme 2

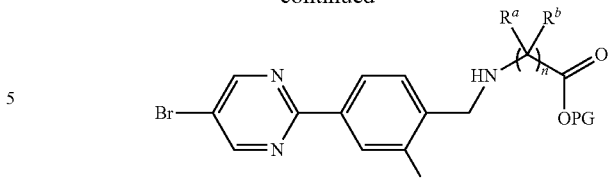

Reagents: PG is a protecting group (i) Pd(dppf)Cl$_2$, Na$_2$CO$_3$ or NaHCO$_3$, dioxane, water; (ii) NBS, AIBN, CHCl$_3$; (iii) DIEA, THF.

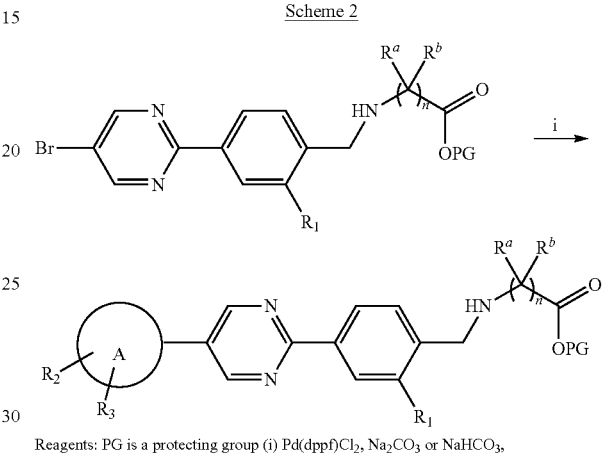

Reagents: PG is a protecting group (i) Pd(dppf)Cl$_2$, Na$_2$CO$_3$ or NaHCO$_3$, dioxane, water.

Scheme 3

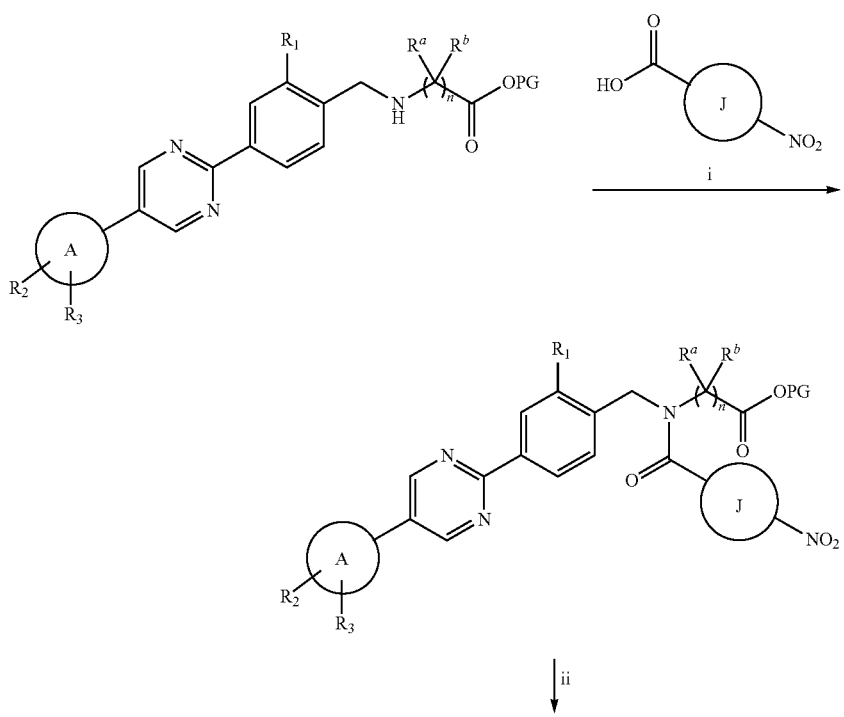

-continued

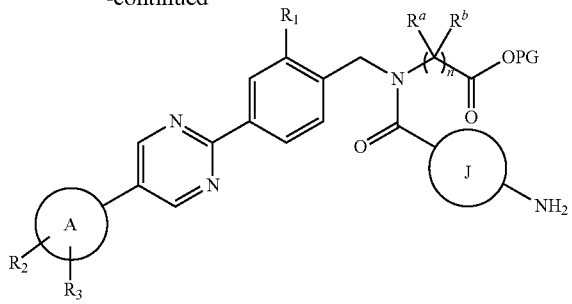

Reagents: PG is a protecting group (i) HATU, DIEA, DMF; (ii) NH₄Cl, iron, THF, EtOH, water.

Scheme 4

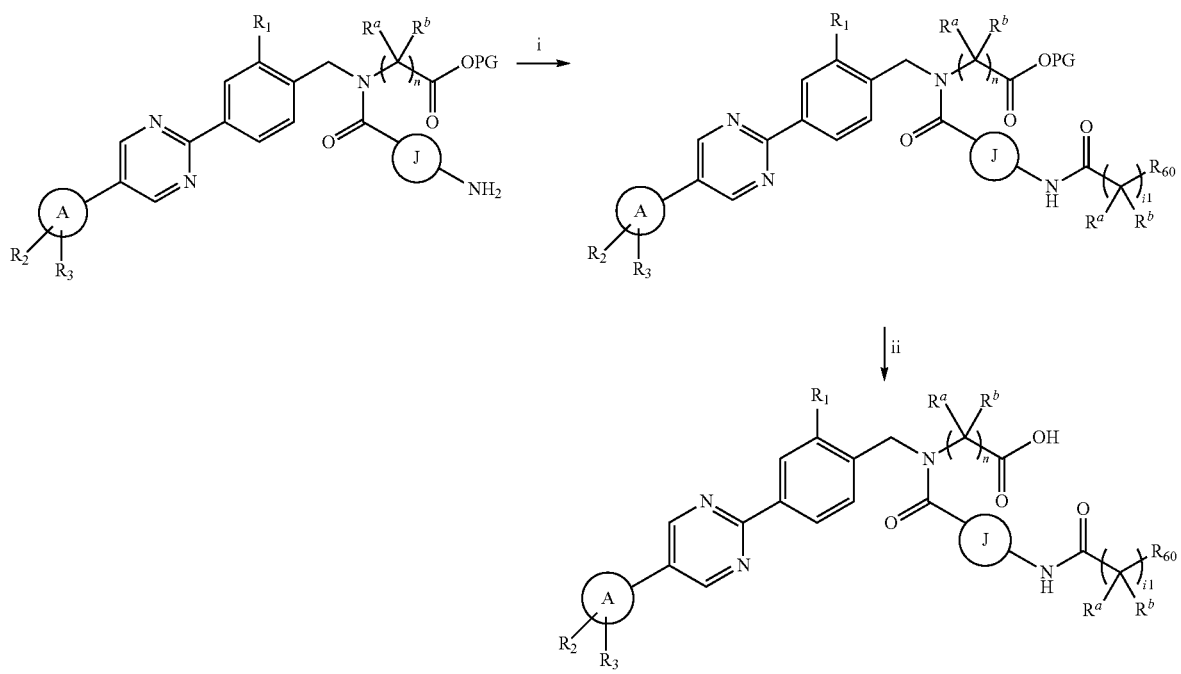

Reagents: PG is a protecting group (i) Coupling with acid: HATU, DIEA, DMF or coupling with acid chloride: DIEA, DCM; (ii) Deprotection of PG: e.g. deprotection of tert-butyl ester: TFA, DCM.

Scheme 5

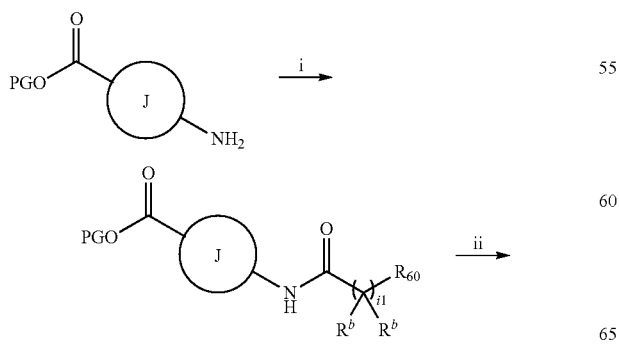

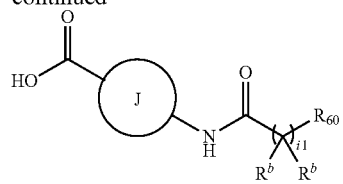

Reagents: PG is a protecting group (i) Coupling with acid: HATU, DIEA, DMF or coupling with acid chloride: DIEA, DCM; (ii) Deprotection of PG: e.g. deprotection of tert-butyl ester: TFA, DCM.

Scheme 6

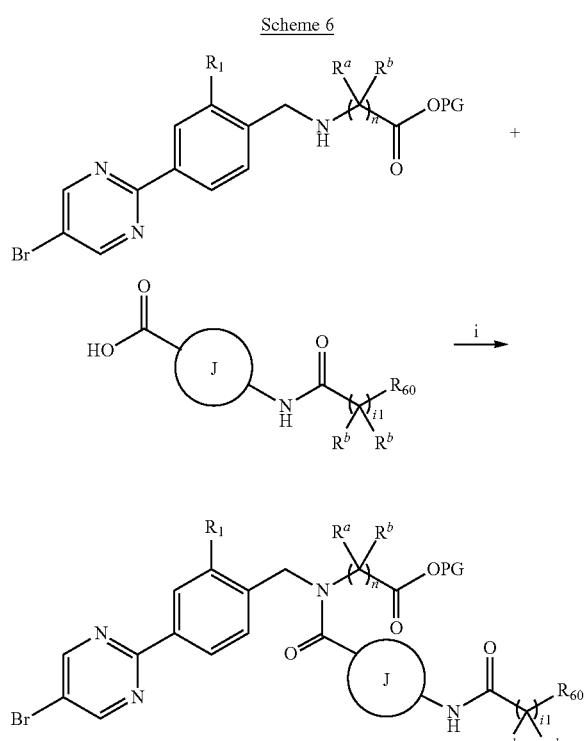

Reagents: PG is a protecting group (i) Coupling with acid: HATU, DIEA, DMF or coupling with acid chloride: DIEA, DCM.

Scheme 7

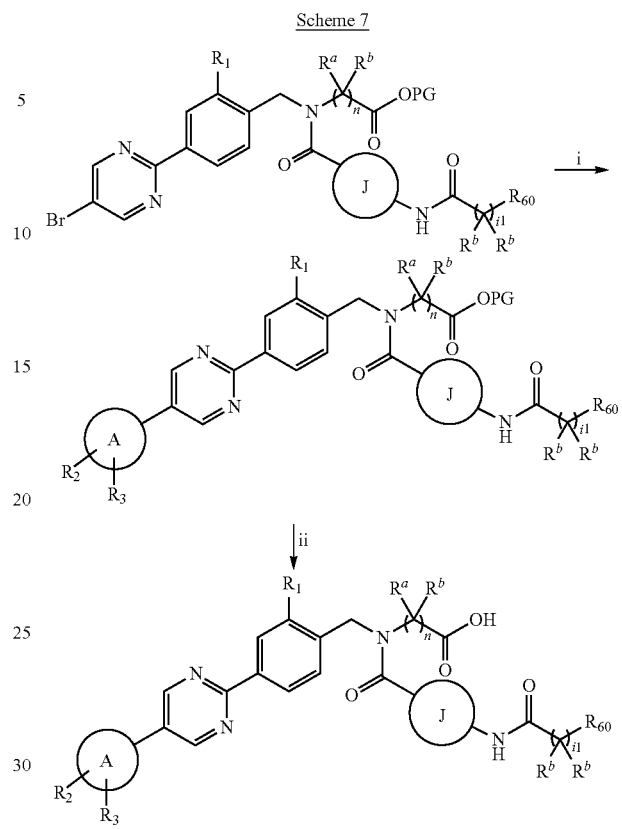

Reagents: PG is a protecting group (i) Pd(dppf)Cl$_2$, Na$_2$CO$_3$ or NaHCO$_3$, dioxane, water, (ii) Deprotection of PG: e.g. deprotection of tert-butyl ester: TFA, DCM.

Scheme 8

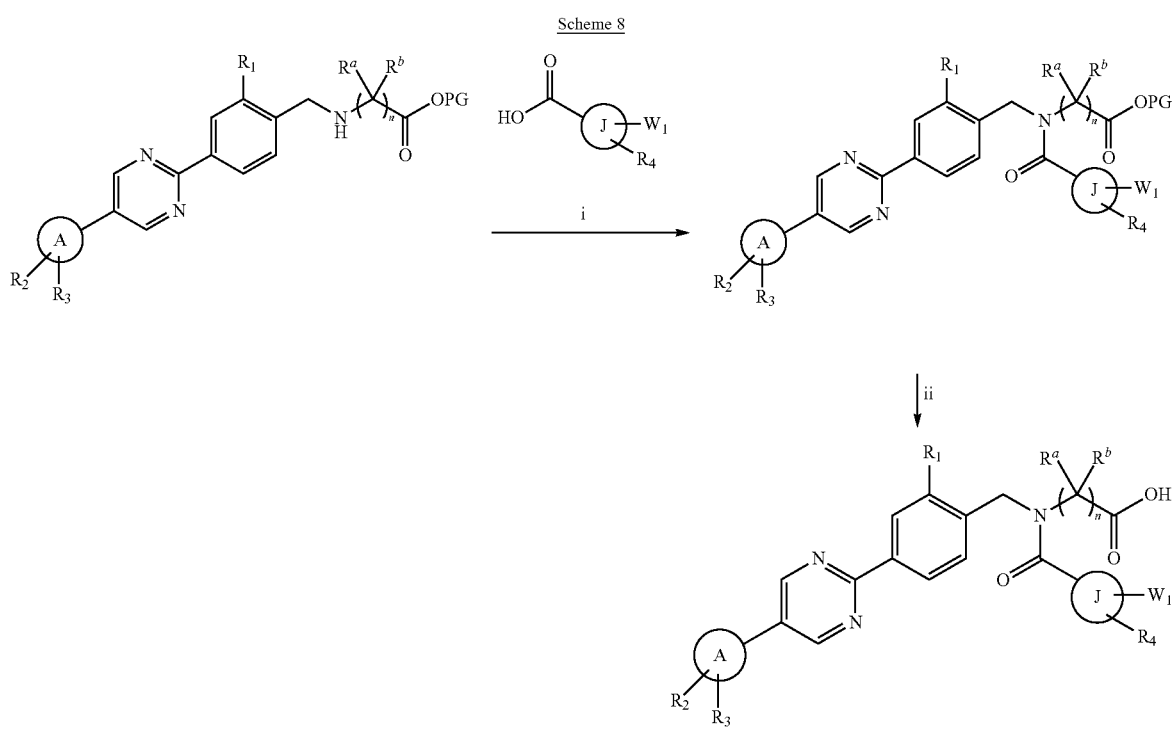

Reagents: PG is a protecting group (i) HATU, DIEA, DMF; (ii) Deprotection of PG: e.g. deprotection of tert-butyl ester: TFA, DCM.

Scheme 9
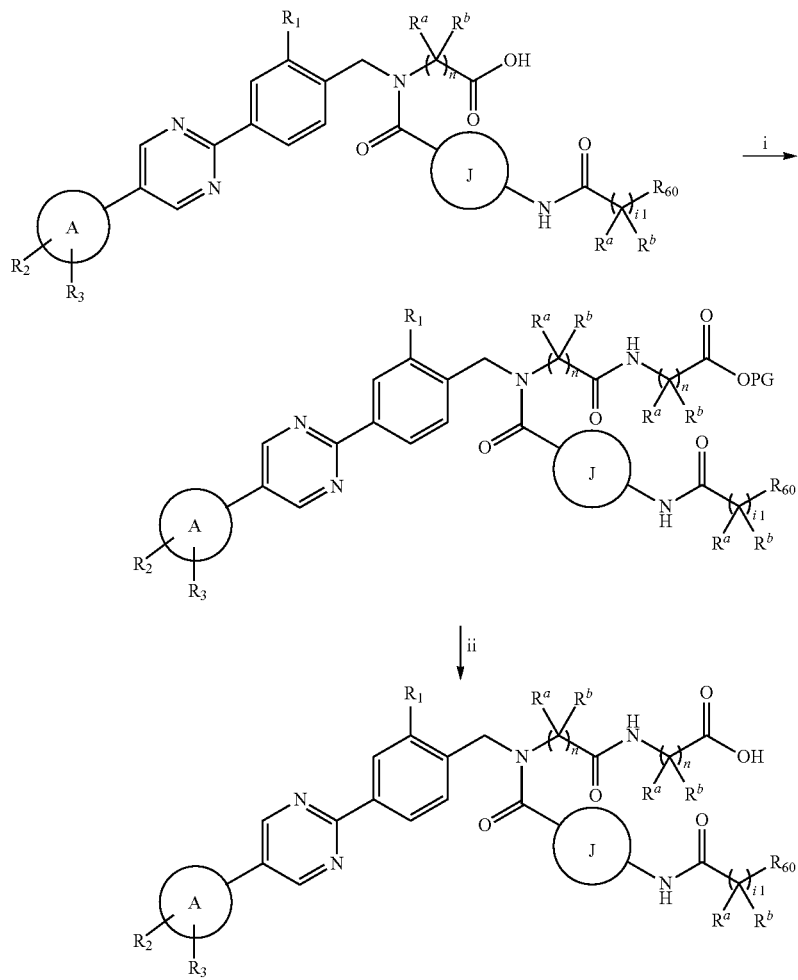
Reagents: PG is a protecting group (i) HATU, DIEA, DMF; (ii) Deprotection of PG: e.g. deprotection of tert-butyl ester: TFA, DCM.
Scheme 10
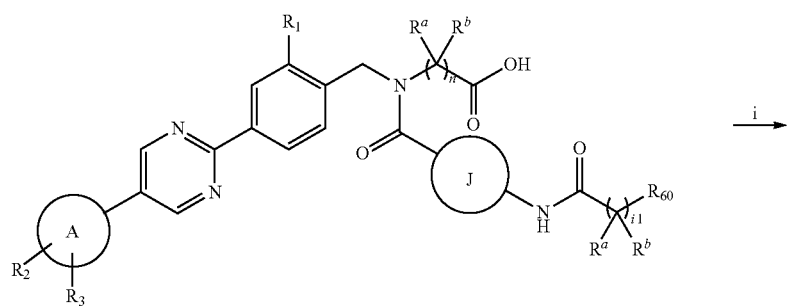

-continued
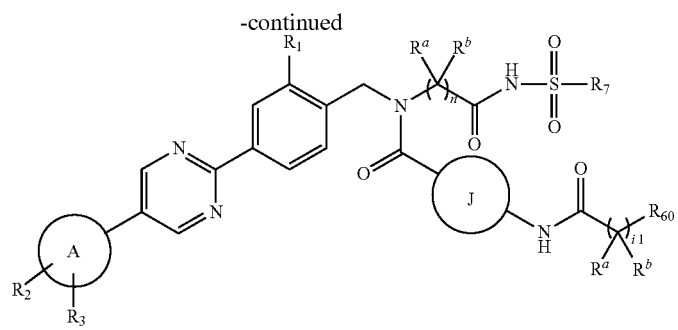
Reagents: (i) 1,1'-carbonyldiimidazole, methanesulfonamide, 1,8-diazabicyclo[5.4.0]undec-7ene, THF.
Scheme 11
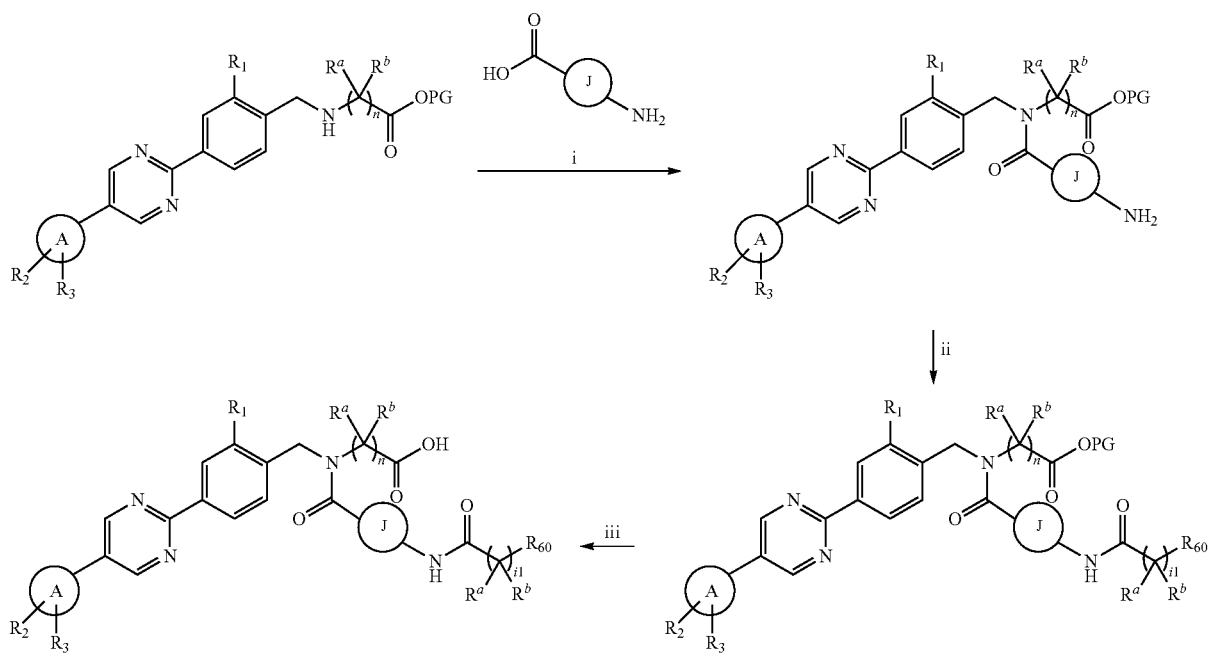
Reagents: PG is a protecting group (i) HATU, DIEA, DMF; (ii) NaH, THF; (iii) Deprotection of PG: e.g deprotection of tert-butyl ester: TFA, DCM.
Scheme 12
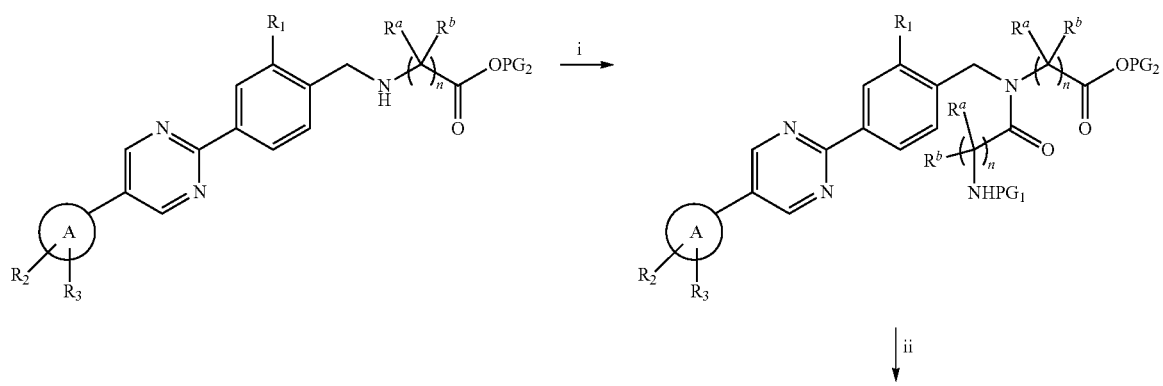

-continued
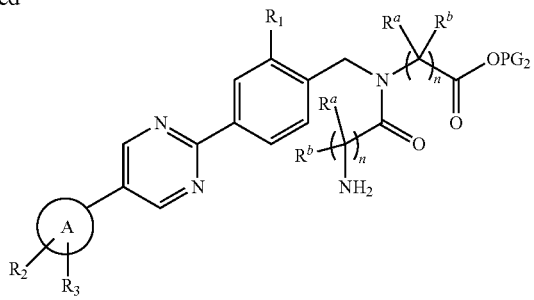
Reagents: PG₁ and PG₂ are protecting groups (i) HATU, DIEA, DMF; (ii) Deprotection of PG1: e.g deprotection of Boc-amine: 5-6N HCl in IPA, DCM.
Scheme 13
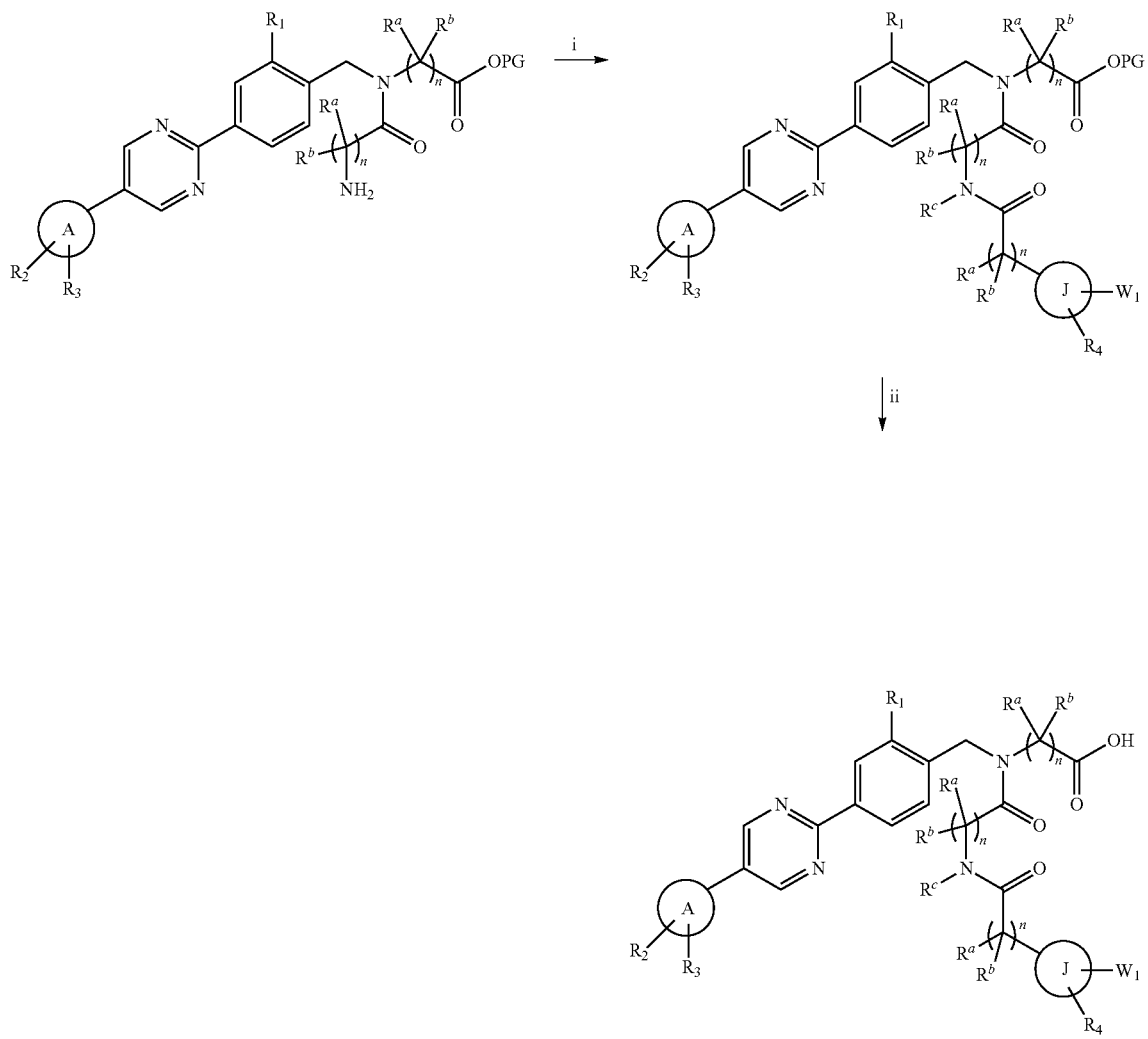
Reagents: PG is a protecting group (i) HATU, DIEA, DMF; (ii) Deprotection of PG: e.g deprotection of tert-butyl ester: TFA, DCM.

Scheme 14
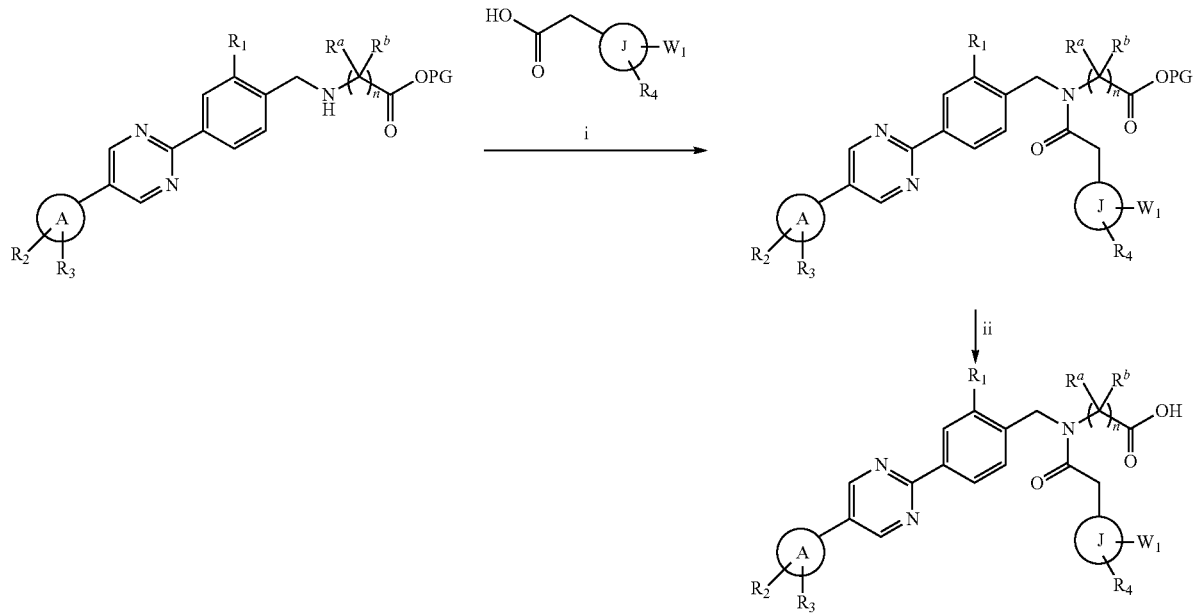
Reagents: PG is a protecting group (i) HATU, DIEA, DMF; (ii) Deprotection of PG:
e.g deprotection of tert-butyl ester: TFA, DCM.
Scheme 15
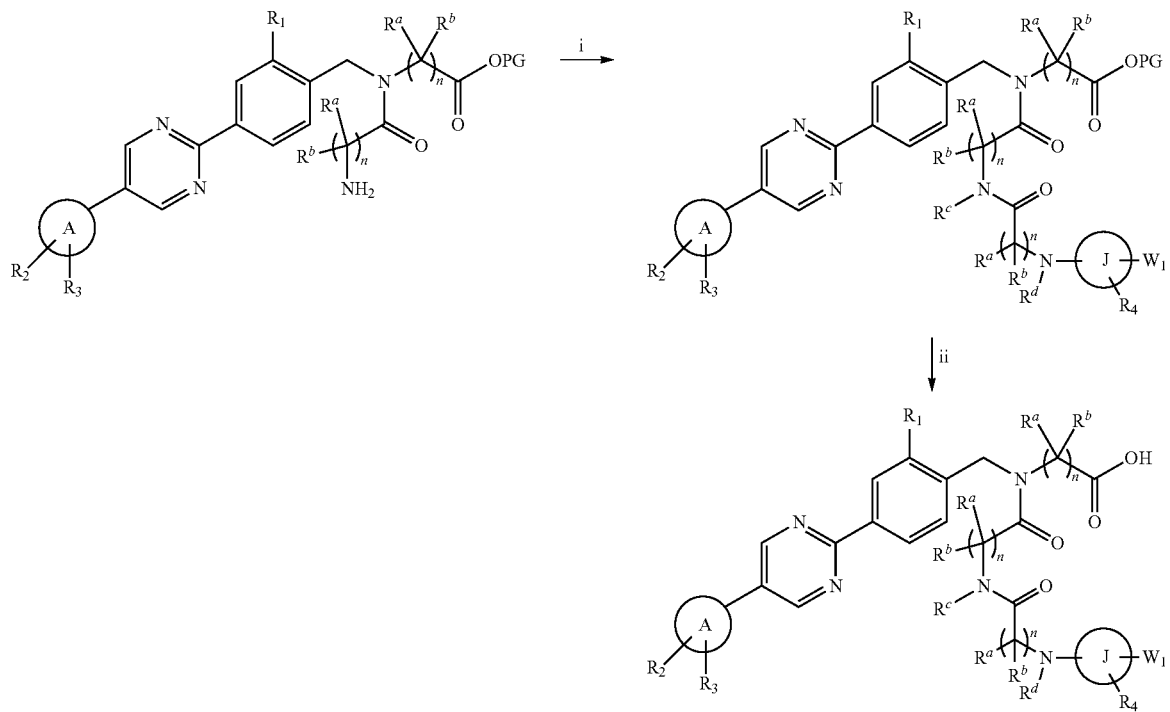
Reagents: PG is a protecting group (i) HATU, DIEA, DMF; (ii) Deprotection of PG:
e.g deprotection of tert-butyl ester: TFA, DCM.

Scheme 16
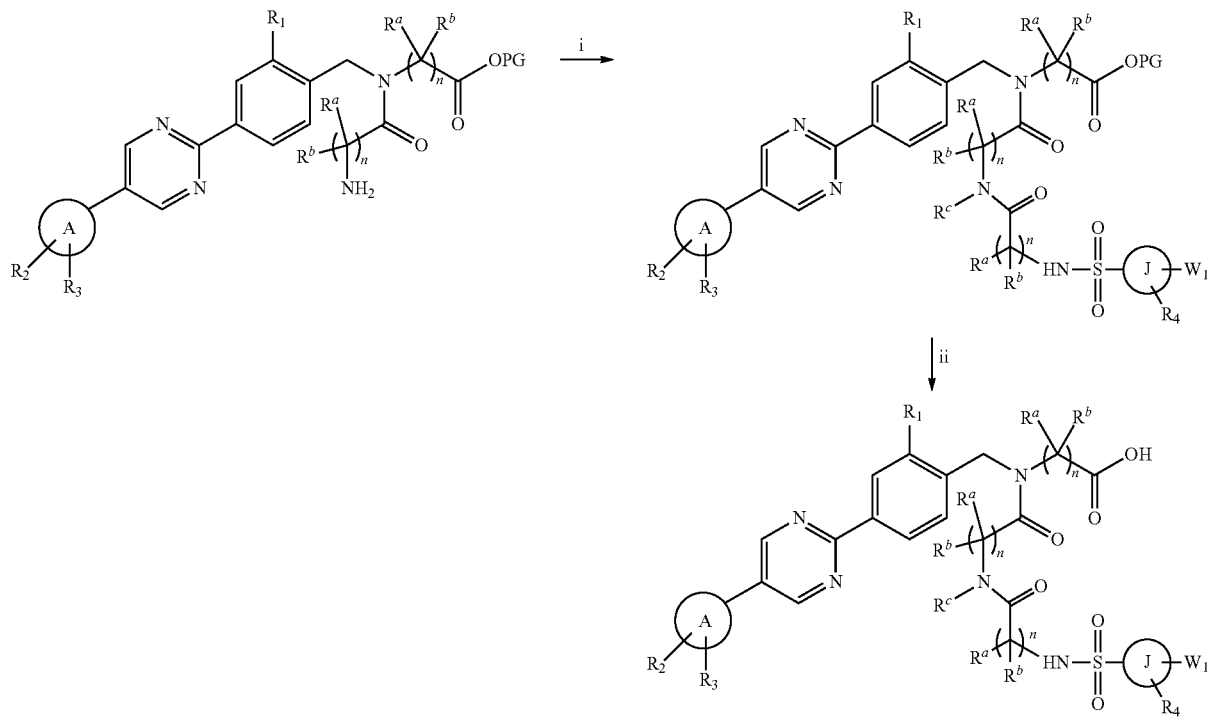
Reagents: PG is protecting group (i) HATU, DIEA, DMF; (ii) Deprotection of PG:
e.g deprotection of tert-butyl ester: TFA, DCM.
Scheme 17
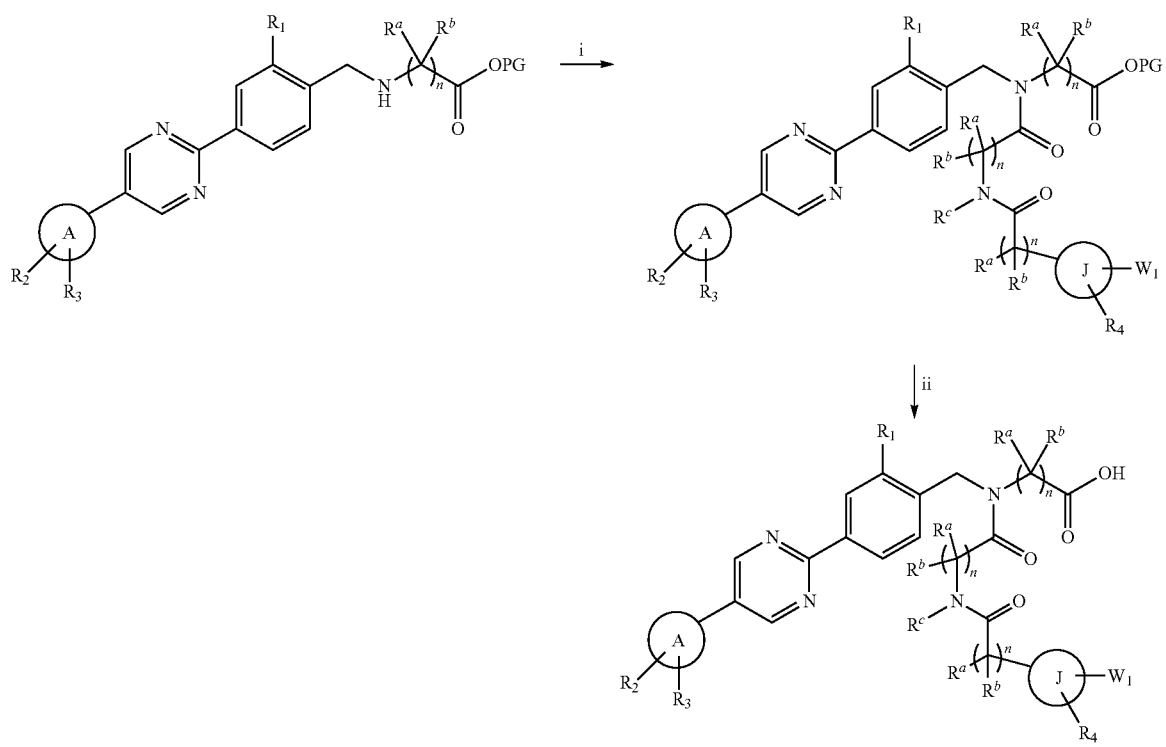
Reagents: PG is a protecting group (i) HATU, DIEA, DMF; (ii) Deprotection of PG:
e.g deprotection of tert-butyl ester: TFA, DCM.

Scheme 18
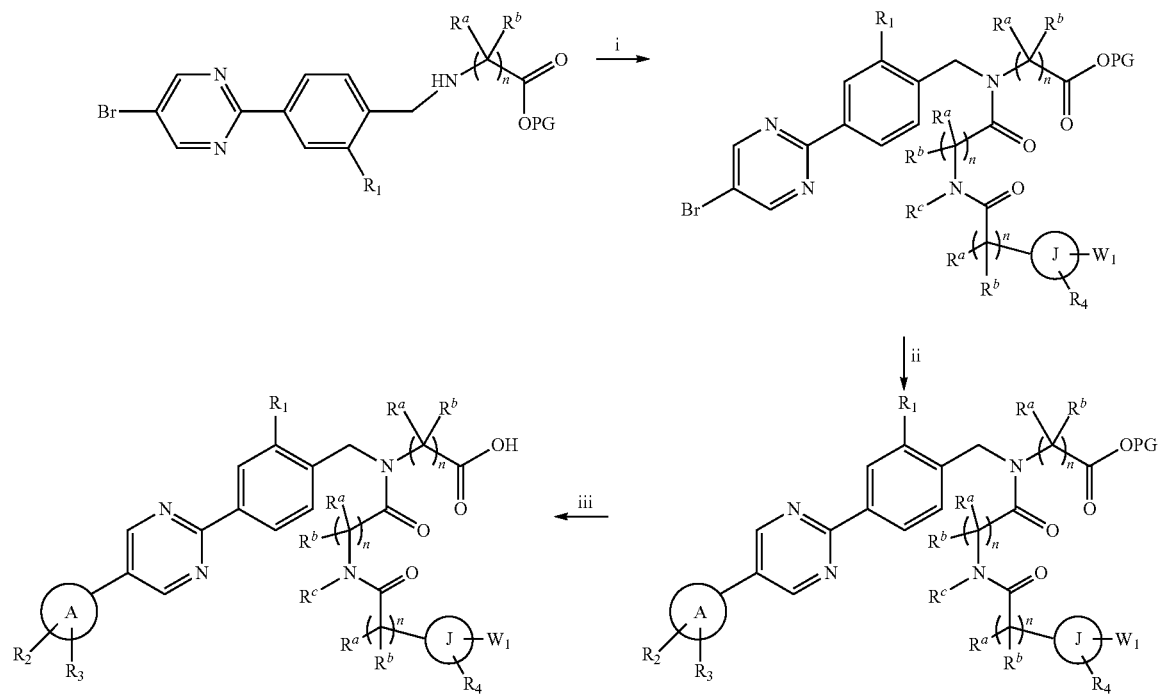
Reagents: PG is protecting group (i) HATU, DIEA, DMF; (ii) Pd(dppf)Cl₂, Na₂CO₃ or NaHCO₃, dioxane, water; (iii) Deprotection of PG: e.g deprotection of tert-butyl ester: TFA, DCM.
Scheme 19
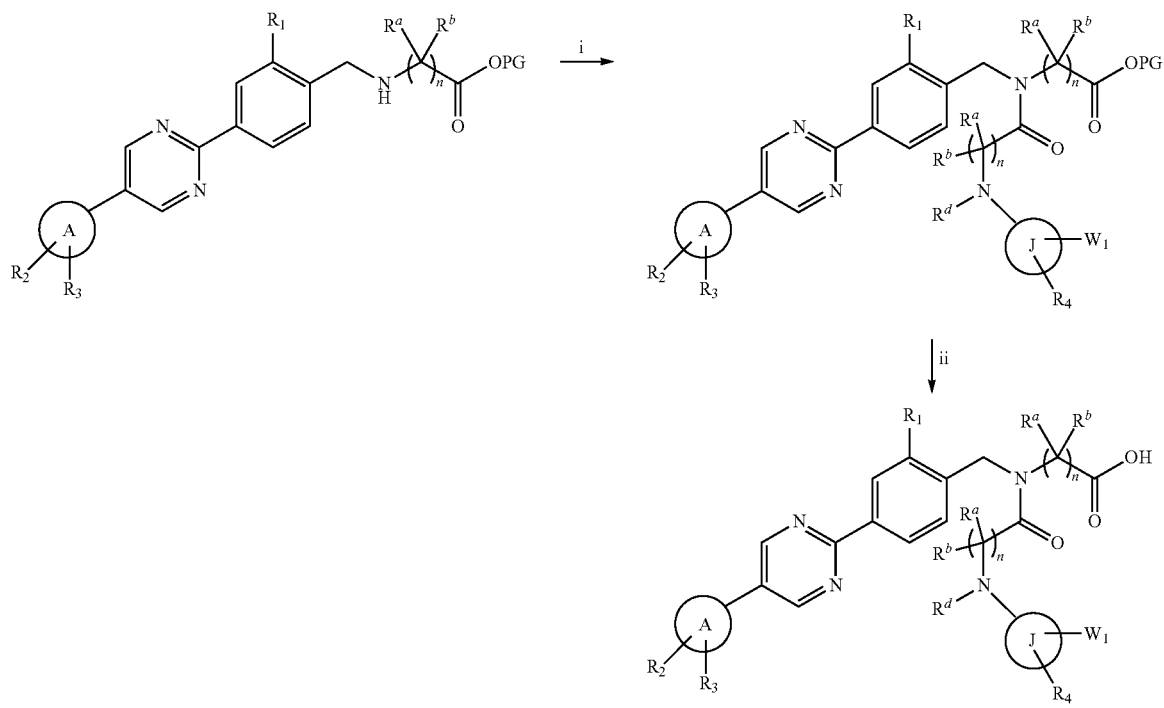
Reagents: PG is a protecting group (i) HATU, DIEA, DMF; (ii) Deprotection of PG: e.g deprotection of tert-butyl ester: TFA, DCM.

Scheme 20

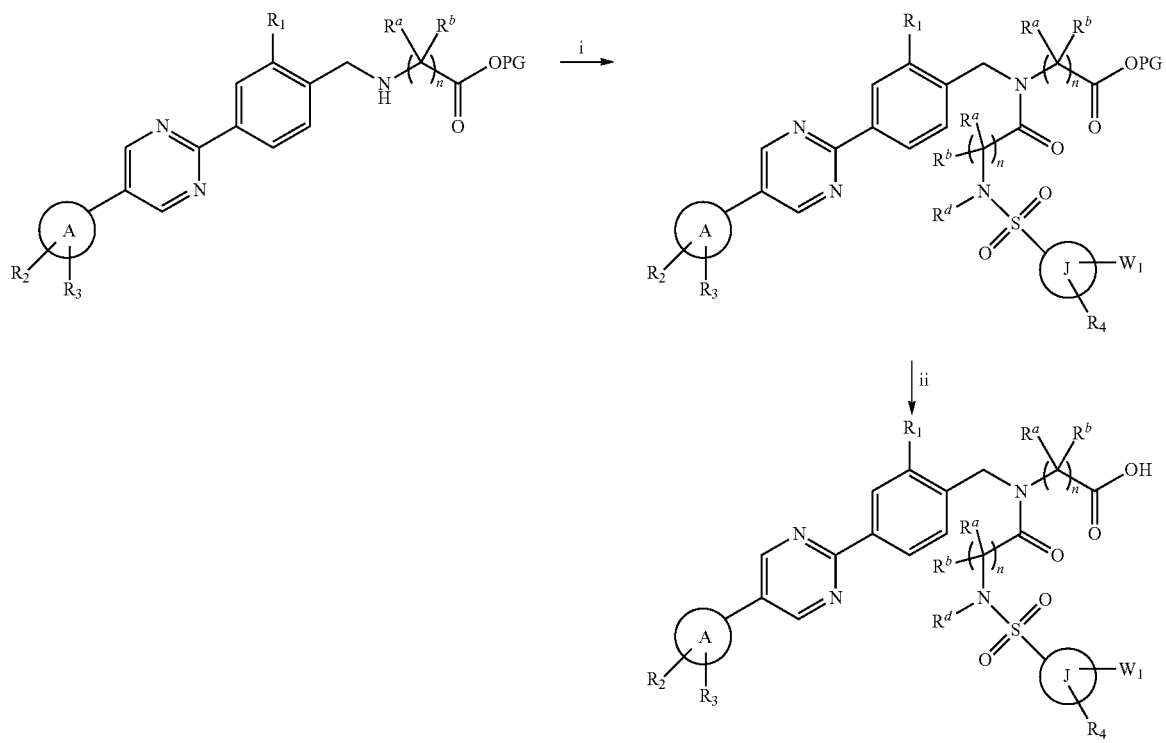

Reagents: PG is a protecting group (i) HATU, DIEA, DMF; (ii) Deprotection of PG: e.g deprotection of tert-butyl ester: TFA, DCM.

EXAMPLES

Compound Synthesis

NMR Spectra $^1$H NMR (400 MHz) and $^{13}$C NMR (100 MHz) were obtained in solution of deuterochloroform (CDCl$_3$) or dimethyl sulfoxide (d$_6$-DMSO). NMR spectra were processed using MestReNova 6.0.3-5604.

LCMS Data

Mass spectra (LCMS) were obtained using one of 2 systems: System 1: Agilent 1100/6110 HPLC system equipped with a Waters X-Bridge C-8, 3.5μ (50×4.6 mm) column using water with 5 mM ammonium acetate as the mobile phase C, and acetonitrile with 5 mM ammonium acetate as the mobile phase D with a flow rate of 1 mL/min. Method 1; 20% D (80% C) to 95% D over 12.0 min. and hold at 95% D for 2.8 min. then 20% D over 0.2 min. Method 2: 20% D (80% C) to 95% D over 3 min. then held at 95% D for 3.8 min. and then to 5% D over 0.2 min. System 2: Agilent 1260 LCMS equipped with a Waters Xselect CSH C18 3.5 μm (4.6×50 mm) column using water with 0.1% formic acid as mobile phase A and acetonitrile with 0.1% formic acid as mobile phase B. Method 3: The gradient was 5-95% mobile phase B over 13.0 min with a flow rate of 2.5 mL/min, then held at 95% for 1.0 min with a flow rate of 4.5 mL/min. Method 4: The gradient was 5-95% mobile phase B over 3.0 min with a flow rate of 2.5 mL/min, then held at 95% for 0.6 min with a flow rate of 4.5 mL/min.

Reaction Conditions and Abbreviations

Pyridine, dichloromethane (DCM), tetrahydrofuran (THF), and toluene used in the procedures were from Aldrich Sure-Seal bottles or Acros AcroSeal dry solvent and kept under nitrogen (N$_2$). All reactions were stirred magnetically and temperatures are external reaction temperatures. The following abbreviations are used: tetrahydrofuran (THF), ethyl acetate (EA), triethylamine (TEA), N-hydroxybenzotriazole (HOBt), 1-ethyl-3-(3-dimethylaminopropyl) carbodiimide hydrochloride (EDC), 1-[Bis(dimethylamino)methylene]-1H-1,2,3-triazolo[4,5-b]pyridinium 3-oxide hexafluorophosphate (HATU), N,N-dimethylformamide (DMF), dimethyl acetamide (DMA), Di-tert-butyl dicarbonate (Boc$_2$O), N,N-Diisopropylethylamine (DIEA), acetic acid (AcOH), hydrochloric acid (HCl), 4-dimethylaminopyridine (DMAP), tert-butanol (t-BuOH), sodium hydride (NaH), sodium triacetoxyborohydride (Na(OAc)$_3$BH), trifluoroacetic acid (TFA), room temperature (RT), dichloromethane (DCM), isopropyl alcohol (IPA), 2,2'-azobis(2-methylpropionitrile) (AIBN).

Purifications

Chromatographies were carried out using a Combiflash Rf flash purification system (Teledyne Isco) equipped with Redisep (Teledyne Isco), Telos (Kinesis) or Grace Resolv (Grace Davison Discovery Sciences) silica gel (SiO$_2$) columns. Preparative HPLC purifications were performed using a Waters Fractionlynx system equipped with either 1) Agilent Prep-C18, 5 μm (21.2×50 mm) column using water containing 0.1% formic acid as mobile phase A, and acetonitrile with 0.1% formic acid as mobile phase B. The gradient was 45-95% mobile phase B over 7.5 min, held at 95% for 1 min, and then returned to 45% over 1.5 min with a flow rate of 28 mL/min or 2) Waters X-Bridge C-8, 5 μm (19×150 mm) column using water containing 0.04% trifluoroacetic acid as mobile phase A, and acetonitrile with 0.04% trifluoroacetic acid as mobile phase B. The gradient was 20-95% mobile phase B over 7 min, held at 95% for 3 min, and then return to 20% over 2 min with flow rate of 28 mL/min. Fractions were collected by UV detection at 254 nm or by mass and evaporated using a Genevac EZ-2.

General Procedure 1. Palladium-Catalyzed Coupling Reactions.

A solution of boronic acid or boronate ester (1.0-1.3 eq), halide (1.0-1.3 eq), sodium bicarbonate or sodium carbonate decahydrate (2.0-2.5 eq), and dichloro[1,1'-bis(di-tert-butylphosphino)ferrocene]palladium(II) or Pd(dppf)Cl$_2$ were combined in THF, acetonitrile, or dioxane (0.1-0.2 M) and water (0.25-0.50 M). The reaction was heated at 80 to 100° C. until complete. The reaction was diluted with EA and washed with saturated aqueous NaHCO$_3$. The organic layer was dried over MgSO$_4$ and concentrated. The product can be purified by chromatography, preparative HPLC, or carried on to the next step without further purification.

General Procedure 2, Preparation of Amides Via Peptide Coupling.

A solution of amine (1.0 eq) and base (DIEA, TEA or NMM) (0-3.0 eq) in DCM or DMF (0.08-0.10 M) was treated with the appropriate carboxylic acid (1.0-1.5 eq). To this mixture was added the coupling reagent. The coupling reagent could be HATU (1.05-2.5 eq) optionally with DMAP (0.01-1 eq), EDC (1.5 eq) with HOBt (1.5 eq) or DMAP (0.01-1 eq), DCC (1.1 eq) with HOBt (1.1 eq) or DCC (1.5 eq) with DMAP (2.0 eq). The reaction mixture was stirred until the reaction was complete. The reaction was diluted with EA and washed with saturated aqueous NaHCO$_3$. The organic layer was dried over MgSO$_4$ and concentrated. The product was purified by chromatography or alternatively can be carried on to the next step without further purification.

General Procedure 3, Hydrolysis of Methyl or Ethyl Esters to Acids.

To a stirring solution of ester (1 eq) in THF or dioxane and water, was added NaOH or LiOH (1-3 eq). The reaction mixture was stirred at up to 60° C. for up to 18 h. The reaction mixture was neutralized with AcOH or HCl and either diluted with water or concentrated. If the reaction mixture was diluted with water, then HCl was added to acidify the reaction mixture to a pH of approximately 2. The resulting precipitate was isolated by filtration to yield product which can be purified by chromatography, preparative HPLC, or used without purification. Alternatively, a solution of the ester (1 eq) in DCE was treated with trimethylstannanol (9 eq) at 80° C. for 24 to 72 h. The mixture was diluted with DCM and water and passed through a phase separator and the organics concentrated to afford product which can be purified by chromatography, preparative HPLC, or used without purification.

General Procedure 4, Deprotection of tert-Butyl Esters to Acids or Deprotection of Boc-Amines.

A solution of the tert-butyl ester or Boc-amine (1 eq) in DCM (0.06 M) was treated with TFA (0.16-0.33 M) or 1-4N HCl in ether or dioxane (10-2 eq). The reaction mixture was stirred at either room temperature or 30° C. until complete. The solvent was removed and the product was purified by chromatography or preparative HPLC. Alternatively, a solution of the tert-butyl ester (1 eq) is treated with formic acid (0.03 M) at room temperature for until the reaction is complete. The reaction was partitioned between DCM and water. The organic layer was dried and concentrated to give the free acid which could be purified by chromatography or preparative HPLC.

General Procedure 5, Preparation of Amides Via Acid Chlorides.

To a solution of amine (1 eq) and base (DIEA, TEA, or pyridine) (2-3 eq) in DCM (0.06-0.30 M) was treated with the appropriate acid chloride (1.0-1.5 eq). The reaction mixture was stirred until the reaction was complete. The reaction was diluted with DCM and washed with saturated aqueous NaHCO$_3$. The organic layer was dried over MgSO$_4$ and concentrated. The product was purified by chromatography. Alternatively, the crude reaction mixture can be carried on to the next step without further purification.

5-Bromo-2-(p-tolyl)pyrimidine

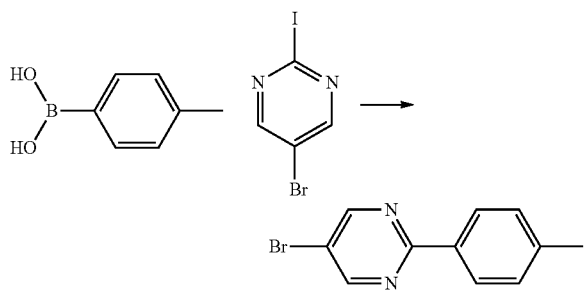

Prepared using General Procedure 1. To a stirring solution of p-tolylboronic acid (14.18 g, 104 mmol) and 5-bromo-2-iodopyrimidine (29.7 g, 104 mmol) in dioxane (140 mL) was added a solution of sodium carbonate (33.2 g, 313 mmol) in water (70 mL). The mixture was de-gassed then treated with Pd(dppf)Cl$_2$ (2.289 g, 3.13 mmol) and heated under reflux. After 16 h, the mixture was allowed to cool then quenched with ice-water (50 mL). 1 M HCl (350 mL) was added slowly and the product extracted with EA (2×350 mL). The combined organic extracts were filtered through Celite then washed successively with 1 M HCl (250 mL) and brine (300 mL), dried over MgSO$_4$ and solvents evaporated. Column chromatography (EA/iso-hexane) gave 15 g (58%) of 5-bromo-2-(p-tolyl)pyrimidine. LCMS-ESI (m/z) calculated for $C_{11}H_9BrN_2$: 248.0; found 249.1 [M+H]$^+$, $t_R$=2.60 min (Method 4). $^1$H NMR (400 MHz, Chloroform-d) δ 8.74 (s, 2H), 8.32-7.99 (m, 2H), 7.27-7.20 (m, 2H), 2.35 (s, 3H).

5-Bromo-2-(4-(bromomethyl)phenyl)pyrimidine

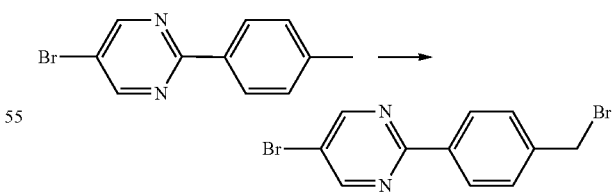

To a stirring solution of 5-bromo-2-(p-tolyl)pyrimidine (5.41 g, 21.72 mmol) in chloroform (100 mL) at reflux was added A-bromosuccinimide (5.08 g, 28.2 mmol) followed by 2,2'-azobis(2-methylpropionitrile) (0.535 g, 3.26 mmol). After 1.5 h, the mixture was allowed to cool and solvent evaporated. Column chromatography (EA/heptane) gave 3.9 g (55%) of 5-bromo-2-(4-(bromomethyl)phenyl)pyrimidine. LCMS-ESI (m/z) calculated for $C_{11}H_8Br_2N_2$: 325.9; found 327.0 [M+H]+, $t_R$=2.62 min (Method 4). $^1$H NMR (400 MHz, DMSO-$d_6$) δ 9.10 (s, 2H), 8.39-8.28 (m, 2H), 7.65-7.56 (m, 2H), 4.79 (s, 2H).

Tert-butyl (4-(5-bromopyrimidin-2-yl)benzyl)glycinate INT-1

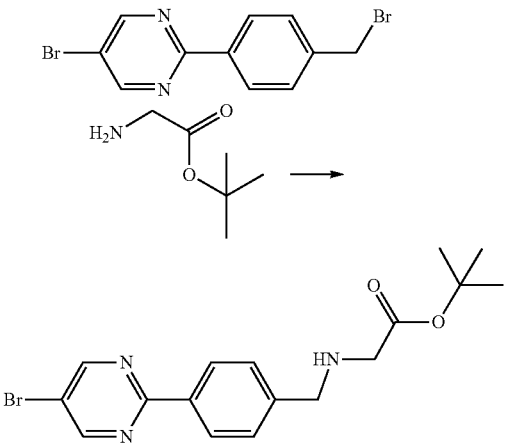

To a stirring solution of 5-bromo-2-(4-(bromomethyl) phenyl)pyrimidine (3.08 g, 9.39 mmol) in THF (100 mL) was added tert-butyl 2-aminoacetate (3.70 g, 28.2 mmol) added followed by DIEA (4.9 mL, 28.2 mmol). The mixture was heated under reflux for 7 h then allowed to cool overnight. The mixture was poured into water (60 mL) and extracted with EA (3×60 mL). The combined organic extracts were washed with brine (100 mL), dried over MgSO$_4$ and solvents evaporated. The residue was re-slurried from diethyl ether to afford 1.46 g (41%) of tert-butyl (4-(5-bromopyrimidin-2-yl)benzyl)glycinate INT-1. LCMS-ESI (m/z) calculated for $C_{17}H_{20}BrN_3O_2$: 377.1; found 378.1 [M+H]+, $t_R$=1.42 min (Method 4).

Tert-butyl (4-(5-((1'r,4'r)-4'-ethyl-[1,1'-bi(cyclohexan)]-3-en-4-yl)pyrimidin-2-yl)benzyl)glycinate INT-2

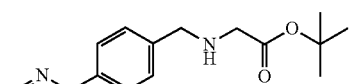

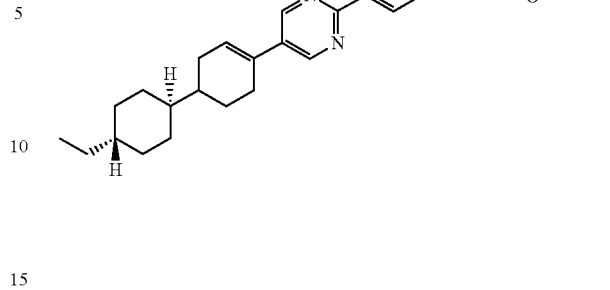

Prepared using General Procedure 1. To a stirring solution of tert-butyl (4-(5-bromopyrimidin-2-yl)benzyl)glycinate INT-1 (0.969 g, 2.56 mmol) and 2-((1'r,4'r)-4'-ethyl-[1,1'-bi(cyclohexan)]-3-en-4-yl)-4,4,5,5-tetramethyl-1,3,2-dioxaborolane (1.06 g, 3.33 mmol) in dioxane (35 mL) was added NaHCO$_3$ (8.5 mL of a 0.9 M aqueous solution, 7.7 mmol). The mixture was de-gassed then treated with PdCl$_2$(dppf) (0.099 g, 0.128 mmol). The mixture was heated to 90° C. for 3 h then allowed to cool and treated with water (30 mL). The mixture was extracted with EA (3×100 mL) and the combined organic extracts washed with brine (150 mL), dried over MgSO$_4$ and solvents evaporated. Column chromatography (EA/DCM/iso-hexane) gave 618 mg (49%) of tert-butyl (4-(5-((1'r,4'r)-4'-ethyl-[1,1'-bi(cyclohexan)]-3-en-4-yl)pyrimidin-2-yl)benzyl)glycinate INT-2. LCMS-ESI (m/z) calculated for $C_{31}H_{43}N_3O_2$: 489.3; found 490.4 [M+H]+, $t_R$=2.58 min (Method 4). $^1$H NMR (400 MHz, Chloroform-d) δ 8.71 (s, 2H), 8.42-8.25 (m, 2H), 7.48 (d, J=8.2 Hz, 2H), 6.36-6.06 (m, 1H), 4.02 (s, 2H), 3.36 (s, 2H), 2.45-2.23 (m, 3H), 1.95-1.90 (m, 2H), 1.74 (app q, J=12.4 Hz, 5H), 1.40-1.30 (m, 10H), 1.21-0.85 (m, 7H), 0.83-0.76 (m, 5H).

Tert-butyl 2-(N-(4-(5-((1'r,4'r)-4'-ethyl-[1,1'-bi(cyclohexan)]-3-en-4-yl)pyrimidin-2-yl)benzyl)-4-nitrobenzamido)acetate

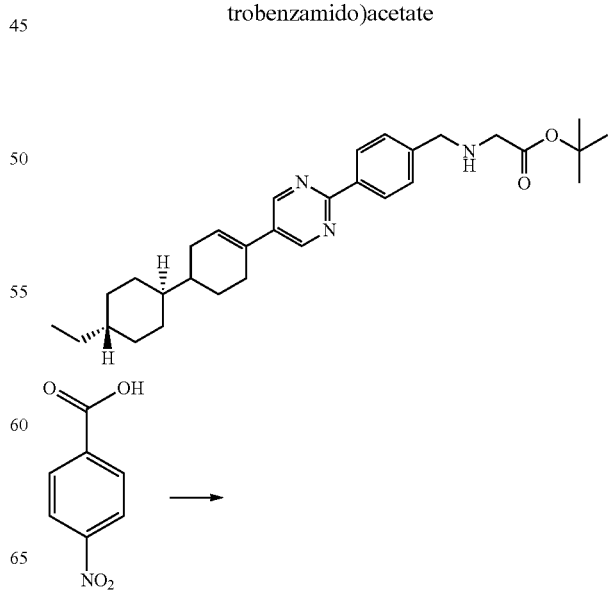

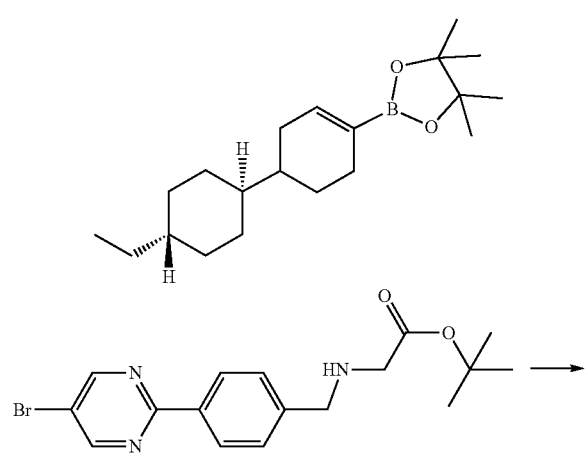

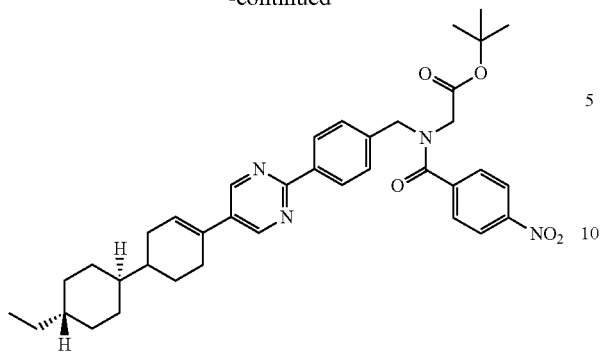

Prepared using General Procedure 2. To a stirring suspension of tert-butyl (4-(5-((1'r,4'r)-4'-ethyl-[1,1'-bi(cyclohexan)]-3-en-4-yl)pyrimidin-2-yl)benzyl)-glycinate INT-2 (2 g, 4.08 mmol) and 4-nitrobenzoic acid (0.975 g, 5.72 mmol) in DMF (60 mL) was added DIEA (3.6 mL, 20.42 mmol) and HATU (2.29 g, 5.72 mmol) and the mixture heated to 80° C. After 1 h, the mixture was allowed to cool then treated with water (50 mL). The precipitate was collected by filtration, washing with toluene (50 mL) to afford 1.35 g (52%) of tert-butyl 2-(N-(4-(5-((1'r,4'r)-4'-ethyl-[1,1'-bi(cyclohexan)]-3-en-4-yl)pyrimidin-2-yl)benzyl)-4-nitrobenzamido)acetate. LCMS-ESI (m/z) calculated for $C_{38}H_{46}N_4O_5$: 638.3; found 639.4 $[M+H]^+$, $t_R$=3.50 min (Method 4). $^1$H NMR (400 MHz, Chloroform-d) δ 8.73 (s, 2H), 8.36 (d, J=7.9 Hz, 2H), 8.20 (app t, J=9.0 Hz, 2H), 7.60 (app dd, J=16.6, 8.6 Hz, 2H), 7.38 (d, J=8.1 Hz, 1H), 7.21 (d, J=8.0 Hz, 1H), 6.24 (br s, 1H), 4.81 (s, 1H), 4.53 (s, 1H), 4.06 (s, 1H), 3.62 (s, 1H), 2.46-2.35 (m, 2H), 2.30-2.23 (m, 1H), 1.98-1.90 (m, 2H), 1.75 (app q, J=12.6 Hz, 4H), 1.44-1.31 (m, 10H), 1.30-0.90 (m, 7H), 0.87-0.76 (m, 5H).

Tert-butyl N-(4-aminobenzoyl)-N-(4-(5-((1'r,4'r)-4'-ethyl-[1,1'-bi(cyclohexan)]-3-en-4-yl)pyrimidin-2-yl)benzyl)glycinate INT-3

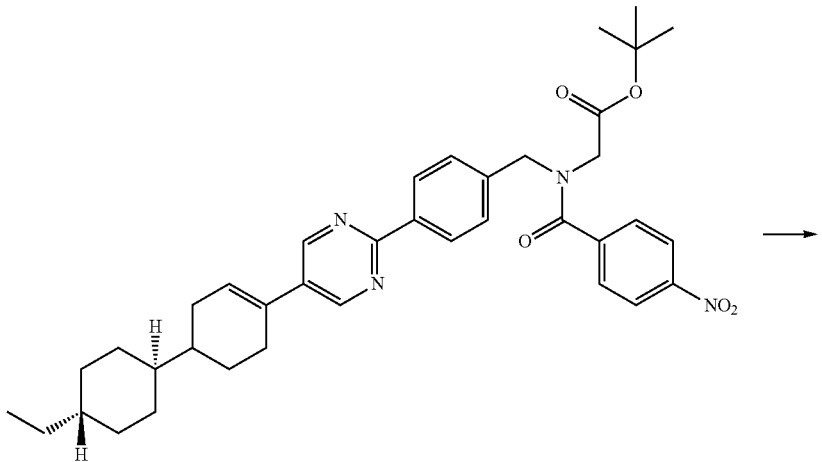

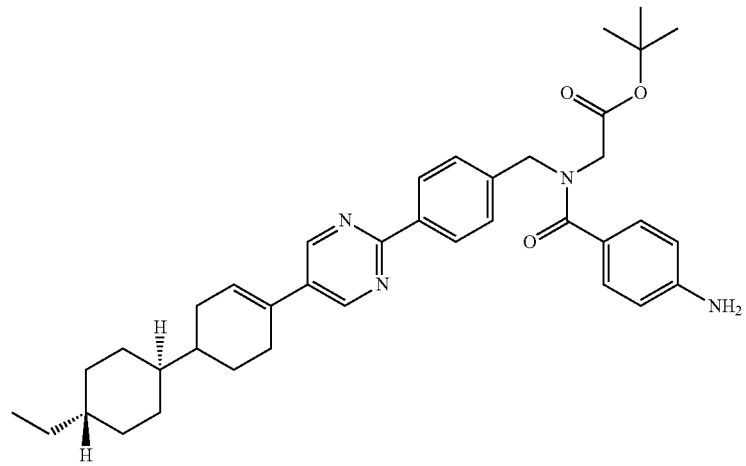

To a stirring suspension of tert-butyl 2-(N-(4-(5-((1'r,4'r)-4'-ethyl-[1,1'-bi(cyclohexan)]-3-en-4-yl)pyrimidin-2-yl)benzyl)-4-nitrobenzamido)acetate (4.3 g, 6.73 mmol) in THF (90 mL), EtOH (90 mL) and water (9 mL) were added a solution of NH$_4$Cl (1.837 g, 33.7 mmol) in water (2 mL) and iron (1.9 g, 33.7 mmol). The suspension was heated under reflux. After 3 h, the mixture was filtered hot through a pad of celite, washing with DCM (100 mL). The mixture was washed with 2 M NaOH (50 mL) and the aqueous further extracted with DCM (2×100 mL). The combined organic extracts were washed with brine (100 mL) and split through a hydrophobic frit. The solvents were evaporated to afford an off-white solid. This was taken up in DCM (300 mL), washed successively with water (100 mL) and brine (2×150 mL) then split through a hydrophobic frit and solvents evaporated to afford 3.72 g (91%) of tert-butyl N-(4-aminobenzoyl)-N-(4-(5-((1'r,4'r)-4'-ethyl-[1,1'-bi(cyclohexan)]-3-en-4-yl)pyrimidin-2-yl)benzyl)glycinate INT-3. LCMS-ESI (m/z) calculated for C$_{38}$H$_{48}$N$_4$O$_3$: 608.4; no mass observed, $t_R$=3.45 min (Method 4).

the cooling bath was removed. After a further 1 h, the mixture was evaporated then re-dissolved in DCM (10 mL). The resulting solution was added dropwise to a stirring suspension of tert-butyl N-(4-aminobenzoyl)-N-(4-(5-((1'r,4'r)-4'-ethyl-[1,1'-bi(cyclohexan)]-3-en-4-yl)pyrimidin-2-yl)benzyl)glycinate INT-3 (1.3 g, 2.135 mmol) and DIEA (1.2 mL, 6.41 mmol) in DCM (10 mL) at 0° C. After 10 min, the cooling bath was removed. After a further 0.5 h, the mixture was diluted with DCM (100 mL) and washed successively with 1 M HCl (100 mL) and NaHCO$_3$ (100 mL), dried over MgSO$_4$ and evaporated. The residue was taken into DCM (10 mL) and stirred with TFA (8 mL). After 2 h, the mixture was diluted with DCM (50 mL), THF (20 mL) and toluene (20 mL) and washed successively with water (100 mL) then a mixture of water (100 mL) and THF (10 mL). The organics were dried over MgSO$_4$ and solvents evaporated and the residue stripped with toluene (50 mL). The residue was re-crystallized from EA (40 mL) to afford crude product. This was then dissolved in DMSO (30 mL) and THF (20 mL) and treated with water (50 mL). After stirring for 1 h, the precipitate was collected by filtration to afford 1.334 g (81%) of 2-(N-(4-(5-((1'r,4'r)-4'-ethyl-[1,1'-bi(cyclohexan)]-3-en-4-yl)pyrimidin-2-yl)benzyl)-4-(2-(4-methoxy-2-(trifluoromethyl)phenyl)acetamido)benzamido) acetic acid Compound 1. LCMS-ESI (m/z) calculated for 2-(N-(4-(5-(1'r,4'r)-4'-ethyl-[1,1'-bi(cyclohexan)]-3-en-4-yl)pyrimidin-2-yl)benzyl)-4-(2-(4-methoxy-2-(trifluoromethyl)phenyl)acetamido)benzamido)acetic acid Compound 1

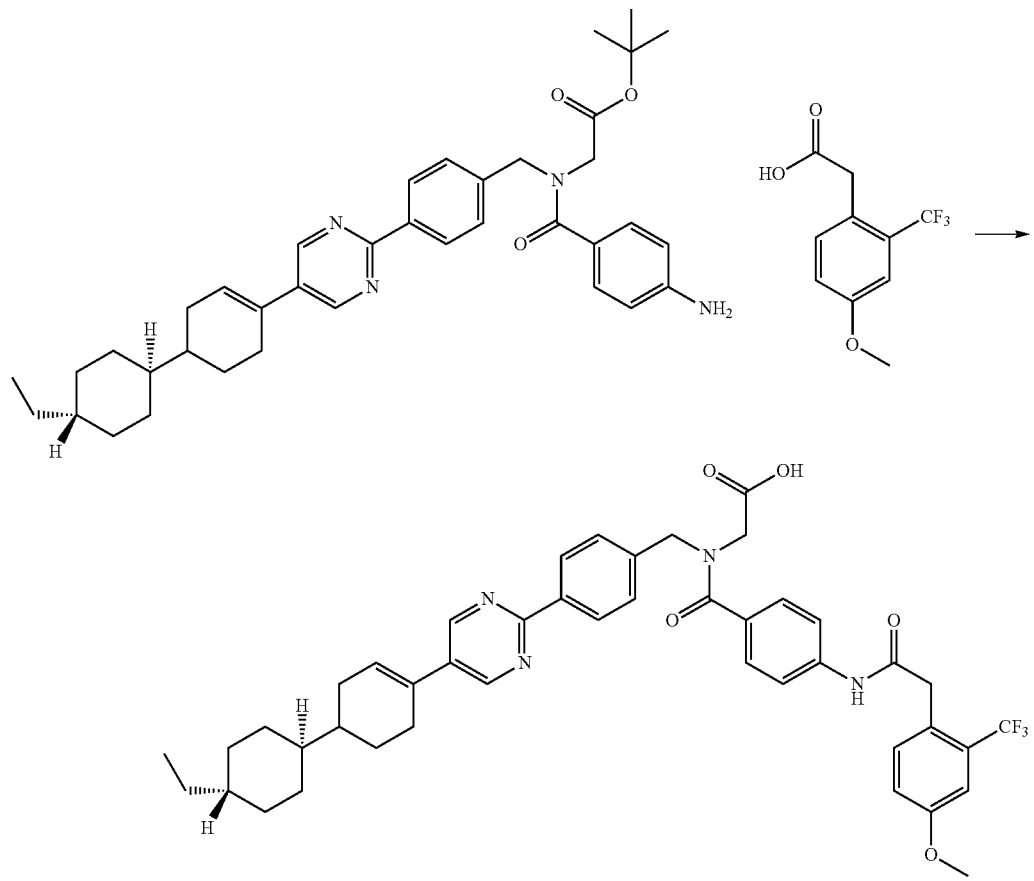

To a stirring solution of 2-(4-methoxy-2-(trifluoromethyl)phenyl)acetic acid (0.750 g, 3.20 mmol) in DCM (10 mL) was added DMF (1 drop) and the mixture cooled to 0° C. Oxalyl chloride (0.22 mL, 2.56 mmol) was added. After 1 h, C$_{44}$H$_{47}$F$_3$N$_4$O$_5$: 768.3; found 769.3 [M+H]$^+$, $t_R$=13.10 min (Method 3). $^1$H NMR (400 MHz, DMSO-d$_6$) δ 12.83 (br s, 1H), 10.35 (s, 1H), 8.95 (s, 2H), 8.52-8.25 (m, 2H), 7.63 (app t, J=10.1 Hz, 2H), 7.54-7.32 (m, 5H), 7.23-7.18 (m, 2H), 6.47 (br s, 1H), 4.73 (s, 1H), 4.65 (s, 1H), 4.01 (s, 1H), 3.93 (s, 1H), 3.86-3.82 (m, 5H), 2.46-2.19 (m, 2H), 2.01-1.94 (m, 2H), 1.84-1.76 (m, 4H), 1.41-1.30 (m, 2H), 1.24-0.93 (m, 7H), 0.91-0.82 (m, 5H).

((4-Methoxy-2-(trifluoromethyl)phenyl)acetamido)benzoic acid

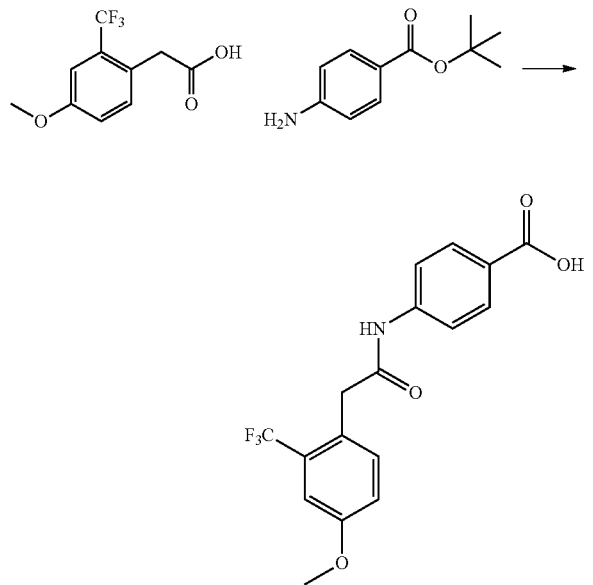

To a stirring solution of 2-(4-methoxy-2-(trifluoromethyl)phenyl)acetic acid (3.25 g, 13.88 mmol) in DCM (30 mL) at 0° C. was added DMF (3 drops) then oxalyl chloride (1.5 mL, 17.4 mmol). After 10 min, the cooling bath was removed. After a further 2 h, solvents were evaporated and the residue taken into DCM (10 mL). The resulting solution was added to a stirring solution of tert-butyl 4-aminobenzoate (2.68 g, 13.88 mmol) and DIEA (3.8 mL, 20.8 mmol) in DCM (10 mL) at −10° C. such that the internal temperature was maintained below −5° C. The mixture was allowed to warm slowly then poured into a mixture of ice-water (200 mL), 1 M HCl (50 mL) and iso-hexane (100 mL). After 10 min, the precipitate was collected by filtration, washing successively with water (2×20 mL), iso-hexane (2×20 mL), and MTBE (5 mL). The filter cake was dried in the vacuum oven then taken up in DCM (30 mL) and treated with TFA (20 mL). After 2 h, the mixture was poured into a mixture of ice-water (100 mL) and iso-hexane (100 mL) and the product collected by filtration washing successively with water (2×20 mL), iso-hexane (2×20 mL) and MTBE (5 mL). The filter cake was dried in the vacuum oven to afford 3.86 g (79%) of 4-(2-(4-methoxy-2-(trifluoromethyl)phenyl)acetamido)benzoic acid. LCMS-ESI (m/z) calculated for $C_{17}H_{14}F_3NO_4$: 353.1; found 354.0 [M+H]⁺, $t_R$=1.94 min (Method 4).

Methyl 2-((4-(5-bromopyrimidin-2-yl)benzyl)amino)acetate

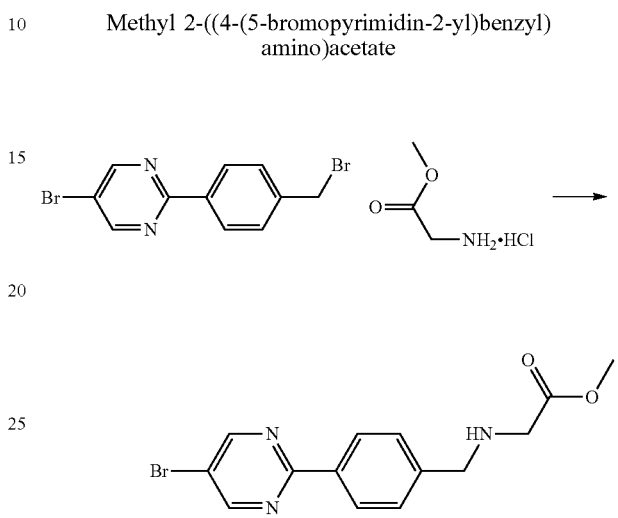

To a stirring mixture of 5-bromo-2-(4-(bromomethyl)phenyl)pyrimidine (1 g, 2.44 mmol) in THF (10 mL) and DMF (10 mL) was added methyl 2-aminoacetate, HCl (0.928 g, 7.32 mmol) followed by DIEA (1.3 mL, 7.32 mmol) and the reaction mixture heated to 65° C. After 1.5 h, the mixture was allowed to cool then poured into NaHCO₃ (40 mL) and extracted with EA (3×20 mL). The combined organic extracts were washed with brine (50 mL), dried over MgSO₄ and solvents evaporated. Column chromatography (EA/iso-hexane) gave 590 mg (72%) of methyl 2-((4-(5-bromopyrimidin-2-yl)benzyl)amino)acetate. LCMS-ESI (m/z) calculated for $C_{14}H_{14}BrN_3O_2$: 335.0; found 336.1 [M+H]⁺, $t_R$=1.06 min (Method 4). ¹H NMR (400 MHz, DMSO-d₆) δ 9.07 (s, 2H), 8.34-8.22 (m, 2H), 7.52-7.33 (m, 2H), 3.80 (s, 2H), 3.63 (s, 3H), 3.35 (s, 2H), 2.61 (br s, 1H).

N-(4-(5-Bromopyrimidin-2-yl)benzyl)-N-(4-(2-(4-methoxy-2-(trifluoromethyl)phenyl)-acetamido)benzoyl)glycinate INT-4

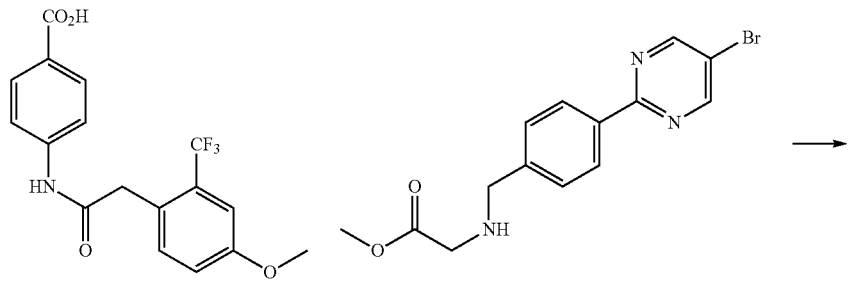

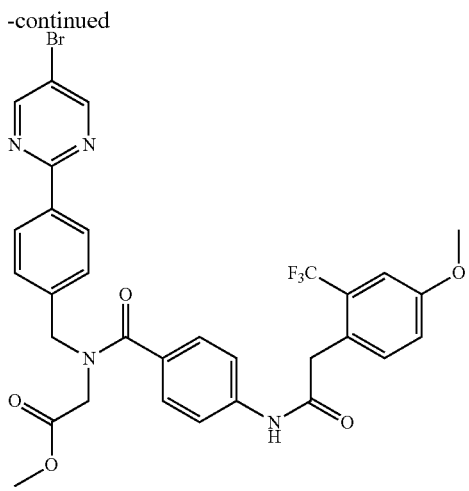

Prepared using General Procedure 2. To a stirring solution of 4-(2-(4-methoxy-2-(trifluoromethyl)phenyl)acetamido) benzoic acid (410 mg, 1.16 mmol) and DIEA (0.5 mL, 2.9 mmol) in DMF (15 mL), was added HATU (455 mg, 1.16 mmol). After 15 min a solution of methyl 2-((4-(5-bromopyrimidin-2-yl)benzyl)amino)acetate (325 mg, 0.97 mmol) in DMF (15 mL) was added. After 16 h, the mixture was poured into water (50 mL) and extracted with EA (3×100 mL). The combined organic extracts were washed with brine (50 mL), dried over MgSO$_4$ and solvents evaporated. Column chromatography (EA/iso-hexane) gave 649 mg (100%) of N-(4-(5-bromopyrimidin-2-yl)benzyl)-N-(4-(2-(4-methoxy-2-(trifluoro-methyl)phenyl)acetamido)benzoyl) glycinate INT-4. LCMS-ESI (m/z) calculated for $C_{31}H_{26}BrF_3N_4O_5$: 670.1; found 671.1 [M+H]$^+$, $t_R$=2.64 min (Method 4).

Compound 2 was prepared from methyl N-(4-(5-bromopyrimidin-2-yl)benzyl)-N-(4-(2-(4-methoxy-2-(trifluoromethyl)phenyl)acetamido)benzoyl)-glycinate INT-4 using General Procedures 1 then 3.

Compounds 3-10, 125, and 148-152 were prepared from tert-butyl (4-(5-(((1'r,4'r)-4'-ethyl-[1,1'-bi(cyclohexan)]-3-en-4-yl)pyrimidin-2-yl)benzyl)glycinate INT-2 using General Procedures 2 then 4.

Compounds 11 and 12 were prepared from Compound 1 using General Procedures 2 then 4.

Compounds 13, 14, 15, 112, and 113 were prepared from Compound 1 using General Procedures 2 then 3.

Tert-butyl N-(4-(5-bromopyrimidin-2-yl)benzyl)-N-(4-(2-(4-methoxy-2-(trifluoromethyl)phenyl)acetamido) benzoyl)glycinate INT-5

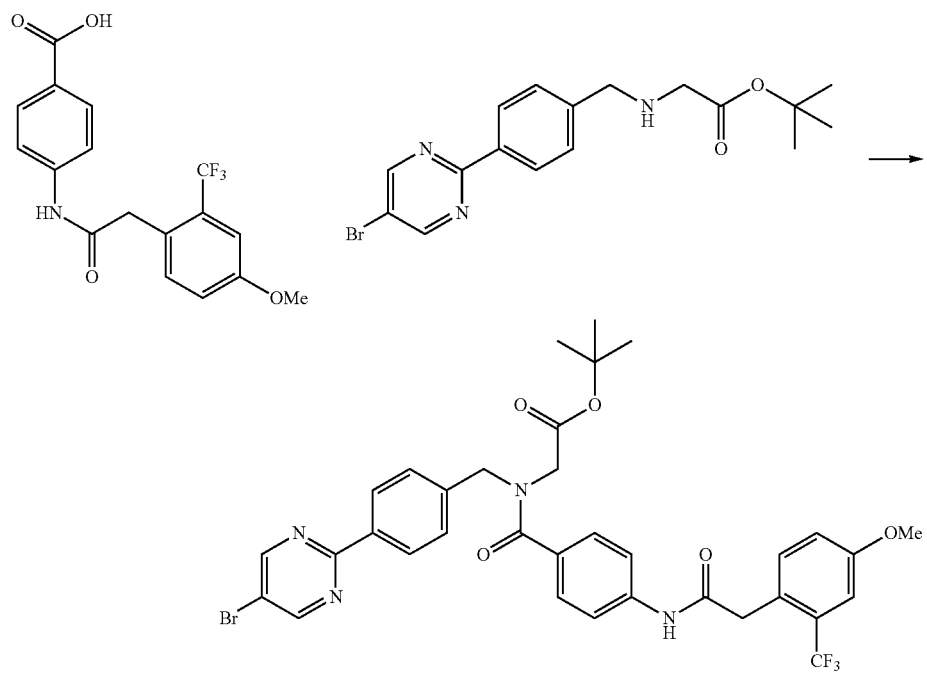

Prepared using General Procedure 2. To a stirring solution of DIEA (0.97 mL, 5.55 mmol) and 4-(2-(4-methoxy-2-(trifluoromethyl)phenyl)acetamido)-benzoic acid (0.560 g, 1.586 mmol) in DMF (15 mL) was added HATU (0.784 g, 2.062 mmol). After 5 min tert-butyl (4-(5-bromopyrimidin-2-yl)benzyl)glycinate INT-1 (0.600 g, 1.586 mmol) was added. After 16 h, the mixture was poured onto 0.5 M HCl (50 mL) and extracted with EA (50 mL then 2×20 mL). The combined organic extracts were washed with brine (30 mL), dried over MgSO$_4$ and solvents evaporated. Column chromatography (EA/iso-hexane) gave 0.35 g (31%) of tert-butyl N-(4-(5-bromopyrimidin-2-yl)benzyl)-N-(4-(2-(4-methoxy-2-(trifluoromethyl)-phenyl)acetamido) benzoyl)glycinate INT-5. LCMS-ESI (m/z) calculated for $C_{34}H_{32}BrF_3N_4O_5$: 712.2; found 713.1 [M+H]$^+$, $t_R$=2.97 min (Method 4). $^1$H NMR (400 MHz, DMSO-d$_6$) δ 10.35 (s, 1H), 9.09 (s, 2H), 8.47-8.16 (m, 2H), 7.63 (br s, 2H), 7.53 (d, J=7.8 Hz, 1H), 7.43 (br s, 2H), 7.40-7.34 (m, 2H), 7.28-7.14 (m, 2H), 4.73 (s, 1H), 4.63 (s, 1H), 3.99 (s, 1H), 3.95 (s, 1H), 3.85-3.82 (m, 5H), 1.42 (s, 5H), 1.32 (s, 4H).

Compounds 16, 17, 77-81, and 94-96 were prepared from tert-butyl N-(4-(5-bromopyrimidin-2-yl)benzyl)-N-(4-(2-(4-methoxy-2-(trifluoromethyl)phenyl)-acetamido) benzoyl)glycinate INT-5 using General Procedures 1 then 4.

1-(3-(4-methoxy-2-(trifluoromethyl)phenyl)propanoyl)piperidine-4-carboxylic acid (carboxylic acid for Compound 18) was prepared from methyl piperidine-4-carboxylate and 3-(4-methoxy-2-(trifluoromethyl)phenyl)propanoic acid using General Procedures 2 then 3.

1-(2-(4-methoxy-2-(trifluoromethyl)phenyl)acetyl)piperidine-4-carboxylic acid (carboxylic acid for Compound 19) was prepared from methyl piperidine-4-carboxylate and 2-(4-methoxy-2-(trifluoromethyl)phenyl)acetic acid using General Procedures 2 then 3.

3-chloro-4-(2-(4-methoxy-2-(trifluoromethyl)phenyl)acetamido)-benzoic acid (carboxylic acid for Compound 20) was prepared from 2-(4-methoxy-2-(trifluoromethyl)phenyl)acetyl chloride and 4-amino-3-chlorobenzoic acid using General Procedure 5.

3-methoxy-4-(2-(4-methoxy-2-(trifluoromethyl)phenyl)acetamido)-benzoic acid (carboxylic acid for Compound 21) was prepared from 2-(4-methoxy-2-(trifluoromethyl)phenyl)acetyl chloride and 4-amino-3-methoxybenzoic acid using General Procedure 5.

2-methoxy-4-(2-(4-methoxy-2-(trifluoromethyl)phenyl)acetamido)-benzoic acid (carboxylic acid for Compound 22) was prepared from 2-(4-methoxy-2-(trifluoromethyl)phenyl)acetyl chloride and 4-amino-2-methoxybenzoic acid using General Procedure 5.

5-(2-(4-methoxy-2-(trifluoromethyl)phenyl)acetamido) picolinic acid (carboxylic acid for Compound 23) was prepared from 2-(4-methoxy-2-(trifluoromethyl)phenyl)acetyl chloride and 5-aminopicolinic acid using General Procedure 5.

2-chloro-4-(2-(4-methoxy-2-(trifluoromethyl)phenyl)acetamido)-benzoic acid (carboxylic acid for Compound 24) was prepared from 2-(4-methoxy-2-(trifluoromethyl)phenyl)acetyl chloride and 4-amino-2-chlorobenzoic acid using General Procedure 5.

3-cyano-4-(2-(4-methoxy-2-(trifluoromethyl)phenyl)acetamido)-benzoic acid (carboxylic acid for Compound 32) was prepared from 2-(4-methoxy-2-(trifluoromethyl)phenyl)acetyl chloride and 4-amino-3-cyanobenzoic acid using General Procedure 5.

2-bromo-4-(2-(4-methoxy-2-(trifluoromethyl)phenyl)acetamido)-benzoic acid (carboxylic acid for Compound 33) was prepared from 2-(4-methoxy-2-(trifluoromethyl)phenyl)acetyl chloride and methyl 4-amino-2-bromobenzoate using General Procedures 5 then 3.

6-(2-(4-methoxy-2-(trifluoromethyl)phenyl)acetamido) nicotinic acid (carboxylic acid for Compound 46) was prepared from 2-(4-methoxy-2-(trifluoromethyl)phenyl) acetyl chloride and methyl 6-aminonicotinate using General Procedures 5 then 3.

6-(2-(4-methoxyphenyl)acetamido)pyridazine-3-carboxylic acid (carboxylic acid for Compound 57) was prepared from 2-(4-methoxyphenyl)acetyl chloride and methyl 6-aminopyridazine-3-carboxylate using General Procedures 5 then 3.

6-(2-(4-methoxy-2-(trifluoromethyl)phenyl)acetamido) pyridazine-3-carboxylic acid (carboxylic acid for Compound 58) was prepared from 2-(4-methoxy-2-(trifluoromethyl)phenyl)acetyl chloride and methyl 6-aminopyridazine-3-carboxylate using General Procedures 5 then 3.

5-(2-(4-methoxy-2-(trifluoromethyl)phenyl)acetamido) pyrazine-2-carboxylic acid (carboxylic acid for Compound 64) was prepared from 2-(4-methoxy-2-(trifluoromethyl) phenyl)acetyl chloride and methyl 5-aminopyrazine-2-carboxylate using General Procedures 5 then 3.

2,3-dichloro-4-(2-(4-methoxy-2-(trifluoromethyl)phenyl) acetamido)-benzoic acid (carboxylic acid for Compound 67) was prepared from 2-(4-methoxy-2-(trifluoromethyl)phenyl)acetyl chloride and 4-amino-2,3-dichlorobenzoic acid using General Procedure 5.

2,3-dichloro-4-(2-(4-methoxyphenyl)acetamido)benzoic acid (carboxylic acid for Compound 68) was prepared from 2-(4-methoxyphenyl)acetyl chloride and 4-amino-2,3-dichlorobenzoic acid using General Procedure 5.

3-(2-(4-methoxyphenyl)acetamido)propanoic acid (carboxylic acid for Compound 72) was prepared from tert-butyl 3-aminopropanoate and 2-(4-methoxyphenyl)acetic acid using General Procedures 2 then 4.

(2-(4-methoxyphenyl)acetyl)-L-proline (carboxylic acid for Compound 73) was prepared from tert-butyl A-prolinate and 2-(4-methoxyphenyl)acetic acid using General Procedures 2 then 4.

1-(2-(4-methoxyphenyl)acetyl)azetidine-3-carboxylic acid (carboxylic acid for Compound 82) was prepared from tert-butyl azetidine-3-carboxylate and 2-(4-methoxyphenyl)acetic acid using General Procedures 2 then 4.

5-(2-(4-methoxyphenyl)acetamido)furan-2-carboxylic acid (carboxylic acid for Compound 83) was prepared from methyl 5-aminofuran-2-carboxylate and 2-(4-methoxyphenyl)acetyl chloride using General Procedures 5 then 3.

5-(2-(4-methoxyphenyl)acetamido)thiophene-2-carboxylic acid (carboxylic acid for Compound 84) was prepared from methyl 5-aminothiophene-2-carboxylate and 2-(4-methoxyphenyl)acetyl chloride using General Procedures 5 then 3.

5-(2-(4-methoxyphenyl)acetamido)-1,3,4-thiadiazole-2-carboxylic acid (carboxylic acid for Compound 97) was prepared from methyl 5-amino-1,3,4-thiadiazole-2-carboxylate and 2-(4-methoxyphenyl)acetyl chloride using General Procedures 5 then 3.

(2-(4-methoxyphenyl)acetyl)-L-alanine (carboxylic acid for Compound 98) was prepared from tert-butyl L-alaninate and 2-(4-methoxyphenyl)acetic acid using General Procedures 2 then 4.

(2-(4-methoxyphenyl)acetyl)-L-valine (carboxylic acid for Compound 99) was prepared from tert-butyl A-valinate and 2-(4-methoxyphenyl)acetic acid using General Procedures 2 then 4.

5-(2-(4-methoxy-phenyl)acetamido)pyrimidine-2-carboxylic acid (carboxylic acid for Compound 105) was prepared from 2-(4-methoxy-phenyl)acetyl chloride and methyl 5-aminopyrimidine-2-carboxylate using General Procedures 5 then 3.

5-(2-(4-methoxy-2-(trifluoromethyl)phenyl)acetamido)pyrimidine-2-carboxylic acid (carboxylic acid for Compound 106) was prepared from 2-(4-methoxy-2-(trifluoromethyl)phenyl)acetyl chloride and methyl 5-aminopyrimidine-2-carboxylate using General Procedures 5 then 3.

2-(2-(4-methoxyphenyl)acetamido)cyclopentane-1-carboxylic acid (carboxylic acid for Compound 107) was prepared from 2-(4-methoxyphenyl)acetyl chloride and 2-aminocyclopentane-1-carboxylic acid using General Procedure 5.

(2-(4-methoxyphenyl)acetyl)-L-tyrosine (carboxylic acid for Compound 108) was prepared from methyl L-tyrosinate and 2-(4-methoxyphenyl)acetyl chloride using General Procedures 5 then 3.

3-(2-(4-methoxyphenyl)acetamido)cyclopentane-1-carboxylic acid (carboxylic acid for Compound 109) was prepared from 2-(4-methoxyphenyl)acetyl chloride and 3-aminocyclopentane-1-carboxylic acid using General Procedure 5.

2-(2-(4-methoxyphenyl)acetamido)oxazole-5-carboxylic acid (carboxylic acid for Compound 110) was prepared from 2-(4-methoxyphenyl)acetyl chloride and 2-aminooxazole-5-carboxylic acid using General Procedure 5.

(2-(4-methoxyphenyl)acetyl)-L-phenylalanine (carboxylic acid for Compound 114) was prepared from methyl L-phenyl alaninate and 2-(4-methoxyphenyl)acetyl chloride using General Procedures 5 then 3.

(2-(4-methoxyphenyl)acetyl)-D-alanine (carboxylic acid for Compound 115) was prepared from tert-butyl D-alaninate and 2-(4-methoxyphenyl)acetic acid using General Procedures 2 then 4.

(R)-2-(2-(4-methoxyphenyl)acetamido)butanoic acid (carboxylic acid for Compound 116) was prepared from tert-butyl (R)-2-aminobutanoate and 2-(4-methoxyphenyl)acetic acid using General Procedures 2 then 4.

Compounds 18-24, 32, 33, 46, 57, 58, 64, 67, 68, 72, 73, 82-84, 97-99, 105-110, 114-116 were prepared from tert-butyl (4-(5-((1'r,4'r)-4'-ethyl-[1,1'-bi(cyclohexan)]-3-en-4-yl)pyrimidin-2-yl)benzyl)glycinate INT-2 with the appropriate carboxylic acid using General Procedures 2 then 4.

Methyl 2-bromo-4-(2-(4-methoxy-2-(trifluoromethyl)phenyl)acetamido)benzoate

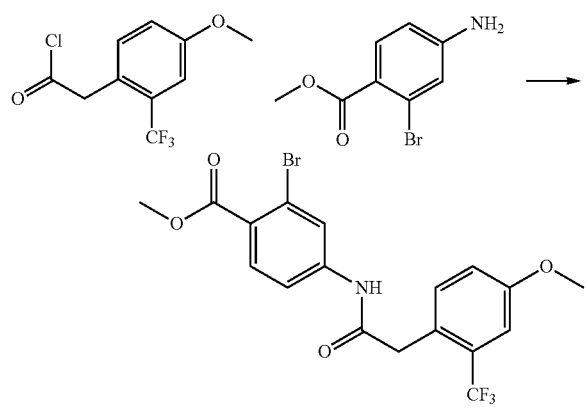

Prepared using General Procedure 5 from 2-(4-methoxy-2-(trifluoromethyl)phenyl)acetyl chloride (800 mg, 3.17 mmol) and methyl 4-amino-2-bromobenzoate (730 mg, 3.17 mmol) to give 550 mg (33%) of methyl 2-bromo-4-(2-(4-methoxy-2-(trifluoromethyl)phenyl)acetamido)benzoate. LCMS-ESI (m/z) calculated for $C_{18}H_{15}BrF_3NO_4$: 445.0, found 446.0 [M+H]$^+$, $t_R$=2.49 minutes (Method 4).

2-cyano-4-(2-(4-methoxy-2-(trifluoromethyl)phenyl)acetamido)benzoic acid

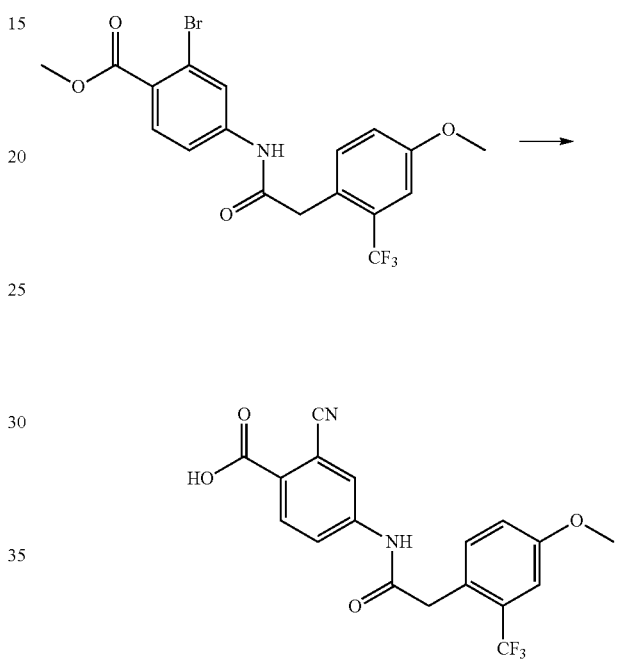

Methyl 2-bromo-4-(2-(4-methoxy-2-(trifluoromethyl)phenyl)-acetamido) benzoate (290 mg, 0.65 mmol) in NMP (7.22 mL) was treated with copper cyanide (87 mg, 0.975 mmol) and heated to 150° C. for 18 hours. Water (10 mL) was added to the mixture and the layers were separated. The aqueous layer was extracted with EA (2×10 mL). The combined organic layers were dried over magnesium sulfate, filtered, concentrated, and purified by column chromatography (0-60% EA in iso-hexanes) to give 0.140 g (52%) methyl 2-cyano-4-(2-(4-methoxy-2-(trifluoromethyl)phenyl)acetamido)benzoate.

Prepared using General Procedure 5. To a solution of methyl 2-cyano-4-(2-(4-methoxy-2-(trifluoromethyl)phenyl)-acetamido)benzoate (0.140 g, 0.357 mmol) in THF (2.55 mL) was added 0.4 M LiOH (1.37 mL, 0.54 mmol) at 0° C. After 4 hours, the reaction mixture was evaporated under reduced pressure to give 0.138 g (99%) of 2-cyano-4-(2-(4-methoxy-2-(trifluoromethyl)phenyl)-acetamido) benzoic acid.

Tert-butyl 2-(2-cyano-N-(4-(5-((1'r,4'r)-4'-ethyl-[1,1'-bi(cyclohexan)]-3-en-4-yl)pyrimidin-2-yl)benzyl)-4-(2-(4-methoxy-2-(trifluoromethyl)phenyl)-acetamido)benzamido)acetate

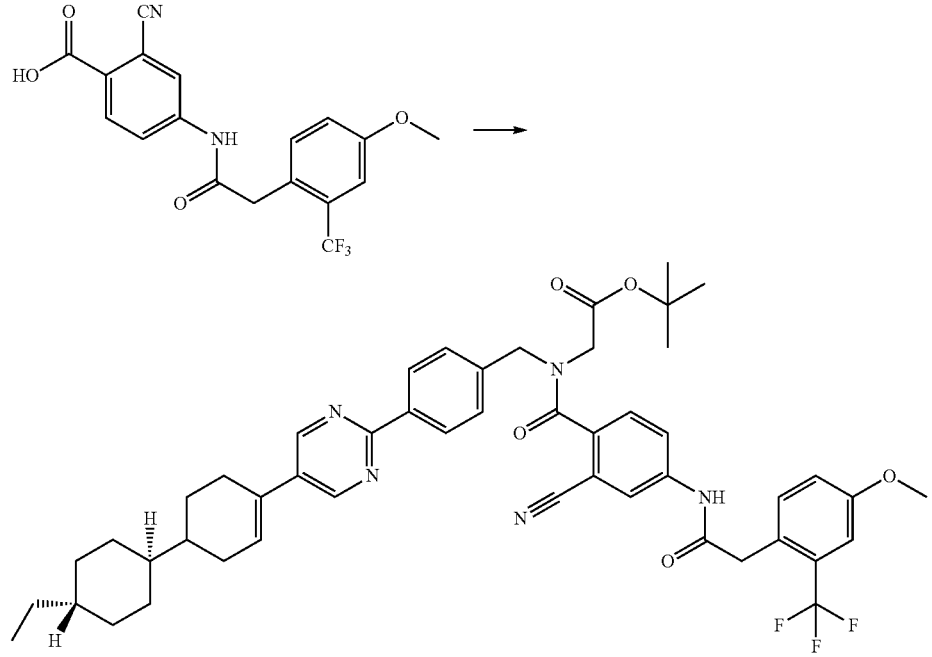

Prepared using General Procedure 2. To a stirring mixture of tert-butyl (4-(5-((1'r,4'r)-4'-ethyl-[1,1'-bi(cyclohexan)]-3-en-4-yl)pyrimidin-2-yl)benzyl)-glycinate INT-2 (0.117 g, 0.238 mmol) and 2-cyano-4-(2-(4-methoxy-2-(trifluoromethyl)phenyl)acetamido) benzoic acid (0.357 g, 0.135 mmol) in DMF (3 mL) at 0° C. was added DIEA (0.246 mL, 1.43 mmol) followed by HATU (0.286 g, 0.714 mmol) and the reaction was stirred at RT for 18 h. EA (10 mL) and 1M HCl (10 mL) were added and the layers were separated. The aqueous layer was extracted with EA (10 mL) and the combined organic layers were washed with saturated sodium bicarbonate (10 mL) and brine (10 mL). The organic layer was dried over magnesium sulfate, filtered, concentrated, and purified by column chromatography (0-60% EA in DCM/iso-hexanes) to give 0.109 g (50%) of tert-butyl 2-(2-cyano-N-(4-(5-((1'r,4')-4'-ethyl-[1,1'-bi(cyclohexan)]-3-en-4-yl)pyrimidin-2-yl)benzyl)-4-(2-(4-methoxy-2-(trifluoromethyl)phenyl)acetamido)benzamido)-acetate.

LCMS-ESI (m/z) calculated for $C_{49}H_{54}F_3N_5O_5$: 849.4, no mass observed, $t_R$=3.48 minutes (Method 4).

N-(2-cyano-4-(2-(4-methoxy-2-(trifluoromethyl)phenyl)acetamido)benzoyl)-N-(4-(5-((1'r,4'r)-4'-ethyl-[1,1'-bi(cyclohexan)]-3-en-4-yl)pyrimidin-2-yl)benzyl)glycine Compound 47

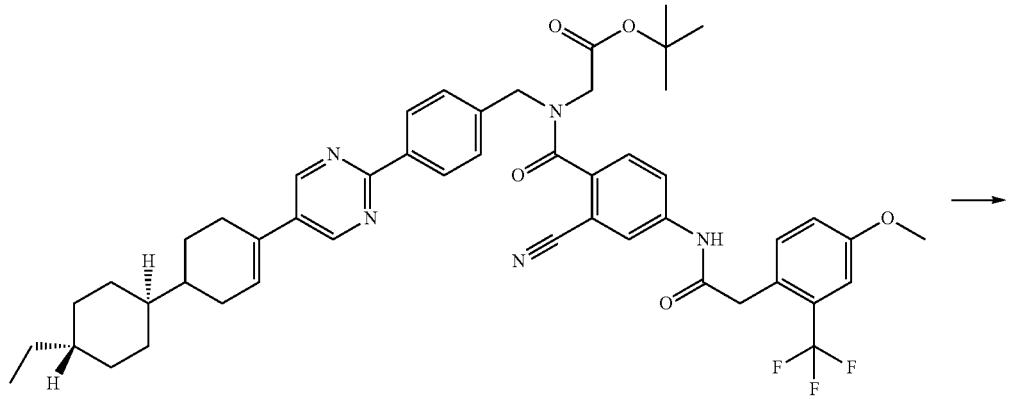

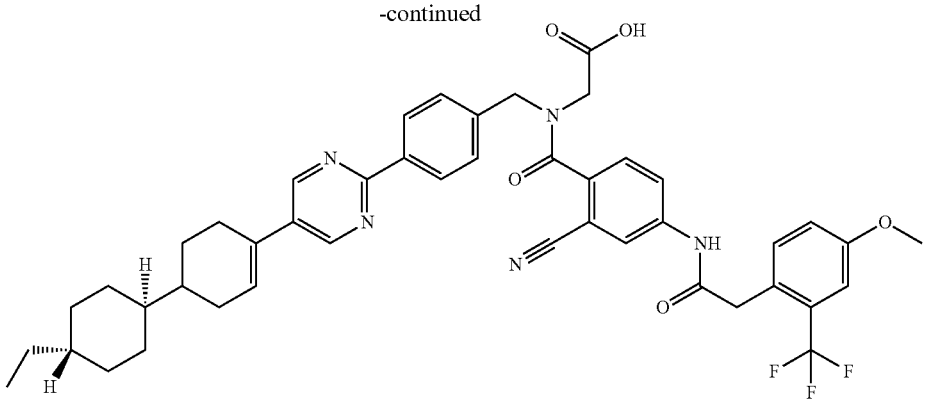

A sample of tert-butyl 2-(2-cyano-N-(4-(5-((1'r,4'r)-4'-ethyl-[1, 1'-bi(cyclohexan)]-3-en-4-yl)pyrimidin-2-yl)benzyl)-4-(2-(4-methoxy-2-(trifluoro-methyl)phenyl)acetamido) benzamido)acetate (0.047 g, 0.056 mmol) was stirred in formic acid (2 mL, 0.056 mmol) for 7 h at room temperature. DCM (5 mL) and water (5 mL) were added and the layers were separated. The organic layer was collected and evaporated under reduced pressure and purified by column chromatography (0-50% EA (1% acetic) in DCM/iso-hexanes) to provide 0.006 g (13%) of N-(2-cyano-4-(2-(4-methoxy-2-(trifluoromethyl)phenyl)acetamido)-benzoyl)-N-(4-(5-((1'r,4'r)-4'-ethyl-[1,1'-bi(cyclohexan)]-3-en-4-yl)pyrimidin-2-yl)benzyl)glycine Compound 47. LCMS-ESI (m/z) calculated for $C_{45}H_{46}F_3N_5O_5$: 793.4, found 794 $[M+H]^+$, $t_R$=11.42 minutes (Method 3).

Compounds 25-28, 30, 31, 34-45, 48-51, 53, 55, 56, 65, 66, 69, 74-76, 85, 92, 93 and 153 were prepared from tert-butyl N-(4-aminobenzoyl)-N-(4-(5-((1'r,4'r)-4'-ethyl-[1, 1'-bi(cyclohexan)]-3-en-4-yl)pyrimidin-2-yl)benzyl)glycinate INT-3 with the appropriate carboxylic acid using General Procedures 2 then 4.

4-(2-(4-methoxyphenyl)acetamido)benzoic acid

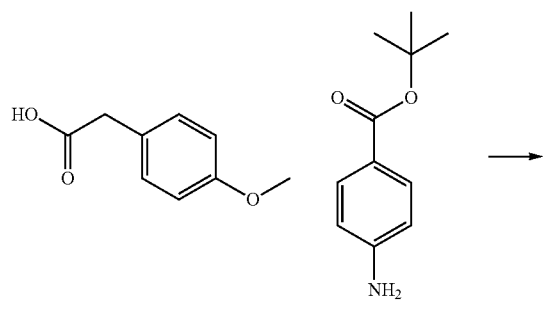

Prepared using General Procedure 2. To a stirring solution of 2-(4-methoxyphenyl)acetic acid (1 g, 6.02 mmol), tert-butyl 4-aminobenzoate (1.16 g, 6.02 mmol) and triethylamine (2.2 mL, 15.04 mmol) in DMF (20 mL) was added HATU (2.477 g, 6.32 mmol). After 2 h, additional 2-(4-methoxyphenyl)acetic acid (100 mg, 0.60 mmol) and HATU (247 mg, 0.63 mmol) were added. After a further 1 h, the mixture was diluted with EA (50 mL) and washed successively with $NaHCO_3$ (2×50 mL), 1 M HCl (100 mL) and brine (50 mL), dried over $MgSO_4$ and solvents evaporated. The residue was taken into DCM (30 mL) and stirred with TFA (15 mL). After 4 h, the mixture was washed with water (50 mL) and split through a hydrophobic frit. Solvents were evaporated to afford 1.02 g (59%) of 4-(2-(4-methoxyphenyl)acetamido)benzoic acid. LCMS-ESI (m/z) calculated for $C_{16}H_{15}NO_4$: 285.1; found 286.0 $[M+H]^+$, $t_R$=1.70 min (Method 4). $^1$H NMR (400 MHz, DMSO-$d_6$) δ 12.70 (s, 1H), 10.49 (s, 1H), 8.00-7.81 (m, 2H), 7.80-7.60 (m, 2H), 7.37-7.14 (m, 2H), 6.99-6.82 (m, 2H), 3.73 (s, 3H), 3.61 (s, 2H).

Tert-butyl 2-(N-(4-(5-((1'r,4'r)-4'-ethyl-[1,1'-bi(cyclohexan)]-3-en-4-yl)pyrimidin-2-yl)benzyl)-4-(2-(4-methoxyphenyl)acetamido)benzamido)acetate

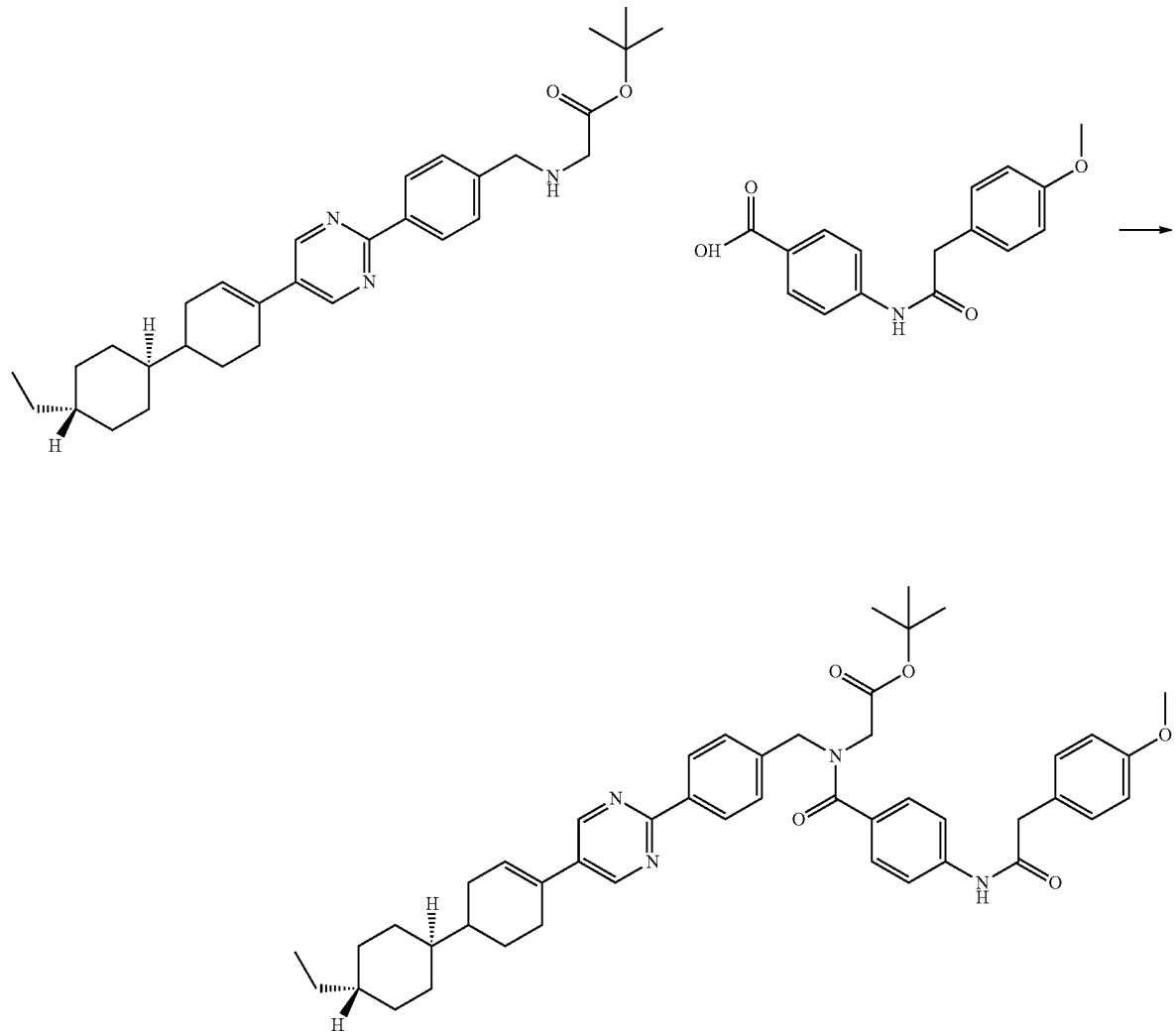

Prepared using General Procedure 2. To a stirring mixture of tert-butyl (4-(5-((1'r,4'r)-4'-ethyl-[1,1'-bi(cyclohexan)]-3-en-4-yl)pyrimidin-2-yl)benzyl)-glycinate INT-2 (2 g, 4.08 mmol), DIEA (2.1 mL, 12.25 mmol) and 4-(2-(4-methoxyphenyl)-acetamido)benzoic acid (1.28 g, 4.49 mmol) in DMF (40 mL) and DCM (20 mL), was added HATU (1.96 g, 4.90 mmol). After 16 h, solvents were evaporated and the residue re-slurried from ACN (100 mL). Column chromatography (EA/DCM/iso-hexane) gave 1.905 g (62%) of tert-butyl 2-(N-(4-(5-((1'r,4'r)-4'-ethyl-[1,1'-bi(cyclohexan)]-3-en-4-yl)pyrimidin-2-yl)benzyl)-4-(2-(4-methoxyphenyl)acetamido)benzamido)acetate. LCMS-ESI (m/z) calculated for $C_{47}H_{56}N_4O_5$: 756.4; no m/z observed, $t_R$=3.47 min (Method 4).

2-(N-(4-(5-((1'r,4'r)-4'-ethyl-[1,1'-bi(cyclohexan)]-3-en-4-yl)pyrimidin-2-yl)benzyl)-4-(2-(4-methoxyphenyl)acetamido)benzamido)acetic acid Compound 29

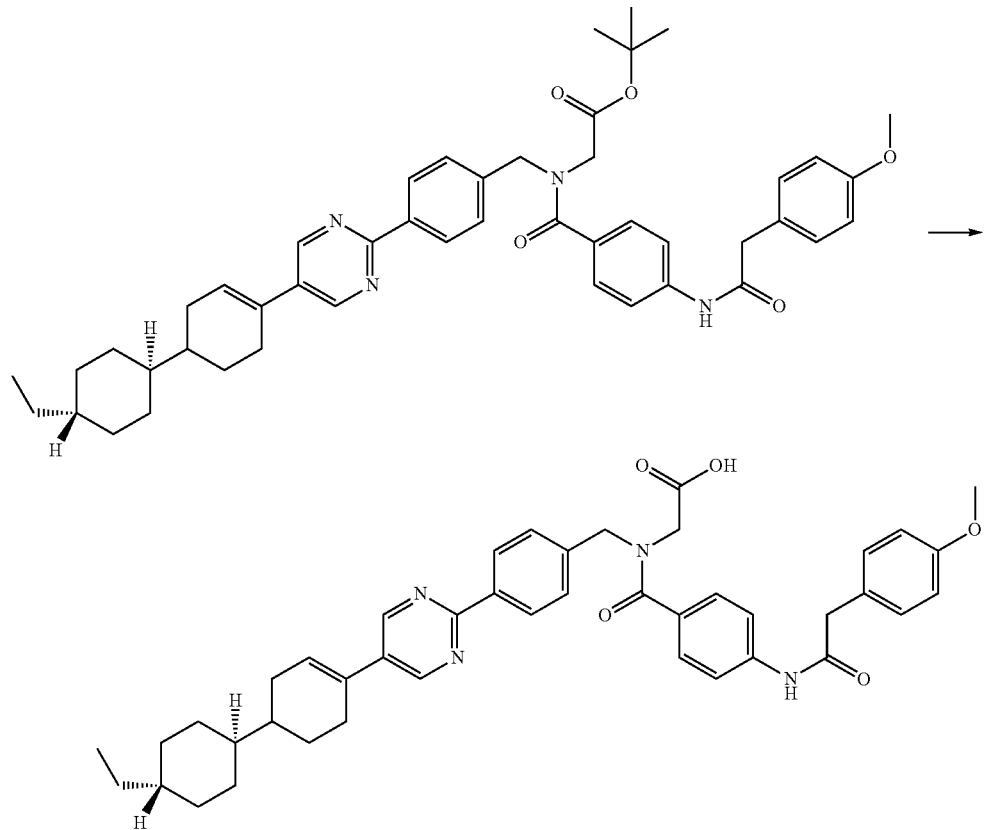

Prepared using General Procedure 4. To a stirring mixture of tert-butyl 2-(N-(4-(5-((1'r,4'r)-4'-ethyl-[1,1'-bi(cyclohexan)]-3-en-4-yl)pyrimidin-2-yl)-benzyl)-4-(2-(4-methoxyphenyl)acetamido)benzamido)acetate (1.9 g, 2.51 mmol) in DCM (50 mL) was added TFA (20 mL). After 2 h, solvents were evaporated and the residue re-slurried from ACN (100 mL) to afford 1.5 g (85%) of 2-(N-(4-(5-((1'r,4'r)-4'-ethyl-[1,1'-bi(cyclohexan)]-3-en-4-yl)pyrimidin-2-yl)benzyl)-4-(2-(4-methoxyphenyl)acetamido)benzamido) acetic acid Compound 29. LCMS-ESI (m/z) calculated for $C_{43}H_{48}N_4O_5$: 700.4; found 701.1 [M+H]$^+$, $t_R$=3.30 min (Method 4).

N-(4-(5-((1'r,4'r)-4'-ethyl-[1,1'-bi(cyclohexan)]-3-en-4-yl)pyrimidin-2-yl)benzyl)-4-(2-(4-methoxyphenyl)acetamido)-N-(2-(methylsulfonamido)-2-oxoethyl)benzamide Compound 52

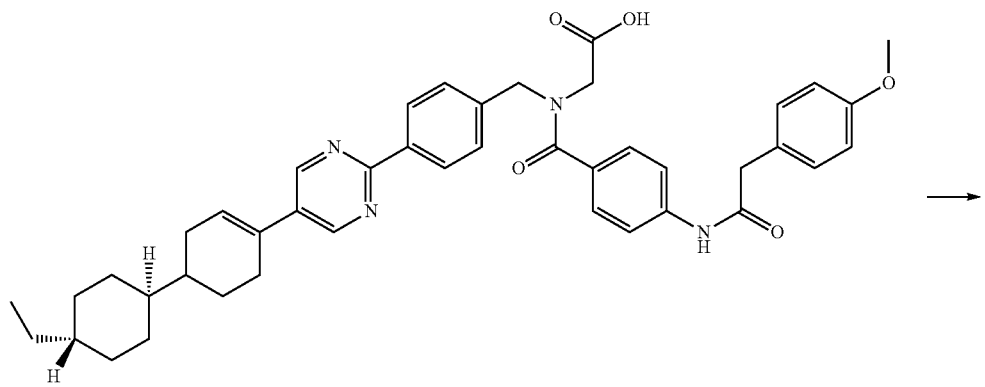

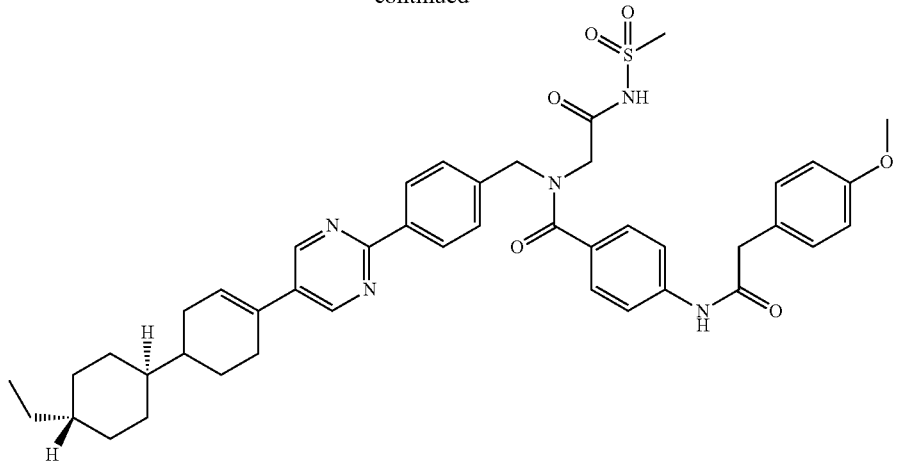

To a stirring solution of 2-(N-(4-(5-((1'r,4'r)-4'-ethyl-[1,1'-bi(cyclohexan)]-3-en-4-yl)pyrimidin-2-yl)benzyl)-4-(2-(4-methoxyphenyl)-acetamido)benzamido)acetic acid Compound 29 (1.3 g, 1.855 mmol) in THF (25 mL) at 40° C. was added 1,1'-carbonyldiimidazole (1.203 g, 7.42 mmol). After 1.5 h, the mixture was treated with a solution of methanesulfonamide (1.080 g, 11.13 mmol) and 1,8-diazabicyclo[5.4.0]undec-7-ene (1.7 mL, 11.13 mmol) in THF (3 mL). After 4 h, the mixture was allowed to cool then diluted with DCM (50 mL), washed successively with 1 M HCl (50 mL) and brine (50 mL), dried over MgSO$_4$ and solvents evaporated. Column chromatography (DCM/MeOH/AcOH) gave 1.05 g (73%) of N-(4-(5-((1'r,4'r)-4'-ethyl-[1,1'-bi(cyclohexan)]-3-en-4-yl)pyrimidin-2-yl)benzyl)-4-(2-(4-methoxyphenyl)acetamido)-N-(2-(methylsulfonamido)-2-oxoethyl)benzamide Compound 52. LCMS-ESI (m/z) calculated for $C_{44}H_{51}N_5O_6S$: 777.4; found 778.1 [M+H]$^+$, $t_R$=10.83 min (Method 3). $^1$H NMR (400 MHz, DMSO-d$_6$) δ 11.85 (br s, 1H), 10.31 (s, 1H), 8.95 (s, 2H), 8.51-8.22 (m, 2H), 7.67-7.63 (m, 2H), 7.56-7.31 (m, 4H), 7.25-7.22 (m, 2H), 6.93-6.83 (m, 2H), 6.46 (dt, J=5.3, 2.4 Hz, 1H), 4.72 (s, 1H), 4.64 (s, 1H), 4.09 (s, 1H), 3.97 (s, 1H), 3.72 (s, 3H), 3.57 (s, 2H), 3.25 (s, 2H), 3.18 (s, 1H), 2.56-2.26 (m, 3H), 2.04-1.89 (m, 2H), 1.87-1.70 (m, 4H), 1.41-1.27 (m, 2H), 1.24-0.91 (m, 6H), 0.90-0.81 (m, 5H).

Compounds 54 and 61 were prepared from Compound 29 using General Procedures 2 then 4.

Compounds 59, 60, and 62 were prepared from Compound 29 using General Procedures 2 then 3.

Tert-butyl N-(5-aminopyrazine-2-carbonyl)-N-(4-(5-(1'r,4'r)-4'-ethyl-[1,1'-bi(cyclohexan)]-3-en-4-yl)pyrimidin-2-yl)benzyl)glycinate

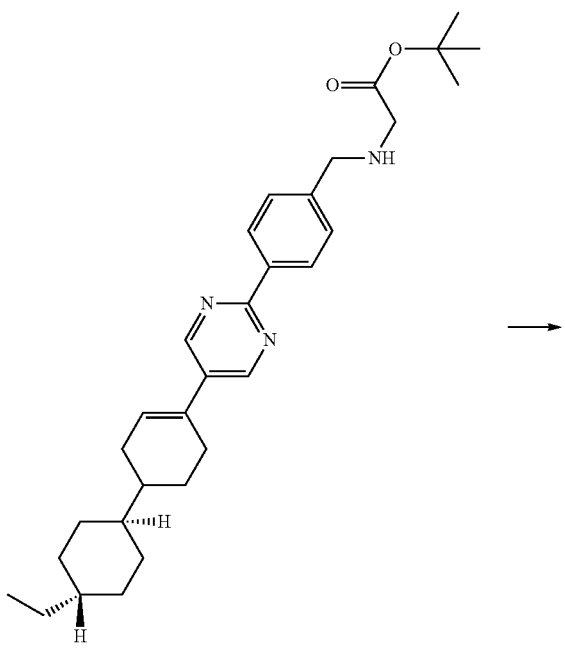

217

-continued

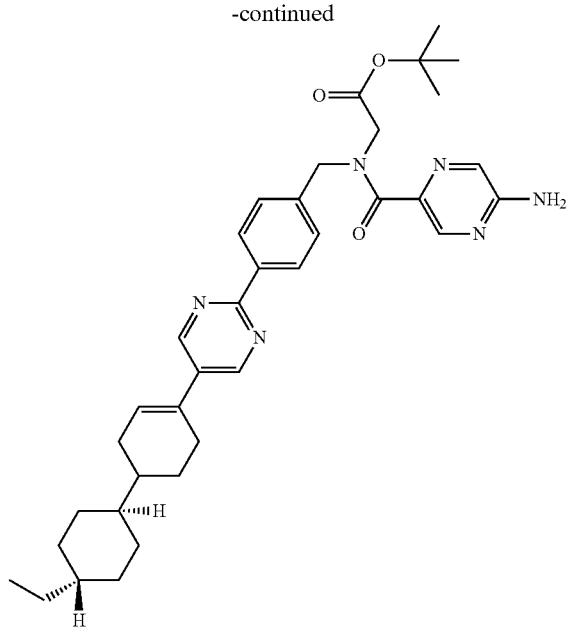

218

Tert-butyl N-(4-(5-(1'r,4'r)-4'-ethyl-[1,1'-bi(cyclohexan)]-3-en-4-yl)pyrimidin-2-yl)benzyl)-N-(5-(2-(4-methoxyphenyl)acetamido)pyrazine-2-carbonyl) glycinate

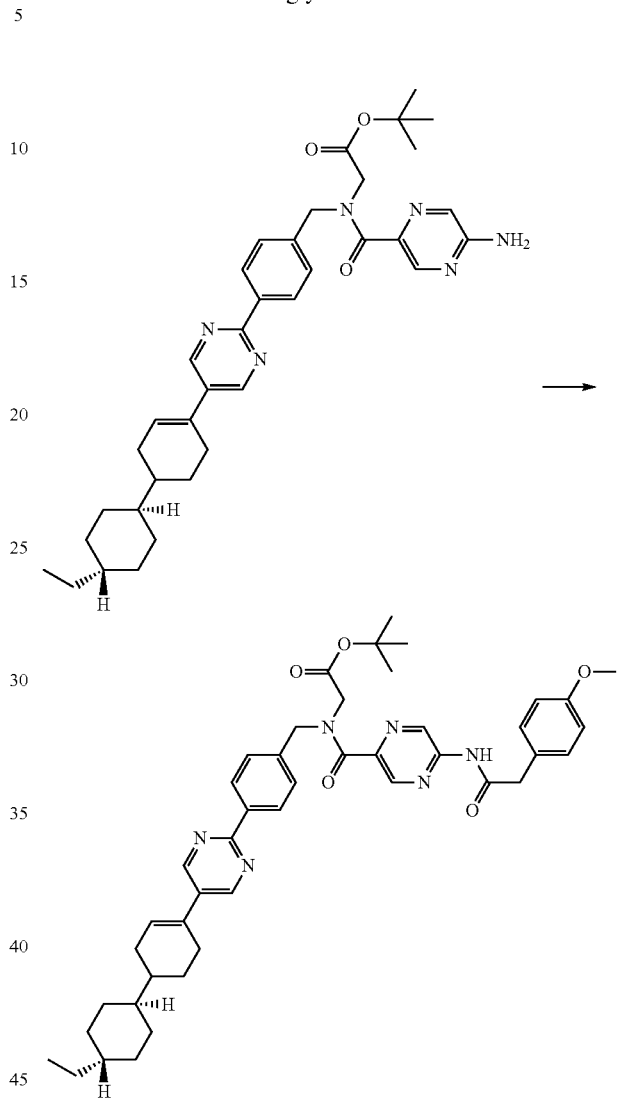

To a solution of 5-aminopyrazine-2-carboxylic acid (225.4 mg, 1.62 mmol) and DIEA (418.7 mg, 3.24 mmol) in DMF (10 mL) was added HATU (381.1 mg, 1.62 mmol). The reaction mixture was stirred 1 h at RT and tert-butyl (4-(5-((1'r,4'r)-4'-ethyl-[1,1'-bi(cyclohexan)]-3-en-4-yl)pyrimidin-2-yl)benzyl)glycinate INT-2 (530.0 mg, 1.08 mmol) was added. The reaction mixture stirred at room temperature for 3 h. The reaction mixture was diluted with EA then washed with saturated aqueous NaHCO$_3$ and water. The organic layer was dried over anhydrous sodium sulfate, concentrated, and purified by chromatography (EA/hexanes from 0 to 70%) to provide 628 mg (95%) of tert-butyl N-(5-aminopyrazine-2-carbonyl)-N-(4-(5-((1'r,4'r)-4'-ethyl-[1,1'-bi(cyclohexan)]-3-en-4-yl)pyrimidin-2-yl)benzyl) glycinate as a white solid. LCMS-ESI (m/z) calculated for $C_{36}H_{46}N_6O_3$: 610.8; found 611.1[M+H]$^+$, $t_R$=4.873 minutes (Method 2).

To a solution of tert-butyl N-(5-aminopyrazine-2-carbonyl)-N-(4-(5-((1'r,4'r)-4'-ethyl-[1,1'-bi(cyclohexan)]-3-en-4-yl)pyrimidin-2-yl)benzyl)glycinate (600.0 mg, 0.98 mmol) in anhydrous THF (20 mL) was added sodium hydride (47.04 mg, 1.96 mmol, 60% dispersion in mineral oil). The reaction mixture stirred at 0° C. for 2 h and then at RT for 1 h. The 2-(4-methoxyphenyl)acetyl chloride (542.78 mg, 2.94 mmol) was added to above solution at 0° C. and the reaction mixture was allowed to warm to RT. The mixture stirred was stirred for 18 h. After evaporated THF solvent, the reaction mixture was diluted with EA then washed with saturated aqueous NaHCO$_3$ and water. The organic layer was dried over anhydrous sodium sulfate, concentrated, and purified by chromatography (EA/hexanes from 0 to 70%) to provide 350 mg (47%) of tert-butyl N-(4-(5-((1'r,4'r)-4'-ethyl-[1,1'-bi(cyclohexan)]-3-en-4-yl)pyrimidin-2-yl)benzyl)-N-(5-(2-(4-methoxy-phenyl)acetamido)pyrazine-2-carbonyl)glycinate. LCMS-ESI (m/z) calculated for $C_{45}H_{54}N_6O_5$: 758.9; found 759.3 [M+H]$^+$, $t_R$=5.053 minutes (Method 2).

N-(4-(5-((1'r,4'r)-4'-ethyl-[1,1'-bi(cyclohexan)]-3-en-4-yl)pyrimidin-2-yl)benzyl)-N-(5-(2-(4-methoxyphenyl)acetamido)pyrazine-2-carbonyl)glycine Compound 63

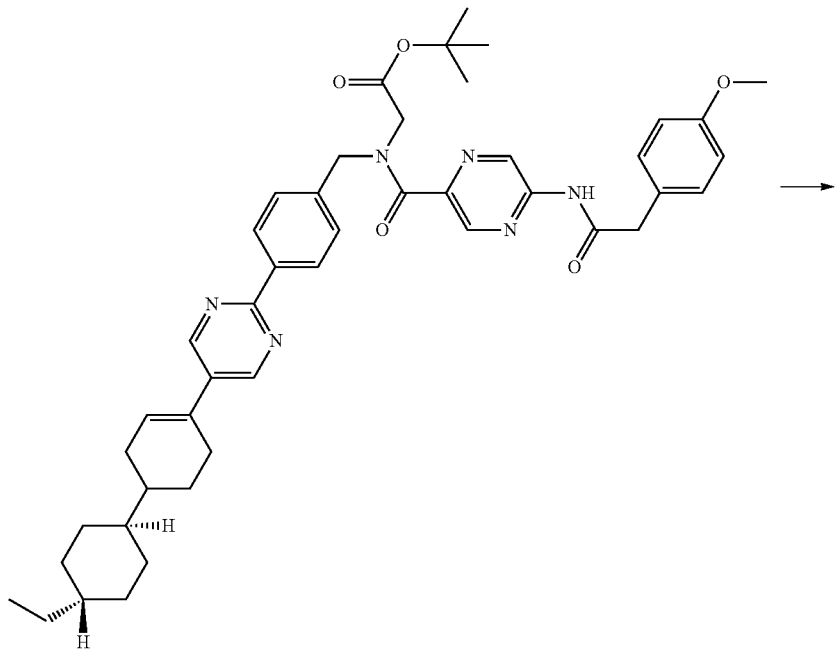

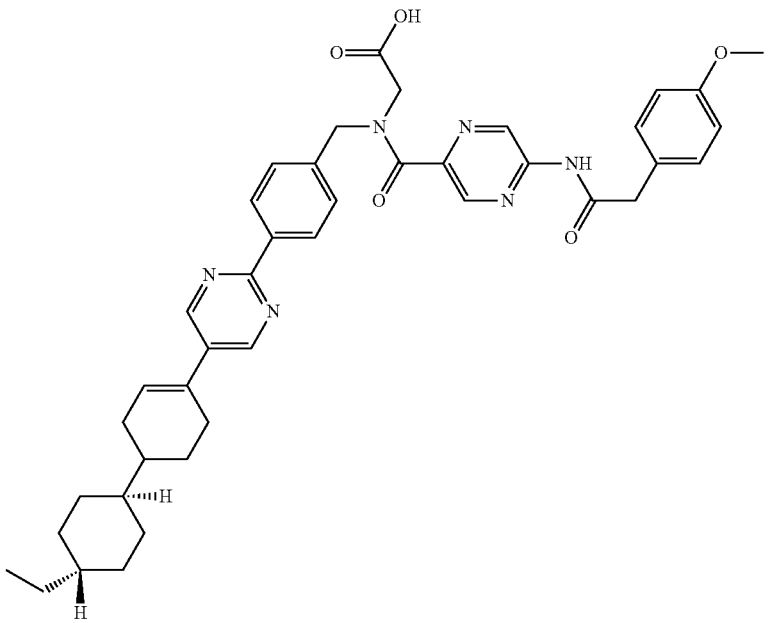

To a solution of tert-butyl N-(4-(5-((1'r,4'r)-4'-ethyl-[1,1'-bi(cyclohexan)]-3-en-4-yl)pyrimidin-2-yl)benzyl)-N-(5-(2-(4-methoxyphenyl)-acetamido)pyrazine-2-carbonyl)glycinate (350.0 mg, 0.461 mmol) in DCM (25 mL) was added TFA (1 mL) at room temperature and the mixture was stirred for 4 hours. The solvent was removed and the residue was diluted with EA and washed with saturated aqueous NaHCO$_3$ and H$_2$O. The organic layer was dried over anhydrous sodium sulfate, concentrated, and purified by chromatography (DCM/MeOH from 0 to 10%) to provide 183 mg (57%) of N-(4-(5-((1'r,4'r)-4'-ethyl-[1,1'-bi(cyclohexan)]-3-en-4-yl)pyrimidin-2-yl)benzyl)-N-(5-(2-(4-methoxyphenyl)-acetamido)pyrazine-2-carbonyl)glycine Compound 63. LCMS-ESI (m/z) calculated for $C_{41}H_{46}N_6O_5$: 702.8; found 703.0 [M+H]$^+$, $t_R$=8.797 minutes (Method 1).

221

Tert-butyl N-(4-(5-bromopyrimidin-2-yl)benzyl)-N-(4-(2-(4-methoxyphenyl)-acetamido)benzoyl)glycinate (INT-6)

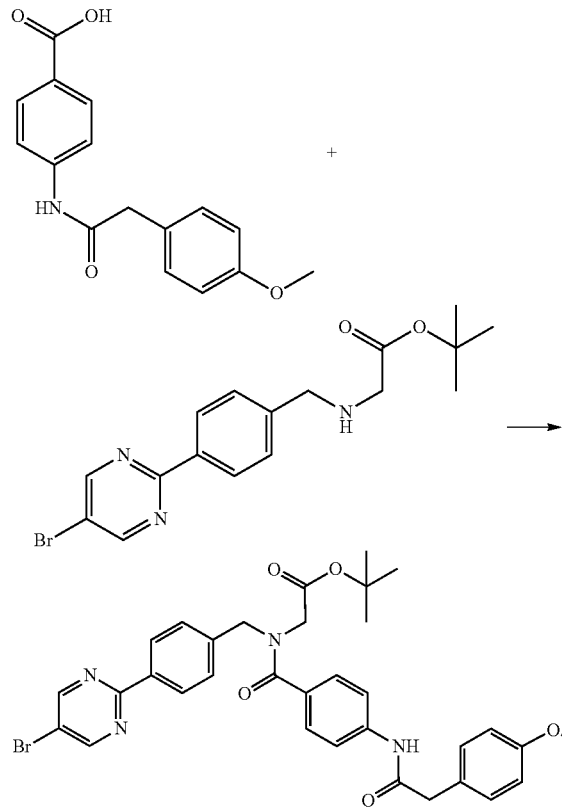

Prepared using General Procedure 2. A stirred solution of 4-(2-(4-methoxyphenyl)acetamido)benzoic acid (1.0 g, 3.50 mmol), tert-butyl (4-(5-bromopyrimidin-2-yl)benzyl)glycinate INT-1 (1.99 g, 80% pure, 4.2 mmol) and DIEA (1.35 g, 10.50 mmol) in DMF (20 mL) was treated with HATU (1.23 g, 5.25 mmol) added portionwise. The reaction mixture was stirred at RT for 2 h then diluted with EA (50 mL)). The combined organic layers were washed with saturated sodium bicarbonate solution (2×50 mL) dried over magnesium sulfate and concentrated. The crude product was purified by column chromatography (0-70% EA in Hexane) to afford 1.39 g (61.8%) of tert-butyl N-(4-(5-bromopyrimidin-2-yl)benzyl)-N-(4-(2-(4-methoxyphenyl)acetamido) benzoyl)-glycinate INT-6. LCMS-ESI (m/z) calculated for $C_{33}H_{33}BrN_4O_5$: 644.2, found 644.8 $[M+H]^+$, $t_R$=3.859 minutes (Method 2).

Compounds 70, 86-91, and 100-103 were prepared from tert-butyl N-(4-(5-bromopyrimidin-2-yl)benzyl)-N-(4-(2-(4-methoxyphenyl)acetamido)benzoyl)glycinate INT-6 using General Procedures 1 then 4.

(2-(4-methoxyphenyl)acetyl)glycine

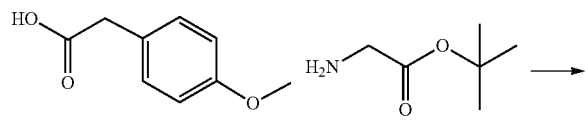

222

-continued

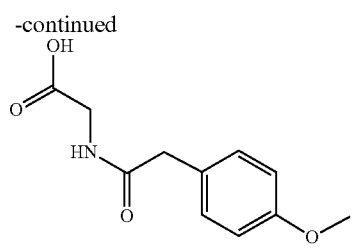

Prepared using General Procedure 2. To a stirring solution of 2-(4-methoxyphenyl)acetic acid (4 g, 24.1 mmol) in DMF (20 mL) was added HATU (8.50 g, 36.15 mmol) and the mixture was stirred at RT for 1 h. Tert-butyl glycinate hydrochloride (4.02 g, 24.1 mmol) and DIEA (9.34 g, 72.3 mmol) were added and stirred for 3 h. The mixture was diluted with EA (50 mL) and washed with NaHCO$_3$ (10 mL), dried over MgSO$_4$ and solvents evaporated. The intermediate was purified by chromatography (0-100% EA in hexane) to give 3.5 g of tert-butyl (2-(4-methoxyphenyl) acetyl)glycinate. This intermediate was dissolved in DCM (10 mL) and treated with TFA (2 mL) for 18 h. The solvent was removed under reduced pressure to give 2.79 g (52%) of (2-(4-methoxyphenyl)acetyl)glycine. LCMS-ESI (m/z) calculated for $C_{11}H_{13}NO_4$: 223.1; found 224.3 $[M+H]^+$, $t_R$=0.63 min (Method 2).

Tert-butyl N-(4-(5-bromopyrimidin-2-yl)benzyl)-N-((2-(4-methoxyphenyl)acetyl)-glycyl)glycinate

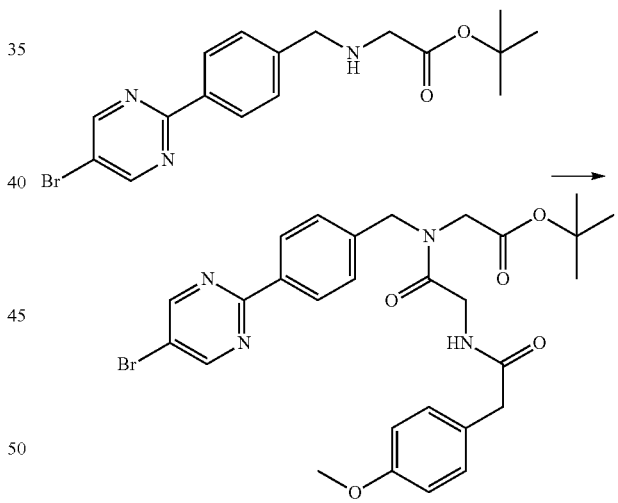

Prepared using General Procedure 2. To a stirring solution of (2-(4-methoxyphenyl)acetyl)glycine (2.9 g, 12.1 mmol) in DMF (20 mL) was added HATU (4.27 g, 18.15 mmol) and the mixture was stirred at RT for 1 h. Tert-butyl (4-(5-bromopyrimidin-2-yl)benzyl)glycinate INT-1 (4.11 g, 10.89 mmol) and DIEA (4.69 g, 36.3 mmol) were added and stirred for 3 h. The mixture was diluted with EA (50 mL) and washed with NaHCO$_3$ (10 mL), dried over MgSO$_4$ and solvents evaporated. The intermediate was purified by chromatography (0-100% EA in hexane) to give 3.82 g (54%) of tert-butyl N-(4-(5-bromopyrimidin-2-yl)benzyl)-N-((2-(4-methoxyphenyl)acetyl)glycyl) glycinate. LCMS-ESI (m/z) calculated for $C_{28}H_{31}BrN_4O_5$: 583.5; found 584.3 $[M+H]^+$, $t_R$=3.82 min (Method 2).

223

Tert-butyl N-(4-(5-((1'r,4'r)-4'-ethyl-[1,1'-bi(cyclohexan)]-3-en-4-yl)pyrimidin-2-yl)benzyl)-N-((2-(4-methoxyphenyl)acetyl)glycyl)glycinate

224

Prepared using General Procedure 1. To a stirring solution of tert-butyl N-(4-(5-bromopyrimidin-2-yl)benzyl)-N-((2-(4-methoxyphenyl)acetyl)glycyl) glycinate (1.0 g, 1.71 mmol) and 2-((1'r,4'r)-4'-ethyl-[1,1'-bi(cyclohexan)]-3-en-4-yl)-4,4,5,5-tetramethyl-1,3,2-dioxaborolane (0.82 g, 2.57 mmol) in dioxane (10.3 mL) and water (3.4 mL) was added sodium carbonate decahydrate (0.98 g, 3.43 mmol). The mixture was degassed with nitrogen for 5 min then PdCl$_2$ (dppf) (70 mg, 0.086 mmol) was added and the mixture was heated to 80° C. for 2 h. The reaction was cooled to RT and water (100 mL) was added. The resulting precipitate was filtered and the dark brown solid was dissolved in DCM, loaded onto Celite and purified by chromatography (0-100% EA in hexane) to give 542 mg (45%) of tert-butyl N-(4-(5-((1'r,4'r)-4'-ethyl-[1,1'-bi(cyclohexan)]-3-en-4-yl)pyrimidin-2-yl)benzyl)-N-((2-(4-methoxyphenyl)acetyl) glycyl)glycinate. LCMS-ESI (m/z) calculated for $C_{42}H_{54}N_4O_5$: 694.4, found 695.1 [M+H]$^+$, $t_R$=12.30 minutes (Method 1).

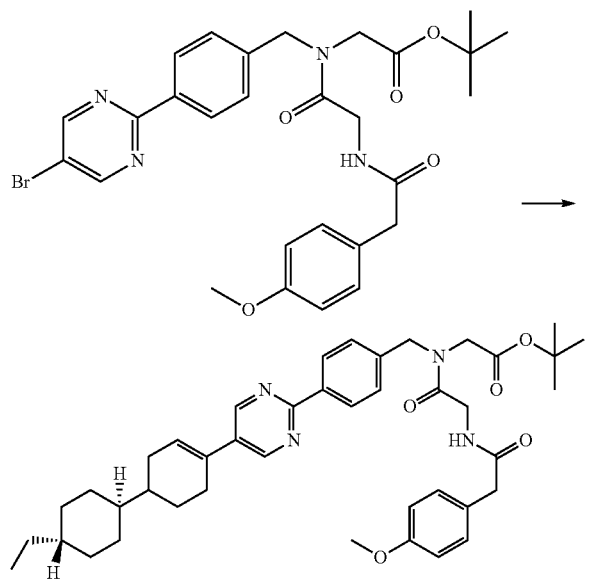

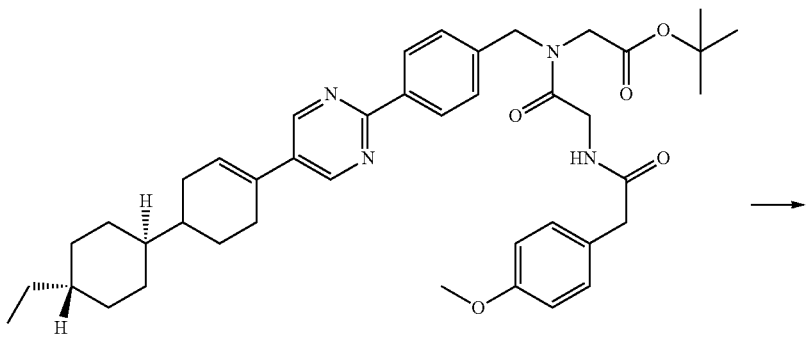

N-(4-(5-(1'r,4'r)-4'-ethyl-[1,1'-bi(cyclohexan)]-3-en-4-yl)pyrimidin-2-yl)benzyl)-N-((2-(4-methoxyphenyl)acetyl)glycyl)glycine Compound 71

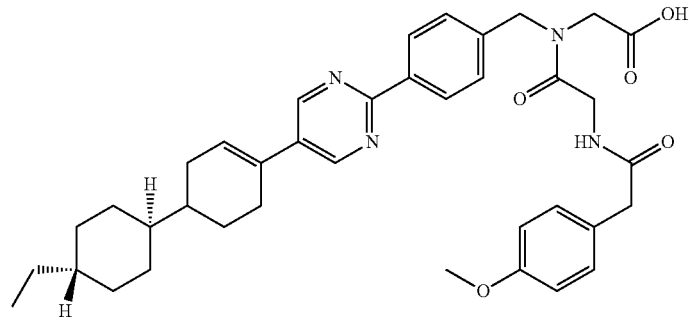

Prepared using General Procedure 4. To a stirring solution of tert-butyl N-(4-(5-((1'r,4'r)-4'-ethyl-[1,1'-bi(cyclohexan)]-3-en-4-yl)pyrimidin-2-yl)benzyl)-N-((2-(4-methoxyphenyl)acetyl) glycyl)glycinate (329 mg, 0.47 mmol) in DCM (4 mL) was added TFA (1 mL). The mixture was stirred at RT for 18 h. The solvent was removed and the residue was azeotroped with acetonitrile (3×10 mL). The residue was dissolved in DCM (2 mL) and added dropwise to a stirring solution of acetonitrile (20 mL) and water (10 mL). The resulting precipitate was filtered and dried to give 280 mg (93%) of N-(4-(5-((1'r,4'r)-4'-ethyl-[1,1'-bi(cyclohexan)]-3-en-4-yl)pyrimidin-2-yl)benzyl)-N-((2-(4-methoxyphenyl) acetyl)glycyl)glycine Compound 71. LCMS-ESI (m/z) calculated for $C_{38}H_{46}N_4O_5$: 638.4, found 639.1 $[M+H]^+$, $t_R$=8.09 minutes (Method 1).

Compounds 104 and 111 were prepared from Compound 1 using General Procedures 2, 3, then 4.

Compounds 117-121 were prepared from tert-butyl N-(4-(5-bromopyrimidin-2-yl)benzyl)-N-((2-(4-methoxyphenyl) acetyl)glycyl)glycinate using General Procedures 1 then 4.

Tert-butyl N-((tert-butoxycarbonyl)glycyl)-N-(4-(5-((1'r,4'r)-ethyl-[1,1'-bi(cyclohexan)]-3-en-4-yl)pyrimidin-2-yl)benzyl)glycinate

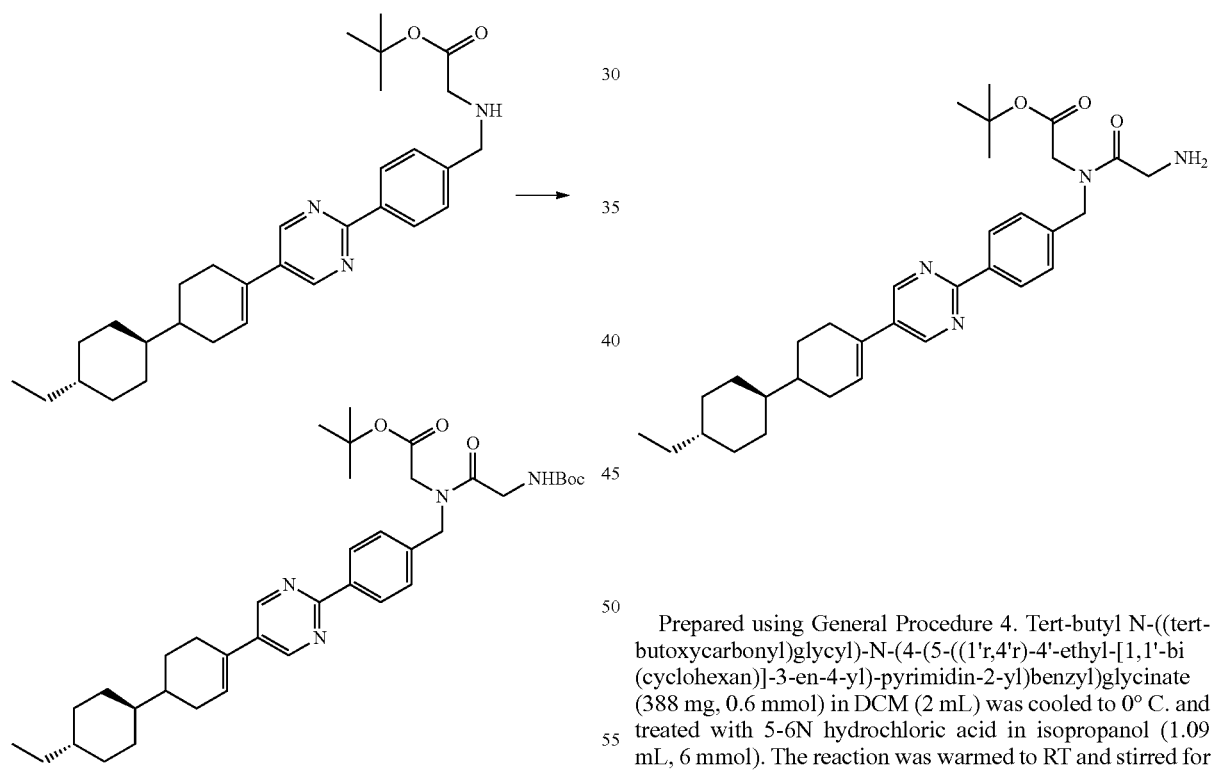

Prepared using General Procedure 2. A stirred solution of (tert-butoxycarbonyl)glycine (300 mg, 1.715 mmol) and DIEA (427 μL, 2.45 mmol) in DMF (3 mL) was treated with HATU (629 mg, 1.654 mmol) added in one portion. The reaction mixture turned yellow and was allowed to stir at RT for 5 min. Tert-butyl (4-(5-((1'r,4'r)-4'-ethyl-[1,1'-bi(cyclohexan)]-3-en-4-yl)pyrimidin-2-yl)benzyl)-glycinate INT-2 (600 mg, 1.225 mmol) and DMF (2 mL) was added and the reaction was allowed to stir at RT for 1 h. Water (60 mL) was added and the precipitate was filtered and washed with water (20 mL). The precipitate was dissolved in DCM, dried over magnesium sulfate and purified by chromatography (0-100% EA in hexanes) to give 583 mg (73.5%) of tert-butyl N-((tert-butoxycarbonyl)glycyl)-N-(4-(5-((1'r,4'r)-4'-ethyl-[1,1'-bi(cyclohexan)]-3-en-4-yl)-pyrimidin-2-yl)benzyl)glycinate. LCMS-ESI (m/z) calculated for $C_{38}H_{54}N_4O_5$: 646.4, found 547.1 $[M-Boc]^+$, $t_R$=5.246 minutes (Method 2).

Tert-butyl N-(4-(5-(1'r,4'r)-4'-ethyl-[1,1'-bi(cyclohexan)]-3-en-4-yl)pyrimidin-2-yl)benzyl)-N-glycylglycinate (INT-7)

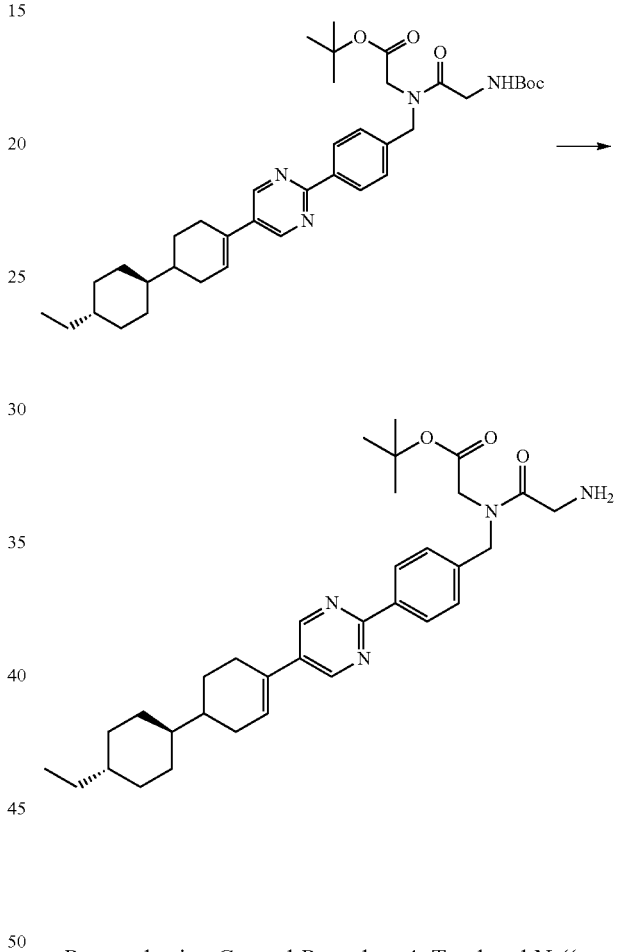

Prepared using General Procedure 4. Tert-butyl N-((tert-butoxycarbonyl)glycyl)-N-(4-(5-((1'r,4'r)-4'-ethyl-[1,1'-bi(cyclohexan)]-3-en-4-yl)-pyrimidin-2-yl)benzyl)glycinate (388 mg, 0.6 mmol) in DCM (2 mL) was cooled to 0° C. and treated with 5-6N hydrochloric acid in isopropanol (1.09 mL, 6 mmol). The reaction was warmed to RT and stirred for 2 h. All the solvent was removed to give 340 mg (97%) of tert-butyl N-(4-(5-((1'r,4'r)-4'-ethyl-[1,1'-bi(cyclohexan)]-3-en-4-yl)pyrimidin-2-yl)benzyl)-N-glycylglycinate INT-7 as the hydrochloride salt which contained ~12% material where the tert-butyl ester was removed. LCMS-ESI (m/z) calculated for $C_{33}H_{46}N_4O_3$: 546.4, found 547.1 $[M+H]^+$, $t_R$=4.982 minutes (Method 2).

Compounds 122-124, 127, and 129-147 were prepared from tert-butyl N-(4-(5-((1'r,4'r)-ethyl-[1,1'-bi(cyclohexan)]-3-en-4-yl)pyrimidin-2-yl)benzyl)-N-glycylglycinate INT-7 using General Procedures 2 then 4.

5-bromo-2-(3-methoxy-4-methylphenyl)pyrimidine

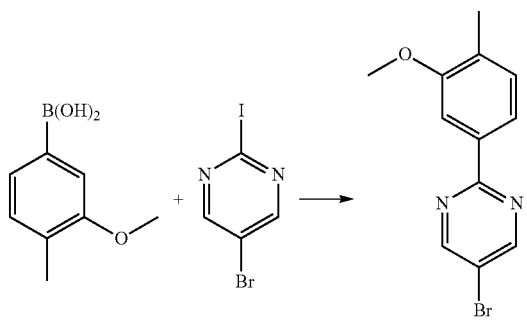

Prepared using General Procedure 1 from (3-methoxy-4-methylphenyl)boronic acid (500 mg, 3.0 mmol) and 5-bromo-2-iodopyrimidine (858 mg, 3.0 mmol) to give 654 mg (49%) of 5-bromo-2-(3-methoxy-4-methylphenyl)pyrimidine. LCMS-ESI (m/z) calculated for $C_{12}H_{11}BrN_2O$: 278.01, found 278.9 $[M+H]^+$, $t_R$=2.66 minutes (Method 4).

Tert-butyl 2-((4-(5-bromopyrimidin-2-yl)-2-methoxybenzyl)amino)acetate

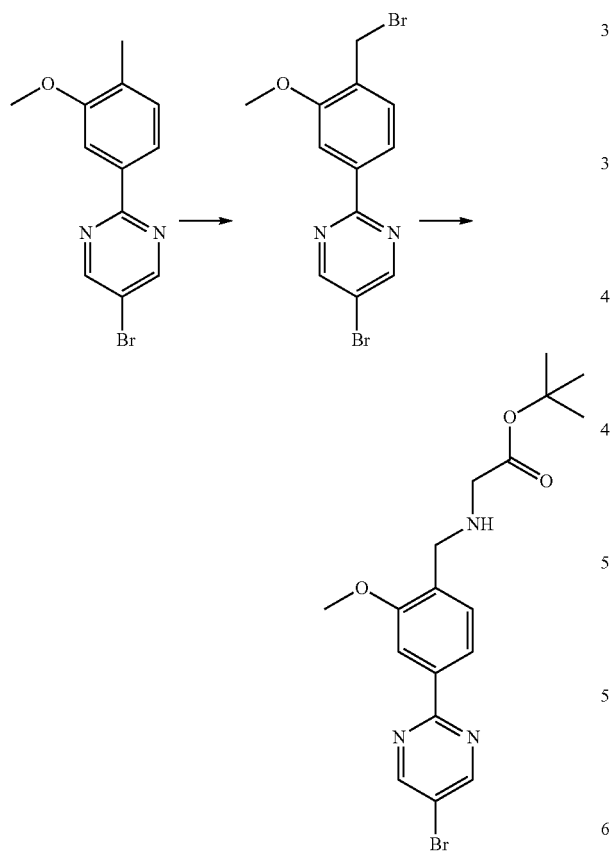

To a round bottom flask containing 5-bromo-2-(3-methoxy-4-methylphenyl)pyrimidine (654 mg, 2.34 mmol) in chloroform (11.7 mL) was added 1-bromopyrrolidine-2,5-dione (541 mg, 3.04 mmol) and (E)-2,2'-(diazene-1,2-diyl)bis(2-methylpropanenitrile) (57.6 mg, 0.35 mmol). The reaction mixture was stirred and heated at reflux for 1 h. The reaction mixture was allowed to cool to RT and the solvent was removed in vacuo to give 838 mg of crude 5-bromo-2-(4-(bromomethyl)-3-methoxyphenyl)pyrimidine.

To a round bottom flask containing 5-bromo-2-(4-(bromomethyl)-3-methoxyphenyl)pyrimidine (838 mg, 2.34 mmol) and tert-butyl 2-aminoacetate hydrochloride (1177 mg, 7.02 mmol) in THF (19.51 mL) was added N-ethyl-N-isopropylpropan-2-amine (1.215 mL, 7.02 mmol). The reaction mixture was heated at 70° C. for 30 min. The reaction mixture was cooled to room temperature and diluted with water (50 mL) and EA (50 mL). The layers were partitioned and the aqueous layer was further extracted with EA (2×20 mL). The combined organic phases were washed with brine (30 mL), dried over anhydrous magnesium sulfate, filtered and the solvent was removed. The residue was purified by chromatography (0% to 10% THF in DCM) to afford 147 mg of tert-butyl 2-((4-(5-bromopyrimidin-2-yl)-2-methoxybenzyl)amino)acetate (14.61%) as a colorless solid. LCMS-ESI (m/z) calculated for $C_{18}H_{22}BrN_3O_3$: 407.08, found 407.9 $[M+H]^+$, $t_R$=1.54 minutes (Method 4).

Tert-butyl (4-(5-((1'r,4'r)-4'-ethyl-[1,1'-bi(cyclohexan)]-3-en-4-yl)pyrimidin-2-yl)-2-methoxybenzyl)glycinate

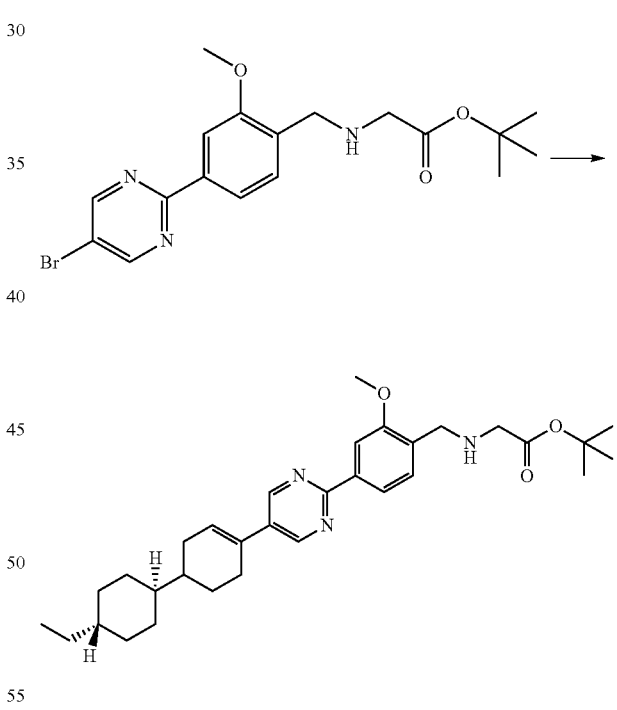

Prepared using General Procedure 1 from tert-butyl 2-((4-(5-bromopyrimidin-2-yl)-2-methoxybenzyl)amino)acetate (147 mg, 0.36 mmol) and 2-((1'r,4'r)-4'-ethyl-[1,1'-bi(cyclohexan)]-3-en-4-yl)-4,4,5,5-tetramethyl-1,3,2-dioxaborolane (152 mg, 0.478 mmol) to give 46 mg (24%) of tert-butyl (4-(5-((1'r,4'r)-4'-ethyl-[1,1'-bi(cyclohexan)]-3-en-4-yl)pyrimidin-2-yl)-2-methoxybenzyl)-glycinate. LCMS-ESI (m/z) calculated for $C_{32}H_{45}N_3O_3$: 519.35, found 520.2 $[M+H]^+$, $t_R$=2.62 minutes (Method 4).

N-(4-(5-((1'r,4'r)-4'-ethyl-[1,1'-bi(cyclohexan)]-3-en-4-yl)pyrimidin-2-yl)-2-methoxybenzyl)-N-((2-(4-methoxyphenyl)acetyl)glycyl)glycine Compound 126)

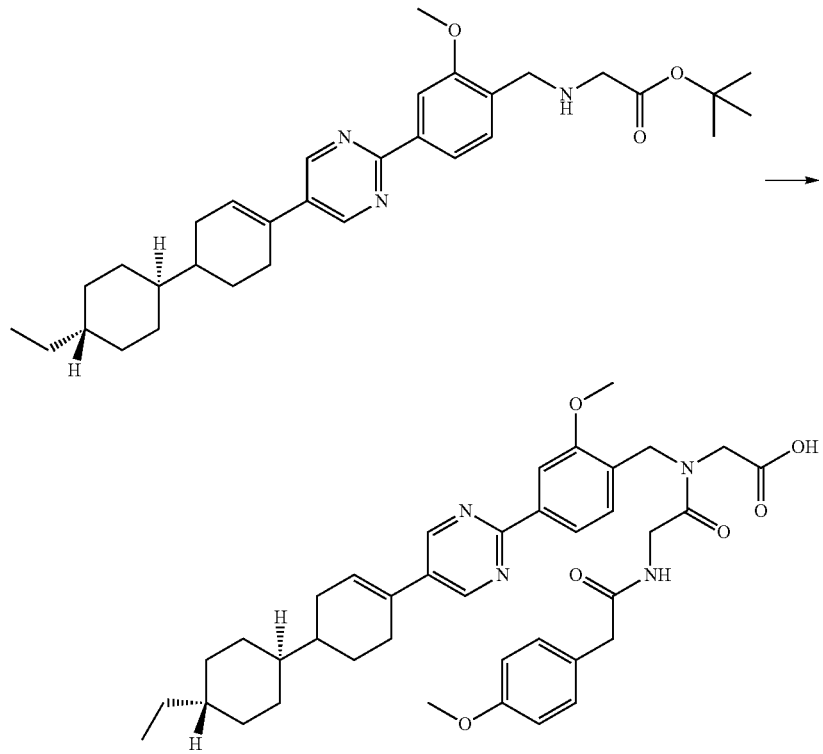

Prepared using General Procedure 2 from tert-butyl (4-(5-((1'r,4'r)-4'-ethyl-[1,1'-bi(cyclohexan)]-3-en-4-yl)pyrimidin-2-yl)-2-methoxybenzyl)glycinate (46 mg, 0.09 mmol) and 2-(2-(4-methoxyphenyl)acetamido)acetic acid (21.8 mg, 0.10 mmol) to give 50 mg (75%) of tert-butyl N-(4-(5-((1'r,4'r)-4'-ethyl-[1,1'-bi(cyclohexan)]-3-en-4-yl)pyrimidin-2-yl)-2-methoxybenzyl)-N-((2-(4-methoxy-phenyl)acetyl)glycyl)glycinate which was treated according to General Procedure 4 to give 37 mg (79%) of N-(4-(5-((1'r,4'r)-4'-ethyl-[1,1'-bi(cyclohexan)]-3-en-4-yl)pyrimidin-2-yl)-2-methoxybenzyl)-N-((2-(4-methoxyphenyl)acetyl)glycyl)glycine (Compound 126). LCMS-ESI (m/z) calculated for $C_{39}H_{48}N_4O_6$: 668.4, found 669.1 [M+H]$^+$, $t_R$=10.62 minutes (Method 3).

Tert-butyl N-((2-(1,1-dioxido-3-oxobenzo[d]isothiazol-2(3H)-yl)acetyl)glycyl)-N-(4-(5-(1'r,4'r)-4'-ethyl-[1,1'-bi(cyclohexan)]-3-en-4-yl)pyrimidin-2-yl)benzyl)glycinate

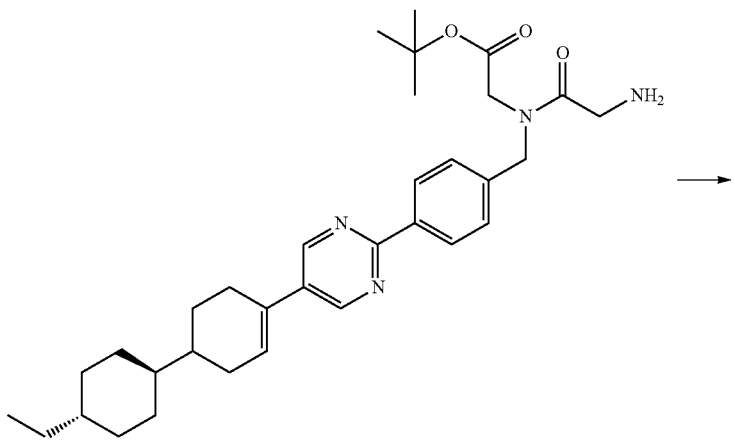

-continued

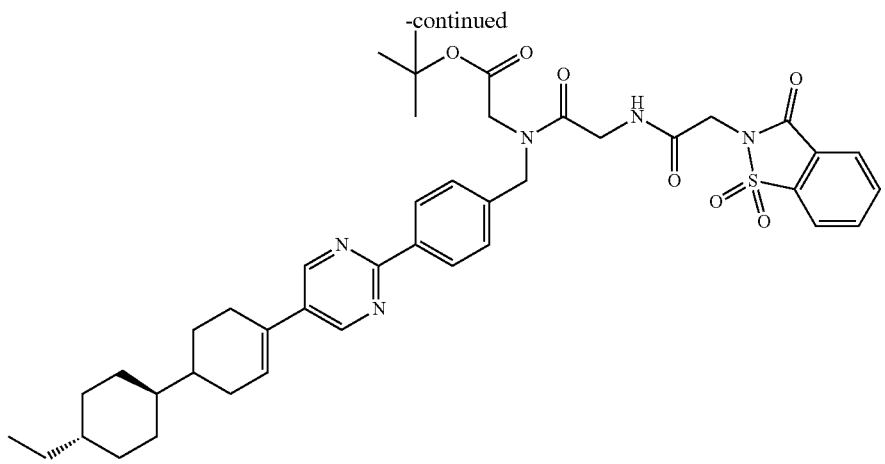

Prepared using General Procedure 1. To a stirring solution of 2-(1,1-dioxido-3-oxobenzo[d]isothiazol-2(3H)-yl)acetic acid (174 mg, 0.72 mmol) in DMF (1.2 mL) at 0° C. was added DIEA (209 µL, 0.72 mmol) and HATU (274 mg, 0.72 mmol). The mixture was stirred at 0° C. for 10 min then added to a stirring mixture of tert-butyl N-(4-(5-((1'r,4'r)-4'-ethyl-[1,1'-bi(cyclohexan)]-3-en-4-yl)pyrimidin-2-yl)benzyl)-N-glycylglycinate (INT-7) (328 mg, 0.6 mmol) in DMF (1.2 mL). After stirring at 0° C. for 1 h, the reaction mixture was warmed to RT and stirred for 3 h. Additional DIEA (209 µL, 0.72 mmol) was added. In a separate flask, additional 2-(1,1-dioxido-3-oxobenzo[d]isothiazol-2(3H)-yl)acetic acid (174 mg, 0.72 mmol) in DMF (1.2 mL) at 0° C. was treated with DIEA (209 µL, 0.72 mmol) and HATU (274 mg, 0.72 mmol) and stirred at 0° C. for 10 min. This activated acid was added to the original reaction mixture and stirred at RT for 15 min. Water (40 mL) was added and the solid was filtered and dried to give crude material which was purified by chromatography (0-100% EA in DCM/hexane) to give 275 mg (60%) of tert-butyl N-((2-(1,1-dioxido-3-oxobenzo[d]isothiazol-2(3H)-yl)acetyl)glycyl)-N-(4-(5-((1'r,4'r)-4'-ethyl-[1,1'-bi(cyclohexan)]-3-en-4-yl)pyrimidin-2-yl)benzyl)glycinate. LCMS-ESI (m/z) calculated for $C_{42}H_{51}N_5O_7S$: 769.4, found 770.0 $[M+H]^+$, $t_R$=4.80 minutes (Method 2).

N-((2-(1,1-dioxido-3-oxobenzo[d]isothiazol-2(3H)-yl)acetyl)glycyl)-N-(4-(5-(1'r,4'r)-4'-ethyl-[1,1'-bi(cyclohexan)]-3-en-4-yl)pyrimidin-2-yl)benzyl)glycine Compound 128

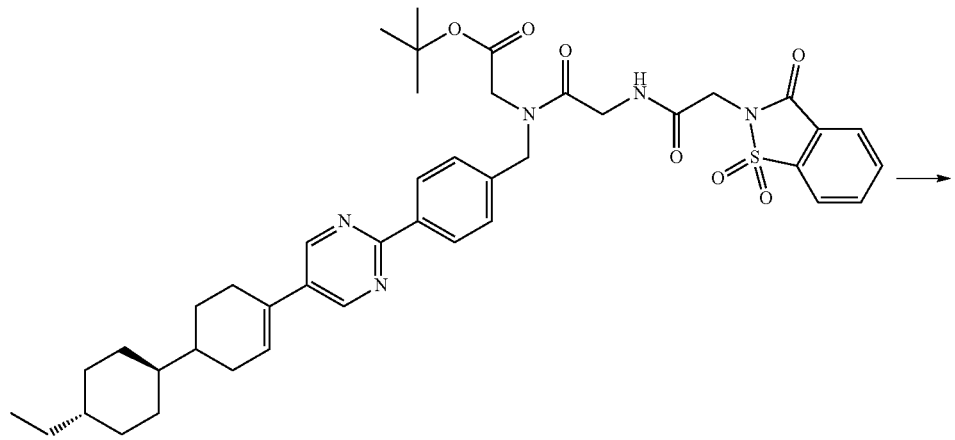

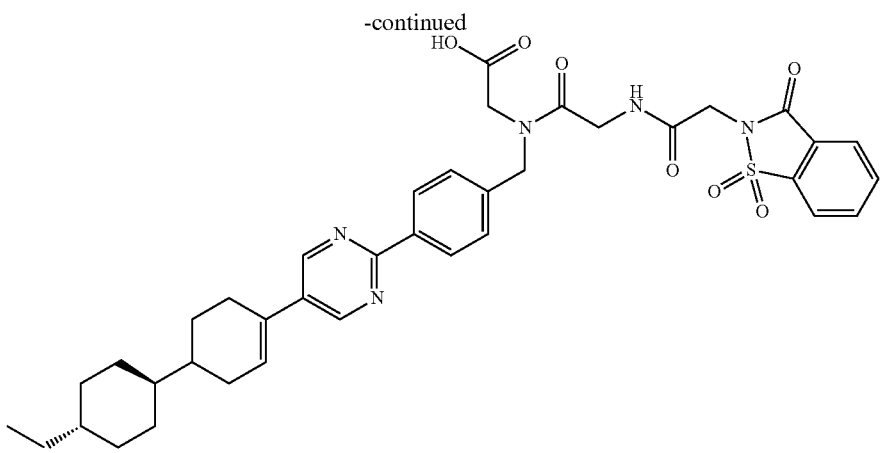

Prepared using General Procedure 4. Tert-butyl N-((2-(1,1-dioxido-3-oxobenzo[d]isothiazol-2(3H)-yl)acetyl)glycyl)-N-(4-(5-((1'r,4'r)-4'-ethyl-[1,1'-bi(cyclohexan)]-3-en-4-yl)pyrimidin-2-yl)benzyl)glycinate (275 mg, 0.357 mmol) in DCM (1 mL) was treated with TFA (1 mL) and stirred at RT for 2 h. The solvent was removed and the residue was azeotroped with DCM (3×5 mL) and acetonitrile (2×5 mL) to give 240 mg (94%) of N-((2-(1,1-dioxido-3-oxobenzo[d]isothiazol-2(3H)-yl)acetyl)glycyl)-N-(4-(5-((1'r,4'r)-4'-ethyl-[1,1'-bi(cyclohexan)]-3-en-4-yl)pyrimidin-2-yl)benzyl)glycine Compound 128. LCMS-ESI (m/z) calculated for $C_{38}H_{43}N_5O_7S$: 713.3, found 714.0 [M+H]$^+$, $t_R$=7.44 minutes (Method 1).

Representative compounds and their corresponding analytical data are shown in Table 2, where the LCMS data was collected using Methods 1 and 3 (see General Methods above).

TABLE 2

Analytical Data for Representative Compounds

| CPD. NO. | LCMS RETENTION TIME (min) | PURITY METHOD |
|---|---|---|
| 1 | 11.55 | 3 |
| 2 | 10.33 | 3 |
| 3 | 11.80 | 3 |
| 4 | 11.86 | 3 |
| 5 | 10.92 | 3 |
| 6 | 11.42 | 3 |
| 7 | 11.45 | 3 |
| 8 | 12.37 | 3 |
| 9 | 12.78 | 3 |
| 10 | 10.5 | 3 |
| 11 | 10.93 | 3 |
| 12 | 10.87 | 3 |
| 13 | 11.01 | 3 |
| 14 | 11.10 | 3 |
| 15 | 11.08 | 3 |
| 16 | 9.89 | 3 |
| 17 | 8.66 | 3 |
| 18 | 11.72 | 3 |
| 19 | 11.49 | 3 |
| 20 | 12.19 | 3 |
| 21 | 12.00 | 3 |
| 22 | 11.64 | 3 |
| 23 | 10.65 | 3 |
| 24 | 12.00 | 3 |
| 25 | 12.59 | 3 |
| 26 | 12.42 | 3 |
| 27 | 12.61 | 3 |
| 28 | 11.06 | 3 |
| 29 | 10.94 | 3 |
| 30 | 11.95 | 3 |
| 31 | 11.22 | 3 |
| 32 | 10.83 | 3 |
| 33 | 11.20 | 3 |
| 34 | 11.18 | 3 |
| 35 | 11.06 | 3 |
| 36 | 11.11 | 3 |
| 37 | 11.49 | 3 |
| 38 | 11.83 | 3 |
| 39 | 11.96 | 3 |
| 40 | 10.84 | 3 |
| 41 | 10.34 | 3 |
| 42 | 11.56 | 3 |
| 43 | 11.30 | 3 |
| 44 | 12.24 | 3 |
| 45 | 10.97 | 3 |
| 46 | 11.56 | 3 |
| 47 | 10.96 | 3 |
| 48 | 11.42 | 3 |
| 49 | 11.49 | 3 |
| 50 | 11.09 | 3 |
| 51 | 11.48 | 3 |
| 52 | 10.84 | 3 |
| 53 | 10.60 | 3 |
| 54 | 9.83 | 3 |
| 55 | 9.88 | 3 |
| 56 | 11.46 | 3 |
| 57 | 11.01 | 3 |
| 58 | 11.50 | 3 |
| 59 | 10.50 | 3 |
| 60 | 9.75 | 3 |
| 61 | 10.30 | 3 |
| 62 | 10.26 | 3 |
| 63 | 11.21 | 3 |
| 64 | 11.67 | 3 |
| 65 | 7.08 | 3 |
| 66 | 10.46 | 3 |
| 67 | 12.40 | 3 |
| 68 | 11.95 | 3 |
| 69 | 11.29 | 3 |
| 70 | 6.16 | 1 |
| 71 | 7.10 | 1 |
| 72 | 6.90 | 1 |
| 73 | 7.10 | 1 |
| 74 | 11.29 | 3 |
| 75 | 11.66 | 3 |
| 76 | 11.22 | 3 |
| 77 | 6.67 | 1 |
| 78 | 6.14 | 1 |
| 79 | 6.49 | 1 |

TABLE 2-continued

Analytical Data for Representative Compounds

| CPD. NO. | LCMS RETENTION TIME (min) | PURITY METHOD |
|---|---|---|
| 80 | 6.01 | 1 |
| 81 | 7.50 | 1 |
| 82 | 7.10 | 1 |
| 83 | 7.50 | 1 |
| 84 | 7.10 | 1 |
| 85 | 11.71 | 3 |
| 86 | 6.09 | 1 |
| 87 | 6.33 | 1 |
| 88 | 7.01 | 1 |
| 89 | 6.32 | 1 |
| 90 | 6.72 | 1 |
| 91 | 7.77 | 1 |
| 92 | 11.29 | 3 |
| 93 | 11.36 | 3 |
| 94 | 8.50 | 1 |
| 95 | 9.28 | 1 |
| 96 | 7.76 | 1 |
| 97 | 7.63 | 1 |
| 98 | 7.10 | 1 |
| 99 | 7.70 | 1 |
| 100 | 7.01 | 1 |
| 101 | 6.54 | 1 |
| 102 | 8.89 | 1 |
| 103 | 8.67 | 1 |
| 104 | 9.59 | 1 |
| 105 | 10.7 | 3 |
| 106 | 11.25 | 3 |
| 107 | 8.20 | 1 |
| 108 | 8.05 | 1 |
| 109 | 8.01 | 1 |
| 110 | 7.80 | 1 |
| 111 | 9.58 | 1 |
| 112 | 9.12 | 1 |
| 113 | 9.12 | 1 |
| 114 | 8.89 | 1 |
| 115 | 8.04 | 1 |
| 116 | 8.27 | 1 |
| 117 | 8.54 | 1 |
| 118 | 8.54 | 1 |
| 119 | 9.46 | 1 |
| 120 | 7.39 | 1 |
| 121 | 7.05 | 1 |
| 122 | 7.90 | 1 |
| 123 | 7.90 | 1 |
| 124 | 8.50 | 1 |
| 125 | 8.50 | 1 |
| 126 | 10.62 | 3 |
| 127 | 8.21 | 1 |
| 128 | 7.73 | 1 |
| 129 | 7.79 | 1 |
| 130 | 7.67 | 1 |
| 131 | 7.70 | 1 |
| 132 | 8.10 | 1 |
| 133 | 8.30 | 1 |
| 134 | 7.86 | 1 |
| 135 | 8.00 | 1 |
| 136 | 8.04 | 1 |
| 137 | 8.60 | 1 |
| 138 | 8.30 | 1 |
| 139 | 8.60 | 1 |
| 140 | 8.60 | 1 |
| 141 | 8.40 | 1 |
| 142 | 8.90 | 1 |
| 143 | 8.70 | 1 |
| 144 | 8.70 | 1 |
| 145 | 8.10 | 1 |
| 146 | 8.10 | 1 |
| 147 | 8.30 | 1 |
| 148 | 8.55 | 1 |
| 149 | 8.37 | 1 |
| 150 | 8.30 | 1 |
| 151 | 8.53 | 1 |
| 152 | 8.99 | 1 |
| 153 | 8.72 | 1 |

Biological Assays $EC_{20}$GLP-1(9-36) PAM cAMP Assay: Dose Response of Compound in the Presence of Fixed Concentration of GLP-1 (9-36)

Human GLP-1R CRE-bla CHO-K1 cells were cultured in growth medium (DMEM-High glucose, 10% dialyzed FBS, 0.1 mM NEAA, 25 mM Hepes, 100 U/mL penicillin/100 μg/mL streptomycin, 5 μg/mL Blasticidin, 600 μg/mL Hygromycin), trypsinized and plated in suspension into 384-well white flat bottom plates at 5000 cells/well in 12 μL assay buffer (Hank's Balanced Salt Solution, 10 mM Hepes, 0.1% BSA, pH 7.4). Each compound at a 5× concentration was diluted to a final concentration range of 10 to 0.01 μM (11 points) in assay buffer containing 1.5 mM IBMX and 4% DMSO. GLP-1(9-36) was diluted from 4.2 μM (30 x) to a final assay concentration of 60 nM in assay buffer containing 1.5 mM IBMX and 4% DMSO. Each compound concentration (5×) was added (3 μL), followed by 0.5 μL of GLP-1(9-36) and cells incubated for 30 minutes at 37° C. The peptide was added to the wells using siliconized tips. The reaction was stopped and levels of cAMP were quantified using the DiscoverX HitHunter cAMP kit according to the manufacturer's instructions and luminescence was detected using a SpectraMax M5 Multi-Mode Microplate reader. Luminescence was converted to total cAMP using a cAMP standard curve and data were analyzed by non-linear regression to determine the EC50 and Emax for each compound.

```
Peptide sequences:
GLP-1 (7-36):
                                    (SEQ ID NO: 1)
HAEGTFTSDVSSYLEGQAAKEFIAWLVKGR-NH2

GLP-1 (9-36):
                                    (SEQ ID NO: 2)
EGTFTSDVSSYLEGQAAKEFIAWLVKGR-NH2
```

GLP-1 (7-36) was purchased from GenScript. GLP-1 (9-36) were purchased from Biopeptide Co., Inc.

Activity data for representative compounds is set forth in Table 3 below. In Table 3, the $EC_{20}$ GLP-1 (9-36) PAM Activity range is denoted as follows: "+" denotes activity <0.8 μM; "++" denotes activity between 0.8 μM and 2.5 μM; "+++" denotes activity between 2.5 to 5 μM; and "++++" denotes activity 5 to 10 μM.

TABLE 3

Activity of Representative Compounds

| Cpd. No. | $EC_{20}$ GLP-1(9-36) PAM Activity |
|---|---|
| 1 | + |
| 2 | + |
| 3 | ++ |
| 4 | ++ |
| 5 | ++ |
| 6 | ++ |
| 7 | +++ |
| 8 | +++ |
| 9 | ++ |
| 10 | ++ |
| 11 | + |
| 12 | + |
| 13 | + |
| 14 | + |
| 15 | + |

TABLE 3-continued

Activity of Representative Compounds

| Cpd. No. | EC$_{20}$ GLP-1(9-36) PAM Activity |
|---|---|
| 16 | ++ |
| 17 | ++++ |
| 18 | + |
| 19 | + |
| 20 | + |
| 21 | + |
| 22 | + |
| 23 | + |
| 24 | + |
| 25 | +++ |
| 26 | + |
| 27 | + |
| 28 | + |
| 29 | + |
| 30 | +++ |
| 31 | + |
| 32 | + |
| 33 | + |
| 34 | + |
| 35 | + |
| 36 | + |
| 37 | ++ |
| 38 | + |
| 39 | +++ |
| 40 | ++ |
| 41 | + |
| 42 | + |
| 43 | + |
| 44 | ++ |
| 45 | + |
| 46 | + |
| 47 | + |
| 48 | + |
| 49 | + |
| 50 | + |
| 51 | + |
| 52 | + |
| 53 | + |
| 54 | + |
| 55 | ++ |
| 56 | ++ |
| 57 | + |
| 58 | + |
| 59 | ++ |
| 60 | + |
| 61 | + |
| 62 | + |
| 63 | + |
| 64 | + |
| 65 | + |
| 66 | + |
| 67 | + |
| 68 | + |
| 69 | + |
| 70 | +++ |
| 71 | + |
| 72 | + |
| 73 | + |
| 74 | + |
| 75 | + |
| 76 | + |
| 77 | +++ |
| 78 | ++++ |
| 79 | +++ |
| 80 | +++ |
| 81 | ++ |
| 82 | + |
| 83 | + |
| 84 | ++ |
| 85 | + |
| 86 | +++ |
| 87 | +++ |
| 88 | ++ |
| 89 | ++ |
| 90 | +++ |
| 91 | ++ |
| 92 | + |
| 93 | + |
| 94 | ++ |
| 95 | ++ |
| 96 | + |
| 97 | + |
| 98 | + |
| 99 | + |
| 100 | + |
| 101 | + |
| 102 | ++ |
| 103 | +++ |
| 104 | +++ |
| 105 | + |
| 106 | + |
| 107 | ++ |
| 108 | ++ |
| 109 | + |
| 110 | + |
| 111 | ++ |
| 112 | + |
| 113 | + |
| 114 | + |
| 115 | ++ |
| 116 | + |
| 117 | ++ |
| 118 | ++ |
| 119 | ++ |
| 120 | ++ |
| 121 | ++ |
| 122 | ++ |
| 123 | + |
| 124 | + |
| 125 | ++++ |
| 126 | ++ |
| 127 | + |
| 128 | + |
| 129 | ++ |
| 130 | + |
| 131 | + |
| 132 | ++ |
| 133 | + |
| 134 | + |
| 135 | ++ |
| 136 | + |
| 137 | + |
| 138 | + |
| 139 | ++ |
| 140 | ++ |
| 141 | ++ |
| 142 | ++ |
| 143 | ++ |
| 144 | ++ |
| 145 | +++ |
| 146 | ++ |
| 147 | ++ |
| 148 | ++ |
| 149 | +++ |
| 150 | +++ |
| 151 | ++++ |
| 152 | + |
| 153 | + |

U.S. Provisional Patent Application No. 62/491,892, filed Apr. 28, 2017, to which the present application claims priority, is hereby incorporated herein by reference in its entirety.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

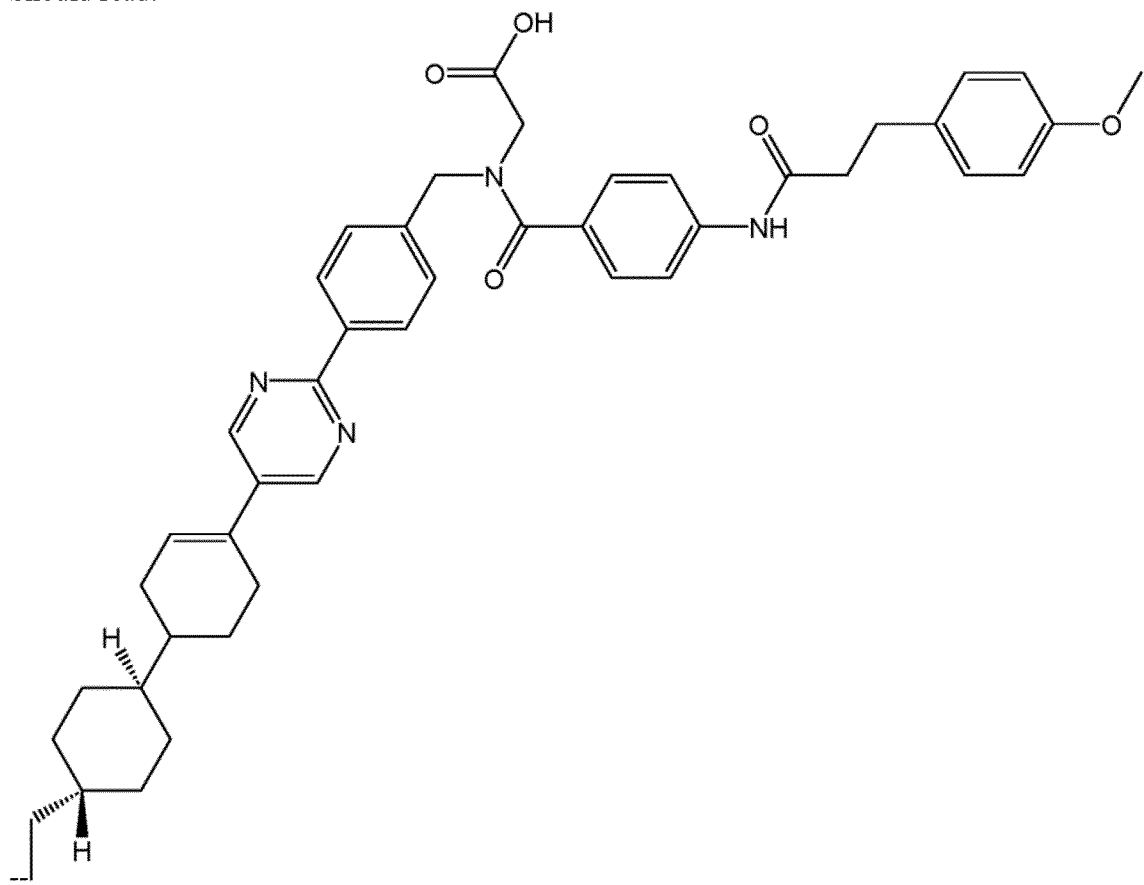

The invention claimed is:

1. A compound having the structure of Formula (I):

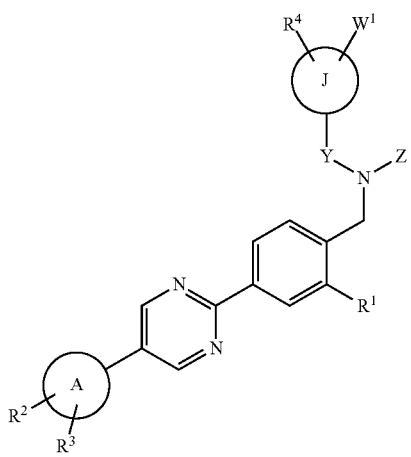

(I)

or a pharmaceutically acceptable salt thereof, wherein:
J is null or has the structure:

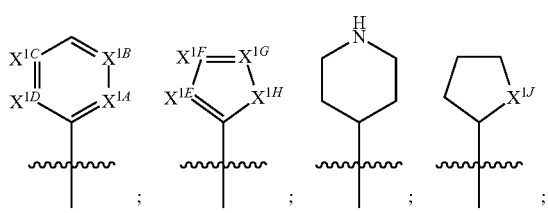

each of $X^{1A}$, $X^{1B}$, $X^{1C}$, $X^{1D}$, $X^{1E}$, $X^{1F}$ and $X^{1G}$ is C, CH or N;

$X^{1H}$ is O or S;

$X^{1J}$ is $CH_2$ or NH;

$R^1$ is H, alkyl or alkoxy;

Y is —C(O)—, —$CH_2$—, —C(O)—$CH_2$—, —$CH_2$—C(O)—, —C(O)—$(CR^aR^b)_n$—$N(R^c)$—C(O)—$(CR^aR^b)_n$—, —C(O)—$(CR^aR^b)_n$—$N(R^d)_w$ here $R^d$ may form a fused ring with J or with a fused J-$R^4$—$W^1$ ring system, —C(O)—$(CR^aR^b)_n$—$N(R^c)$—C(O)—$(CR^aR^b)_n$—$N(R^c)$—$S(O)_k$—$(CR^aR^b)_n$—, —C(O)—$(CR^aR^b)_n$—$N(R^c)$—C(O)—$(CR^aR^b)$—$N(R^d)$— where $R^d$ may form a fused ring with J or with a fused J-$R^4$—$W^1$ ring system, or —C(O)—$(CR^aR^b)_n$—$N(R^c)$—$S(O)_k$—$(CR^aR^b)$—;

Z is —$(CR^aR^b)_n$—C(O)—$R^7$;

$R^7$ is —$OR^{30}$, —$NR^{31}R^{32}$, —$NH(CR^aR^b)_n$—C(O)—$R^7$, —$NHSO_2R^7$ or —(CO)—NH—$SO_2$—$R^7$, or $R^{31}$;

each $R^{30}$ is independently H or alkyl;

each $R^{31}$ and $R^{32}$ is independently H or $C_1$-$C_6$ alkyl optionally substituted with one or more $R^{33}$, or taken together with the N atom to which they are attached can form a 3- to 7-membered heterocyclic ring;

each $R^{33}$ is independently halo, hydroxyl, alkoxy, perhaloalkyl, perhaloalkoxy, carboxyl, —C(O)O—$R^{30}$, —$OR^{30}$, —$N(R^{30})_2$ or heterocyclyl;

each $R^4$ is independently H, alkyl, alkoxy, or alkyl substituted with one or more $R^{43}$, halogen, perhaloalkyl, perhaloalkoxy, —CN, —OR$^{40}$ or —NR$^{41}$R$^{42}$;

each $R^{41}$ and $R^{42}$ is independently H, alkyl, —(CH$_2$)$_n$—C(O)O—R$^{40}$, —C(O)—R$^{40}$, aryl, heteroaryl; or $R^{41}$ and $R^{42}$, taken together with the N atom to which they are attached, can form a 3- to 7-membered heterocyclic ring;

each $R^{43}$ is independently H, halo, hydroxyl, —NR$^{41}$R$^{42}$, or alkoxy;

$W^1$ is —(CR$^a$R$^b$)$_{i_1}$-L$^1$—(CR$^a$R$^b$)$_{j_1}$—R$^{60}$ or R$^4$; or $W^1$ and $R^4$ taken together comprise a 5- or 6-membered carbocyclic or heterocyclic ring fused with the ring to which $W^1$ and $R^4$ are attached and optionally having one, two or three heteroatoms where each such heteroatom is independently selected from O, N, and S, and where any ring atom of such heterocyclic ring may be optionally substituted with one or more —L$^1$—R$^{13}$ or R$^{13}$; or $W^1$ is a 5- or 6-membered heterocyclic ring fused with a phenyl ring and having one, two or three heteroatoms where each such heteroatom is independently selected from O, N, and S, and where any ring atom of such fused heterocyclic ring and phenyl ring moiety may be optionally substituted with one or more $R^{14}$;

$L^1$ is —O—, —C(O)—, —OC(O)—, —C(O)O—, —NR$^{10}$—, —C(O)NR$^{10}$—, —N(R$^{10}$)—(CH$_2$)$_n$—C(O)—, —N(R$^{10}$)—C(O)—N(R$^{10}$)—, —N(R$^{10}$)—S(O)$_2$—, —S(O)$_2$—NR$^{10}$—, or —N(S(O)$_2$—(CH$_2$)$_n$—R$^{60}$)$_2$;

$R^{60}$ is R$^{13}$, —O—(CH$_2$)$_n$—R$^{13}$, or R$^{10}$;

each $R^{10}$, $R^{11}$ and $R^{12}$ is independently H or alkyl;

$R^{13}$ is cycloalkyl, heterocycloalkyl, aryl, or heteroaryl, or a fused bicycle or tricycle of any two or three of such ring moieties, or R$^{13}$ and R$^{10}$ taken together with the N atom to which they are attached form a heterocyclic ring, where any ring atom of R$^{13}$ may be optionally substituted with one or more $R^{14}$ or $R^{15}$;

each $R^{14}$ is independently H, alkyl, halo, hydroxy, cyano, alkoxy, perhaloalkyl, and perhaloalkoxy, —OR$^{10}$,—(CH$_2$)$_n$—C(O)OR$^{10}$, —SR$^{10}$, —SO—R$^{10}$, —S(O)$_2$—R$^{10}$), —(CH$_2$)$_n$—NR$^{11}$R$^{12}$, —NH—C(O)—(CH$_2$)$_n$—R$^{12}$, —N(R$^{11}$)—C(O)—(CH$_2$)$_n$—R$^{12}$, or —NH(CH$_2$)$_n$—R$^{12}$;

$R^{15}$ is cycloalkyl, heterocycloalkyl, aryl, or heteroaryl, or a fused bicycle of any two of such ring moieties, where any ring atom of R$^{15}$ may be optionally substituted with one or more R$^{14}$, each $R^{40}$ is independently H or alkyl;

each $R^a$ and $R^b$ is independently H, hydroxy, alkyl, or aralkyl optionally substituted with hydroxyl; or both R$^a$ and R$^b$ attached to the same carbon are, taken together, oxo, or cycloalkyl;

each $R^c$ and $R^d$ is independently H, hydroxy, alkyl, —S(O)$_k$—R$^7$ or —C(O)—R$^7$;

A is cycloalkyl;

$R^2$ is alkyl, haloalkyl, cycloalkyl, heterocycloalkyl, aryl, heteroaryl, or a fused bicycle of any two of such ring moieties, where any ring atom of R$^2$ may be optionally substituted with one or more R$^3$, each R$^3$ is independently H, alkyl, or perhaloalkyl;

each k is 2;

each n is independently 0, 1, 2, 3 or 4; and each $i_1$ and $j_1$ is independently 0, 1, 2, 3 or 4.

2. The compound of claim 1, wherein the compound has a structure of Formula (II):

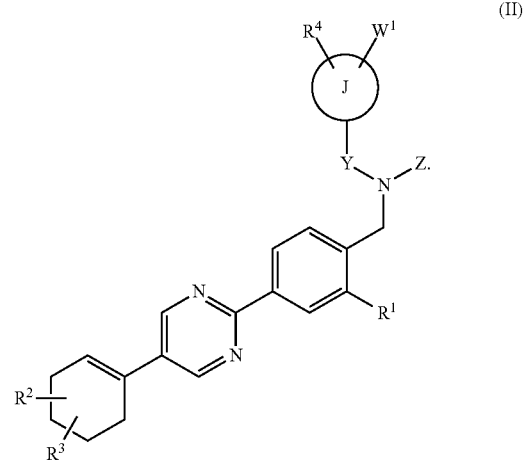

3. The compound of claim 2, wherein the compound has a structure of Formula (III):

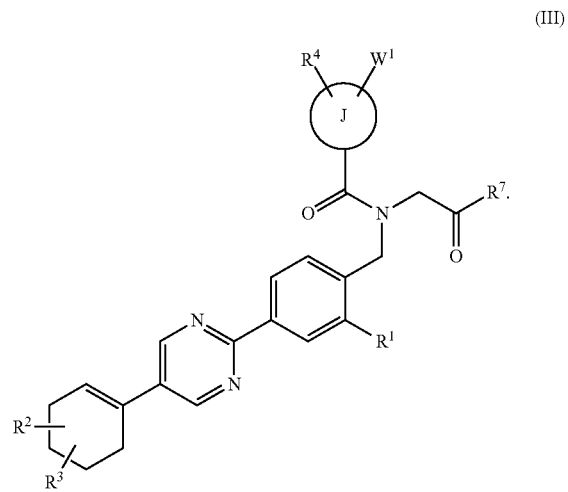

4. The compound of claim 1, wherein the compound has a structure of Formula (IV):

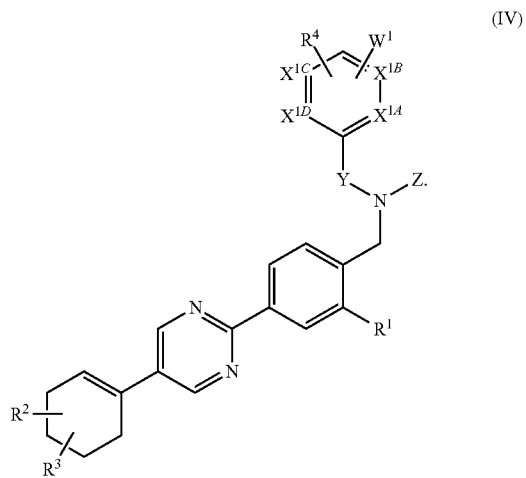

5. The compound of claim 3, wherein the compound has a structure of Formula (V):

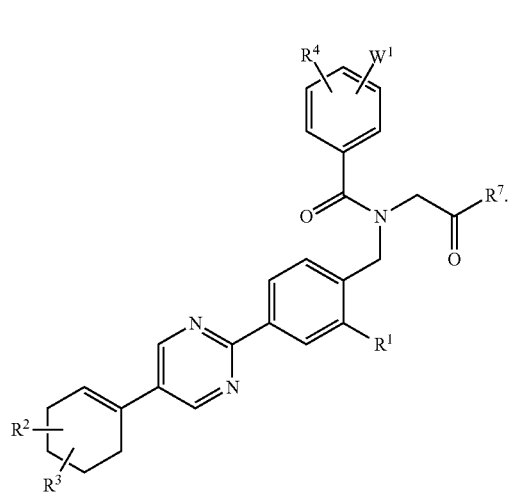

(V)

6. The compound of claim 5, wherein the compound has a structure of Formula (VI):

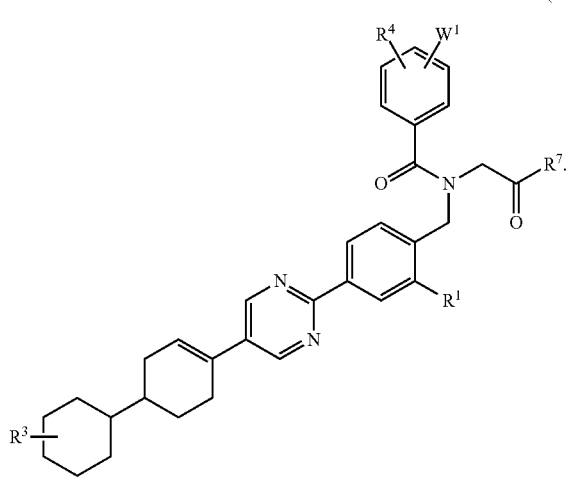

(VI)

7. The compound of claim 2, wherein the compound has a structure of Formula (VII):

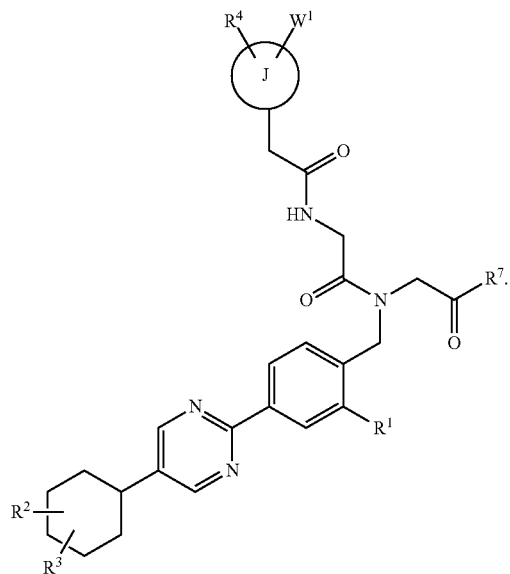

(VII)

8. The compound of claim 7, wherein the compound has a structure of Formula (VIII):

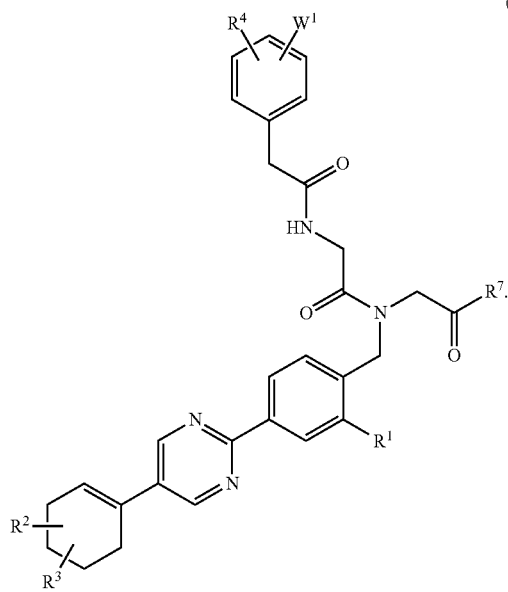

(VIII)

9. The compound of claim 8, wherein the compound has a structure of Formula (IX):

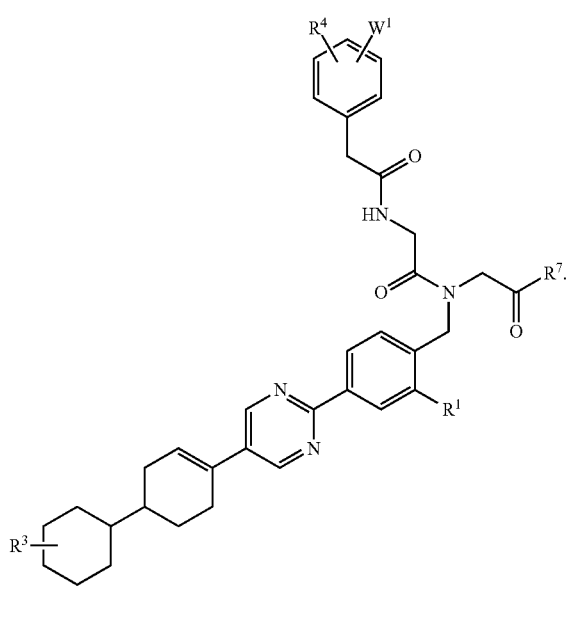

10. The compound of claim 2, wherein the compound has the structure of Formula (X):

11. The compound of claim 10, wherein the compound has the structure of Formula (XI):

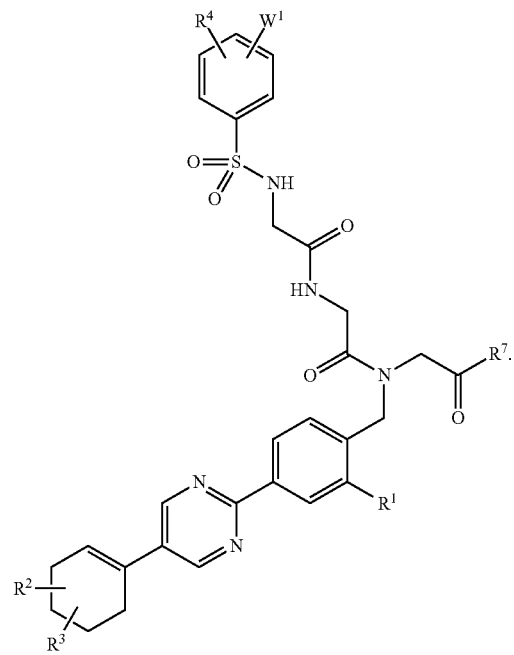

12. The compound of claim 11, wherein the compound has the structure of Formula (XII):

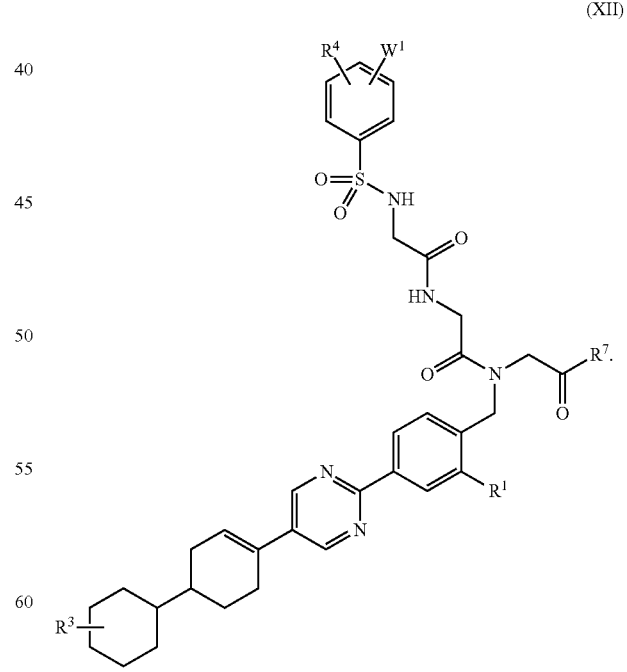

13. The compound of claim 1, wherein the compound is selected from any one of the following compounds or any pharmaceutically acceptable salt thereof:

| Structure | Cpd. No. |
|---|---|
| 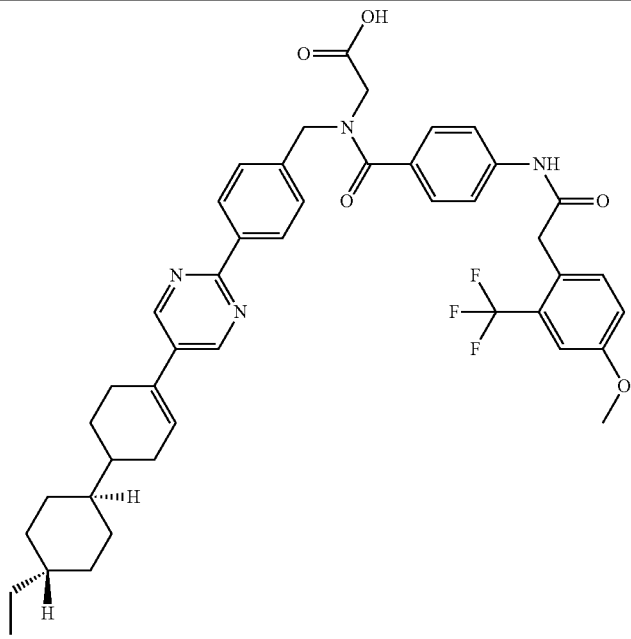 | 1 |
| 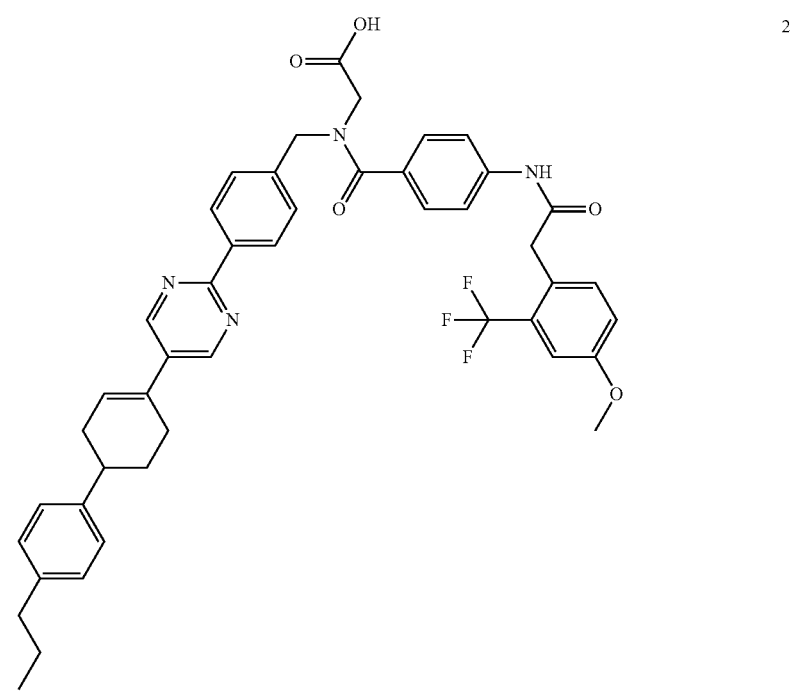 | 2 |

| Structure | Cpd. No. |
|---|---|
| (chemical structure) | 3 |
| (chemical structure) | 4 |

-continued
| Structure | Cpd. No. |
|---|---|
| 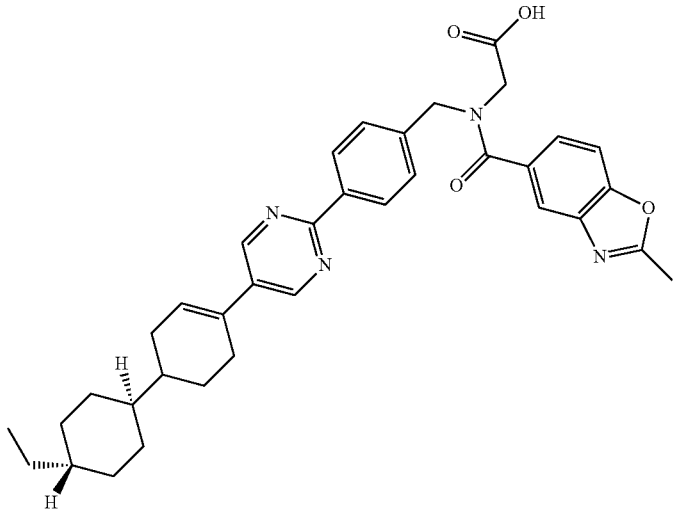 [SMILES: CC[C@H]1CC[C@H](C2CC=C(c3cnc(-c4ccc(CN(CC(=O)O)C(=O)c5ccc6oc(C)nc6c5)cc4)nc3)CC2)CC1] | 5 |
| 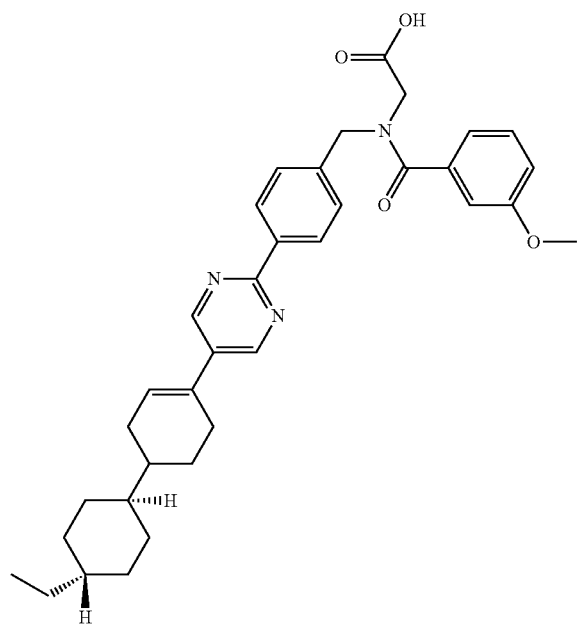 [SMILES: CC[C@H]1CC[C@H](C2CC=C(c3cnc(-c4ccc(CN(CC(=O)O)C(=O)c5cccc(OC)c5)cc4)nc3)CC2)CC1] | 6 |

-continued
| Structure | Cpd. No. |
|---|---|
| 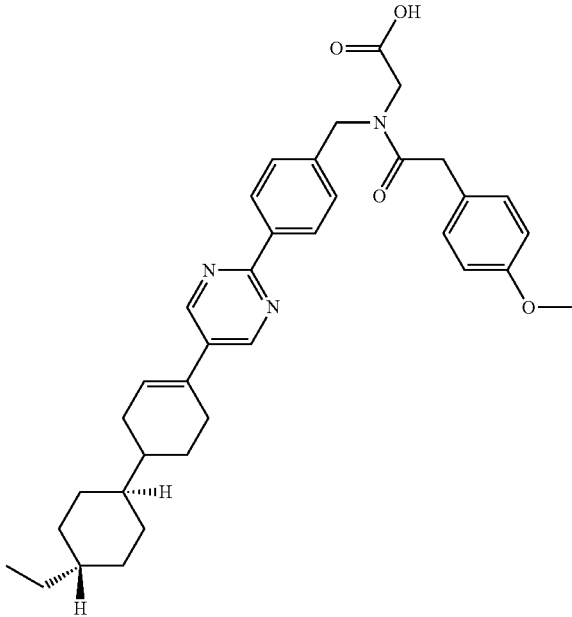 [SMILES: CC[C@H]1CC[C@H](C2CC=C(c3cnc(-c4ccc(CN(CC(=O)O)C(=O)Cc5ccc(OC)cc5)cc4)nc3)CC2)CC1] | 7 |
| 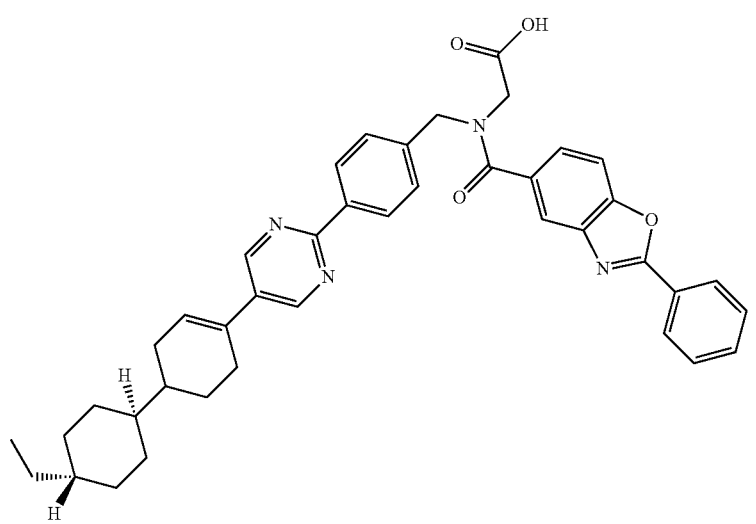 [SMILES: CC[C@H]1CC[C@H](C2CC=C(c3cnc(-c4ccc(CN(CC(=O)O)C(=O)c5ccc6oc(-c7ccccc7)nc6c5)cc4)nc3)CC2)CC1] | 8 |

-continued
| Structure | Cpd. No. |
|---|---|
| 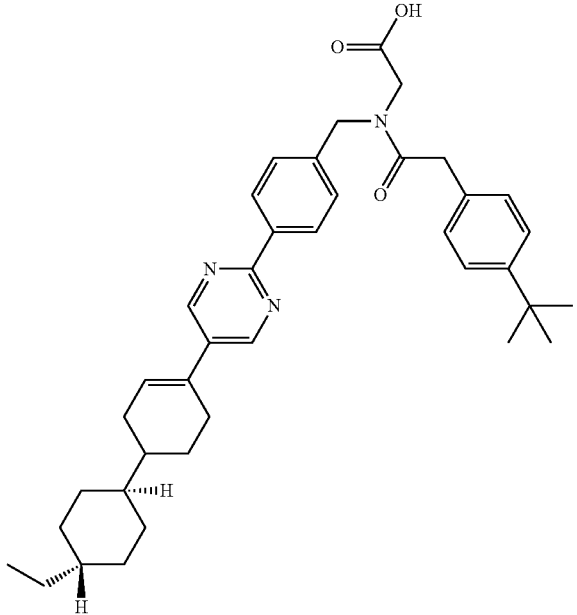 [SMILES: CC[C@H]1CC[C@H](C2CC=C(c3cnc(-c4ccc(CN(CC(=O)O)C(=O)Cc5ccc(C(C)(C)C)cc5)cc4)nc3)CC2)CC1] | 9 |
| 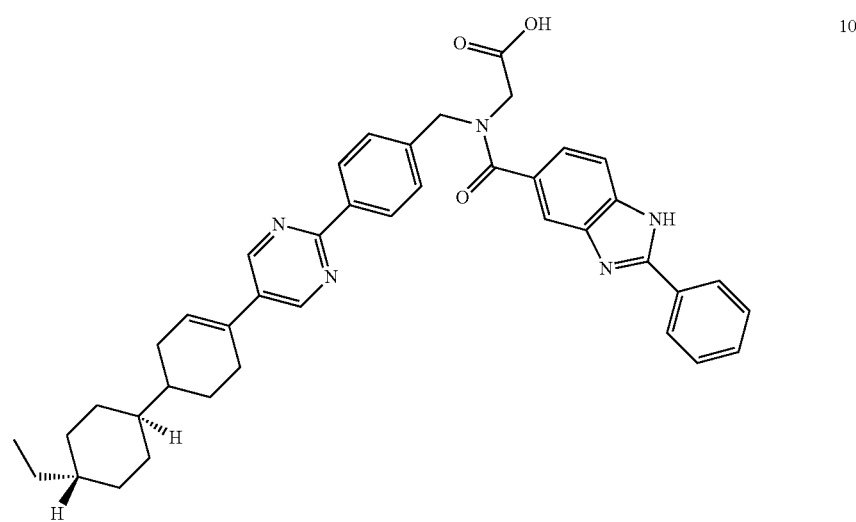 | 10 |

| Structure | Cpd. No. |
|---|---|
| 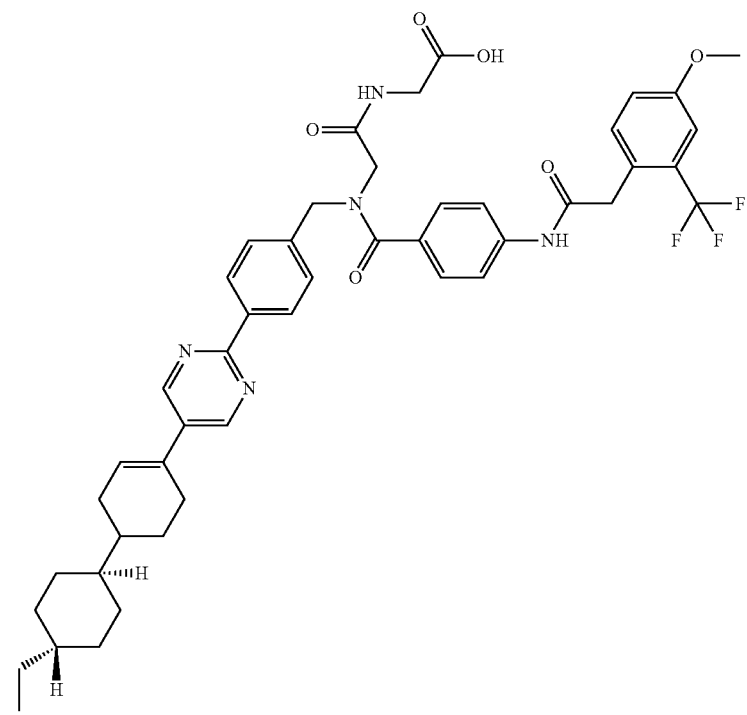 [SMILES: CC[C@H]1CC[C@H](C2CC=C(c3cnc(-c4ccc(CN(CC(=O)NCC(=O)O)C(=O)c5ccc(NC(=O)Cc6ccc(OC)cc6C(F)(F)F)cc5)cc4)nc3)CC2)CC1] | 11 |
| 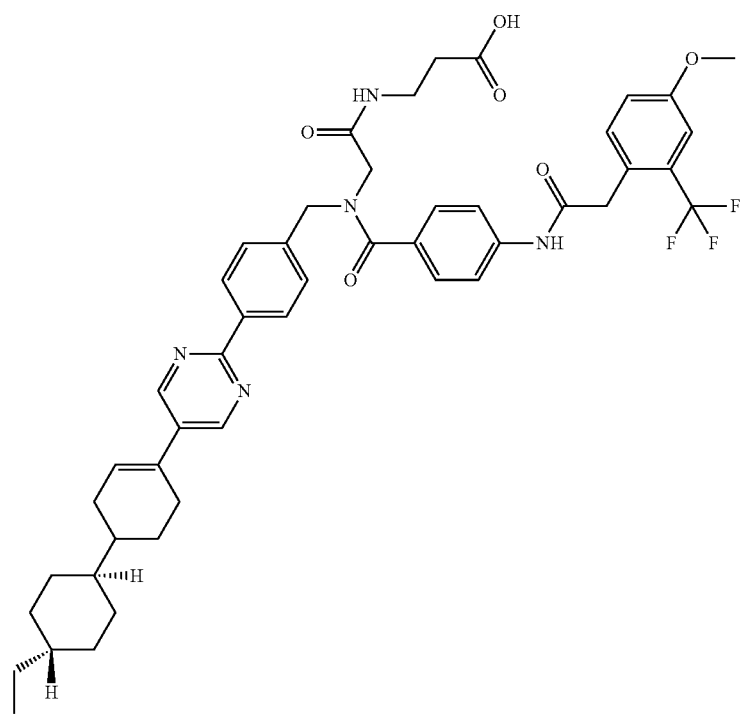 [SMILES: CC[C@H]1CC[C@H](C2CC=C(c3cnc(-c4ccc(CN(CC(=O)NCCC(=O)O)C(=O)c5ccc(NC(=O)Cc6ccc(OC)cc6C(F)(F)F)cc5)cc4)nc3)CC2)CC1] | 12 |

| Structure | Cpd. No. |
|---|---|
| 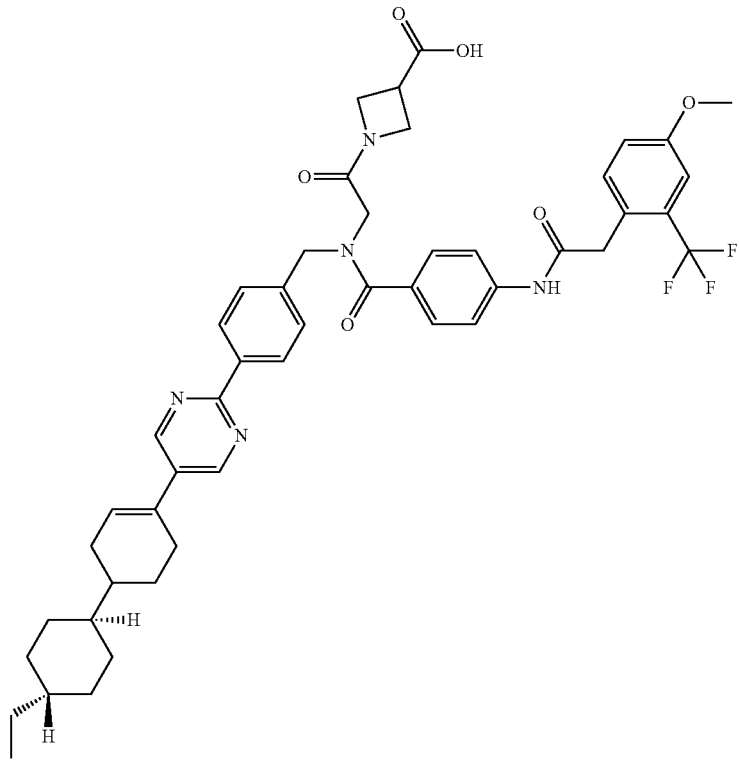 [SMILES: CC[C@H]1CC[C@H](C2CC=C(c3cnc(-c4ccc(CN(CC(=O)N5CC(C(=O)O)C5)C(=O)c5ccc(NC(=O)Cc6ccc(OC)cc6C(F)(F)F)cc5)cc4)nc3)CC2)CC1] | 13 |
| 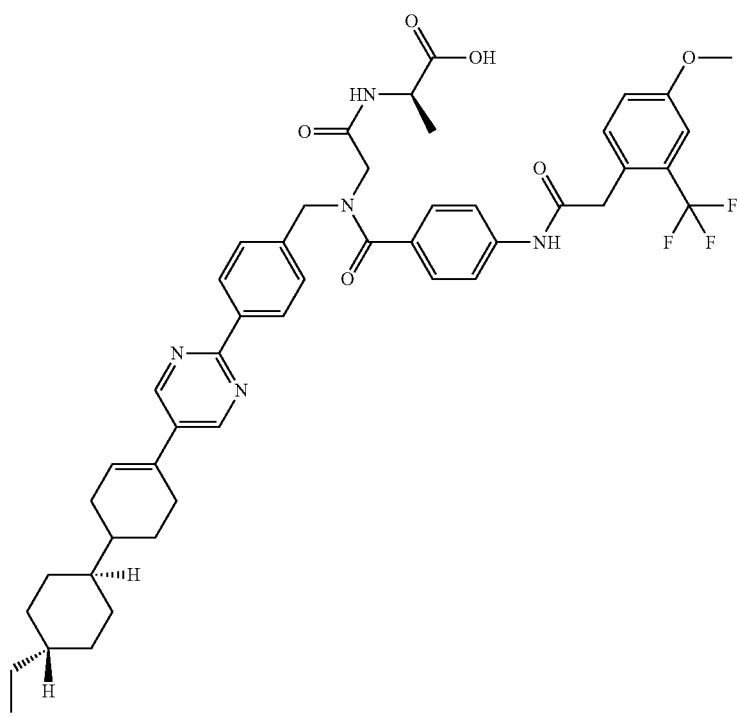 [SMILES: CC[C@H]1CC[C@H](C2CC=C(c3cnc(-c4ccc(CN(CC(=O)N[C@H](C)C(=O)O)C(=O)c5ccc(NC(=O)Cc6ccc(OC)cc6C(F)(F)F)cc5)cc4)nc3)CC2)CC1] | 14 |

| Structure | Cpd. No. |
|---|---|
| 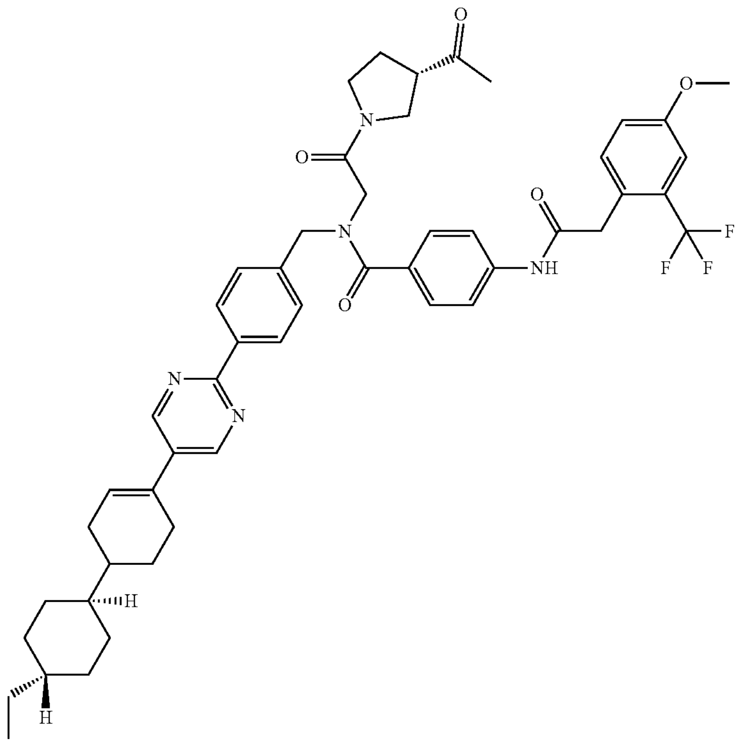 [SMILES: CC[C@H]1CC[C@H](C2CC=C(c3cnc(-c4ccc(CN(CC(=O)N5CC[C@H](C(C)=O)C5)C(=O)c5ccc(NC(=O)Cc6ccc(OC)cc6C(F)(F)F)cc5)cc4)nc3)CC2)CC1] | 15 |
| 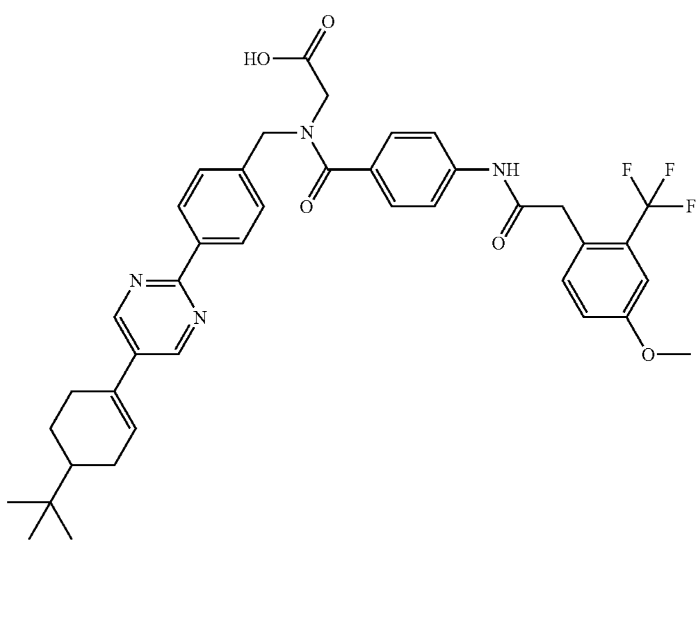 [SMILES: COc1ccc(CC(=O)Nc2ccc(C(=O)N(CC(=O)O)Cc3ccc(-c4ncc(C5=CCC(C(C)(C)C)CC5)cn4)cc3)cc2)c(C(F)(F)F)c1] | 16 |

| Structure | Cpd. No. |
|---|---|
| 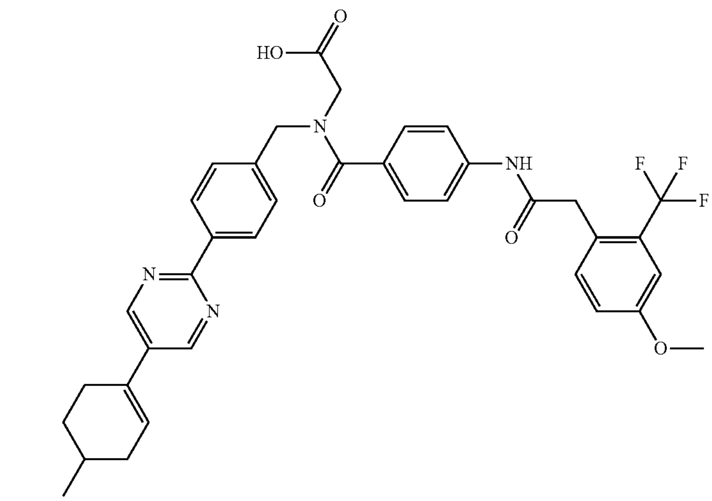 [SMILES: COc1ccc(CC(=O)Nc2ccc(C(=O)N(CC(=O)O)Cc3ccc(-c4ncc(C5=CCC(C)CC5)cn4)cc3)cc2)c(C(F)(F)F)c1] | 17 |
| 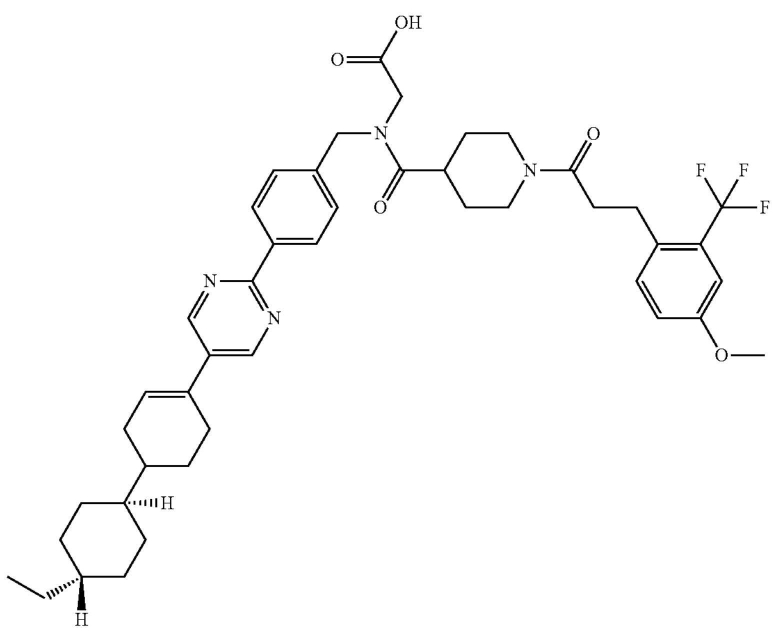 [SMILES: CC[C@H]1CC[C@H](C2CC=C(c3cnc(-c4ccc(CN(CC(=O)O)C(=O)C5CCN(C(=O)CCc6ccc(OC)cc6C(F)(F)F)CC5)cc4)nc3)CC2)CC1] | 18 |

| Structure | Cpd. No. |
|---|---|
| 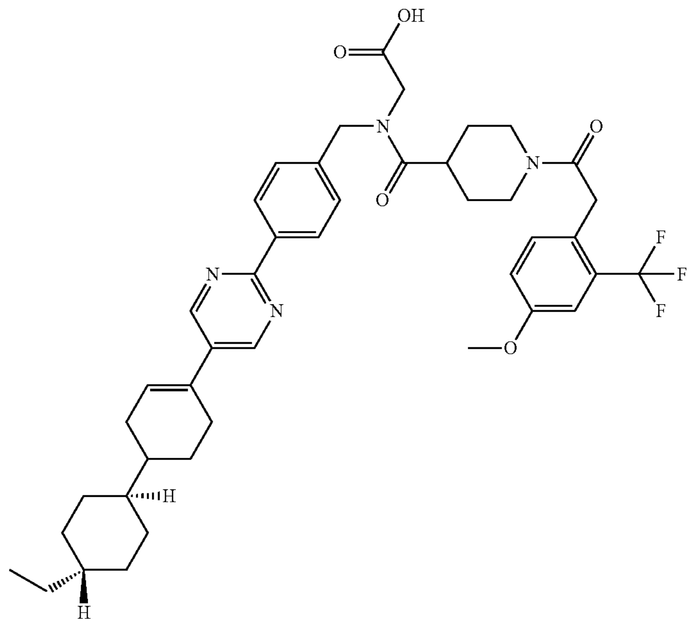 [SMILES: CC[C@H]1CC[C@H](C2CC=C(c3cnc(-c4ccc(CN(CC(=O)O)C(=O)C5CCN(C(=O)Cc6ccc(OC)cc6C(F)(F)F)CC5)cc4)nc3)CC2)CC1] | 19 |
| 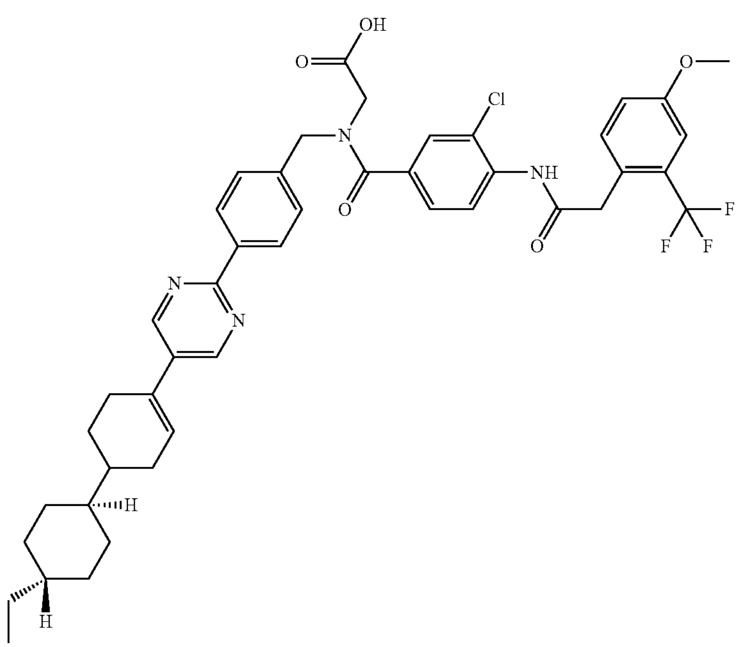 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)c(Cl)c5)cc4)nc3)CC2)CC1] | 20 |

-continued
| Structure | Cpd. No. |
|---|---|
| 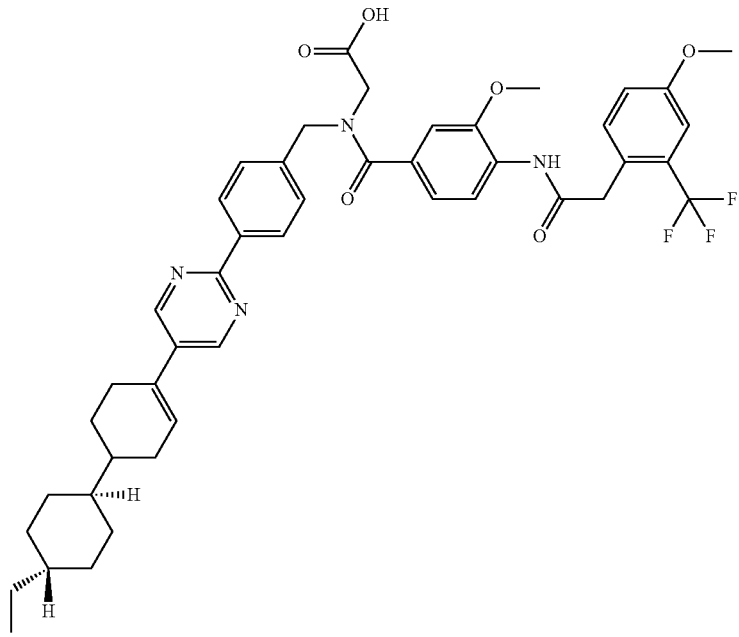 | 21 |
| 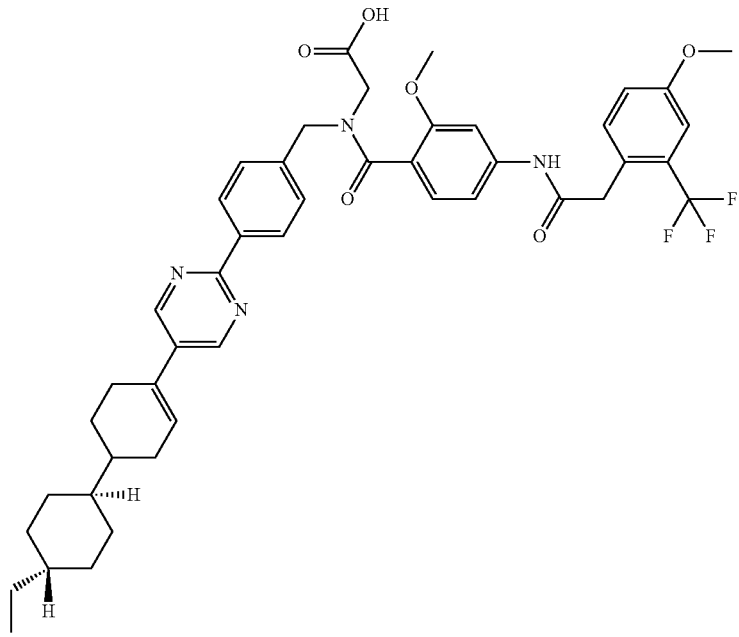 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)cc5OC)cc4)nc3)CC2)CC1] | 22 |

| Structure | Cpd. No. |
| --- | --- |
| 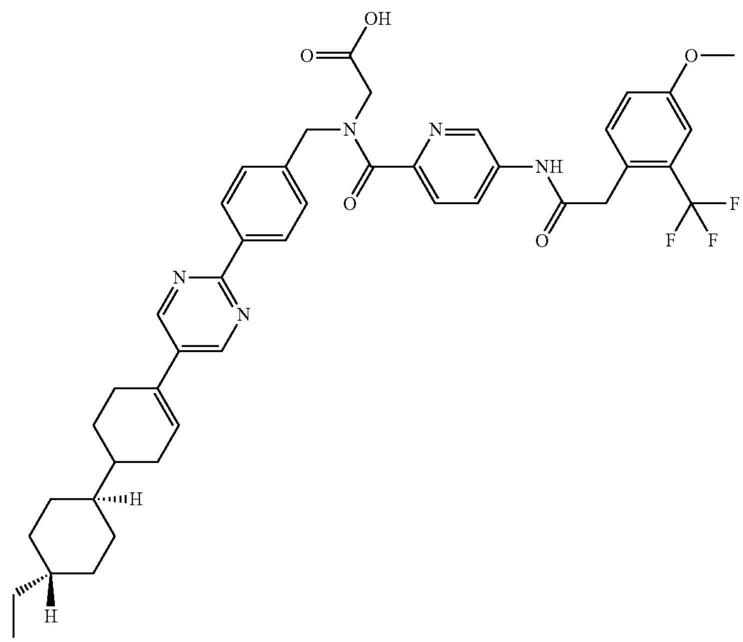 | 23 |
| 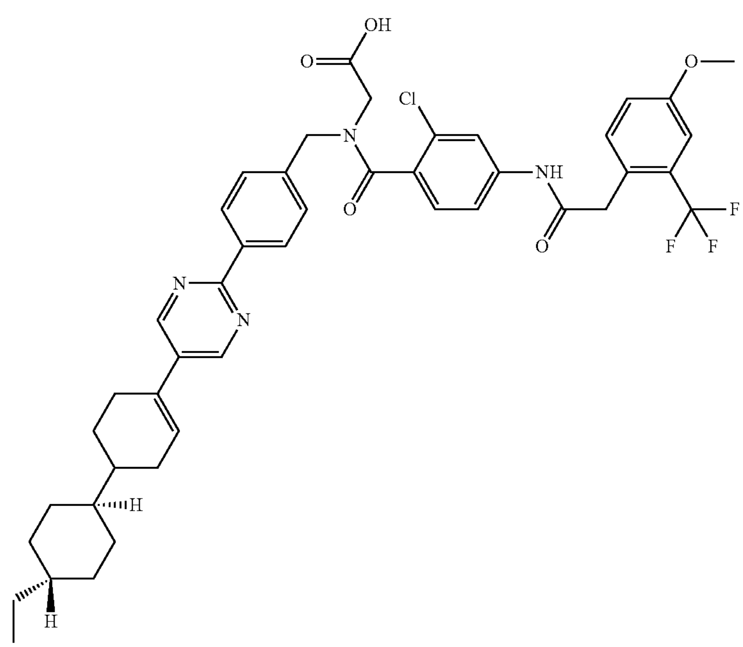 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)cc5Cl)cc4)nc3)CC2)CC1] | 24 |

| Structure | Cpd. No. |
|---|---|
| 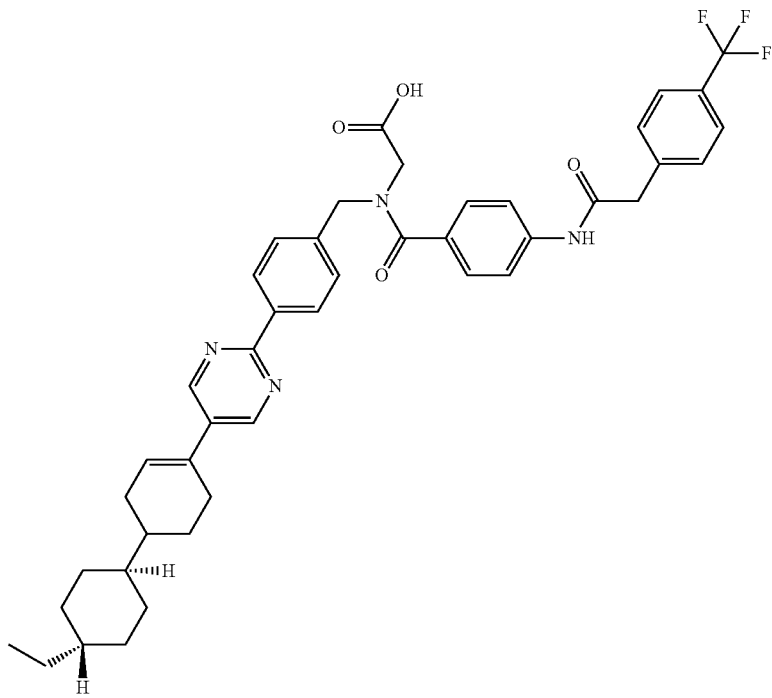 [SMILES: CC[C@H]1CC[C@H](C2CC=C(c3cnc(-c4ccc(CN(CC(=O)O)C(=O)c5ccc(NC(=O)Cc6ccc(C(F)(F)F)cc6)cc5)cc4)nc3)CC2)CC1] | 25 |
| 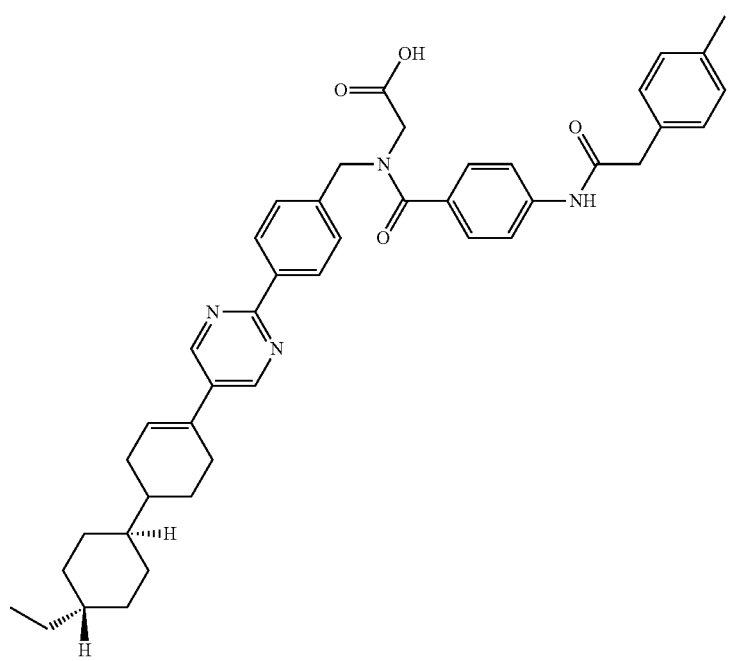 [SMILES: CC[C@H]1CC[C@H](C2CC=C(c3cnc(-c4ccc(CN(CC(=O)O)C(=O)c5ccc(NC(=O)Cc6ccc(C)cc6)cc5)cc4)nc3)CC2)CC1] | 26 |

| Structure | Cpd. No. |
|---|---|
| 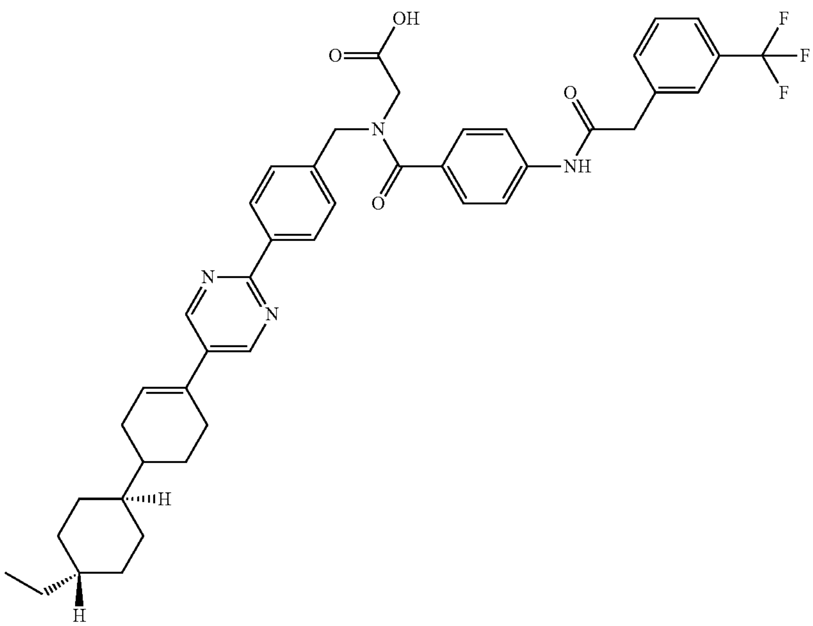 [SMILES: CC[C@H]1CC[C@H](C2CC=C(c3cnc(-c4ccc(CN(CC(=O)O)C(=O)c5ccc(NC(=O)Cc6cccc(C(F)(F)F)c6)cc5)cc4)nc3)CC2)CC1] | 27 |
| 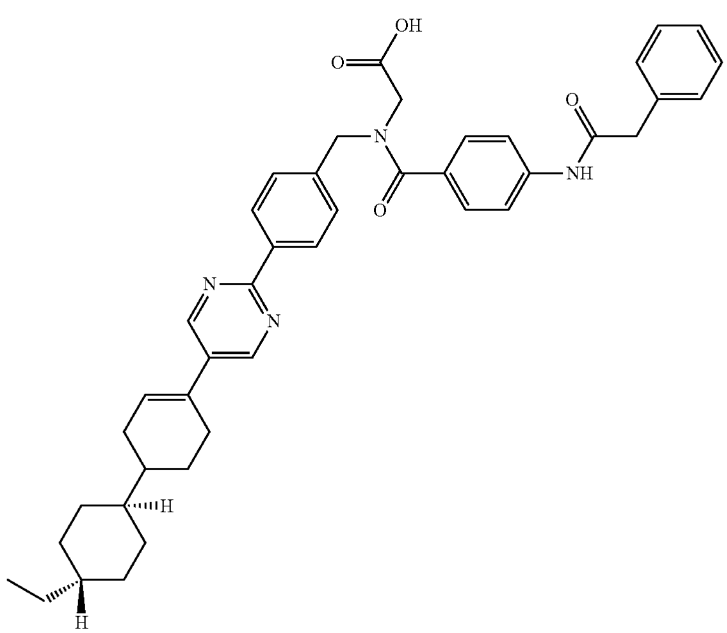 [SMILES: CC[C@H]1CC[C@H](C2CC=C(c3cnc(-c4ccc(CN(CC(=O)O)C(=O)c5ccc(NC(=O)Cc6ccccc6)cc5)cc4)nc3)CC2)CC1] | 28 |

-continued
| Structure | Cpd. No. |
|---|---|
| 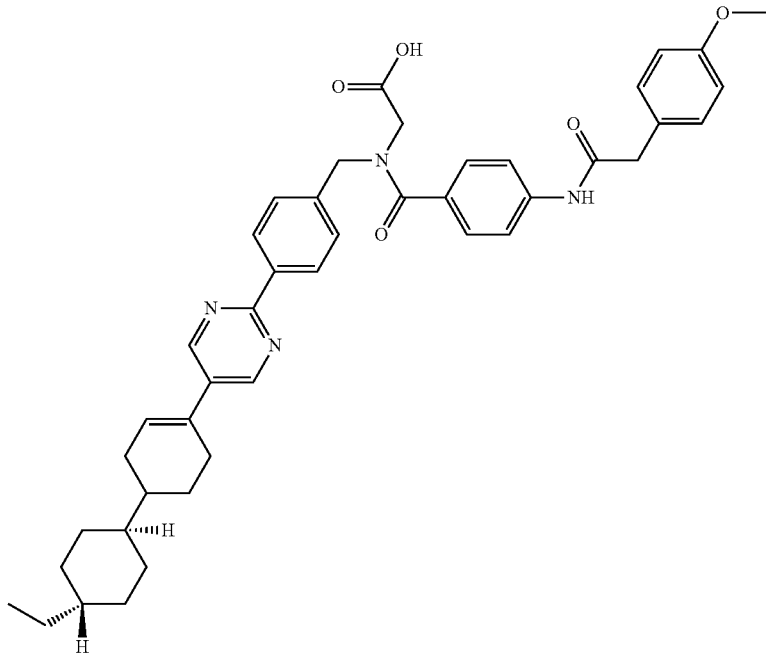 | 29 |
| 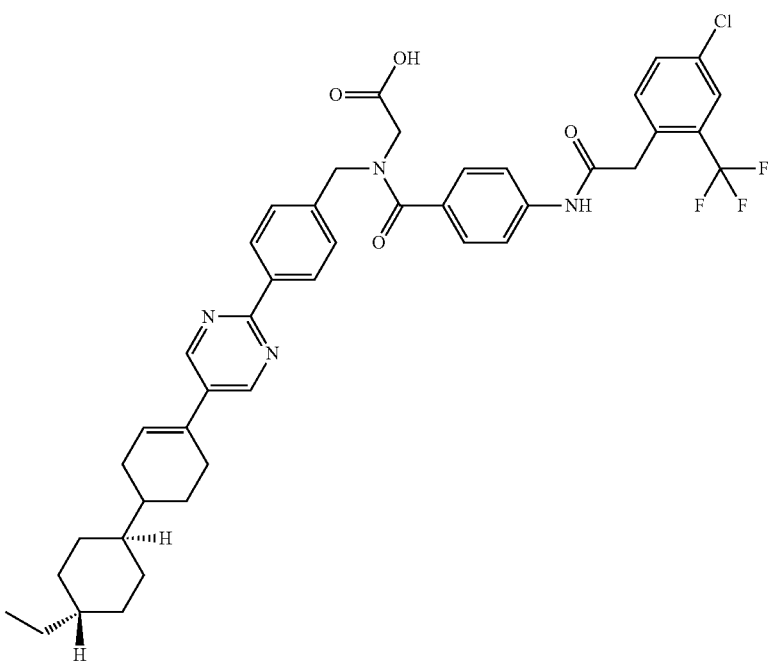 [SMILES: CC[C@H]1CC[C@H](C2CC=C(c3cnc(-c4ccc(CN(CC(=O)O)C(=O)c5ccc(NC(=O)Cc6ccc(Cl)cc6C(F)(F)F)cc5)cc4)nc3)CC2)CC1] | 30 |

| Structure | Cpd. No. |
|---|---|
| 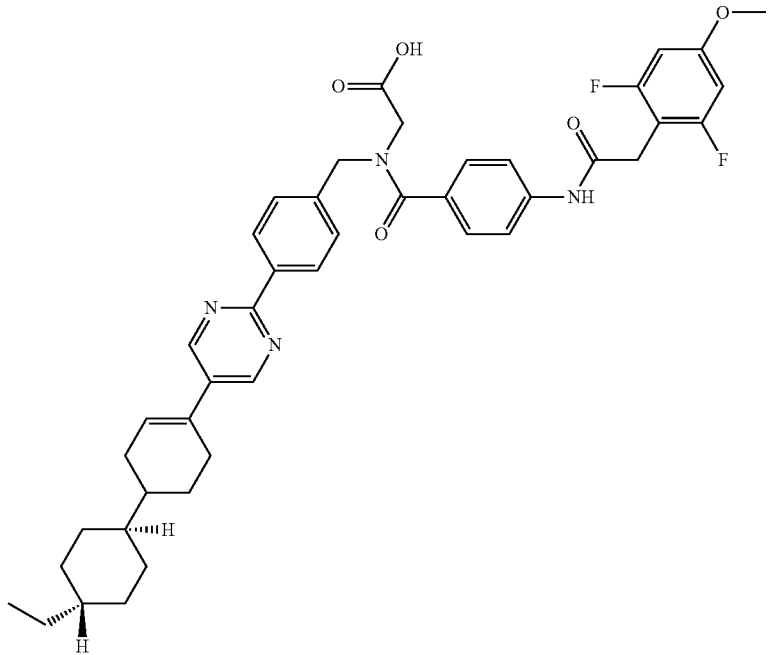 [SMILES: CC[C@H]1CC[C@H](C2CC=C(c3cnc(-c4ccc(CN(CC(=O)O)C(=O)c5ccc(NC(=O)Cc6c(F)cc(OC)cc6F)cc5)cc4)nc3)CC2)CC1] | 31 |
| 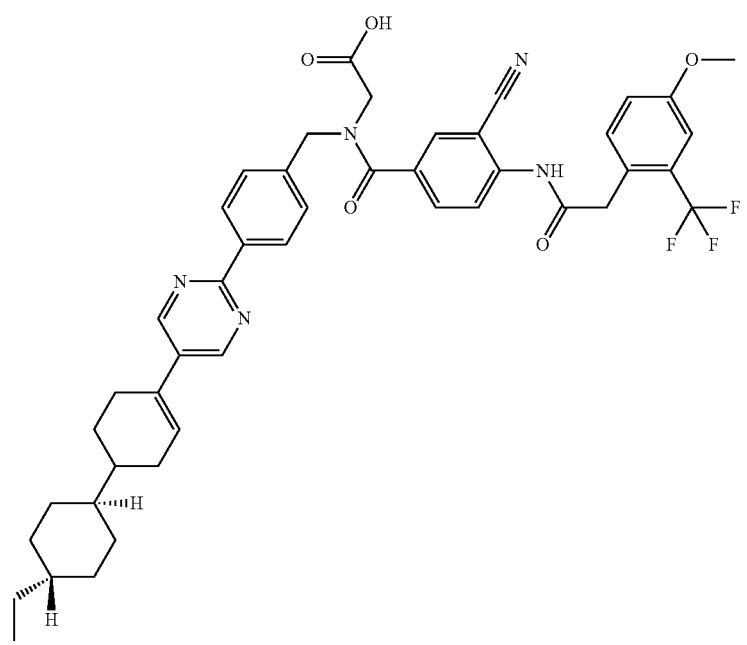 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)c(C#N)c5)cc4)nc3)CC2)CC1] | 32 |

| Structure | Cpd. No. |
|---|---|
| (chemical structure) | 33 |
| (chemical structure) | 34 |

| Structure | Cpd. No. |
| --- | --- |
| 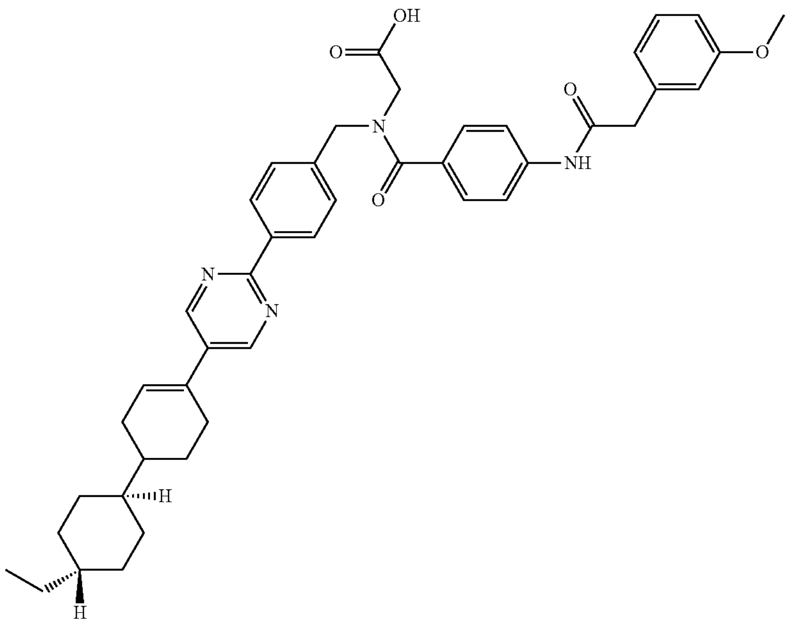 [SMILES: CC[C@H]1CC[C@H](C2CC=C(c3cnc(-c4ccc(CN(CC(=O)O)C(=O)c5ccc(NC(=O)Cc6cccc(OC)c6)cc5)cc4)nc3)CC2)CC1] | 35 |
| 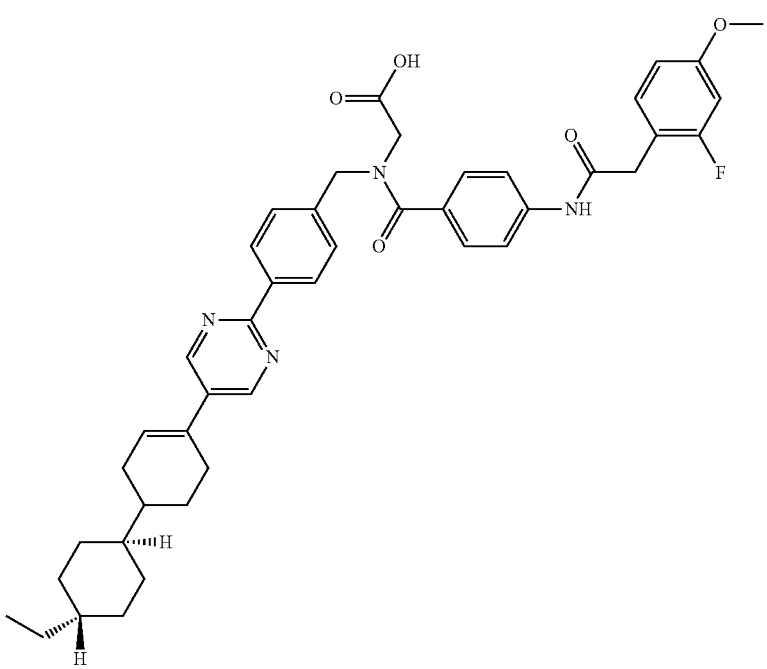 | 36 |

| Structure | Cpd. No. |
|---|---|
| 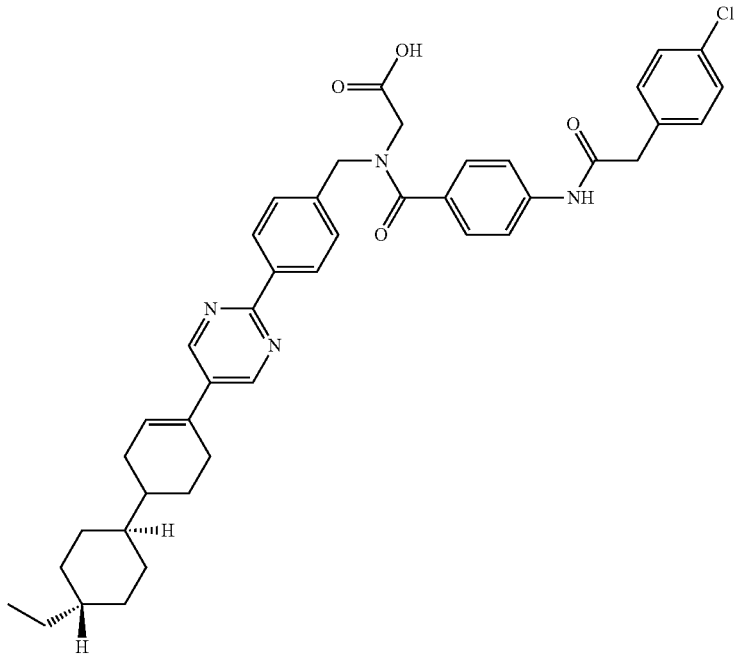 [SMILES: CC[C@H]1CC[C@H](C2CC=C(c3cnc(-c4ccc(CN(CC(=O)O)C(=O)c5ccc(NC(=O)Cc6ccc(Cl)cc6)cc5)cc4)nc3)CC2)CC1] | 37 |
| 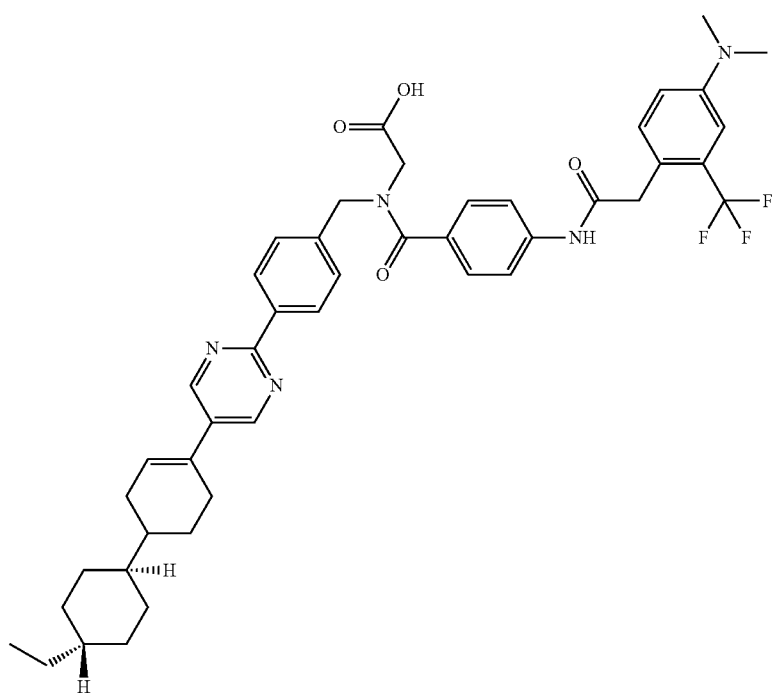 [SMILES: CC[C@H]1CC[C@H](C2CC=C(c3cnc(-c4ccc(CN(CC(=O)O)C(=O)c5ccc(NC(=O)Cc6ccc(N(C)C)cc6C(F)(F)F)cc5)cc4)nc3)CC2)CC1] | 38 |

| Structure | Cpd. No. |
|---|---|
| 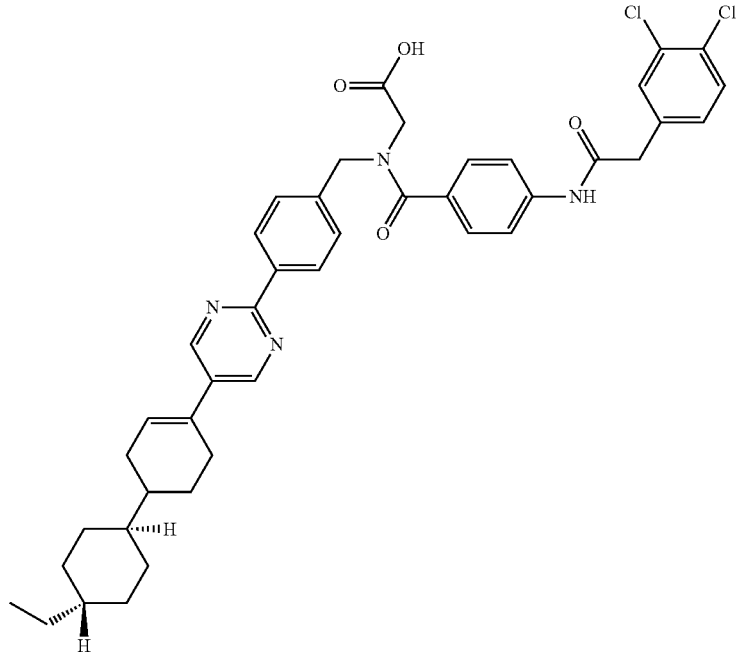 [SMILES: CC[C@H]1CC[C@H](C2CC=C(c3cnc(-c4ccc(CN(CC(=O)O)C(=O)c5ccc(NC(=O)Cc6ccc(Cl)c(Cl)c6)cc5)cc4)nc3)CC2)CC1] | 39 |
| 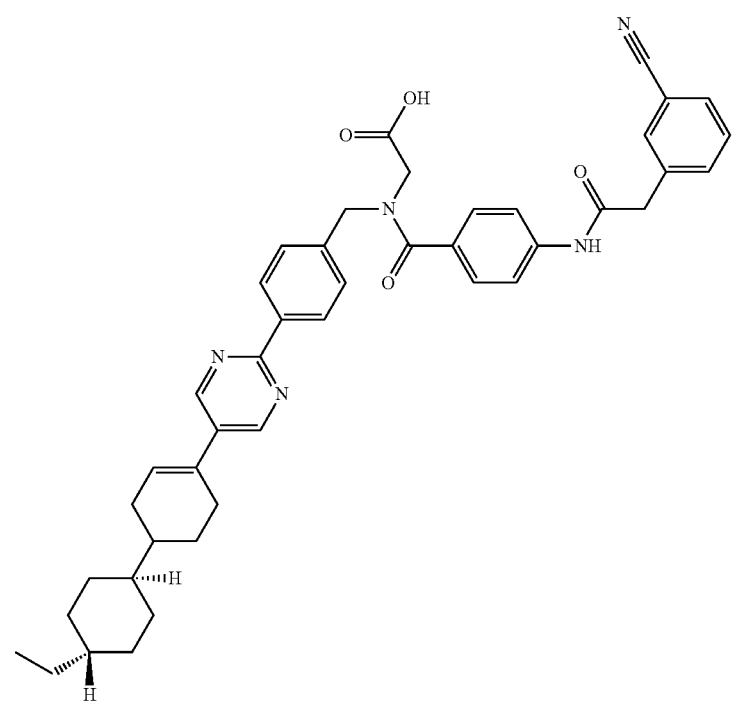 [SMILES: CC[C@H]1CC[C@H](C2CC=C(c3cnc(-c4ccc(CN(CC(=O)O)C(=O)c5ccc(NC(=O)Cc6cccc(C#N)c6)cc5)cc4)nc3)CC2)CC1] | 40 |

| Structure | Cpd. No. |
|---|---|
| 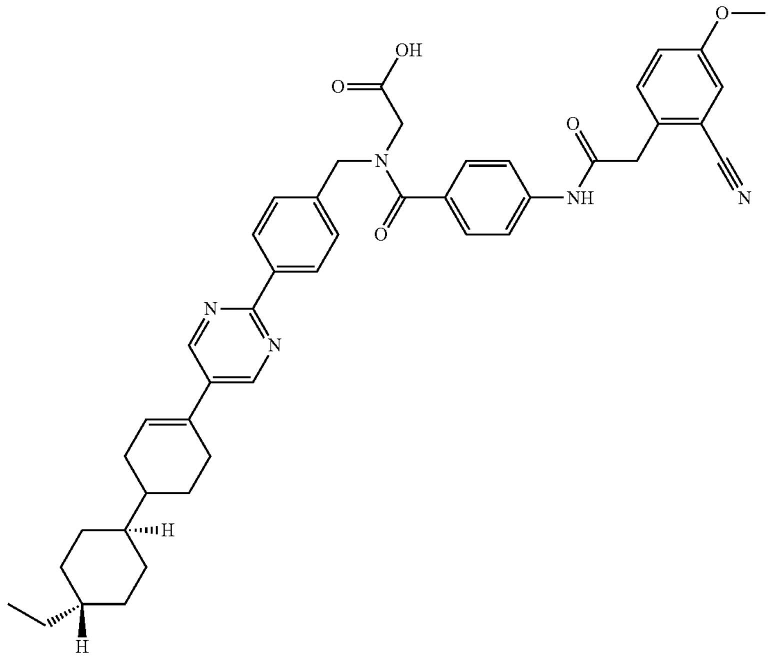 [SMILES: CC[C@H]1CC[C@H](C2CC=C(c3cnc(-c4ccc(CN(CC(=O)O)C(=O)c5ccc(NC(=O)Cc6ccc(OC)cc6C#N)cc5)cc4)nc3)CC2)CC1] | 41 |
| 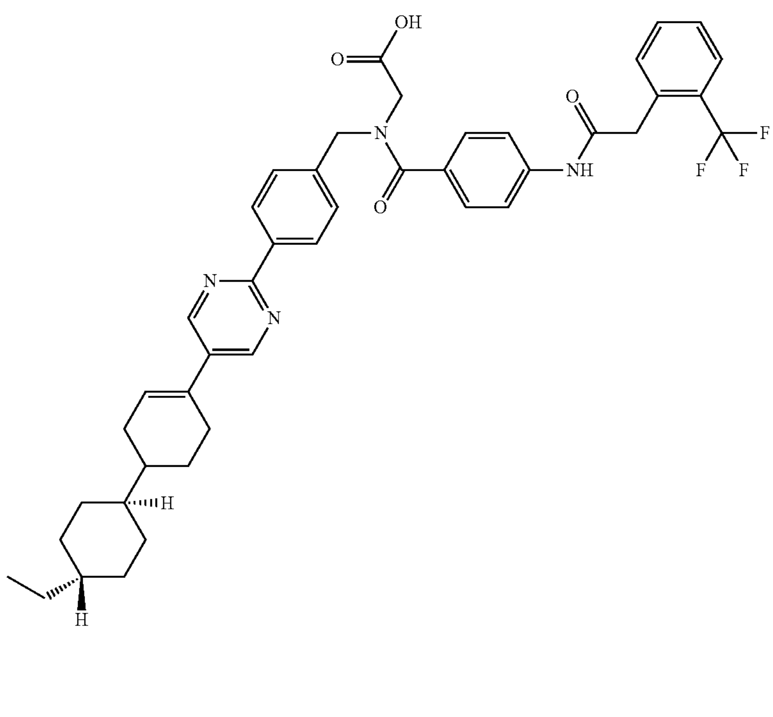 [SMILES: CC[C@H]1CC[C@H](C2CC=C(c3cnc(-c4ccc(CN(CC(=O)O)C(=O)c5ccc(NC(=O)Cc6ccccc6C(F)(F)F)cc5)cc4)nc3)CC2)CC1] | 42 |

| Structure | Cpd. No. |
|---|---|
| 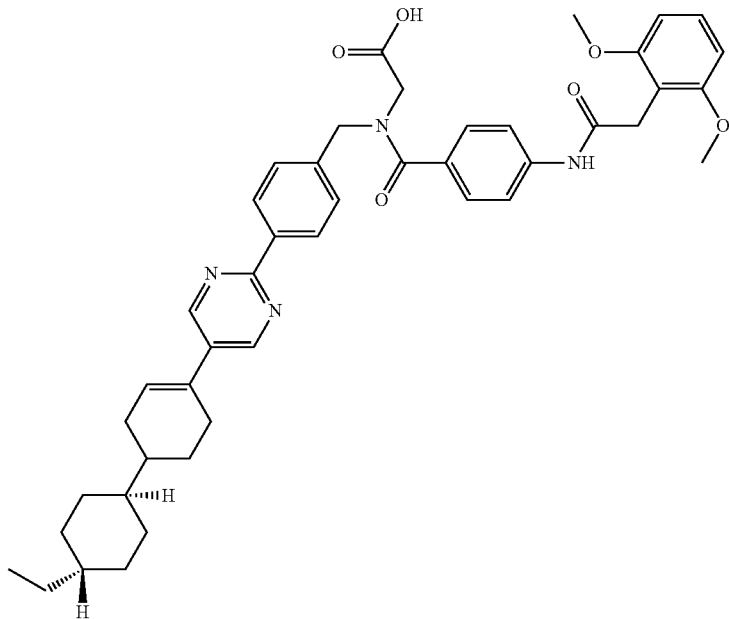 [SMILES: CC[C@H]1CC[C@H](C2CC=C(c3cnc(-c4ccc(CN(CC(=O)O)C(=O)c5ccc(NC(=O)Cc6c(OC)cccc6OC)cc5)cc4)nc3)CC2)CC1] | 43 |
| 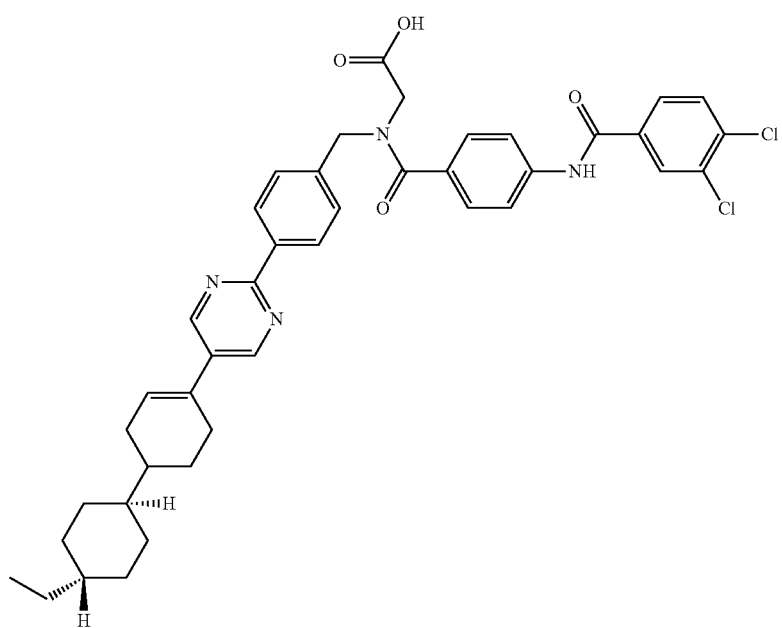 [SMILES: CC[C@H]1CC[C@H](C2CC=C(c3cnc(-c4ccc(CN(CC(=O)O)C(=O)c5ccc(NC(=O)c6ccc(Cl)c(Cl)c6)cc5)cc4)nc3)CC2)CC1] | 44 |

| Structure | Cpd. No. |
|---|---|
| (chemical structure) | 45 |
| (chemical structure) | 46 |

| Structure | Cpd. No. |
|---|---|
| 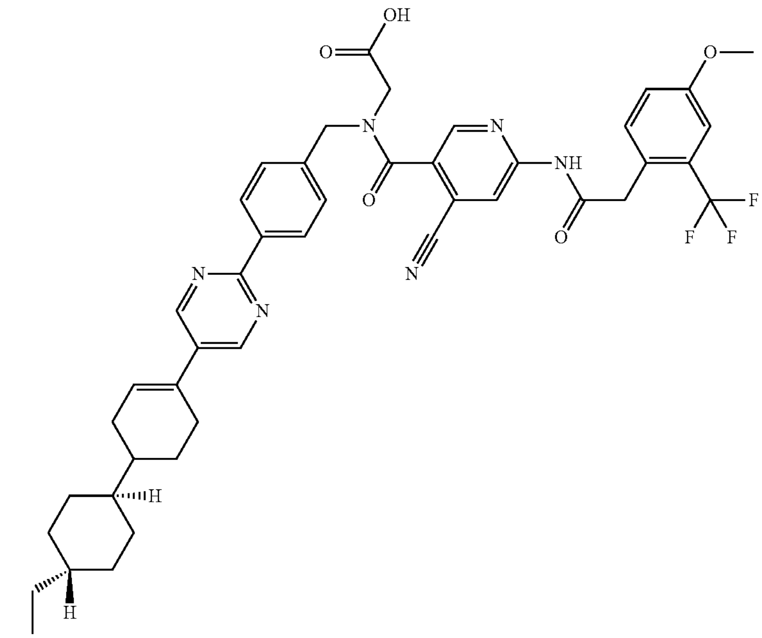 [SMILES: CC[C@H]1CC[C@H](C2CC=C(c3cnc(-c4ccc(CN(CC(=O)O)C(=O)c5cnc(NC(=O)Cc6ccc(OC)cc6C(F)(F)F)cc5C#N)cc4)nc3)CC2)CC1] | 47 |
| 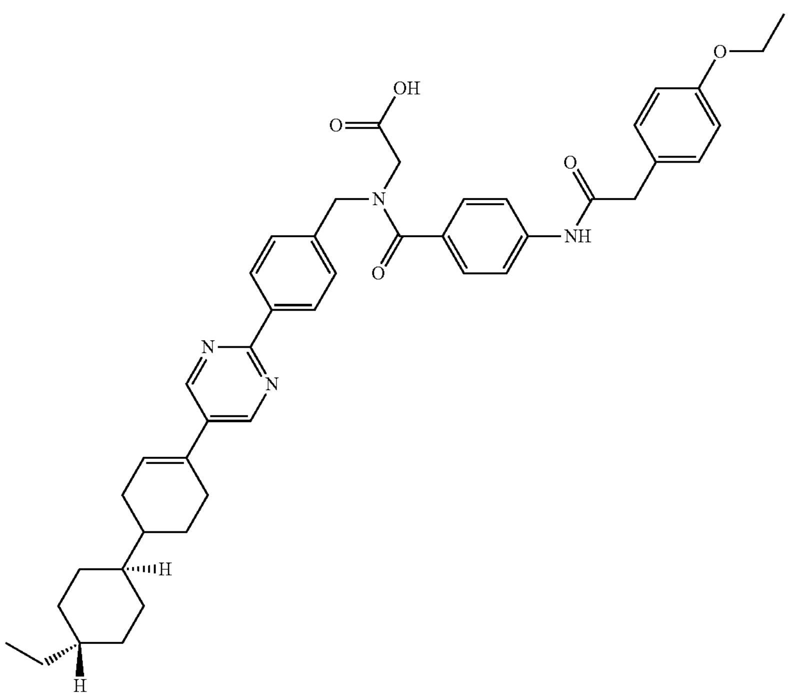 [SMILES: CCOc1ccc(CC(=O)Nc2ccc(C(=O)N(CC(=O)O)Cc3ccc(-c4ncc(C5=CCC([C@H]6CC[C@H](CC)CC6)CC5)cn4)cc3)cc2)cc1] | 48 |

| Structure | Cpd. No. |
|---|---|
| 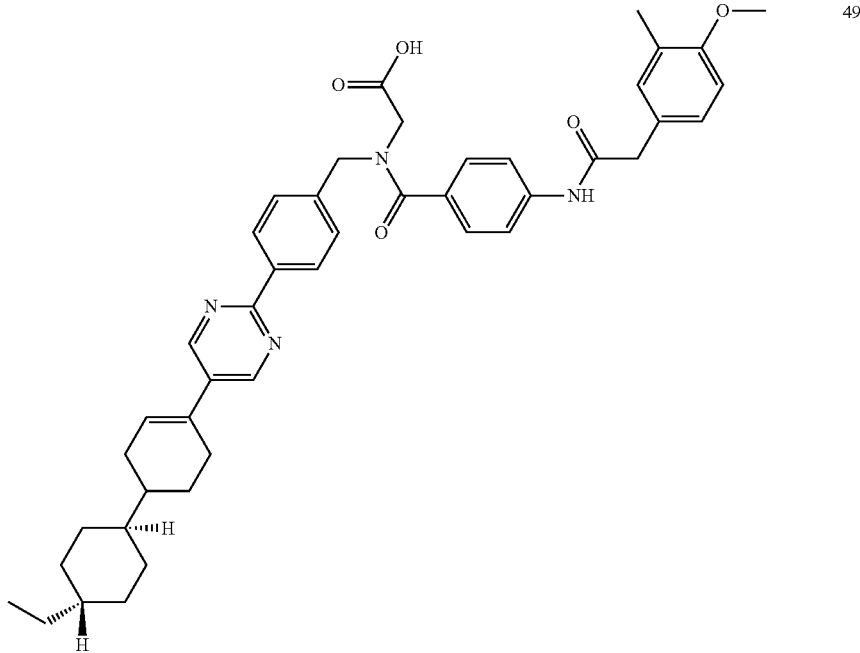 | 49 |
| 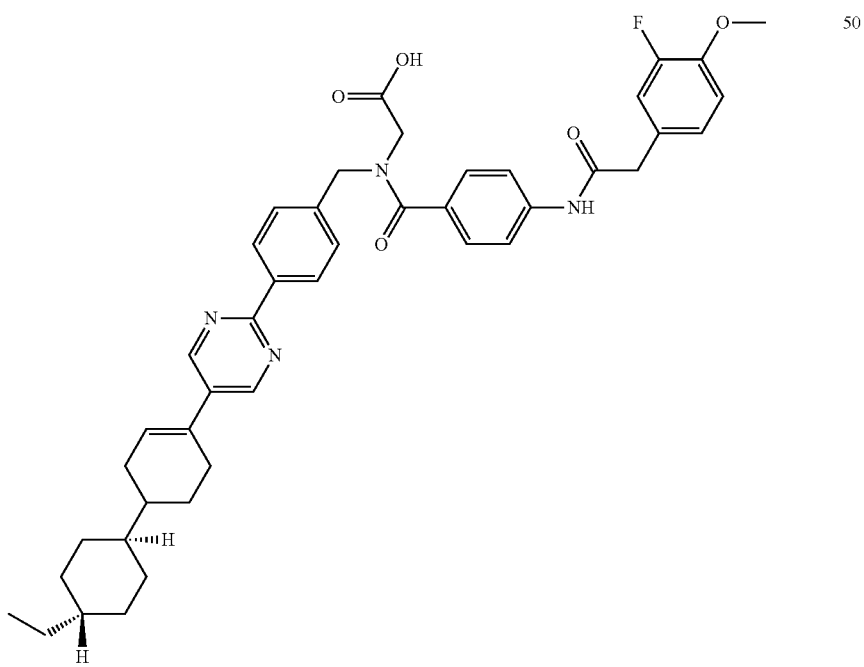 | 50 |

-continued
| Structure | Cpd. No. |
|---|---|
| 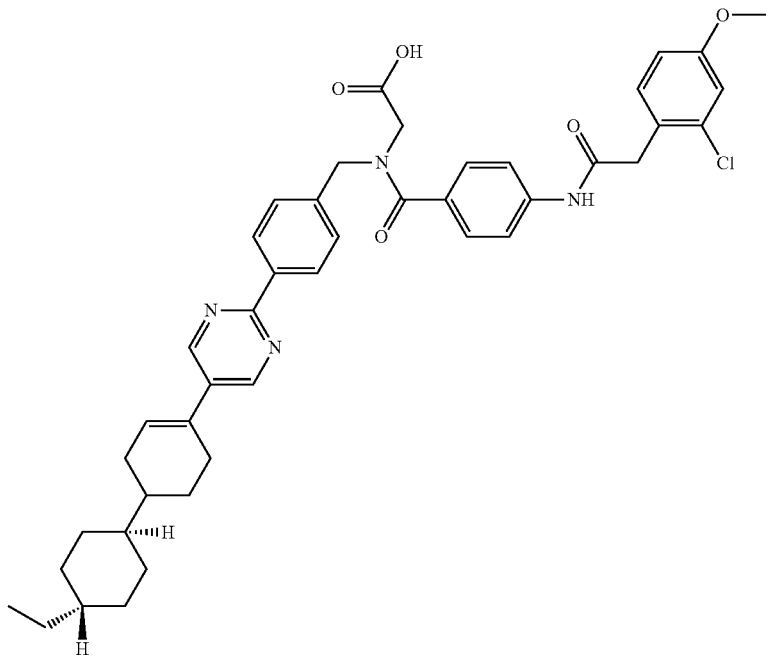 | 51 |
| 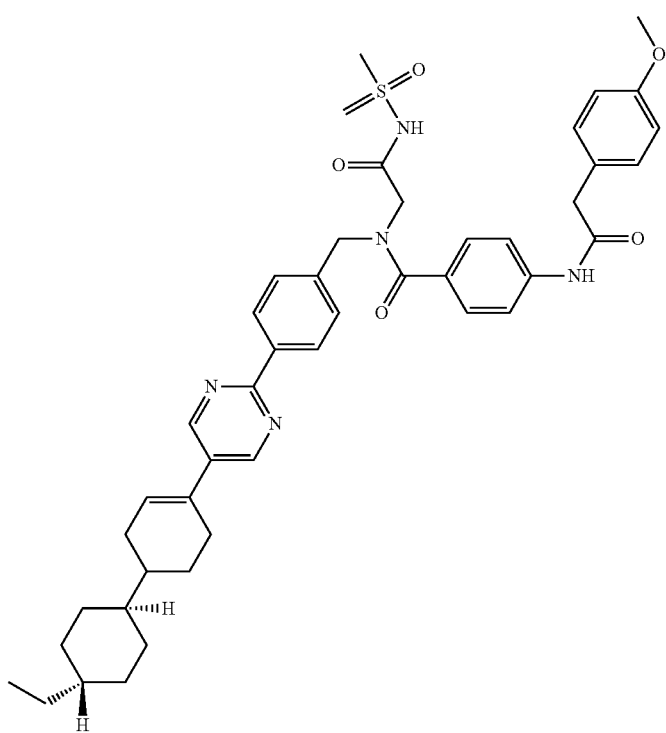 [SMILES: C=S(C)(=O)NC(=O)CN(Cc1ccc(-c2ncc(C3=CCC([C@H]4CC[C@H](CC)CC4)CC3)cn2)cc1)C(=O)c1ccc(NC(=O)Cc2ccc(OC)cc2)cc1] | 52 |

| Structure | Cpd. No. |
|---|---|
| 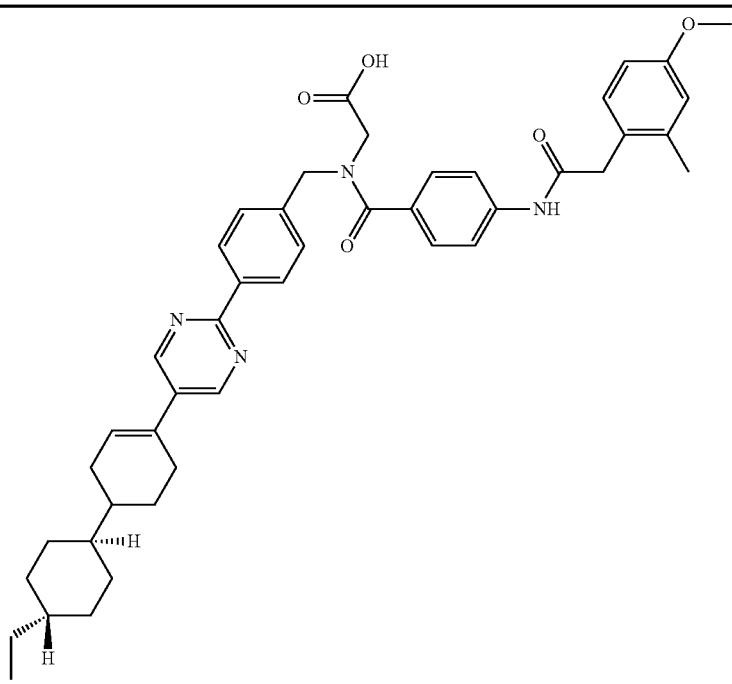 | 53 |
| 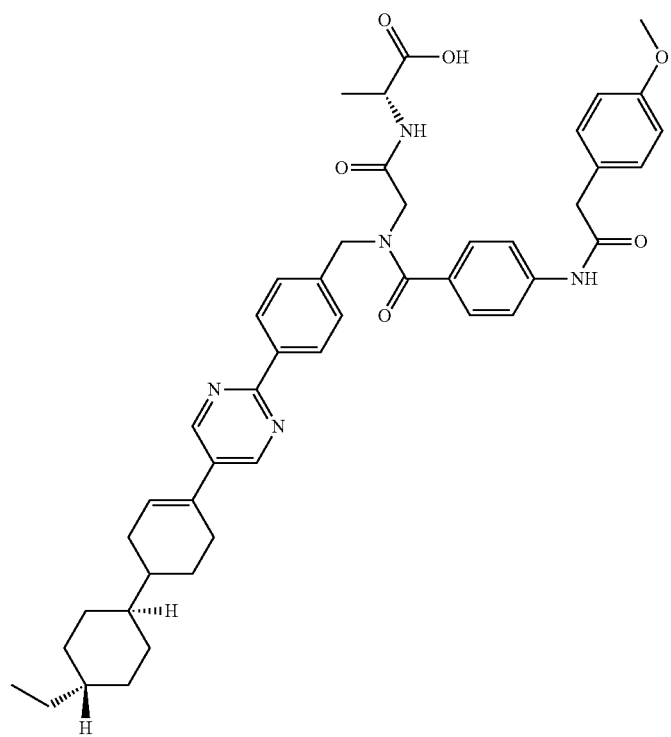 [SMILES: CC[C@H]1CC[C@H](C2CC=C(c3cnc(-c4ccc(CN(CC(=O)N[C@H](C)C(=O)O)C(=O)c5ccc(NC(=O)Cc6ccc(OC)cc6)cc5)cc4)nc3)CC2)CC1] | 54 |

-continued
| Structure | Cpd. No. |
|---|---|
| 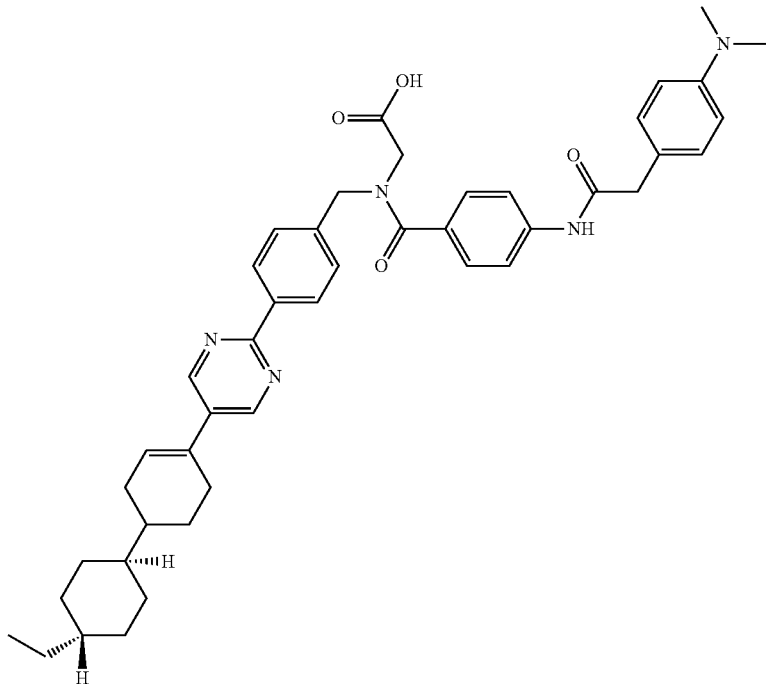 [SMILES: CC[C@H]1CC[C@H](C2CC=C(c3cnc(-c4ccc(CN(CC(=O)O)C(=O)c5ccc(NC(=O)Cc6ccc(N(C)C)cc6)cc5)cc4)nc3)CC2)CC1] | 55 |
| 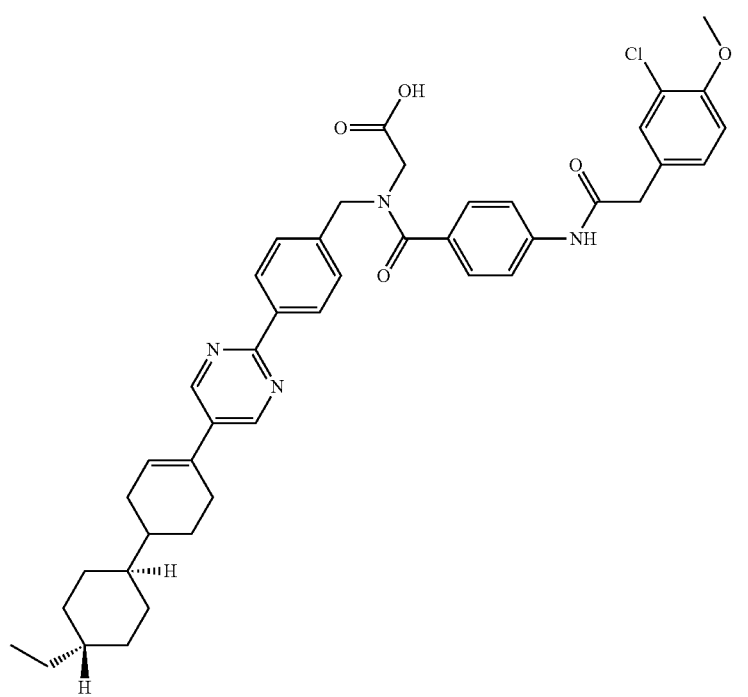 [SMILES: CC[C@H]1CC[C@H](C2CC=C(c3cnc(-c4ccc(CN(CC(=O)O)C(=O)c5ccc(NC(=O)Cc6ccc(OC)c(Cl)c6)cc5)cc4)nc3)CC2)CC1] | 56 |

-continued
| Structure | Cpd. No. |
|---|---|
| 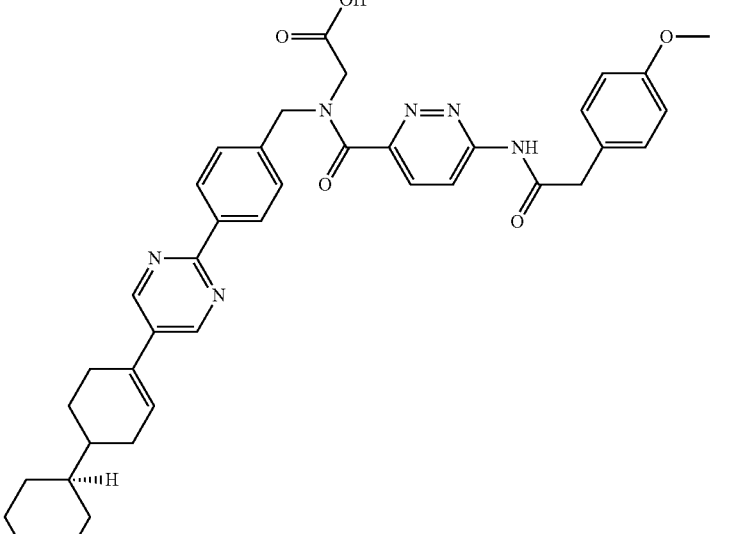 | 57 |
| 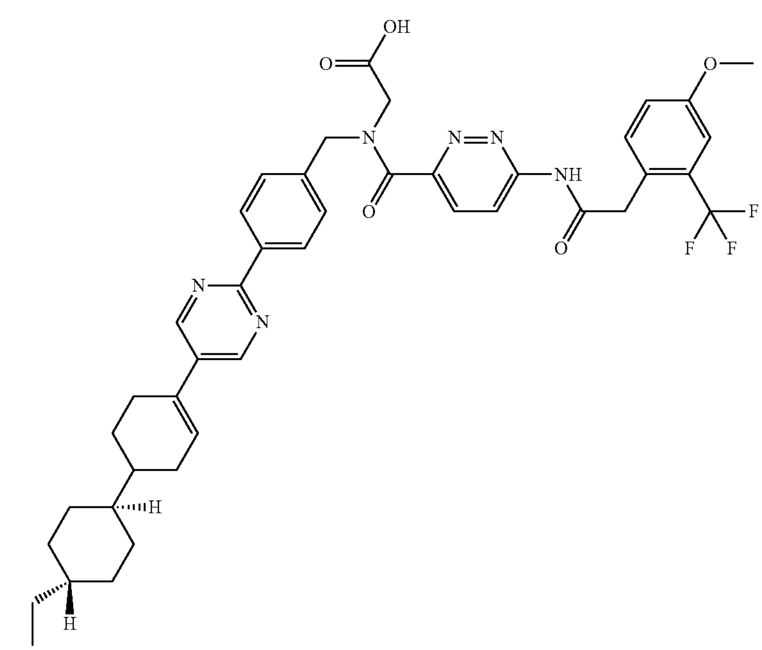 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)nn5)cc4)nc3)CC2)CC1] | 58 |

-continued
| Structure | Cpd. No. |
|---|---|
| 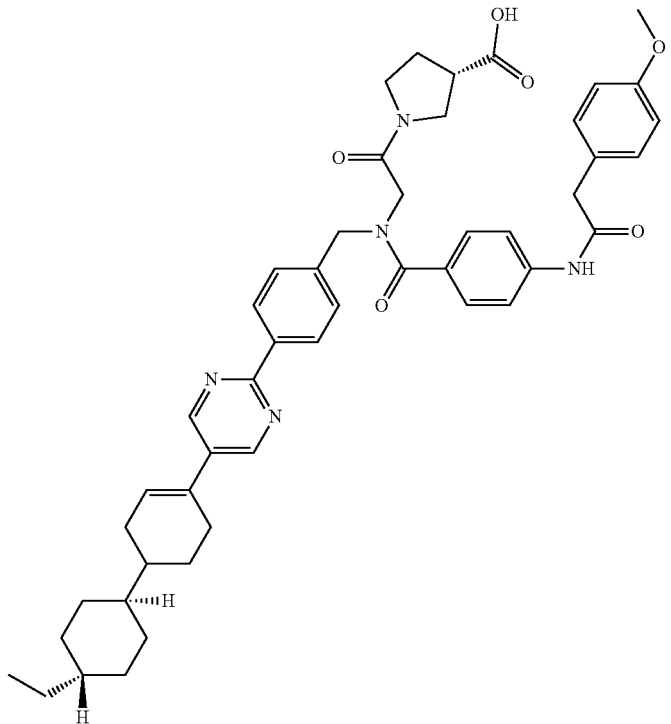 [SMILES: CC[C@H]1CC[C@H](C2CC=C(c3cnc(-c4ccc(CN(CC(=O)N5CC[C@H](C(=O)O)C5)C(=O)c5ccc(NC(=O)Cc6ccc(OC)cc6)cc5)cc4)nc3)CC2)CC1] | 59 |
| 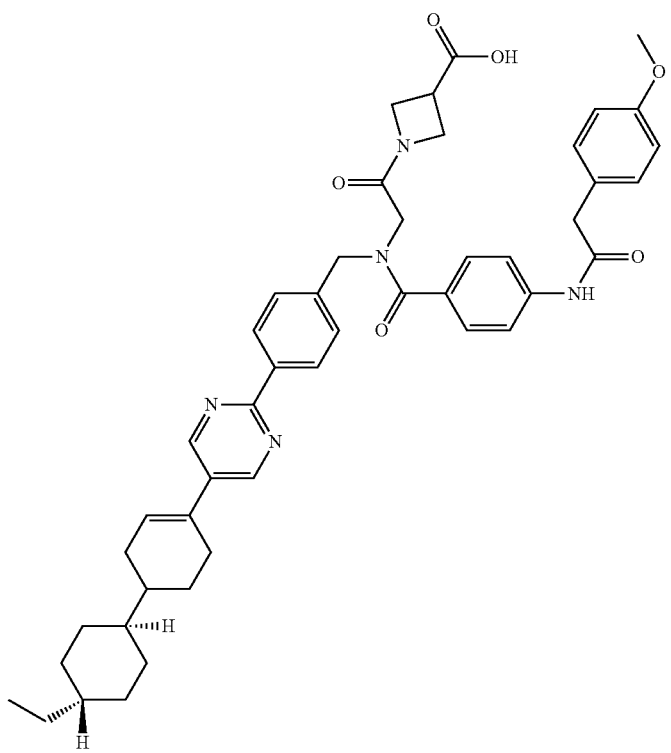 [SMILES: CC[C@H]1CC[C@H](C2CC=C(c3cnc(-c4ccc(CN(CC(=O)N5CC(C(=O)O)C5)C(=O)c5ccc(NC(=O)Cc6ccc(OC)cc6)cc5)cc4)nc3)CC2)CC1] | 60 |

| Structure | Cpd. No. |
|---|---|
| 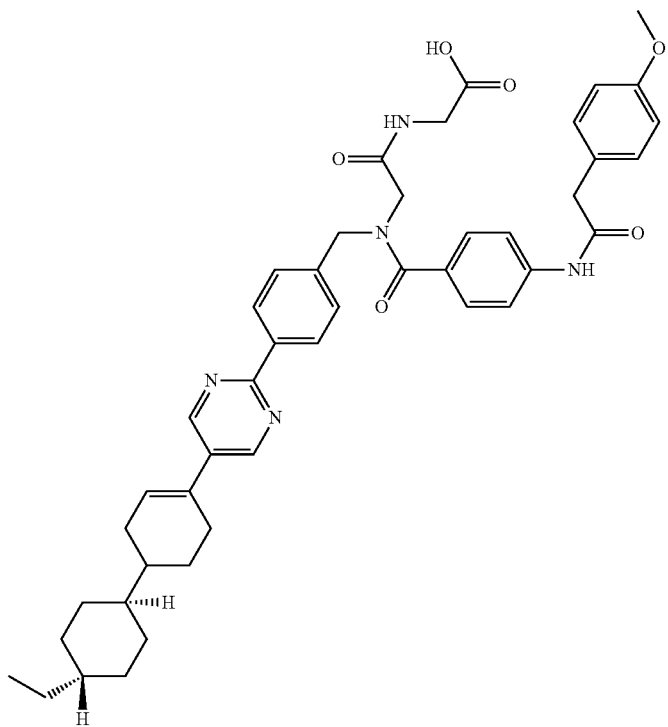 [SMILES: CC[C@H]1CC[C@H](C2CC=C(c3cnc(-c4ccc(CN(CC(=O)NCC(=O)O)C(=O)c5ccc(NC(=O)Cc6ccc(OC)cc6)cc5)cc4)nc3)CC2)CC1] | 61 |
| 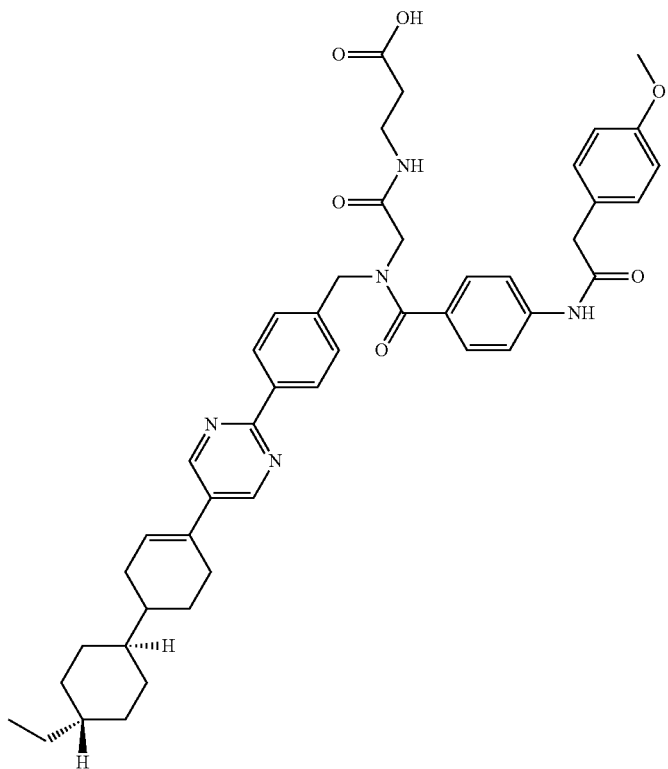 [SMILES: CC[C@H]1CC[C@H](C2CC=C(c3cnc(-c4ccc(CN(CC(=O)NCCC(=O)O)C(=O)c5ccc(NC(=O)Cc6ccc(OC)cc6)cc5)cc4)nc3)CC2)CC1] | 62 |

-continued
| Structure | Cpd. No. |
|---|---|
| 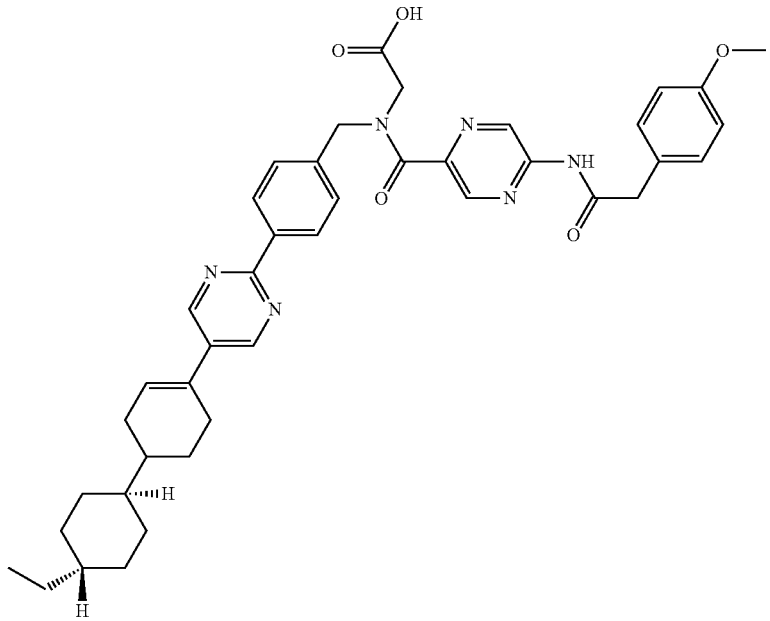 [SMILES: CC[C@H]1CC[C@H](C2CC=C(c3cnc(-c4ccc(CN(CC(=O)O)C(=O)c5cnc(NC(=O)Cc6ccc(OC)cc6)cn5)cc4)nc3)CC2)CC1] | 63 |
| 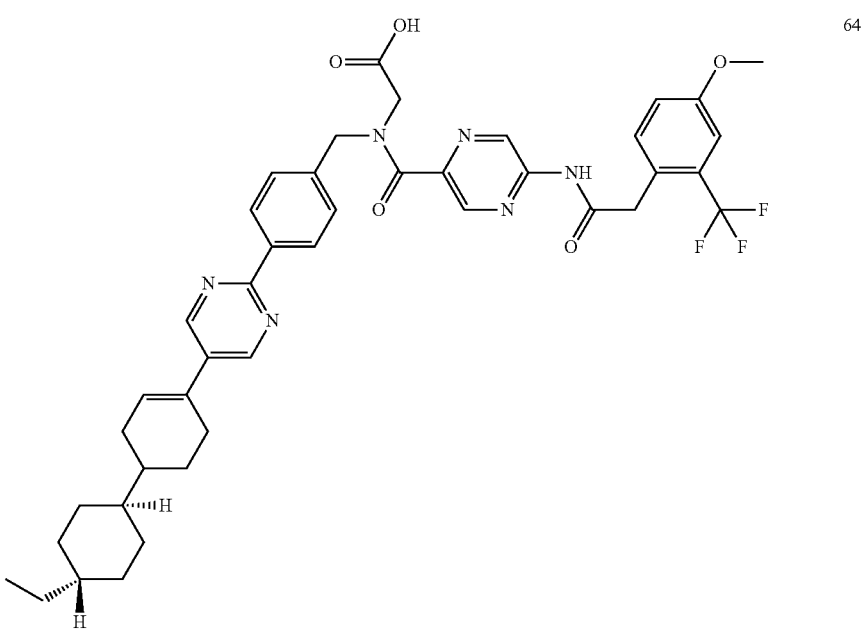 | 64 |

-continued
| Structure | Cpd. No. |
|---|---|
| 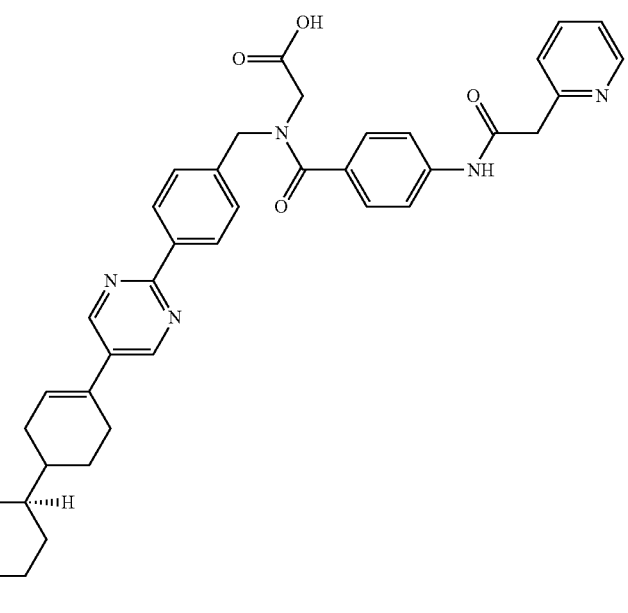 | 65 |
| 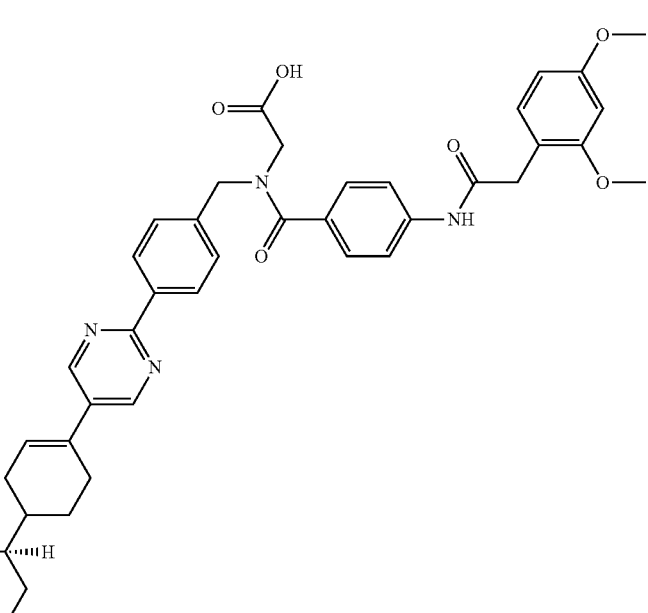 | 66 |

| Structure | Cpd. No. |
| --- | --- |
| 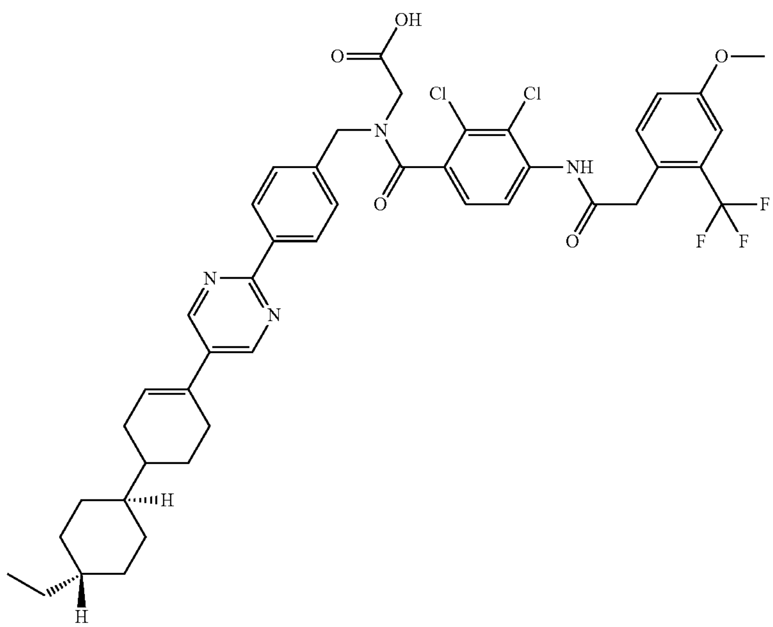 [SMILES: CC[C@H]1CC[C@H](C2CC=C(c3cnc(-c4ccc(CN(CC(=O)O)C(=O)c5ccc(NC(=O)Cc6ccc(OC)cc6C(F)(F)F)c(Cl)c5Cl)cc4)nc3)CC2)CC1] | 67 |
| 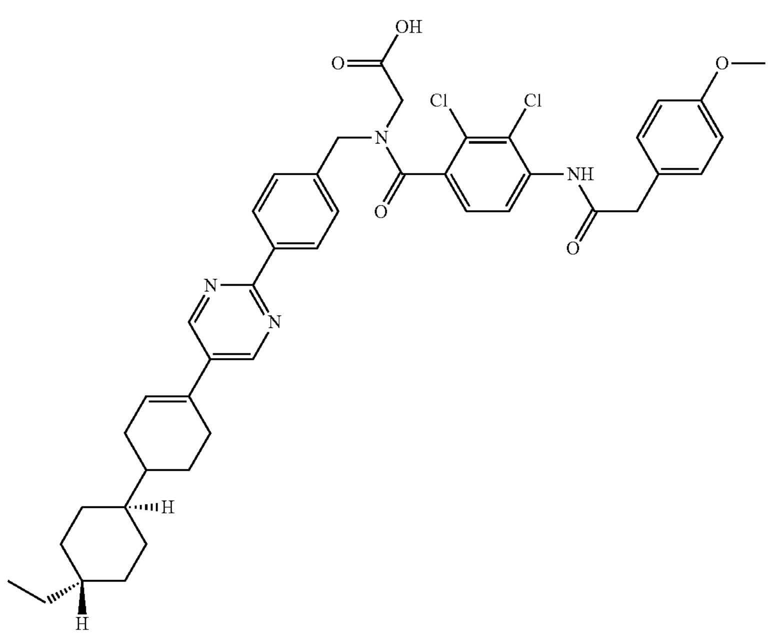 [SMILES: CC[C@H]1CC[C@H](C2CC=C(c3cnc(-c4ccc(CN(CC(=O)O)C(=O)c5ccc(NC(=O)Cc6ccc(OC)cc6)c(Cl)c5Cl)cc4)nc3)CC2)CC1] | 68 |

| Structure | Cpd. No. |
|---|---|
| 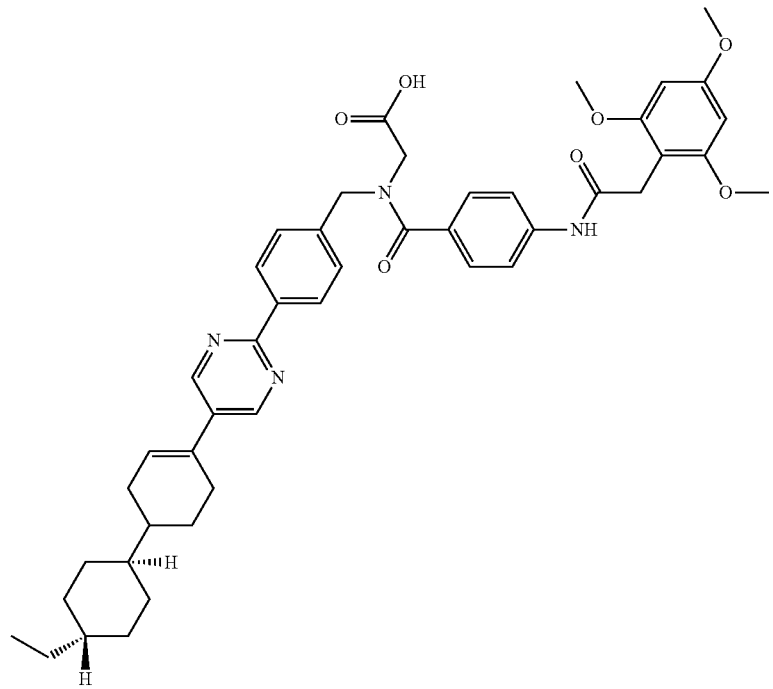 [SMILES: CC[C@H]1CC[C@H](C2CC=C(c3cnc(-c4ccc(CN(CC(=O)O)C(=O)c5ccc(NC(=O)Cc6c(OC)cc(OC)cc6OC)cc5)cc4)nc3)CC2)CC1] | 69 |
| 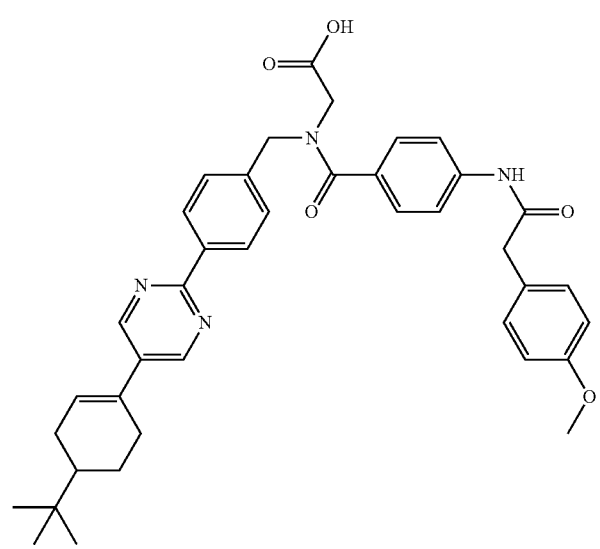 [SMILES: COc1ccc(CC(=O)Nc2ccc(C(=O)N(CC(=O)O)Cc3ccc(-c4ncc(C5=CCC(C(C)(C)C)CC5)cn4)cc3)cc2)cc1] | 70 |

-continued
| Structure | Cpd. No. |
|---|---|
| 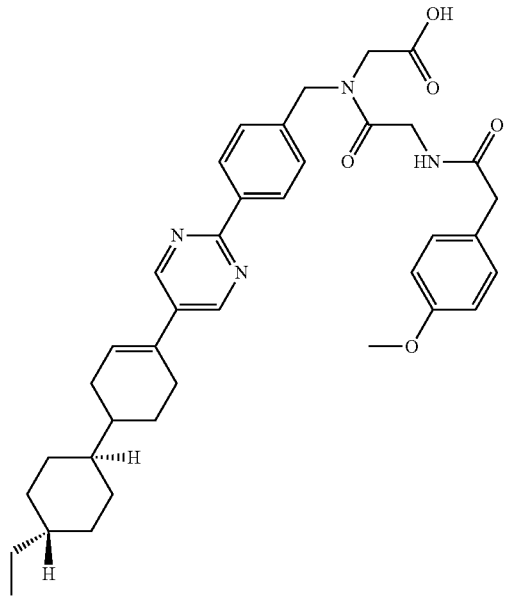 [SMILES: CC[C@H]1CC[C@H](C2CC=C(c3cnc(-c4ccc(CN(CC(=O)O)C(=O)CNC(=O)Cc5ccc(OC)cc5)cc4)nc3)CC2)CC1] | 71 |
| 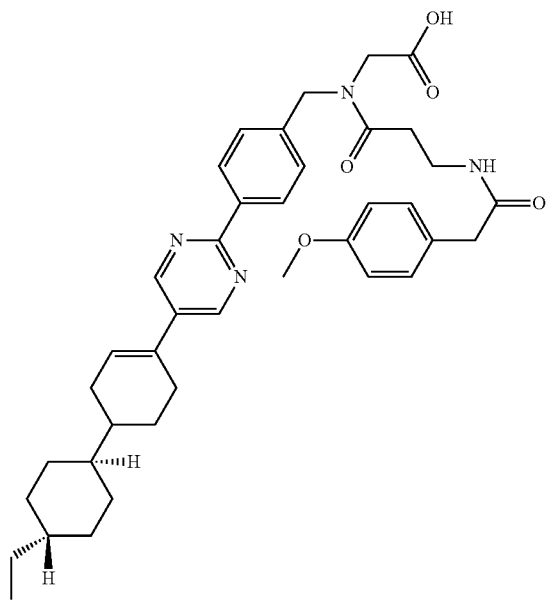 [SMILES: CC[C@H]1CC[C@H](C2CC=C(c3cnc(-c4ccc(CN(CC(=O)O)C(=O)CCNC(=O)Cc5ccc(OC)cc5)cc4)nc3)CC2)CC1] | 72 |

| Structure | Cpd. No. |
|---|---|
| 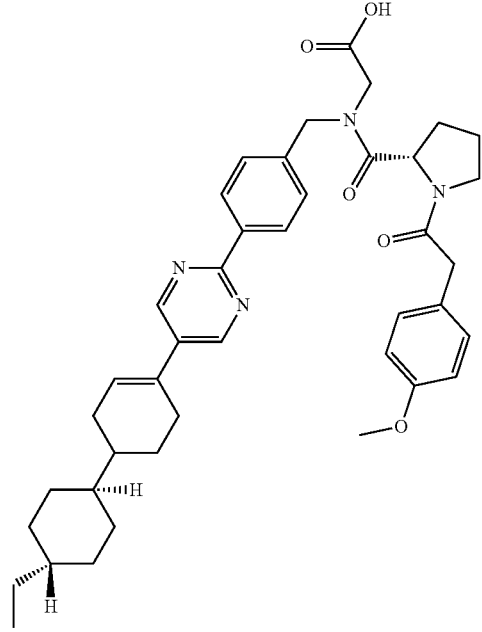 [SMILES: CC[C@H]1CC[C@H](C2CC=C(c3cnc(-c4ccc(CN(CC(=O)O)C(=O)[C@@H]5CCCN5C(=O)Cc5ccc(OC)cc5)cc4)nc3)CC2)CC1] | 73 |
| 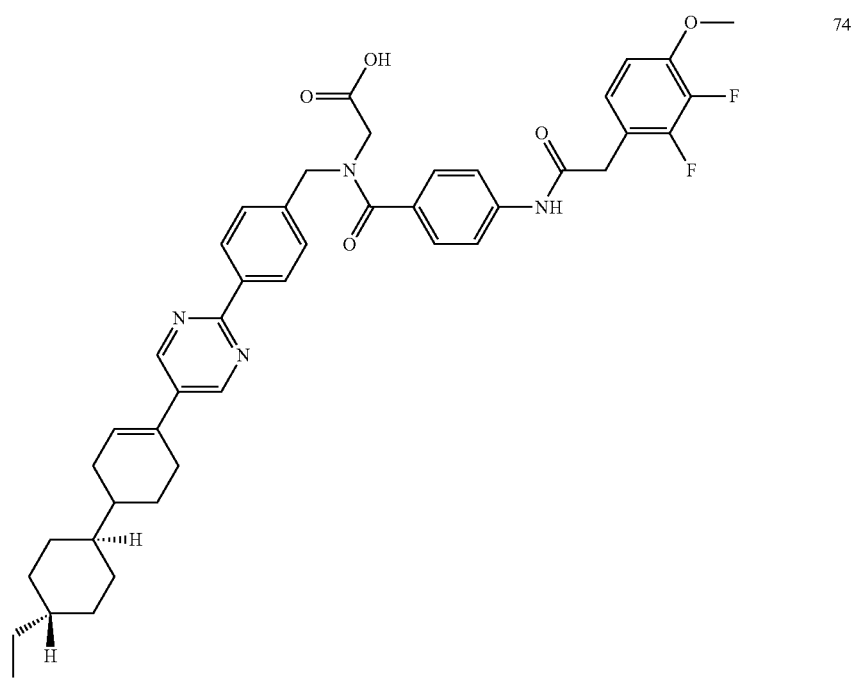 | 74 |

| Structure | Cpd. No. |
|---|---|
| 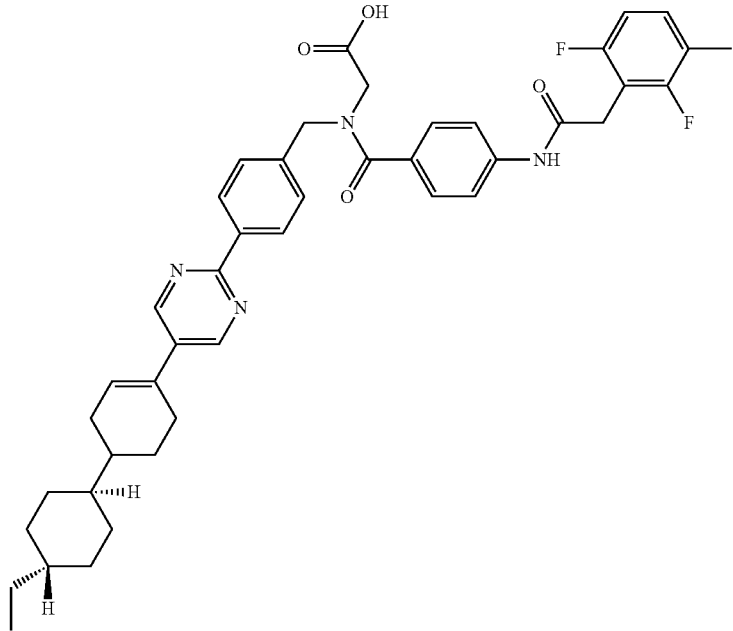 [SMILES: CC[C@H]1CC[C@H](C2CC=C(c3cnc(-c4ccc(CN(CC(=O)O)C(=O)c5ccc(NC(=O)Cc6c(F)ccc(C)c6F)cc5)cc4)nc3)CC2)CC1] | 75 |
| 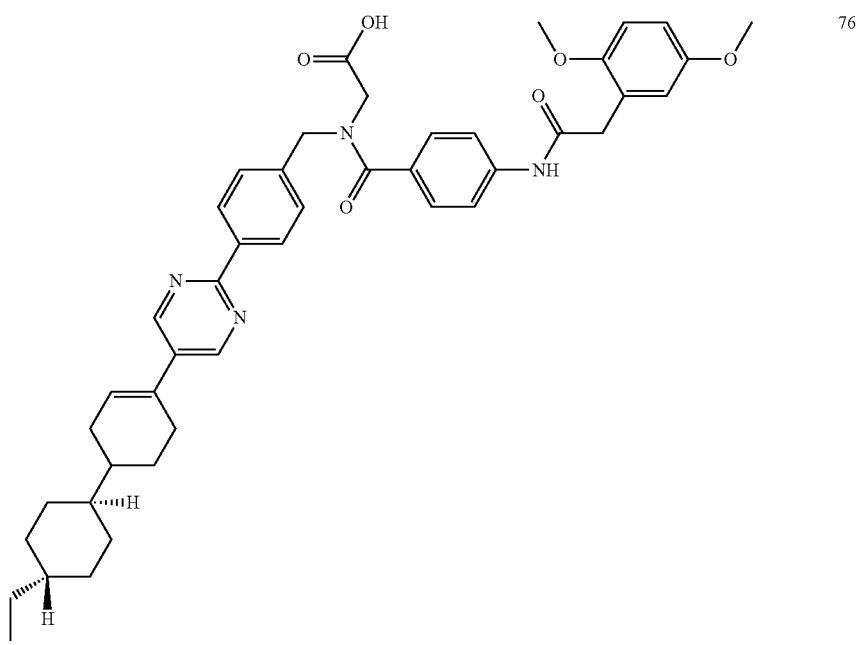 | 76 |

| Structure | Cpd. No. |
|---|---|
| 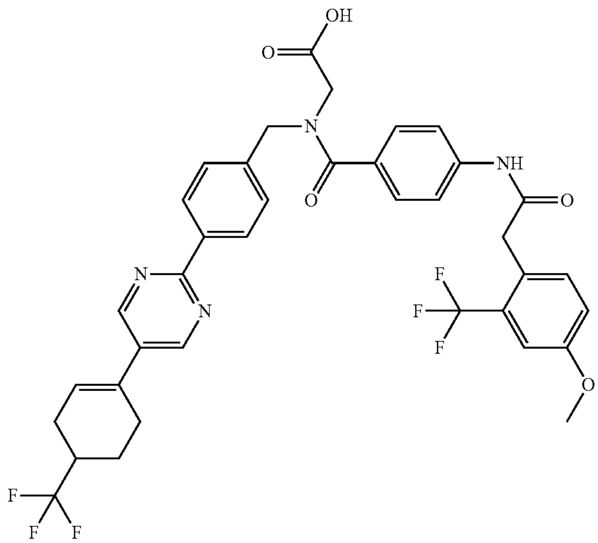 [SMILES: COc1ccc(CC(=O)Nc2ccc(C(=O)N(CC(=O)O)Cc3ccc(-c4ncc(C5=CCC(C(F)(F)F)CC5)cn4)cc3)cc2)c(C(F)(F)F)c1] | 77 |
| 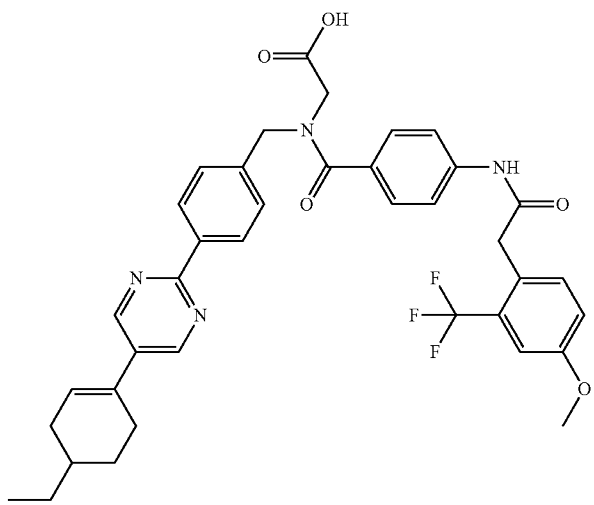 [SMILES: CCC1CC=C(c2cnc(-c3ccc(CN(CC(=O)O)C(=O)c4ccc(NC(=O)Cc5ccc(OC)cc5C(F)(F)F)cc4)cc3)nc2)CC1] | 78 |
| 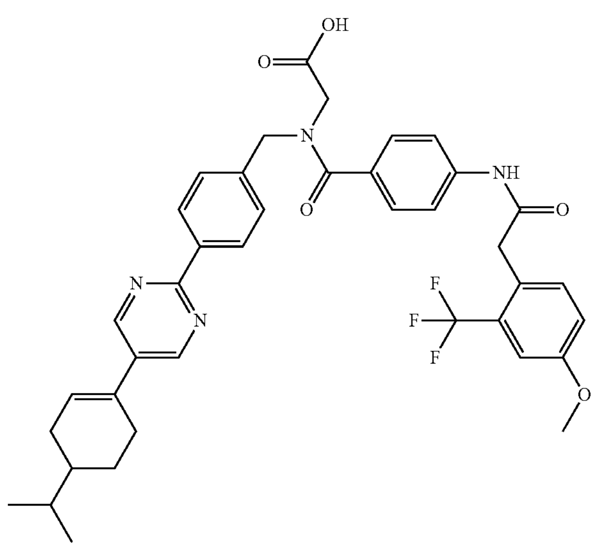 [SMILES: COc1ccc(CC(=O)Nc2ccc(C(=O)N(CC(=O)O)Cc3ccc(-c4ncc(C5=CCC(C(C)C)CC5)cn4)cc3)cc2)c(C(F)(F)F)c1] | 79 |

-continued
| Structure | Cpd. No. |
|---|---|
| 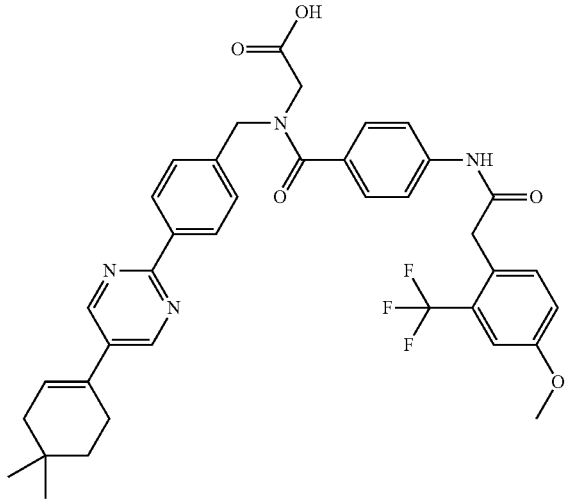 [SMILES: COc1ccc(CC(=O)Nc2ccc(C(=O)N(CC(=O)O)Cc3ccc(-c4ncc(C5=CCC(C)(C)CC5)cn4)cc3)cc2)c(C(F)(F)F)c1] | 80 |
| 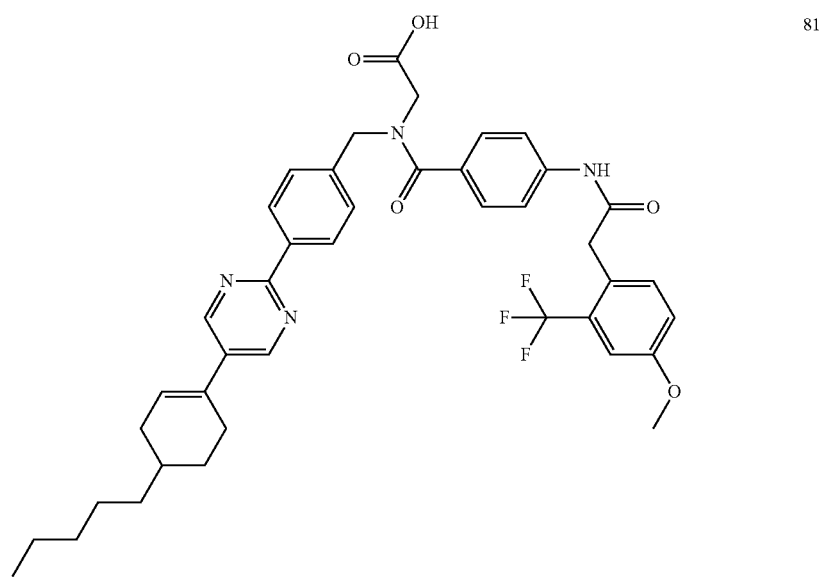 | 81 |

| Structure | Cpd. No. |
|---|---|
| 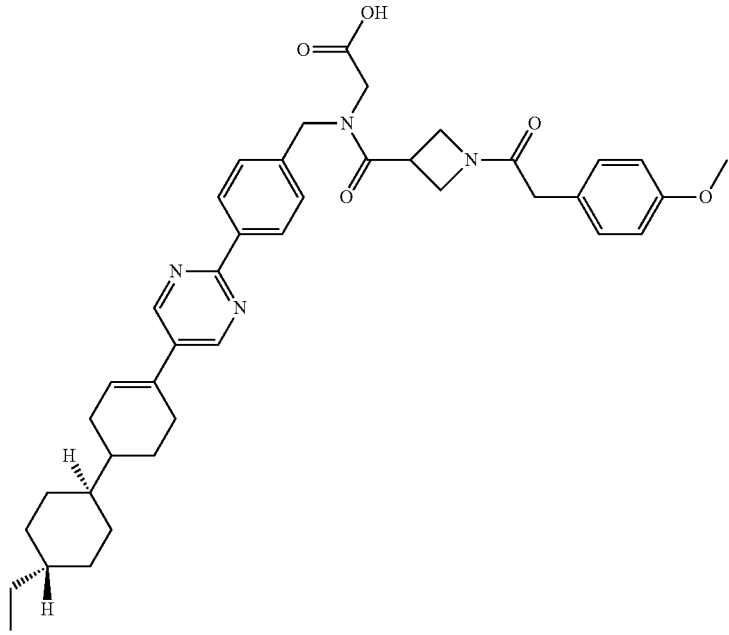 [SMILES: CC[C@H]1CC[C@H](C2CC=C(c3cnc(-c4ccc(CN(CC(=O)O)C(=O)C5CN(C(=O)Cc6ccc(OC)cc6)C5)cc4)nc3)CC2)CC1] | 82 |
| 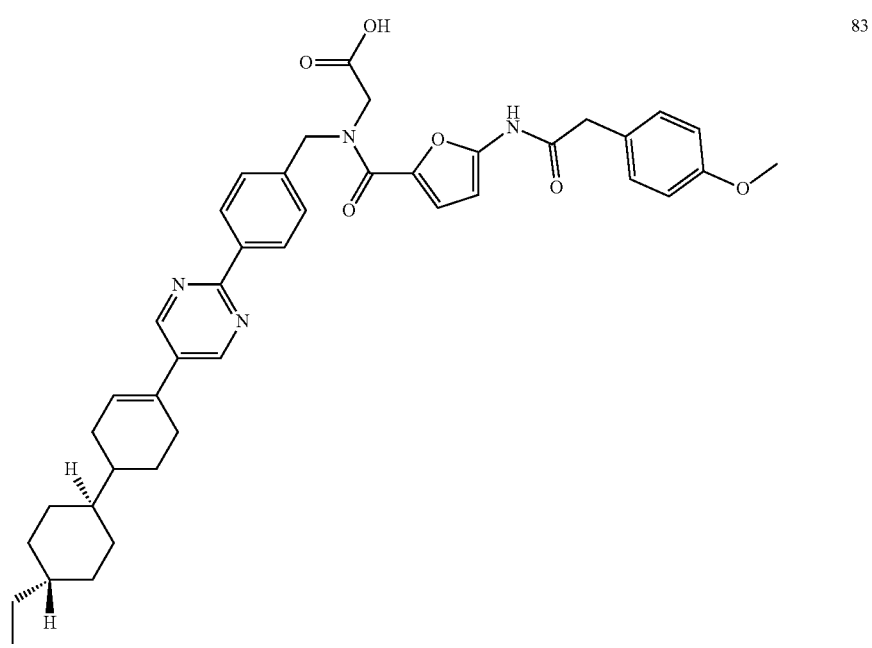 | 83 |

| Structure | Cpd. No. |
|---|---|
| 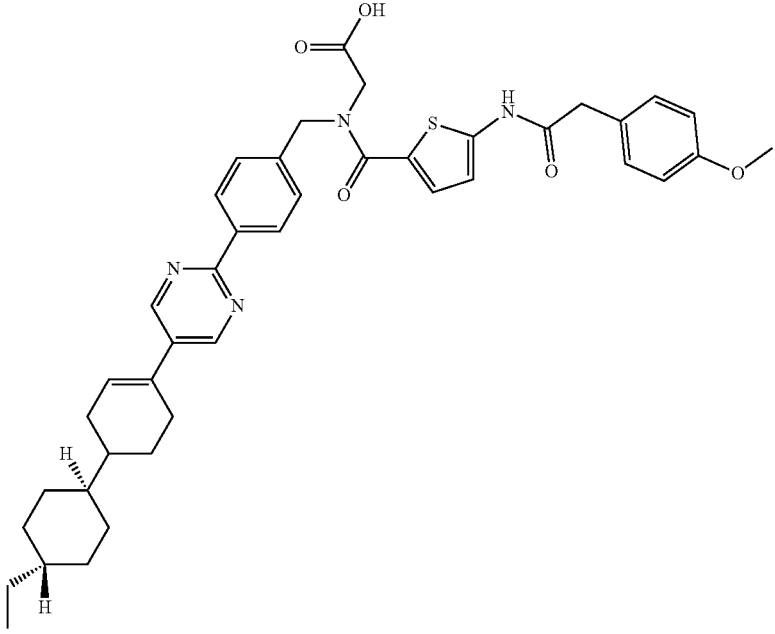 [SMILES: CC[C@H]1CC[C@H](C2CC=C(c3cnc(-c4ccc(CN(CC(=O)O)C(=O)c5ccc(NC(=O)Cc6ccc(OC)cc6)s5)cc4)nc3)CC2)CC1] | 84 |
| 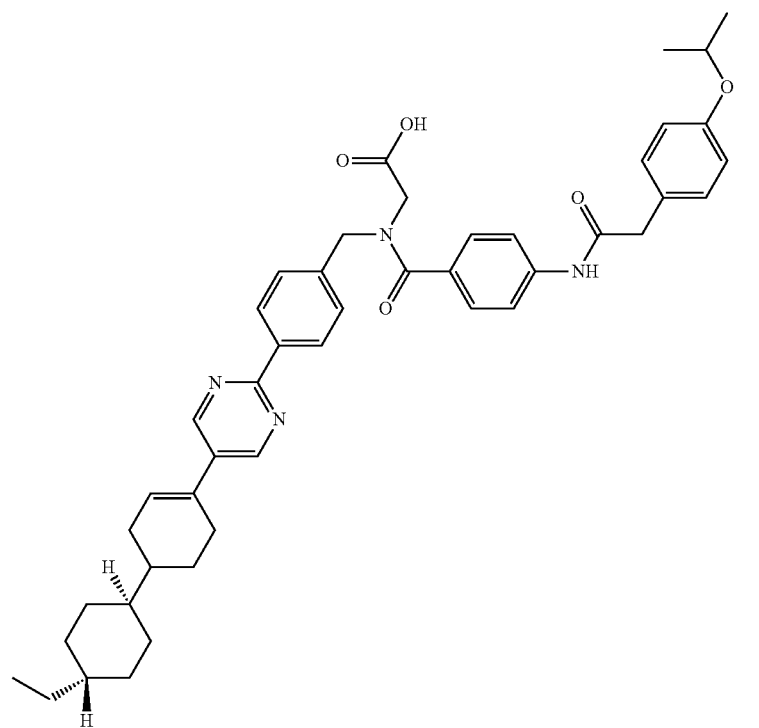 [SMILES: CC[C@H]1CC[C@H](C2CC=C(c3cnc(-c4ccc(CN(CC(=O)O)C(=O)c5ccc(NC(=O)Cc6ccc(OC(C)C)cc6)cc5)cc4)nc3)CC2)CC1] | 85 |

-continued

| Structure | Cpd. No. |
|---|---|
| 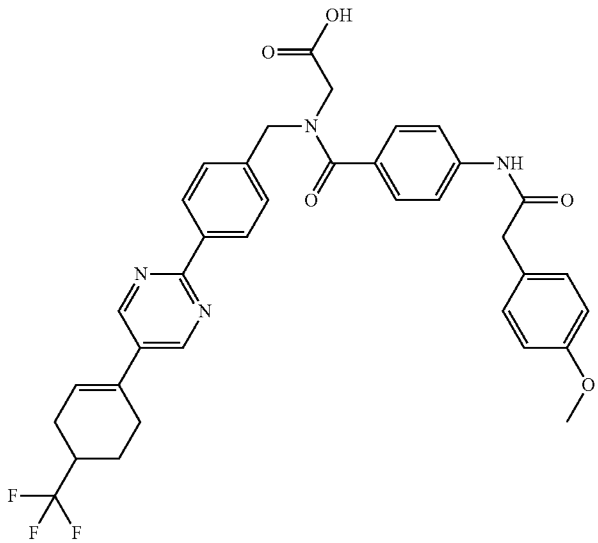 [SMILES: COc1ccc(CC(=O)Nc2ccc(C(=O)N(CC(=O)O)Cc3ccc(-c4ncc(C5=CCC(C(F)(F)F)CC5)cn4)cc3)cc2)cc1] | 86 |
| 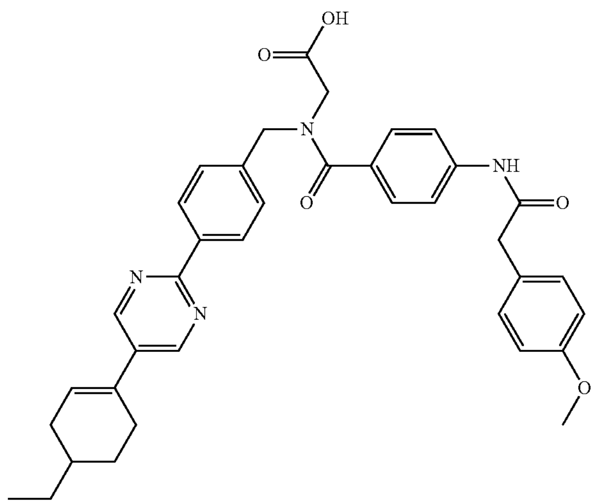 [SMILES: CCC1CC=C(c2cnc(-c3ccc(CN(CC(=O)O)C(=O)c4ccc(NC(=O)Cc5ccc(OC)cc5)cc4)cc3)nc2)CC1] | 87 |
| 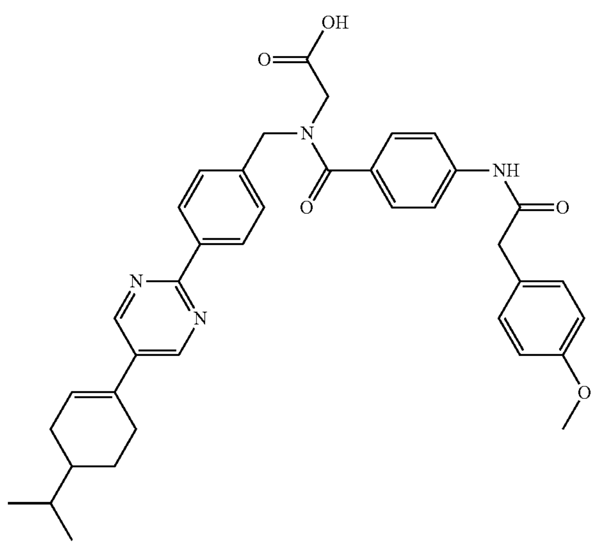 [SMILES: COc1ccc(CC(=O)Nc2ccc(C(=O)N(CC(=O)O)Cc3ccc(-c4ncc(C5=CCC(C(C)C)CC5)cn4)cc3)cc2)cc1] | 88 |

| Structure | Cpd. No. |
|---|---|
| 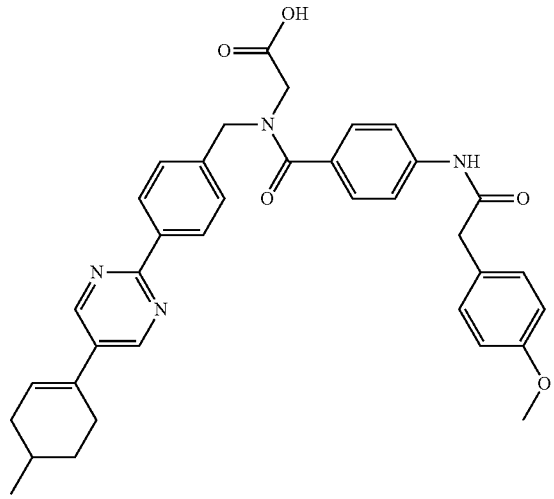 [SMILES: COc1ccc(CC(=O)Nc2ccc(C(=O)N(CC(=O)O)Cc3ccc(-c4ncc(C5=CCC(C)CC5)cn4)cc3)cc2)cc1] | 89 |
| 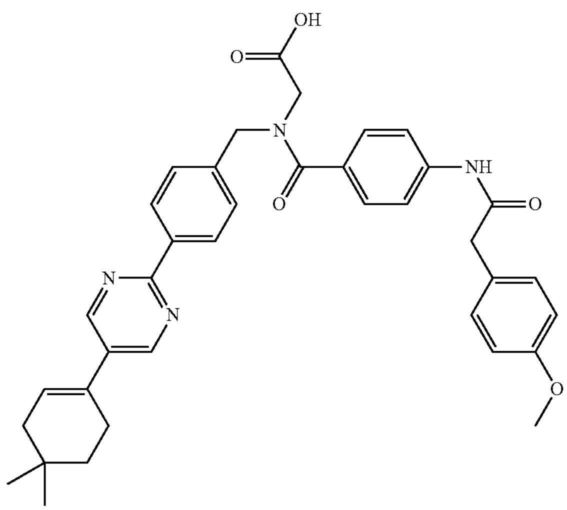 [SMILES: COc1ccc(CC(=O)Nc2ccc(C(=O)N(CC(=O)O)Cc3ccc(-c4ncc(C5=CCC(C)(C)CC5)cn4)cc3)cc2)cc1] | 90 |
| 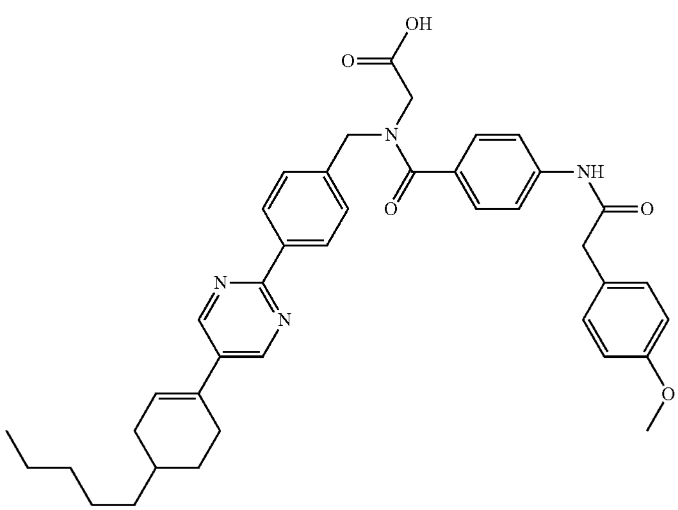 [SMILES: CCCCCC1CC=C(c2cnc(-c3ccc(CN(CC(=O)O)C(=O)c4ccc(NC(=O)Cc5ccc(OC)cc5)cc4)cc3)nc2)CC1] | 91 |

-continued
| Structure | Cpd. No. |
|---|---|
| 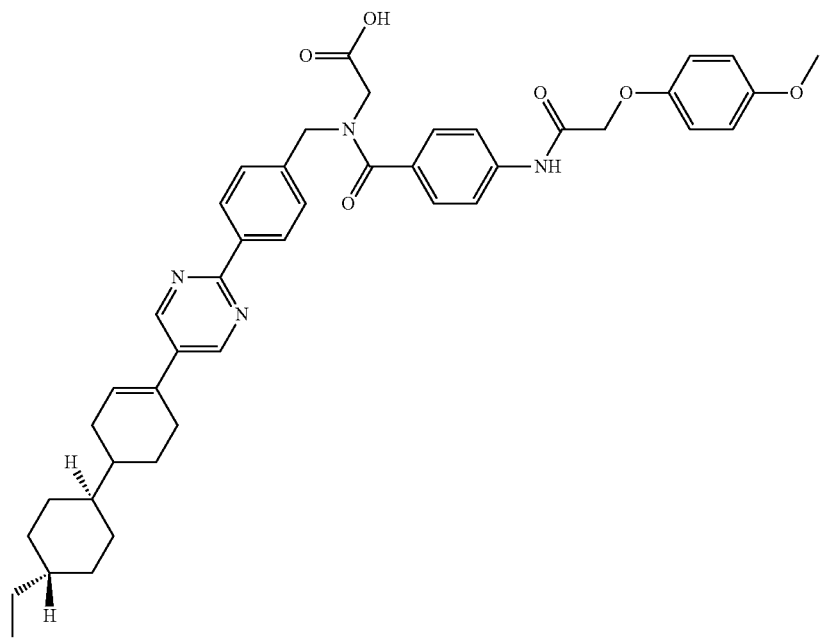 [SMILES: CC[C@H]1CC[C@H](C2CC=C(c3cnc(-c4ccc(CN(CC(=O)O)C(=O)c5ccc(NC(=O)COc6ccc(OC)cc6)cc5)cc4)nc3)CC2)CC1] | 92 |
| 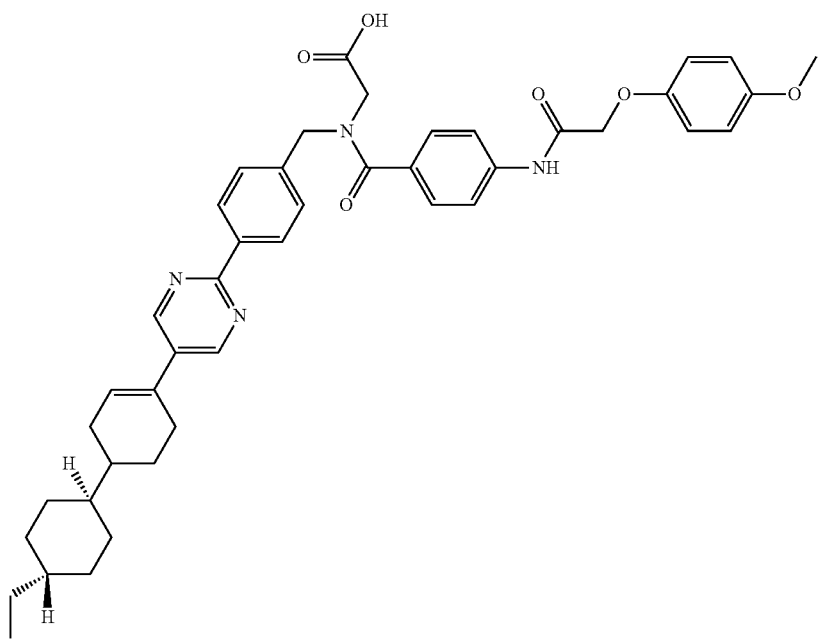 [SMILES: CC[C@H]1CC[C@H](C2CC=C(c3cnc(-c4ccc(CN(CC(=O)O)C(=O)c5ccc(NC(=O)COc6ccc(OC)cc6)cc5)cc4)nc3)CC2)CC1] | 93 |

| Structure | Cpd. No. |
|---|---|
| 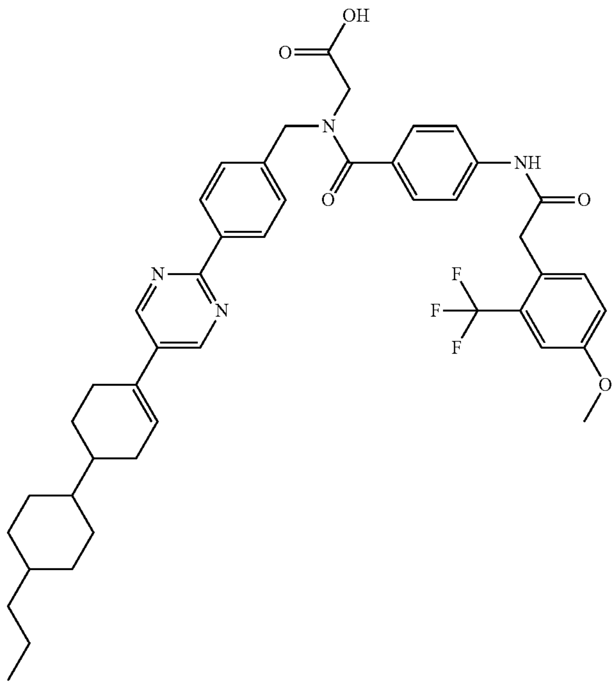 [SMILES: CCCC1CCC(C2CC=C(c3cnc(-c4ccc(CN(CC(=O)O)C(=O)c5ccc(NC(=O)Cc6ccc(OC)cc6C(F)(F)F)cc5)cc4)nc3)CC2)CC1] | 94 |
| 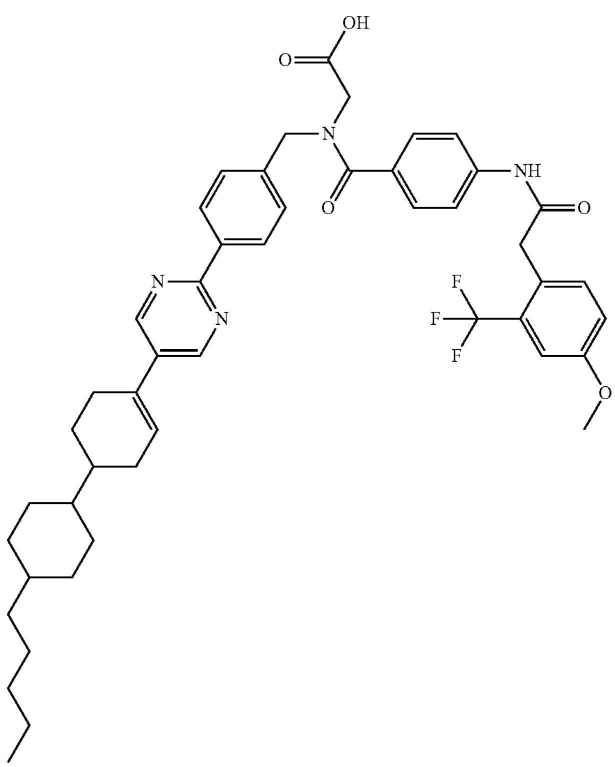 [SMILES: CCCCCC1CCC(C2CC=C(c3cnc(-c4ccc(CN(CC(=O)O)C(=O)c5ccc(NC(=O)Cc6ccc(OC)cc6C(F)(F)F)cc5)cc4)nc3)CC2)CC1] | 95 |

| Structure | Cpd. No. |
| --- | --- |
| 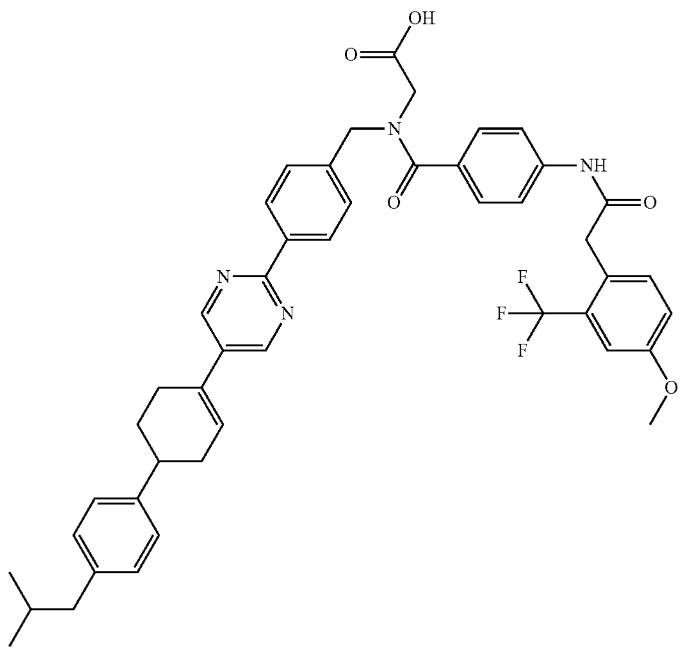 [SMILES: COc1ccc(CC(=O)Nc2ccc(C(=O)N(CC(=O)O)Cc3ccc(-c4ncc(C5=CCC(c6ccc(CC(C)C)cc6)CC5)cn4)cc3)cc2)c(C(F)(F)F)c1] | 96 |
| 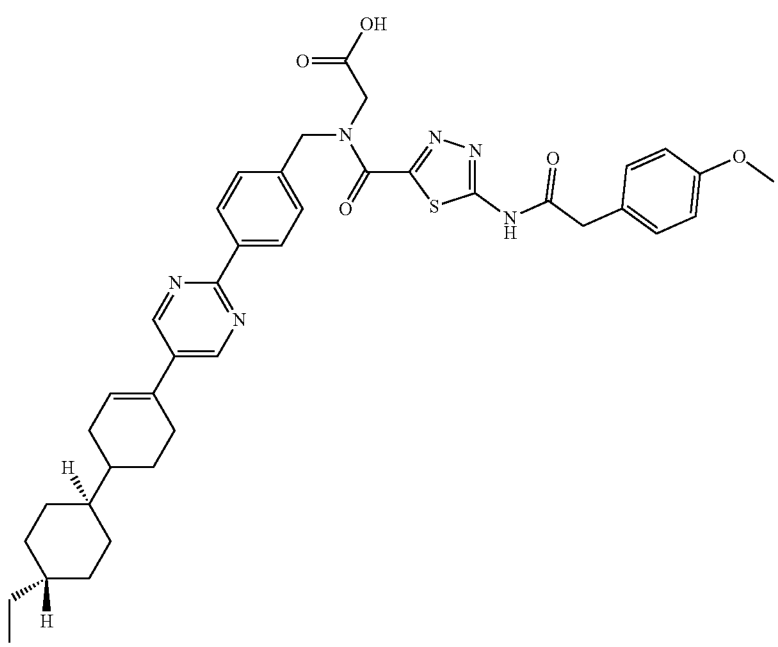 [SMILES: CC[C@H]1CC[C@H](C2CC=C(c3cnc(-c4ccc(CN(CC(=O)O)C(=O)c5nnc(NC(=O)Cc6ccc(OC)cc6)s5)cc4)nc3)CC2)CC1] | 97 |

| Structure | Cpd. No. |
| --- | --- |
| 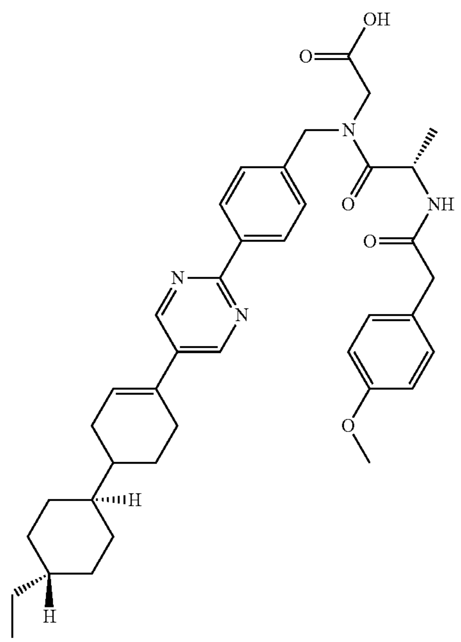 [SMILES: CC[C@H]1CC[C@H](C2CC=C(c3cnc(-c4ccc(CN(CC(=O)O)C(=O)[C@H](C)NC(=O)Cc5ccc(OC)cc5)cc4)nc3)CC2)CC1] | 98 |
| 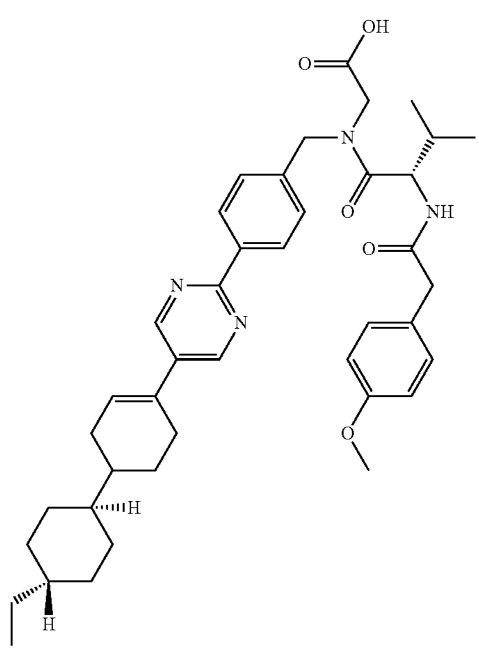 [SMILES: CC[C@H]1CC[C@H](C2CC=C(c3cnc(-c4ccc(CN(CC(=O)O)C(=O)[C@@H](NC(=O)Cc5ccc(OC)cc5)C(C)C)cc4)nc3)CC2)CC1] | 99 |

US 11,530,205 B2
343                                                                                                          344
-continued
| Structure | Cpd. No. |
|---|---|
| 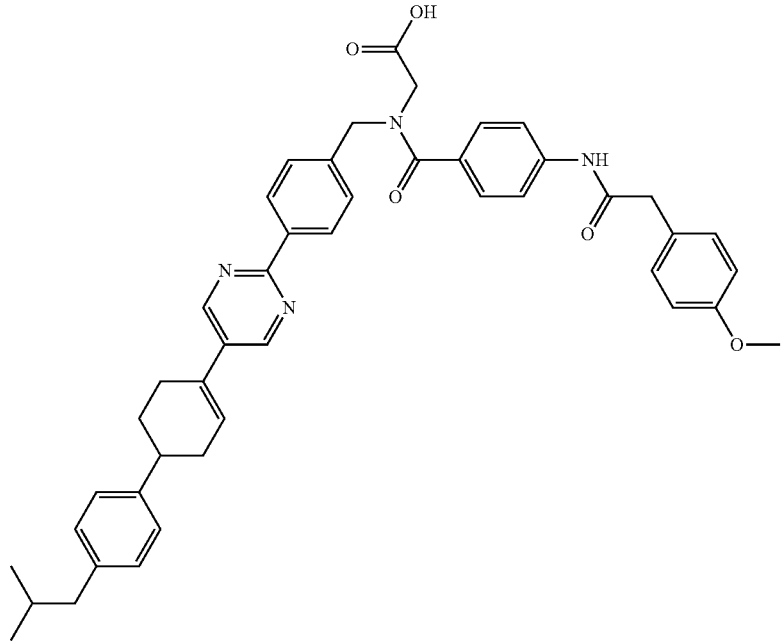 [SMILES: COc1ccc(CC(=O)Nc2ccc(C(=O)N(CC(=O)O)Cc3ccc(-c4ncc(C5=CCC(c6ccc(CC(C)C)cc6)CC5)cn4)cc3)cc2)cc1] | 100 |
| 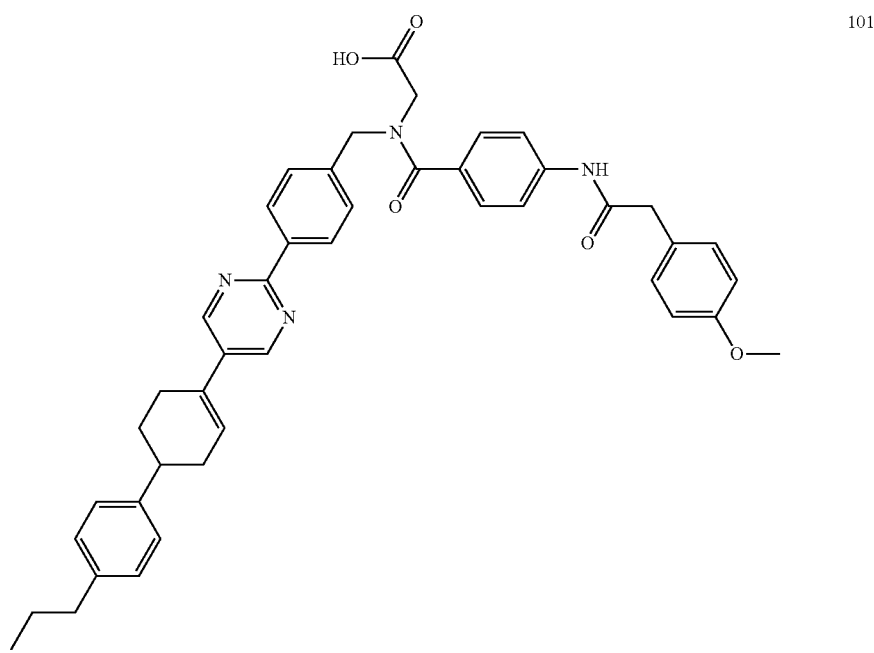 | 101 |

| Structure | Cpd. No. |
|---|---|
| 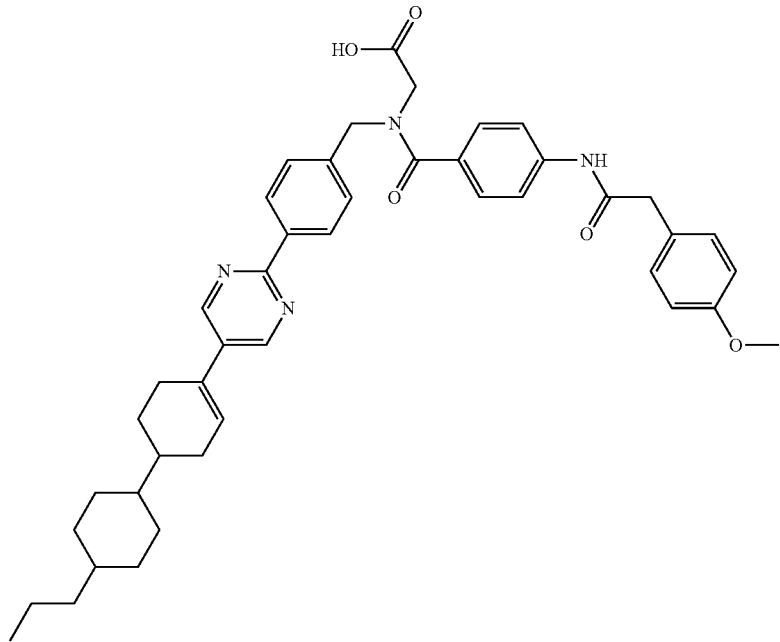 [SMILES: CCCC1CCC(C2CC=C(c3cnc(-c4ccc(CN(CC(=O)O)C(=O)c5ccc(NC(=O)Cc6ccc(OC)cc6)cc5)cc4)nc3)CC2)CC1] | 102 |
| 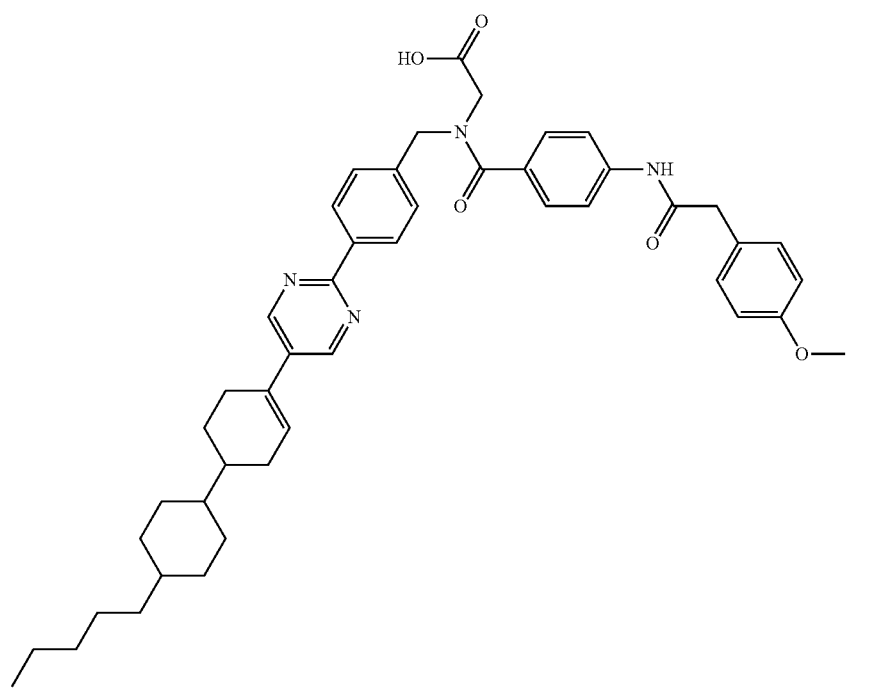 [SMILES: CCCCCC1CCC(C2CC=C(c3cnc(-c4ccc(CN(CC(=O)O)C(=O)c5ccc(NC(=O)Cc6ccc(OC)cc6)cc5)cc4)nc3)CC2)CC1] | 103 |

| Structure | Cpd. No. |
|---|---|
| 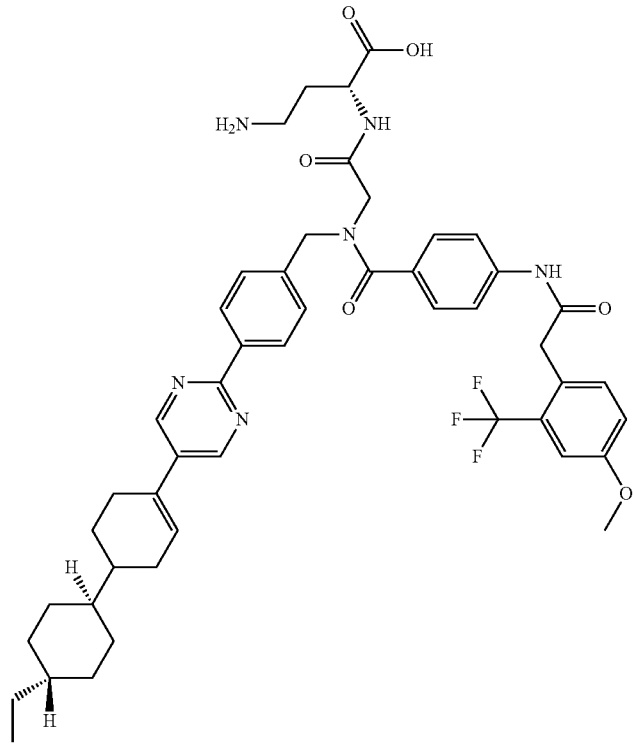 [SMILES: CC[C@H]1CC[C@H](C2CC=C(c3cnc(-c4ccc(CN(CC(=O)N[C@H](CCN)C(=O)O)C(=O)c5ccc(NC(=O)Cc6ccc(OC)cc6C(F)(F)F)cc5)cc4)nc3)CC2)CC1] | 104 |
| 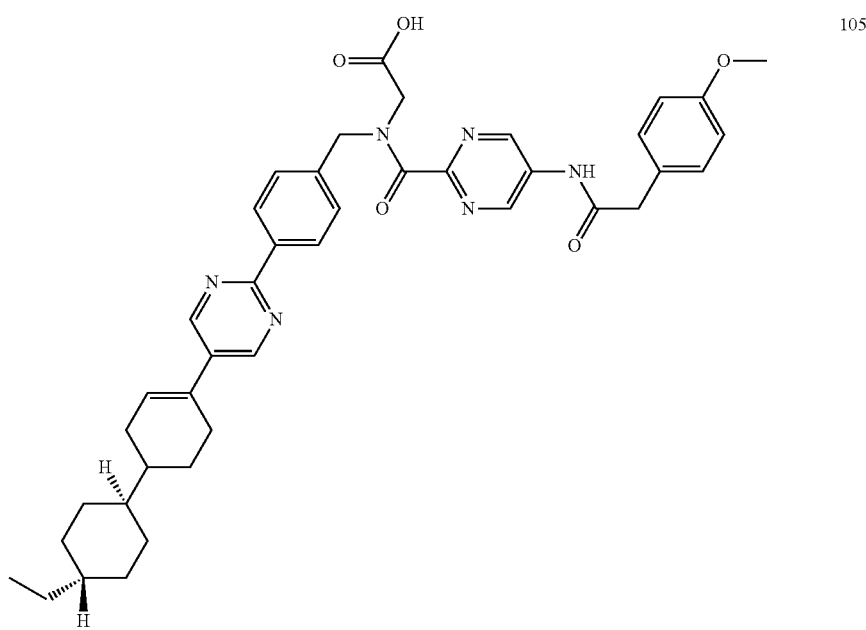 | 105 |

| Structure | Cpd. No. |
|---|---|
| 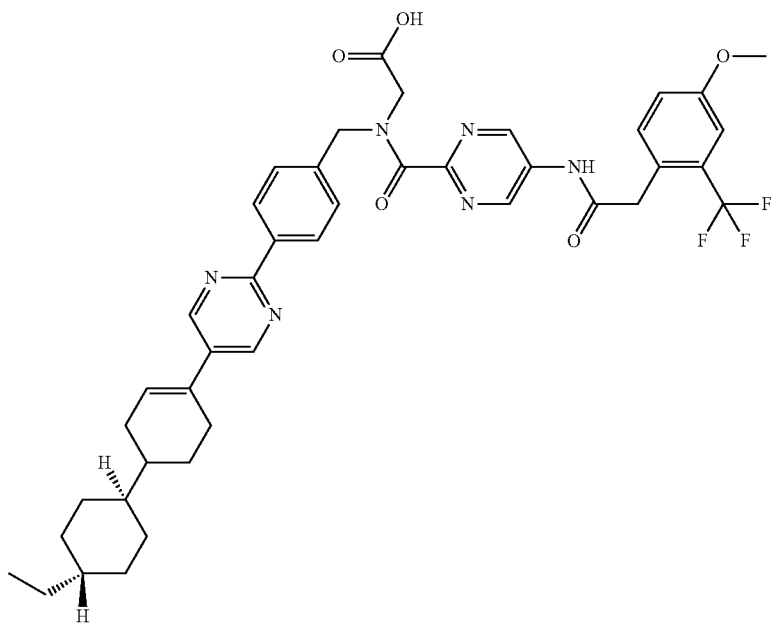 [SMILES: CC[C@H]1CC[C@H](C2CC=C(c3cnc(-c4ccc(CN(CC(=O)O)C(=O)c5ncc(NC(=O)Cc6ccc(OC)cc6C(F)(F)F)cn5)cc4)nc3)CC2)CC1] | 106 |
| 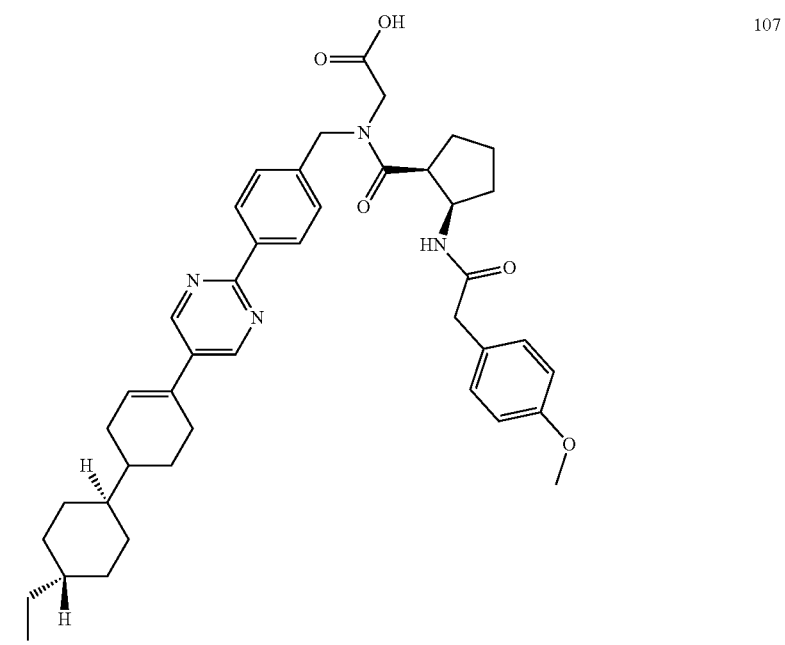 | 107 |

-continued
| Structure | Cpd. No. |
|---|---|
| 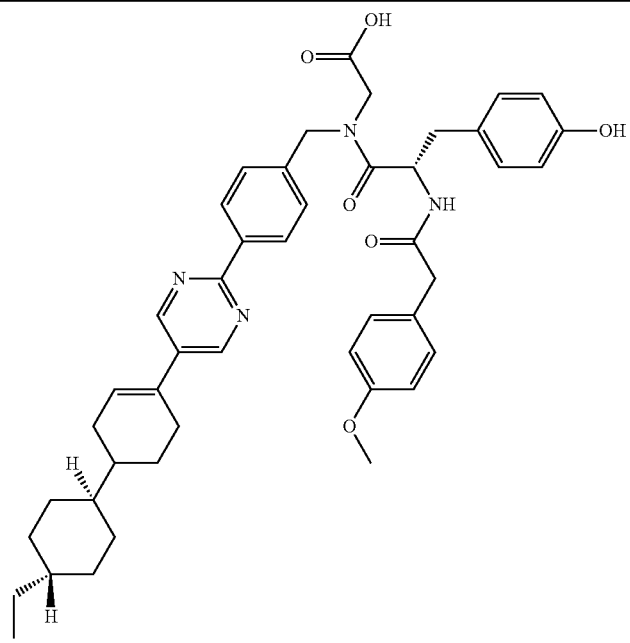 | 108 |
| 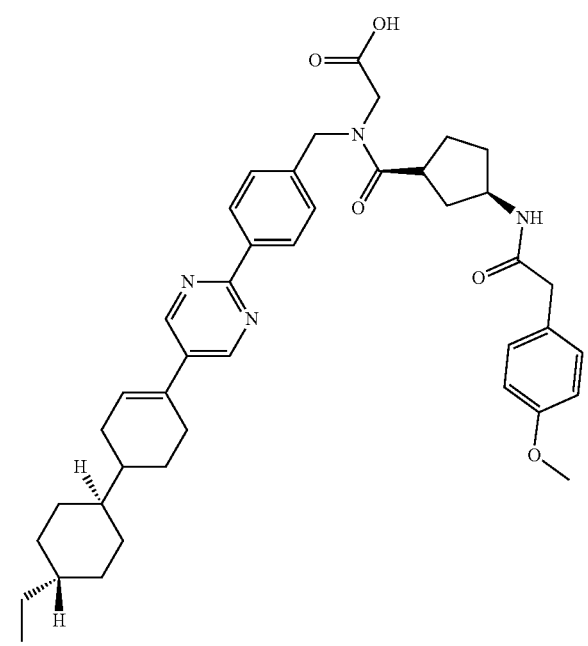 | 109 |

-continued
| Structure | Cpd. No. |
|---|---|
| 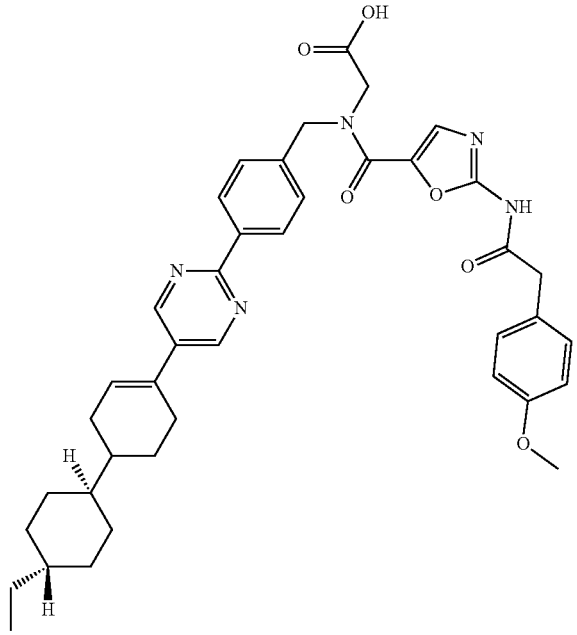 [SMILES: CC[C@H]1CC[C@H](C2CC=C(c3cnc(-c4ccc(CN(CC(=O)O)C(=O)c5cnc(NC(=O)Cc6ccc(OC)cc6)o5)cc4)nc3)CC2)CC1] | 110 |
| 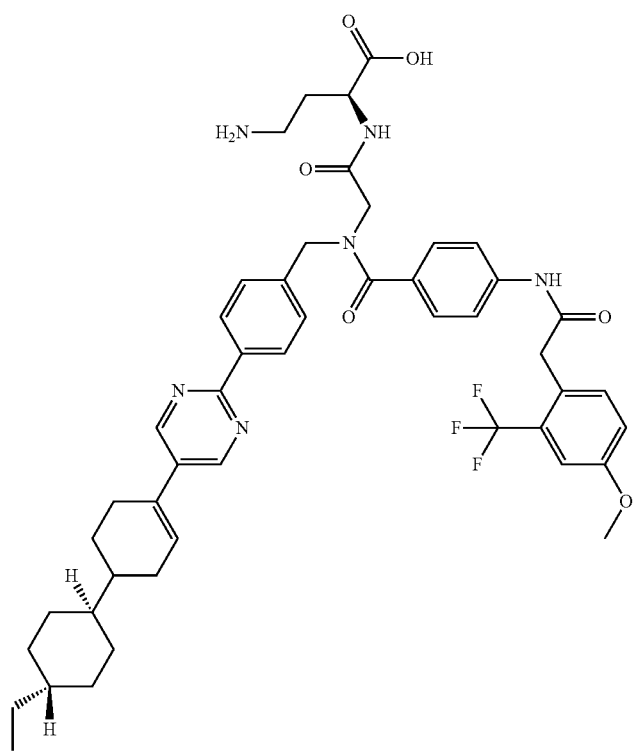 [SMILES: CC[C@H]1CC[C@H](C2CC=C(c3cnc(-c4ccc(CN(CC(=O)N[C@@H](CCN)C(=O)O)C(=O)c5ccc(NC(=O)Cc6ccc(OC)cc6C(F)(F)F)cc5)cc4)nc3)CC2)CC1] | 111 |

| Structure | Cpd. No. |
|---|---|
| 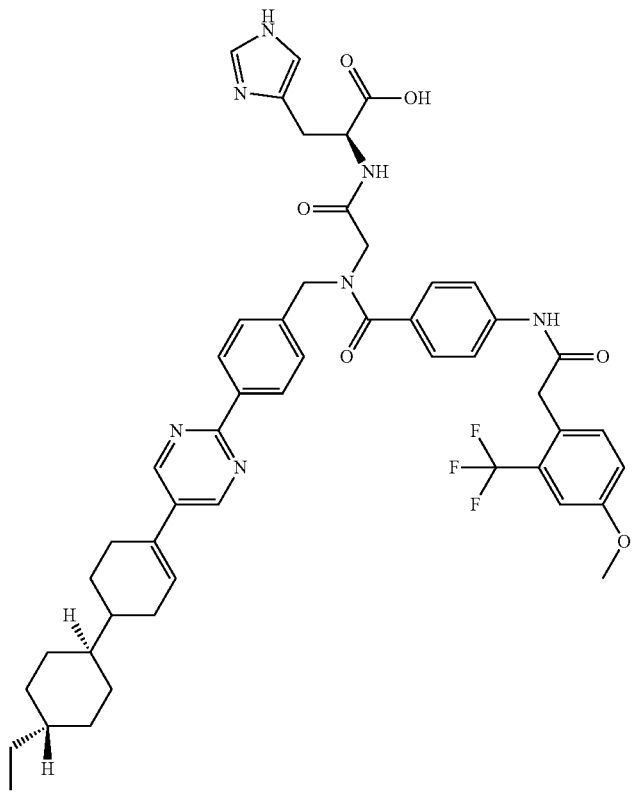 [SMILES: CC[C@H]1CC[C@H](C2CC=C(c3cnc(-c4ccc(CN(CC(=O)N[C@@H](Cc5c[nH]cn5)C(=O)O)C(=O)c5ccc(NC(=O)Cc6ccc(OC)cc6C(F)(F)F)cc5)cc4)nc3)CC2)CC1] | 112 |
| 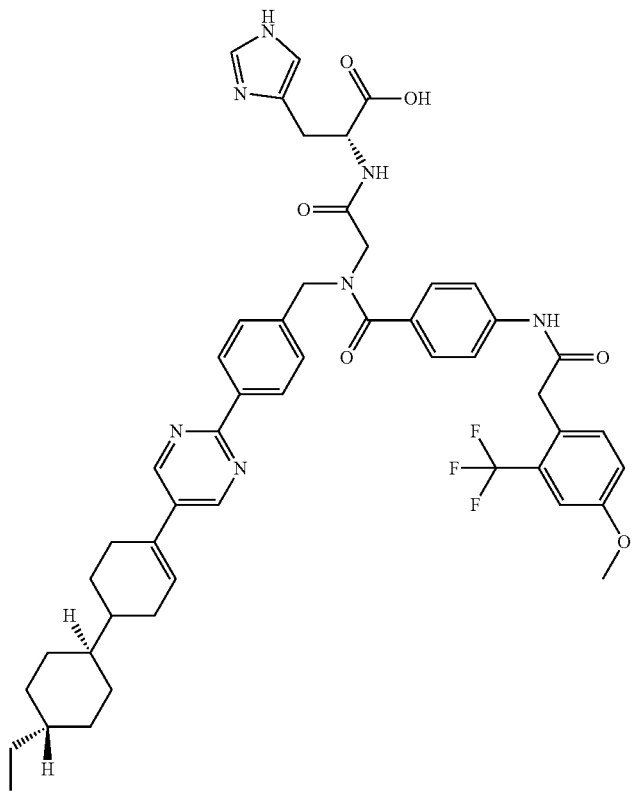 [SMILES: CC[C@H]1CC[C@H](C2CC=C(c3cnc(-c4ccc(CN(CC(=O)N[C@H](Cc5c[nH]cn5)C(=O)O)C(=O)c5ccc(NC(=O)Cc6ccc(OC)cc6C(F)(F)F)cc5)cc4)nc3)CC2)CC1] | 113 |

-continued
| Structure | Cpd. No. |
|---|---|
| 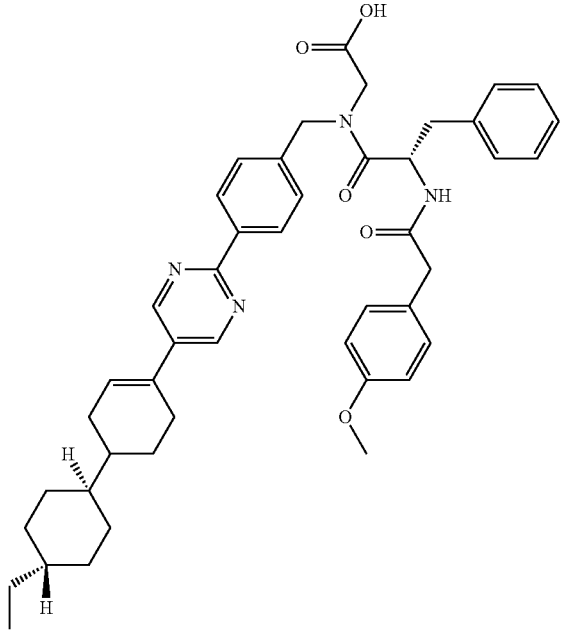 [SMILES: CC[C@H]1CC[C@H](C2CC=C(c3cnc(-c4ccc(CN(CC(=O)O)C(=O)[C@H](Cc5ccccc5)NC(=O)Cc5ccc(OC)cc5)cc4)nc3)CC2)CC1] | 114 |
| 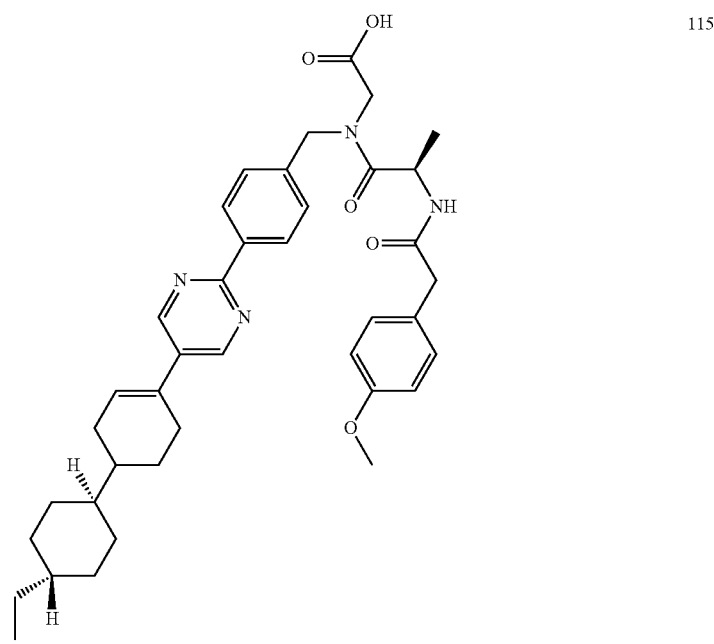 | 115 |

| Structure | Cpd. No. |
|---|---|
| 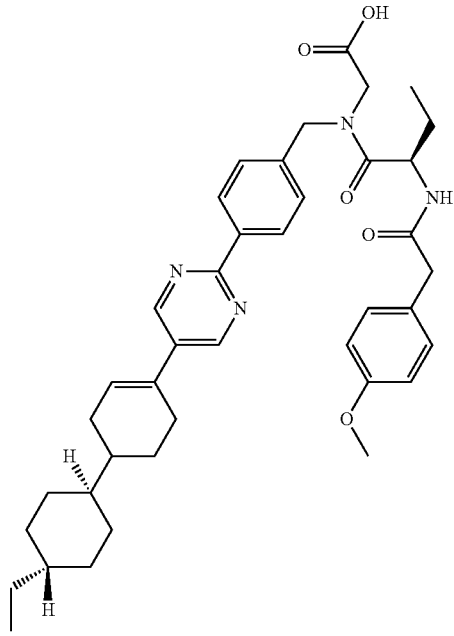 [SMILES: CC[C@@H](NC(=O)Cc1ccc(OC)cc1)C(=O)N(CC(=O)O)Cc1ccc(-c2ncc(C3=CCC([C@H]4CC[C@H](CC)CC4)CC3)cn2)cc1] | 116 |
| 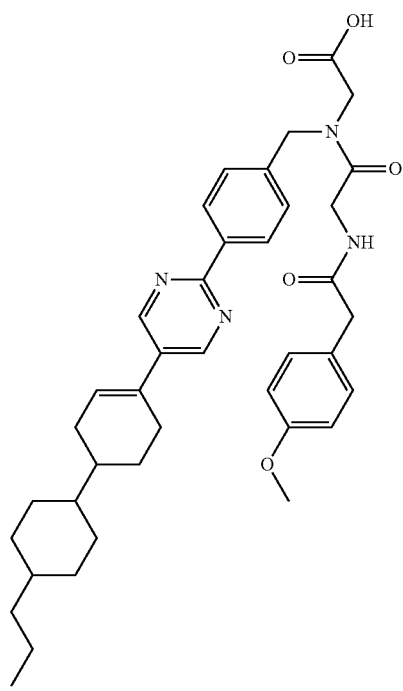 [SMILES: CCCC1CCC(C2CC=C(c3cnc(-c4ccc(CN(CC(=O)O)C(=O)CNC(=O)Cc5ccc(OC)cc5)cc4)nc3)CC2)CC1] | 117 |

| Structure | Cpd. No. |
|---|---|
| 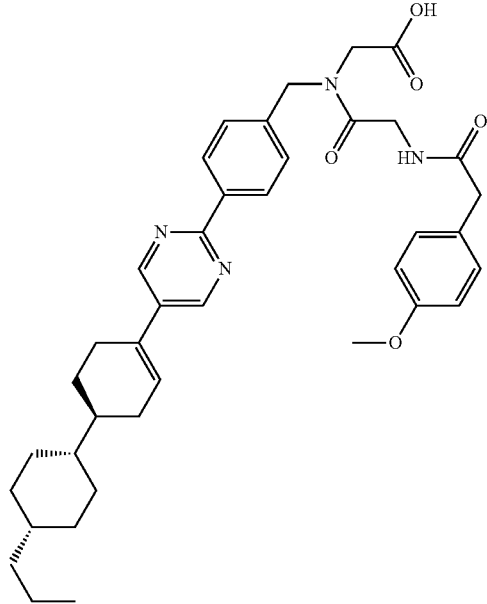 [SMILES: CCC[C@H]1CC[C@@H]([C@@H]2CC=C(c3cnc(-c4ccc(CN(CC(=O)O)C(=O)CNC(=O)Cc5ccc(OC)cc5)cc4)nc3)CC2)CC1] | 118 |
| 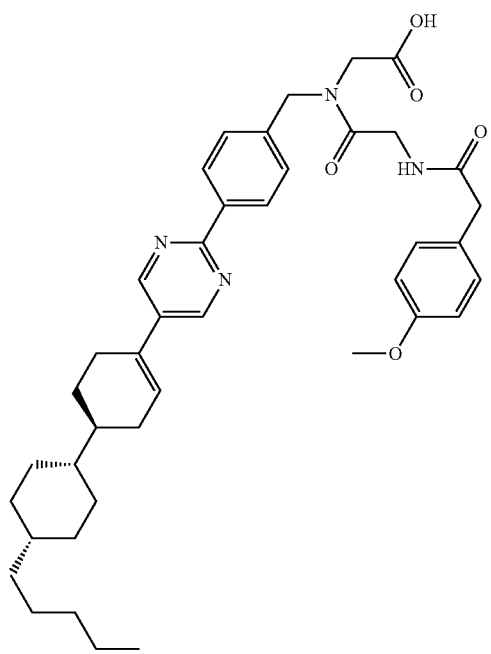 [SMILES: CCCCC[C@H]1CC[C@@H]([C@@H]2CC=C(c3cnc(-c4ccc(CN(CC(=O)O)C(=O)CNC(=O)Cc5ccc(OC)cc5)cc4)nc3)CC2)CC1] | 119 |

| Structure | Cpd. No. |
|---|---|
| 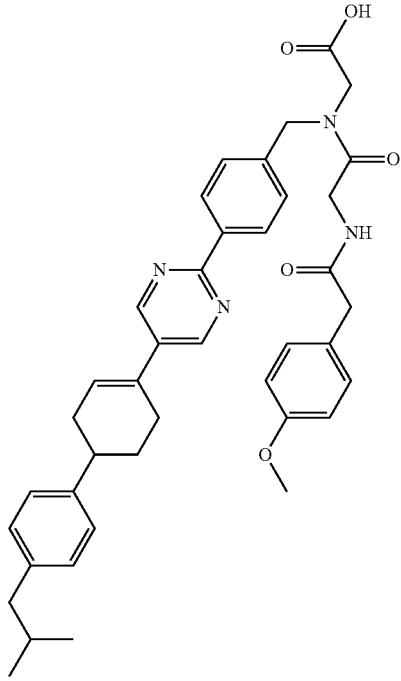 [SMILES: COc1ccc(CC(=O)NCC(=O)N(CC(=O)O)Cc2ccc(-c3ncc(C4=CCC(c5ccc(CC(C)C)cc5)CC4)cn3)cc2)cc1] | 120 |
| 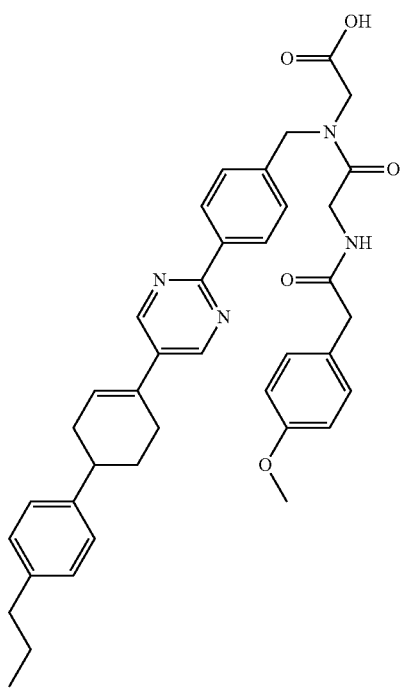 | 121 |

-continued
| Structure | Cpd. No. |
|---|---|
| 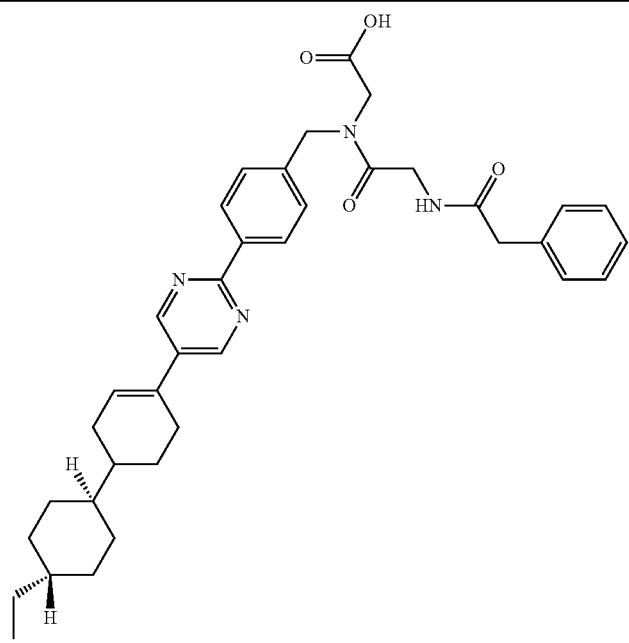 | 122 |
| 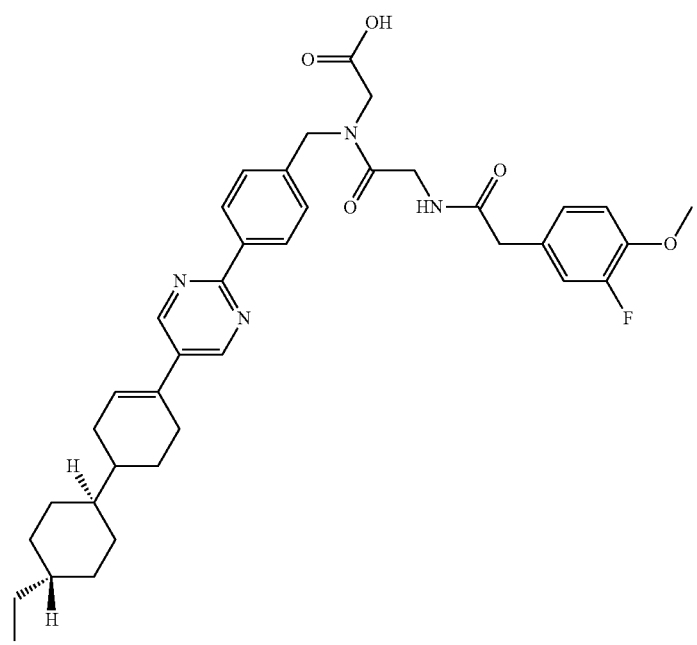 [SMILES: CC[C@H]1CC[C@H](C2CC=C(c3cnc(-c4ccc(CN(CC(=O)O)C(=O)CNC(=O)Cc5ccc(OC)c(F)c5)cc4)nc3)CC2)CC1] | 123 |

-continued
| Structure | Cpd. No. |
|---|---|
| 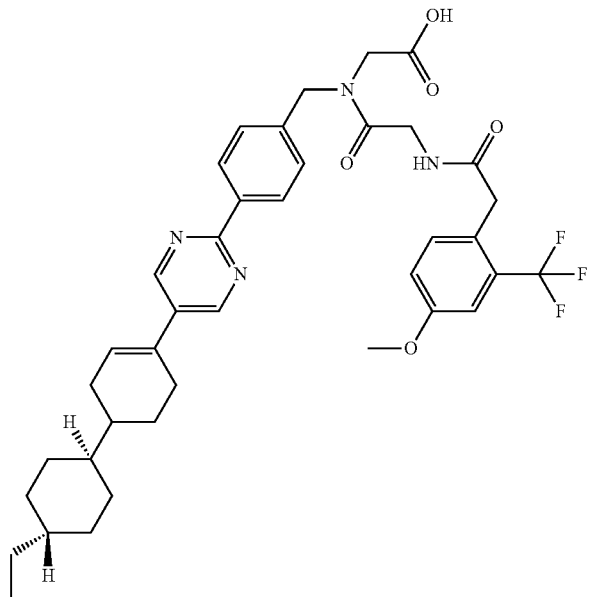 [SMILES: CC[C@H]1CC[C@H](C2CC=C(c3cnc(-c4ccc(CN(CC(=O)O)C(=O)CNC(=O)Cc5ccc(OC)cc5C(F)(F)F)cc4)nc3)CC2)CC1] | 124 |
| 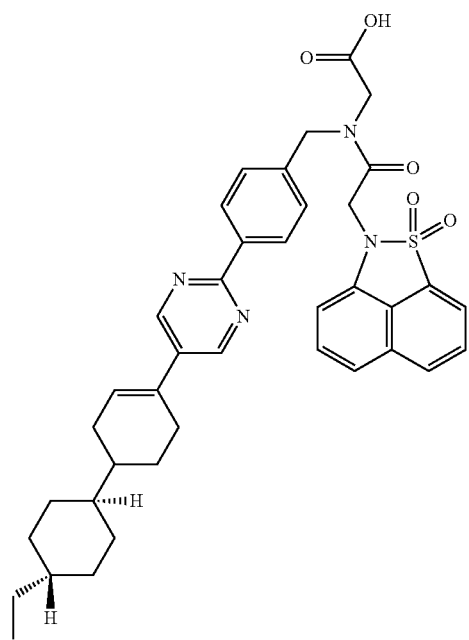 [SMILES: CC[C@H]1CC[C@H](C2CC=C(c3cnc(-c4ccc(CN(CC(=O)O)C(=O)CN5c6cccc7cccc(c67)S5(=O)=O)cc4)nc3)CC2)CC1] | 125 |

| Structure | Cpd. No. |
|---|---|
| 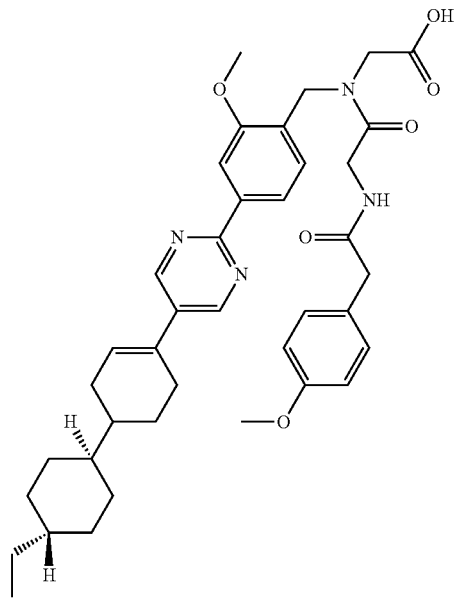 [SMILES: CC[C@H]1CC[C@H](C2CC=C(c3cnc(-c4ccc(CN(CC(=O)O)C(=O)CNC(=O)Cc5ccc(OC)cc5)c(OC)c4)nc3)CC2)CC1] | 126 |
| 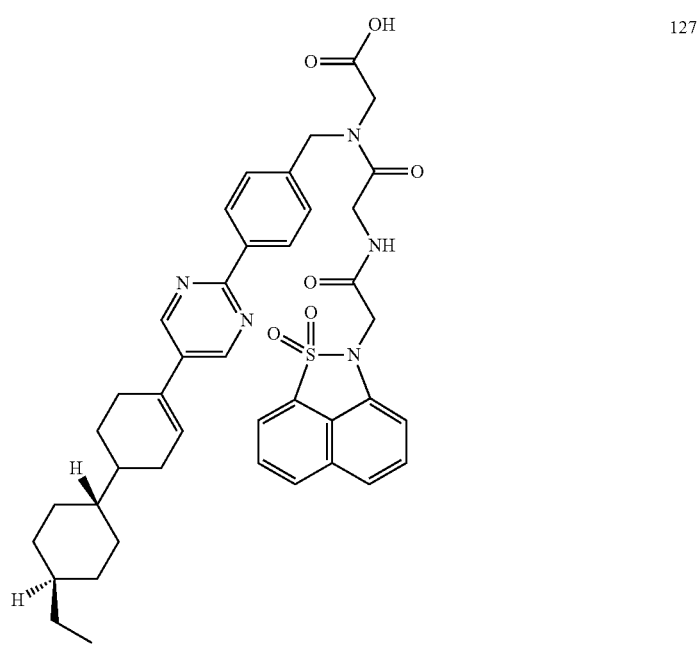 | 127 |

| Structure | Cpd. No. |
|---|---|
| 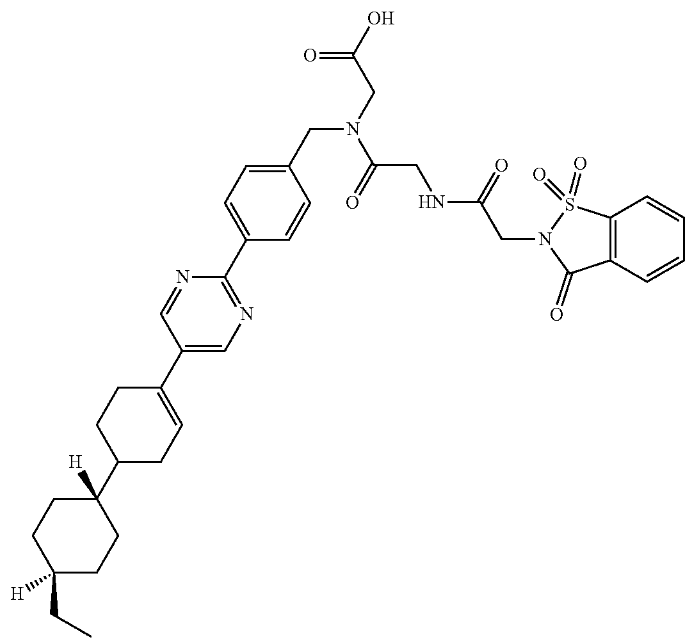 [SMILES: CC[C@H]1CC[C@H](C2CC=C(c3cnc(-c4ccc(CN(CC(=O)O)C(=O)CNC(=O)CN5C(=O)c6ccccc6S5(=O)=O)cc4)nc3)CC2)CC1] | 128 |
| 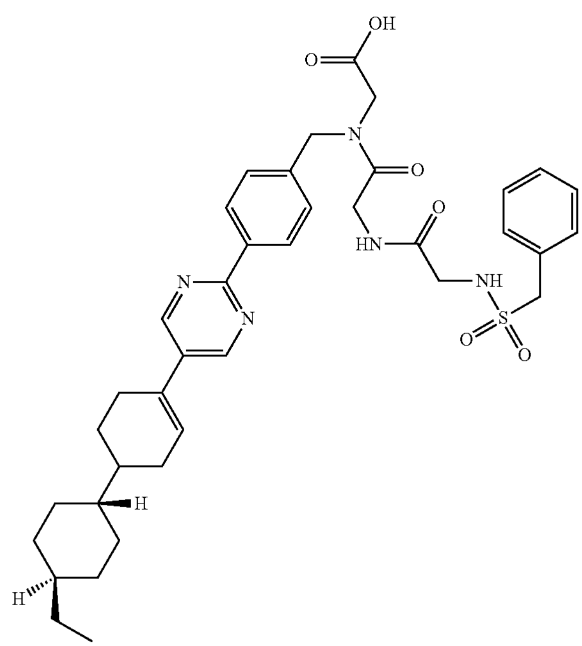 [SMILES: CC[C@H]1CC[C@H](C2CC=C(c3cnc(-c4ccc(CN(CC(=O)O)C(=O)CNC(=O)CNS(=O)(=O)Cc5ccccc5)cc4)nc3)CC2)CC1] | 129 |

| Structure | Cpd. No. |
|---|---|
| (structure) | 130 |
| (structure) | 131 |

| Structure | Cpd. No. |
|---|---|
| 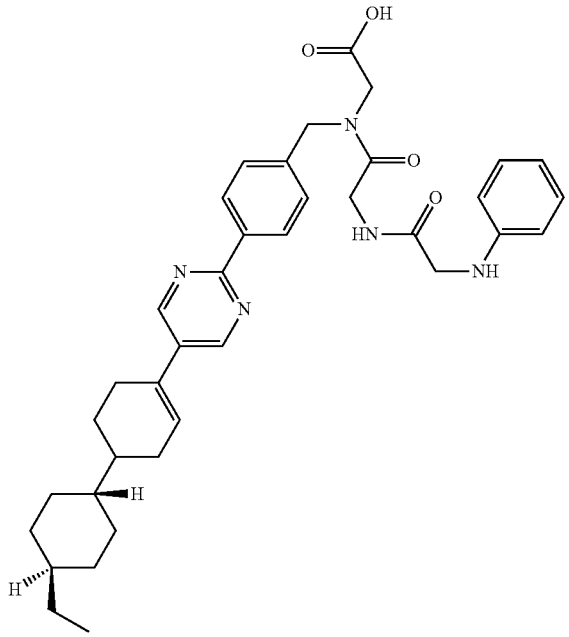 [SMILES: CC[C@H]1CC[C@H](C2CC=C(c3cnc(-c4ccc(CN(CC(=O)O)C(=O)CNC(=O)CNc5ccccc5)cc4)nc3)CC2)CC1] | 132 |
| 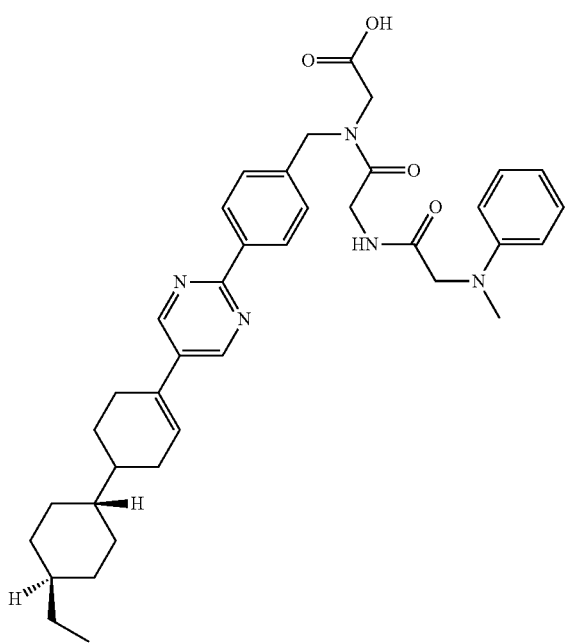 [SMILES: CC[C@H]1CC[C@H](C2CC=C(c3cnc(-c4ccc(CN(CC(=O)O)C(=O)CNC(=O)CN(C)c5ccccc5)cc4)nc3)CC2)CC1] | 133 |

| Structure | Cpd. No. |
|---|---|
| 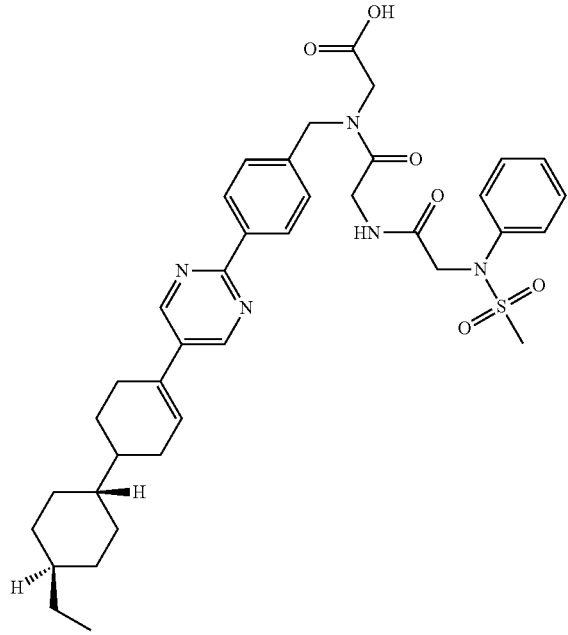 [SMILES: CC[C@H]1CC[C@H](C2CC=C(c3cnc(-c4ccc(CN(CC(=O)O)C(=O)CNC(=O)CN(c5ccccc5)S(C)(=O)=O)cc4)nc3)CC2)CC1] | 134 |
| 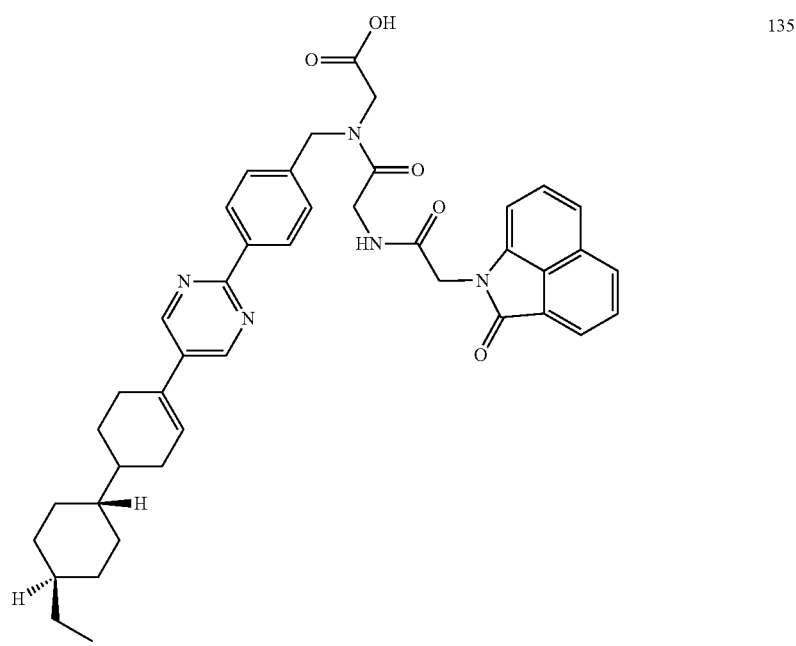 | 135 |

| Structure | Cpd. No. |
|---|---|
| 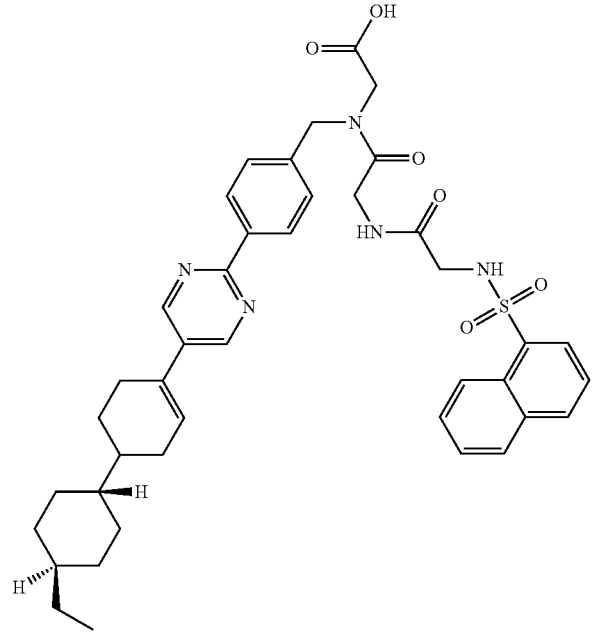 [SMILES: CC[C@H]1CC[C@H](C2CC=C(c3cnc(-c4ccc(CN(CC(=O)O)C(=O)CNC(=O)CNS(=O)(=O)c5cccc6ccccc56)cc4)nc3)CC2)CC1] | 136 |
| 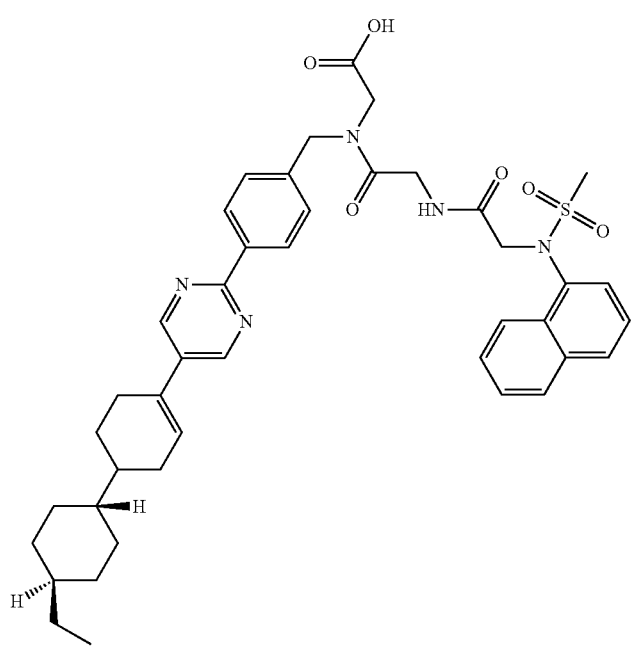 [SMILES: CC[C@H]1CC[C@H](C2CC=C(c3cnc(-c4ccc(CN(CC(=O)O)C(=O)CNC(=O)CN(c5cccc6ccccc56)S(C)(=O)=O)cc4)nc3)CC2)CC1] | 137 |

-continued
| Structure | Cpd. No. |
|---|---|
| 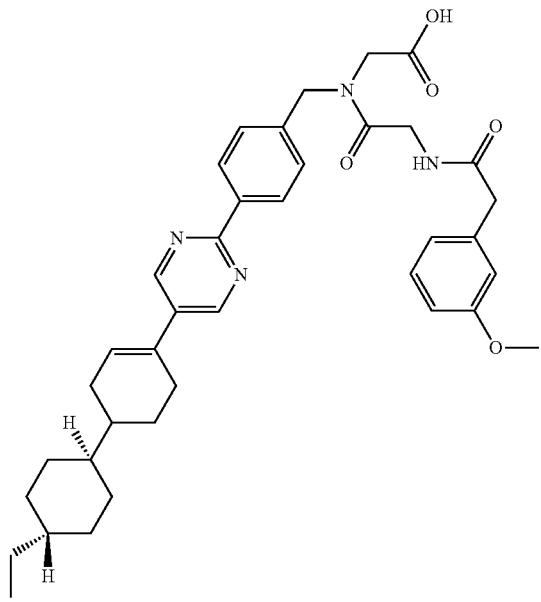 [SMILES: CC[C@H]1CC[C@H](C2CC=C(c3cnc(-c4ccc(CN(CC(=O)O)C(=O)CNC(=O)Cc5cccc(OC)c5)cc4)nc3)CC2)CC1] | 138 |
| 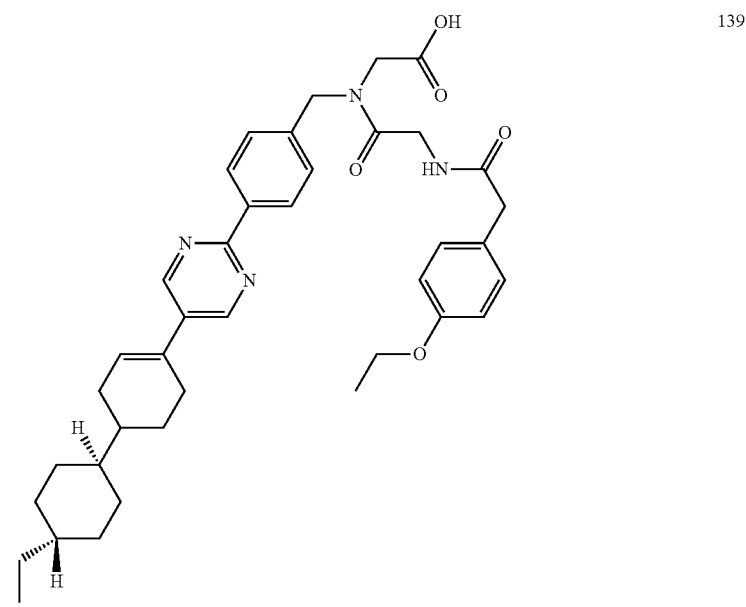 | 139 |

| Structure | Cpd. No. |
|---|---|
| 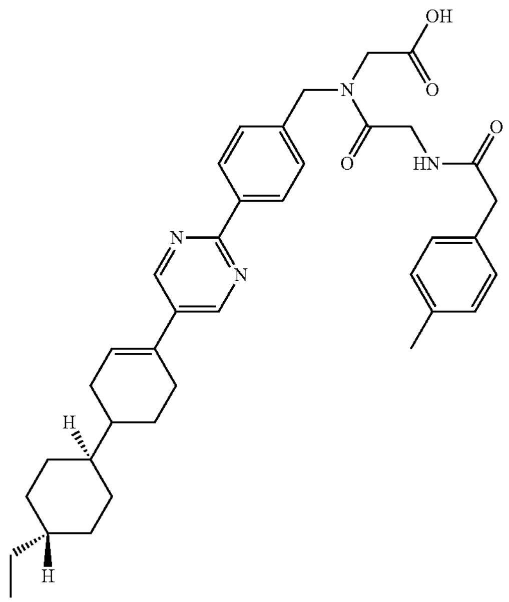 [SMILES: CC[C@H]1CC[C@H](C2CC=C(c3cnc(-c4ccc(CN(CC(=O)O)C(=O)CNC(=O)Cc5ccc(C)cc5)cc4)nc3)CC2)CC1] | 140 |
| 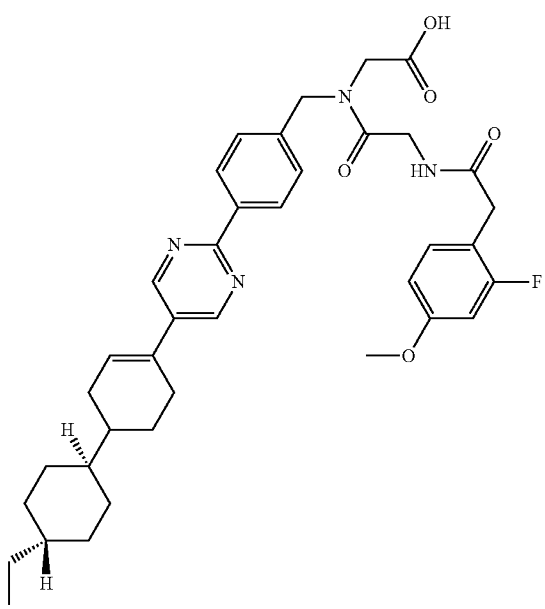 [SMILES: CC[C@H]1CC[C@H](C2CC=C(c3cnc(-c4ccc(CN(CC(=O)O)C(=O)CNC(=O)Cc5ccc(OC)cc5F)cc4)nc3)CC2)CC1] | 141 |

-continued
| Structure | Cpd. No. |
|---|---|
| 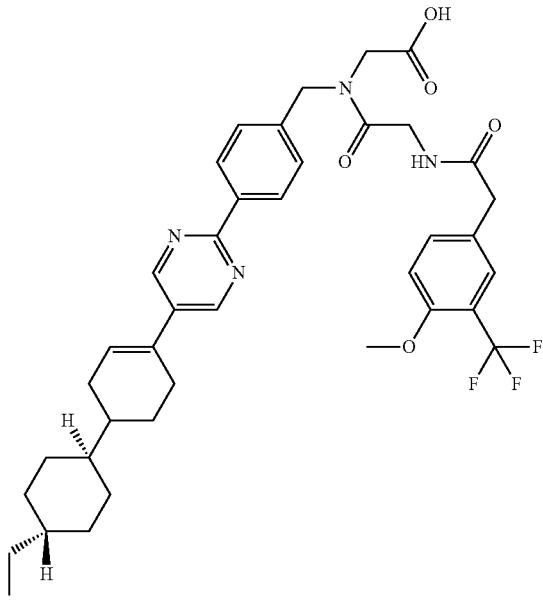 [SMILES: CC[C@H]1CC[C@H](C2CC=C(c3cnc(-c4ccc(CN(CC(=O)O)C(=O)CNC(=O)Cc5ccc(OC)c(C(F)(F)F)c5)cc4)nc3)CC2)CC1] | 142 |
| 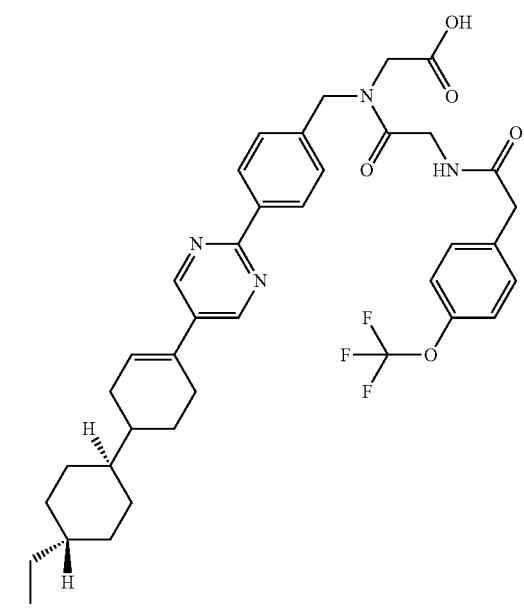 [SMILES: CC[C@H]1CC[C@H](C2CC=C(c3cnc(-c4ccc(CN(CC(=O)O)C(=O)CNC(=O)Cc5ccc(OC(F)(F)F)cc5)cc4)nc3)CC2)CC1] | 143 |

| Structure | Cpd. No. |
|---|---|
| 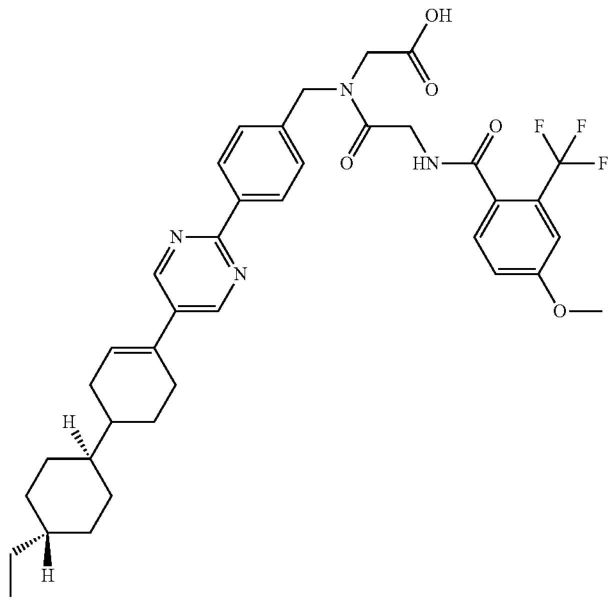 [SMILES: CC[C@H]1CC[C@H](C2CC=C(c3cnc(-c4ccc(CN(CC(=O)O)C(=O)CNC(=O)c5ccc(OC)cc5C(F)(F)F)cc4)nc3)CC2)CC1] | 144 |
| 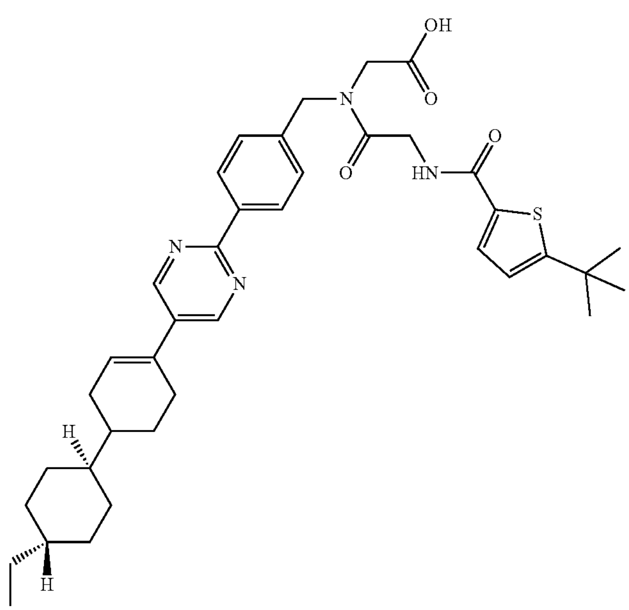 [SMILES: CC[C@H]1CC[C@H](C2CC=C(c3cnc(-c4ccc(CN(CC(=O)O)C(=O)CNC(=O)c5ccc(C(C)(C)C)s5)cc4)nc3)CC2)CC1] | 145 |

| Structure | Cpd. No. |
|---|---|
| 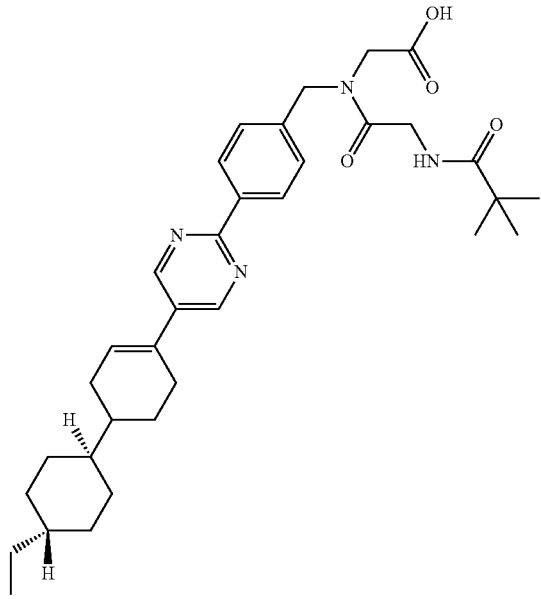 [SMILES: CC[C@H]1CC[C@H](C2CC=C(c3cnc(-c4ccc(CN(CC(=O)O)C(=O)CNC(=O)C(C)(C)C)cc4)nc3)CC2)CC1] | 146 |
| 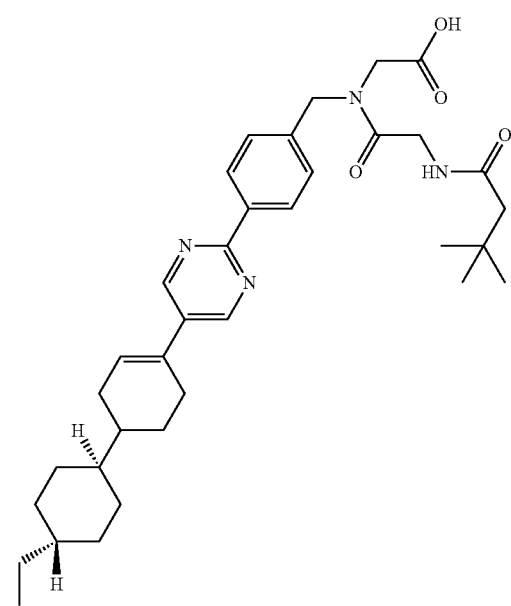 [SMILES: CC[C@H]1CC[C@H](C2CC=C(c3cnc(-c4ccc(CN(CC(=O)O)C(=O)CNC(=O)CC(C)(C)C)cc4)nc3)CC2)CC1] | 147 |

| Structure | Cpd. No. |
|---|---|
| 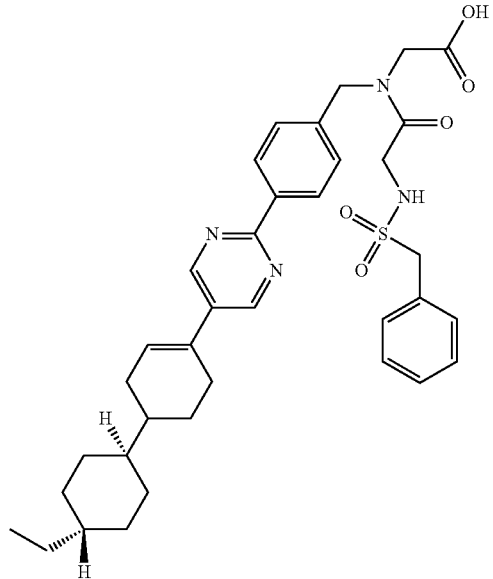 [SMILES: CC[C@H]1CC[C@H](C2CC=C(c3cnc(-c4ccc(CN(CC(=O)O)C(=O)CNS(=O)(=O)Cc5ccccc5)cc4)nc3)CC2)CC1] | 148 |
| 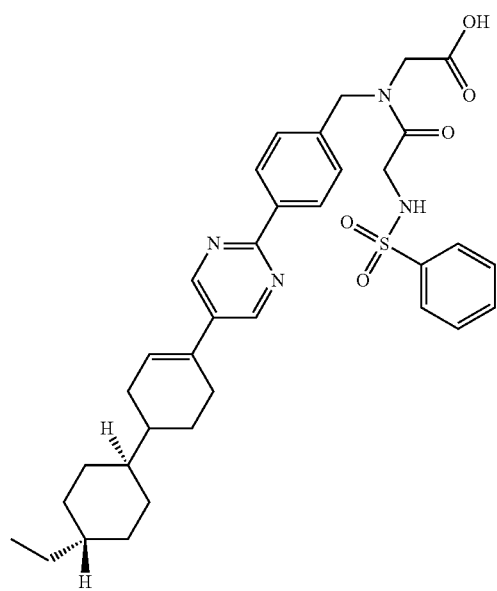 [SMILES: CC[C@H]1CC[C@H](C2CC=C(c3cnc(-c4ccc(CN(CC(=O)O)C(=O)CNS(=O)(=O)c5ccccc5)cc4)nc3)CC2)CC1] | 149 |

-continued
| Structure | Cpd. No. |
|---|---|
| 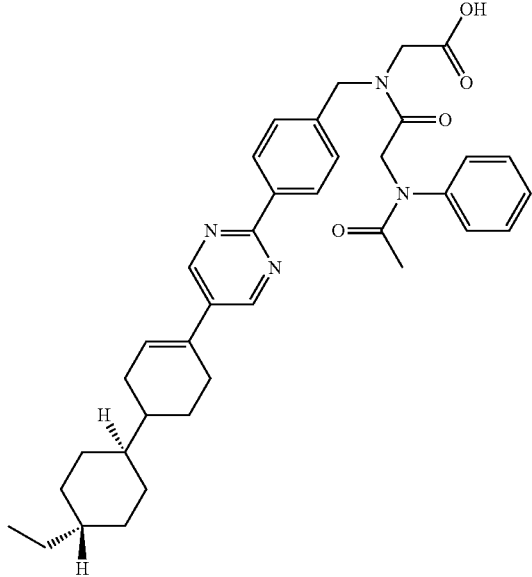 [SMILES: CC[C@H]1CC[C@H](C2CC=C(c3cnc(-c4ccc(CN(CC(=O)O)C(=O)CN(C(C)=O)c5ccccc5)cc4)nc3)CC2)CC1] | 150 |
| 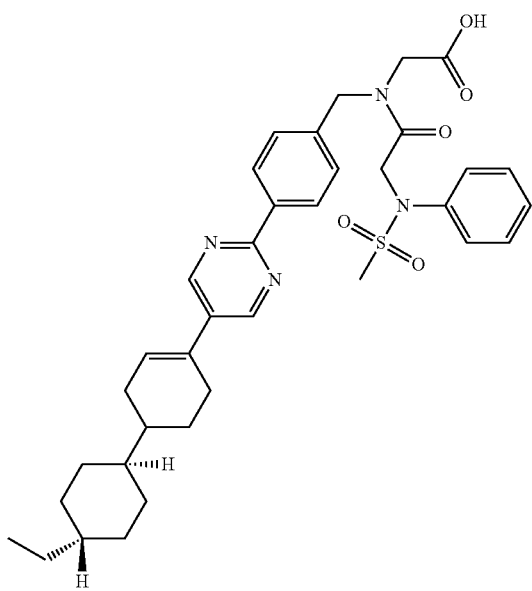 [SMILES: CC[C@H]1CC[C@H](C2CC=C(c3cnc(-c4ccc(CN(CC(=O)O)C(=O)CN(c5ccccc5)S(C)(=O)=O)cc4)nc3)CC2)CC1] | 151 |

-continued
| Structure | Cpd. No. |
|---|---|
| 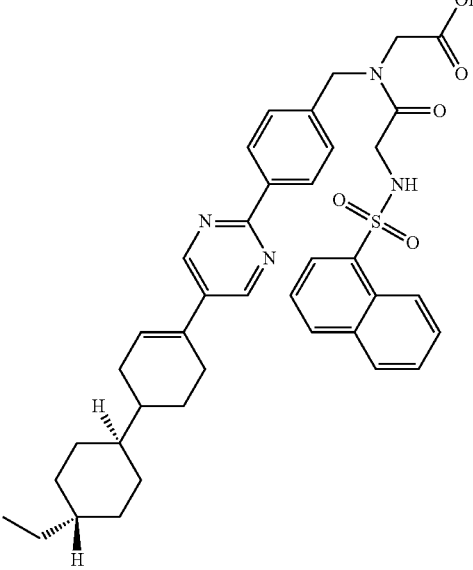 | 152 |
| 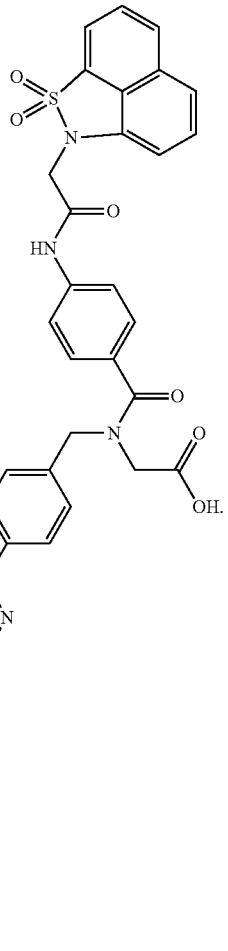 | 153 |
14. A pharmaceutical composition comprising a compound of claim 1 together with at least one pharmaceutically acceptable carrier, diluent or excipient.
15. A method of modulating a glucagon-like peptide 1 receptor comprising contacting the receptor with an effective amount of a compound of claim 1.

16. A method for treating a malcondition in a patient for which modulation of a glucagon-like peptide 1 receptor is medically indicated, comprising administering an effective amount of a compound of claim 1, to the patient at a frequency and for a duration of time sufficient to provide a beneficial effect to the patient.

17. The method of claim 16 wherein the malcondition is type I diabetes, type II diabetes, gestational diabetes, obesity, excessive appetite, insufficient satiety or metabolic disorder.

18. The method of claim 16 wherein the malcondition is non-alcoholic fatty liver disease (NAFLD) or non-alcoholic steatohepatitis (NASH).

\* \* \* \* \*

UNITED STATES PATENT AND TRADEMARK OFFICE
CERTIFICATE OF CORRECTION

| | | |
|---|---|---|
| PATENT NO. | : 11,530,205 B2 | Page 1 of 5 |
| APPLICATION NO. | : 16/608134 | |
| DATED | : December 20, 2022 | |
| INVENTOR(S) | : Junko Tamiya et al. | |

It is certified that error appears in the above-identified patent and that said Letters Patent is hereby corrected as shown below:

In the Claims

Column 241, Claim 1, Line 61:
"more $R^3$, each $R^3$"
Should read:
--more $R^3$; each $R^3$--.

Column 244, Claim 7, Structure (VII):

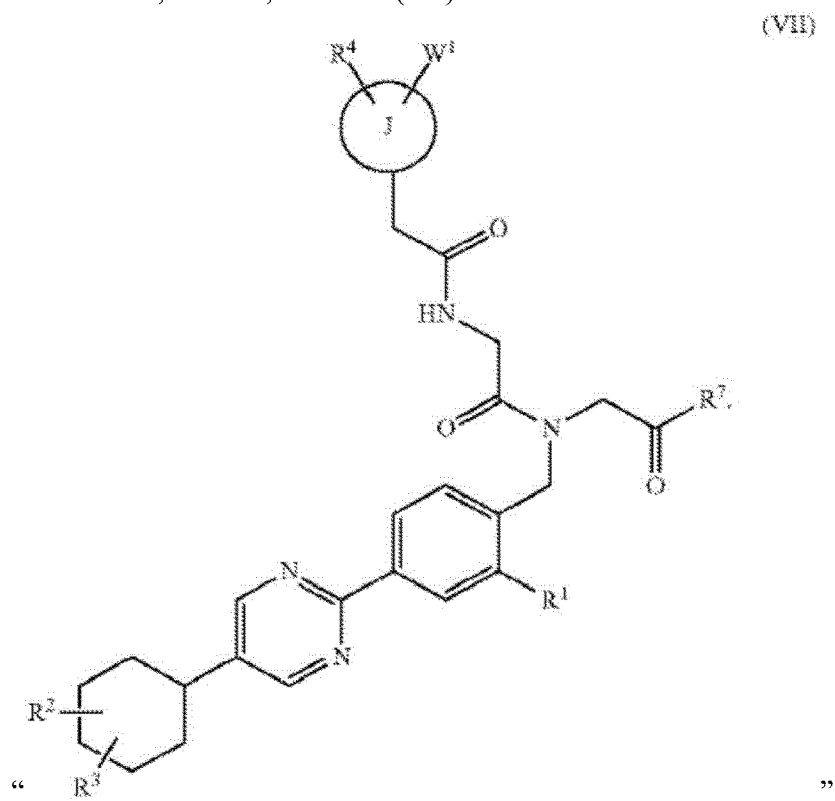

Signed and Sealed this
Seventeenth Day of December, 2024

Derrick Brent
*Acting Director of the United States Patent and Trademark Office*

CERTIFICATE OF CORRECTION (continued)
U.S. Pat. No. 11,530,205 B2

Should read:

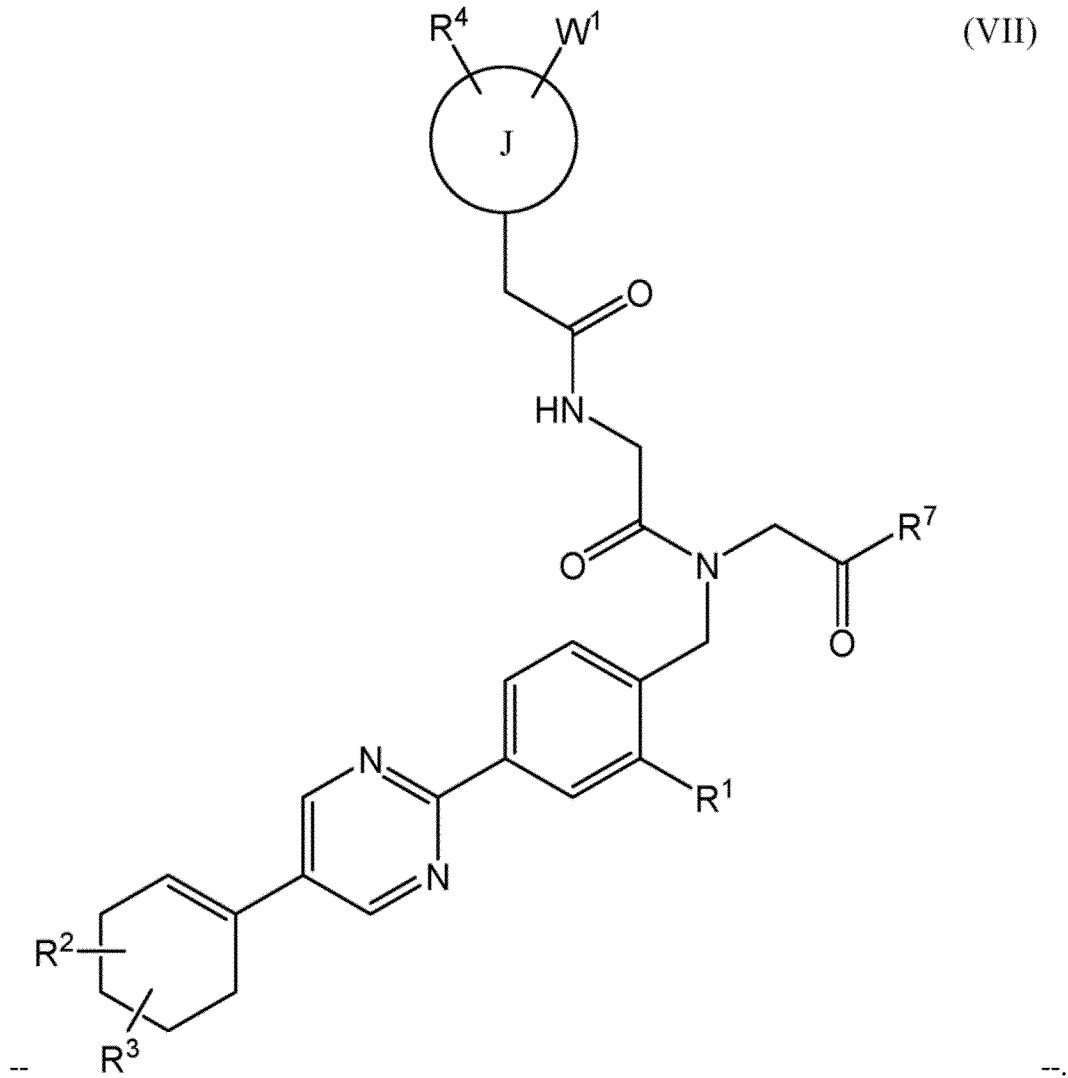

(VII)

--                                                                        --.

CERTIFICATE OF CORRECTION (continued)
U.S. Pat. No. 11,530,205 B2

Page 3 of 5

Columns 297 and 298, Claim 13, Structure 52:

"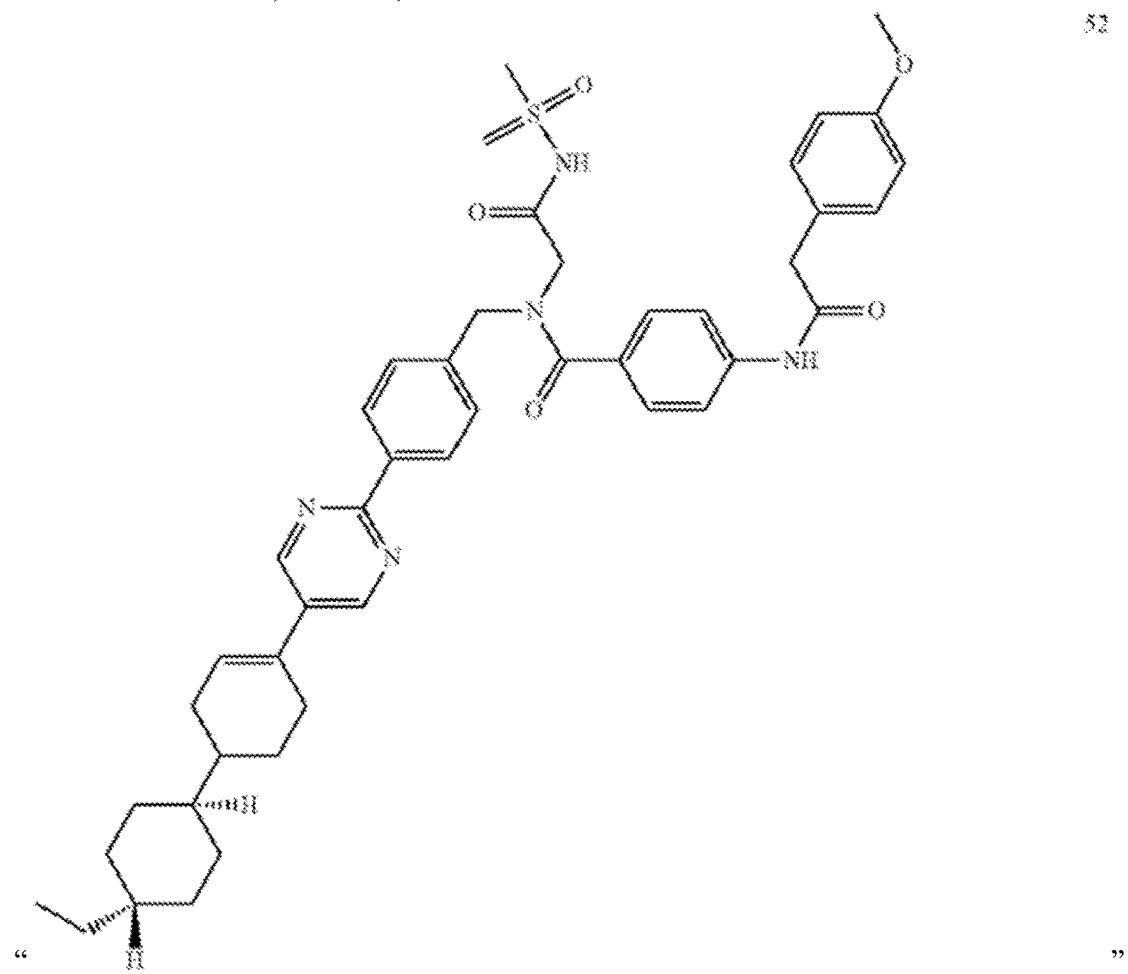"

CERTIFICATE OF CORRECTION (continued)
U.S. Pat. No. 11,530,205 B2

Should read:

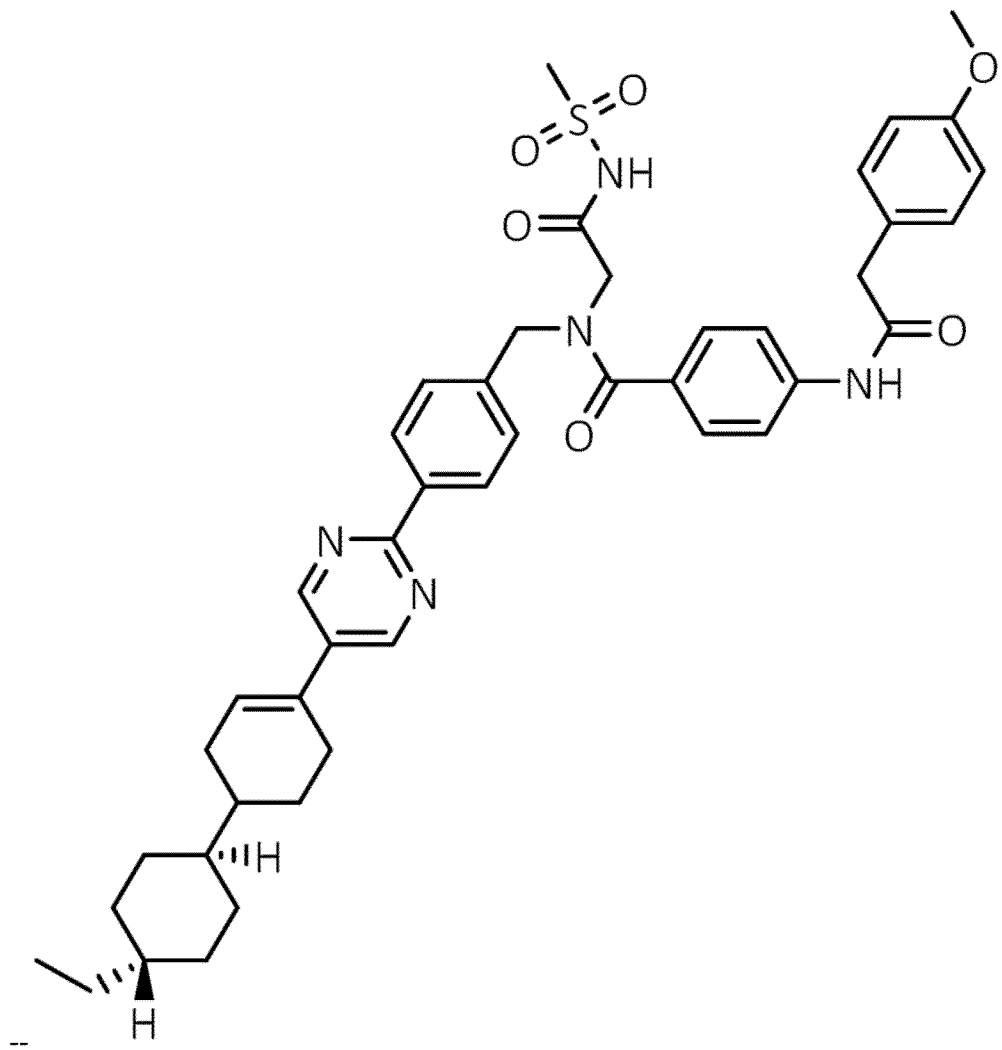

-- 52--.

CERTIFICATE OF CORRECTION (continued)
U.S. Pat. No. 11,530,205 B2

Page 5 of 5

Columns 335 and 336, Claim 13, Structure 93:

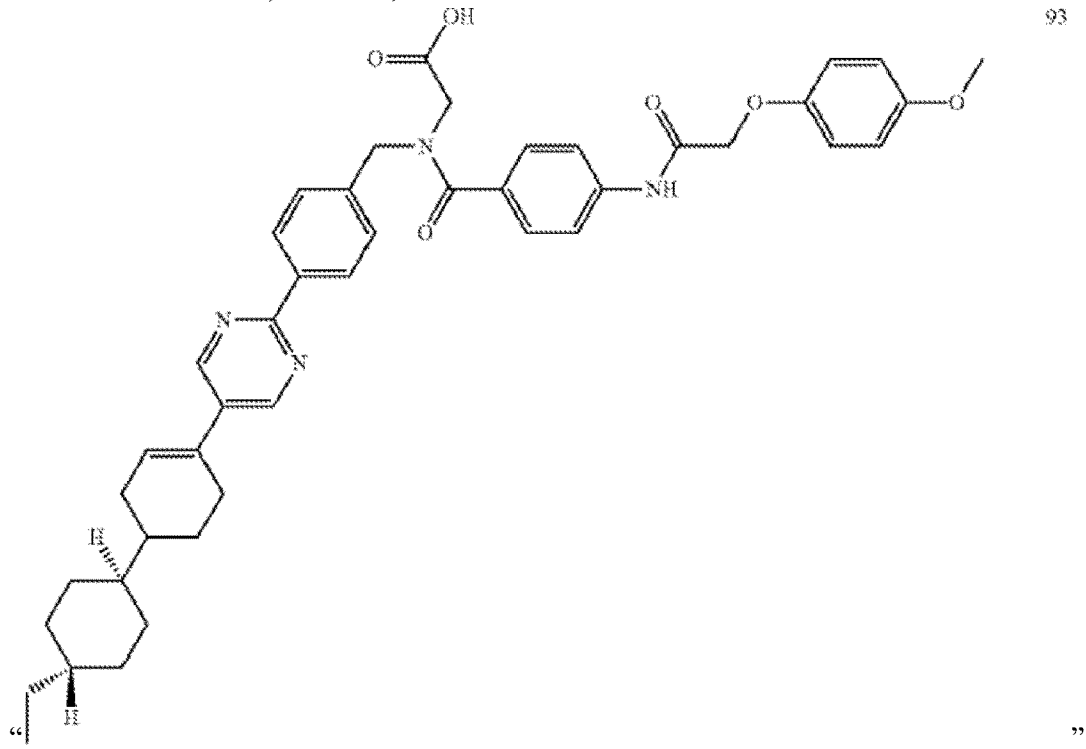

Should read:

SEQUENCE LISTING

```
<160> NUMBER OF SEQ ID NOS: 2

<210> SEQ ID NO 1
<211> LENGTH: 30
<212> TYPE: PRT
<213> ORGANISM: Artificial Sequence
<220> FEATURE:
<223> OTHER INFORMATION: Peptide GLP-1 (7-36)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: Peptide GLP-1 (9-36)

<400> SEQUENCE: 2

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg
            20                  25
```